United States Patent
Amighi et al.

(10) Patent No.: US 10,188,738 B2
(45) Date of Patent: Jan. 29, 2019

(54) FORMULATIONS USEFUL IN THE TREATMENT OF PROLIFERATIVE DISEASES AFFECTING THE RESPIRATORY TRACT

(71) Applicant: Université Libre de Bruxelles, Brussels (BE)

(72) Inventors: Karim Amighi, Brussels (BE); Rémi Rosière, Wezembeek-Oppem (BE); Nathalie Wauthoz, Tournai (BE); Michel Gelbecke, Uccle (BE)

(73) Assignee: Université Libre de Bruxelles, Brussels (BE)

( * ) Notice: Subject to any disclaimer, the term of this patent is extended or adjusted under 35 U.S.C. 154(b) by 0 days.

(21) Appl. No.: 15/029,736

(22) PCT Filed: Oct. 16, 2014

(86) PCT No.: PCT/EP2014/072281
§ 371 (c)(1),
(2) Date: Apr. 15, 2016

(87) PCT Pub. No.: WO2015/055796
PCT Pub. Date: Apr. 23, 2015

(65) Prior Publication Data
US 2016/0263232 A1  Sep. 15, 2016

(30) Foreign Application Priority Data
Oct. 16, 2013  (EP) ................... 13188995

(51) Int. Cl.
| | | |
|---|---|---|
| *A61K 9/51* | (2006.01) | |
| *A61K 31/337* | (2006.01) | |
| *A61K 31/495* | (2006.01) | |
| *A61K 33/24* | (2006.01) | |
| *A61K 9/00* | (2006.01) | |
| *A61K 9/50* | (2006.01) | |
| *A61K 47/48* | (2006.01) | |
| *A61K 47/55* | (2017.01) | |
| *A61K 47/61* | (2017.01) | |
| *A61K 47/69* | (2017.01) | |

(52) U.S. Cl.
CPC ...... *A61K 47/48107* (2013.01); *A61K 9/0075* (2013.01); *A61K 9/50* (2013.01); *A61K 9/5089* (2013.01); *A61K 9/51* (2013.01); *A61K 9/5123* (2013.01); *A61K 9/5161* (2013.01); *A61K 9/5192* (2013.01); *A61K 31/337* (2013.01); *A61K 31/495* (2013.01); *A61K 33/24* (2013.01); *A61K 47/551* (2017.08); *A61K 47/61* (2017.08); *A61K 47/6927* (2017.08); *A61K 47/6939* (2017.08)

(58) Field of Classification Search
CPC ............ A61K 47/48107; A61K 47/551; A61K 47/61; A61K 47/692; A61K 47/6939; A61K 9/0075; A61K 9/50; A61K 9/5089; A61K 9/51; A61K 9/5123; A61K 9/5161; A61K 9/5192; A61K 31/337; A61K 31/495; A61K 31/24
See application file for complete search history.

(56) References Cited

U.S. PATENT DOCUMENTS

| | | | |
|---|---|---|---|
| 4,816,567 A | 3/1989 | Cabilly et al. | |
| 4,921,949 A | 5/1990 | Lang et al. | |
| 6,369,086 B1 | 4/2002 | Davis et al. | |
| 6,369,087 B1 | 4/2002 | Whittle et al. | |
| 6,372,733 B1 | 4/2002 | Caldwell et al. | |
| 6,372,778 B1 | 4/2002 | Tung et al. | |
| 2011/0060036 A1* | 3/2011 | Nie ................... | A61K 47/48169 514/449 |
| 2012/0269729 A1* | 10/2012 | Santra .............. | A61K 47/48107 424/9.1 |

FOREIGN PATENT DOCUMENTS

| | | |
|---|---|---|
| JP | 2005-008598 | 1/2005 |
| WO | WO2011/014821 | 2/2011 |
| WO | WO 2012/174559 | 12/2012 |

OTHER PUBLICATIONS

Jadhav et al. (Int J Pharm Pharm Sci, 4 (3), 163-169).*
Patel et al. J. Pharm. Pharmaceut. Sci. 2010, 13(3), 536-557.*
Manaspon et al. J. Nanomater. 2012, 2012, 1-11.*
Clackson et al., "Making antibody fragments using phage display libraries", Nature, 352(6336): 624-628. (Aug. 1991).
Duret et al., "In vitro and in vivo evaluation of a dry powder endotracheal insufflator device for use in dose-dependent preclinical studies in mice", Eur. J. Pharm Biopharm, 81(3):627-634, (Aug. 2012). Epub (Apr. 2012).
Erhunmwunsee et al., "Surgical managemnet of pulmonary metastases", Ann Thorac Surg, 88(6):2052-2060, (Dec. 2009).
Islam et al., "Dry powder inhalers (DPIs)—a review of device reliability and innovation", Int J Pharm, 360(1-2):1-11, (Aug. 2008). Epub (May 2008).
Jadhav et al., "Design of chitosan based and rographolides microparticles for targetted delivery to lung tumor", International Journal of Pharmacy and Pharmaceutical Sciences, 4(3):163-169. (2012).

(Continued)

*Primary Examiner* — Sreenivasan Padmanabhan
*Assistant Examiner* — Genevieve A Alley
(74) *Attorney, Agent, or Firm* — McDonnell Boehnen Hulbert & Berghoff

(57) ABSTRACT

The present application provides a pharmaceutical formulation comprising a folate receptor (FR)-targeting antineoplastic substance or composition, wherein the pharmaceutical formulation is configured for administration by inhalation, wherein the FR-targeting antineoplastic substance or composition is comprised in a nanoparticle and wherein the nanoparticles are comprised in microparticles, and its use in the treatment of a proliferative disease affecting at least part of the respiratory tract. The present application further provides a pharmaceutical formulation comprising an antineoplastic agent and a FR-targeting excipient, for use in the treatment of a proliferative disease affecting at least part of the respiratory tract.

24 Claims, 10 Drawing Sheets

(56) References Cited

OTHER PUBLICATIONS

Jain, "Drug delivery systems-an overview", Methods Mol Biol, 437:1-50 (2008).
Jiang et al., "The suppression of lung tumorgenesis by aerosol-delivered folate-chitosan-graft-polyethylenimine/Akt 1 shRNA complexes through the Akt signaling pathway" Biomaterials, 30(29):5844-5852. (Oct. 2009).
Kohler et al., "Continuous cultures of fused cells secreting antibody of predefined specificity", Nature, 256(5517): 495-7. (Aug. 1975).
Lu et al., "Folate-mediated delivery of macromolecular anticancertherapeutic agents", Adv Drug Deliv Rev, 54 (5):675-693, (Sep. 2002).
Marks et al., "By-passing immuniction. Human antibodies from V-gene libraries displayed on phage", J Mol Biol, 222 (3): 581-597. (Dec. 1991).
Molina et al., "Non-small cell lung cancer: epidemiology, risk factors, treatment, and survivorship", Mayo Clin Proc 83 (5):584-594, (May 2008).
Parveen et al., "Evaluation of cytotoxicity and mechanism of apoptosis of doxorubicin using folate-decorated chitosan nanoparticles for targeted delivery to retinoblastoma", Cancer Nanotechnology, 1(1-6):47-62. (Oct. 2010).
Pi-Ping et al., "Porous quanternized chitosan nanoparticles containing paclitaxel nanocrystals improved therapeutic efficacy in non-small-cell lung cancer after oral administration", Biomacromolecules, 12(12):4230-4239. (Dec. 2011).
Smyth et al., "Pulmonary Delivery of Anti-cancer Agents", Informa Healthcare, pp. 81-111, (2008).
Wauthoz et al., "In vivo assessment of temozolomide local delivery for lung cancer inhalation therapy", Europ J of Pharmaceutical Sciences, 39(5):402-411. (Mar. 2010).
Xia et al., "Folate-targeted therapies for cancer", J Med Chem, 53(19):6811-6824, (Oct. 2010).
Zhao et al., "Preparation and characterization of camptothecin (CPT)-loaded folate-conjugated dextran nanoparticles for tumor-targeted drug delivery using supercritical antisolvent method", J of Controlled Release, 152(1):E90-E92. (Nov. 2011).
Xu et al., "Preparation and characterization of folate-chitosan-gemcitabine core-shell nanoparticles for potential tumor-targeted drug delivery", J of Nanoscience and Nanotechnology, 13(1):129-138. (Jan. 2013).
Yuning et al., "Synthesis and characterization of folate-conjugated quaternized chitosan as a gene delivery vector", Chemical Industry and Engineering Program, 2542-2547. (2012) [English abstract submitted].
International Search Report issued by the International Searching Authority for International Application No. PCT/EP2014/072281, dated Jan. 21, 2015 (4 pages).
Written Opinion issued by the International Searching Authority for International Application No. PCT/EP2014072281, dated Jan. 21, 2015, (7 pages).
International Preliminary Report On Patentability for International Application No. PCT/EP2014/072281, dated Apr. 19, 2016 (8 pages).
NCBI NP_113617.1 "retbindin isoform 2 [*Homo sapiens*]" published Oct. 6, 2016 [retrieved on Jun. 26, 2017] [retrieved from https://www.ncbi.nlm.nih.gov/protein/NP_113617.1] [2 pages].
NCBI NP_001257369.1 "retbindin isoform 3 [*Homo sapiens*]" published Oct. 6, 2016 [retrieved on Jun. 26, 2017] [retrieved from https://www.ncbi.nlm.nih.gov/protein/NP_001257369.1] [2 pages].
NCBI NP_057936.1 "folate receptor alpha precursor [*Homo sapiens*]" published Jun. 26, 2017 [retrieved on Jun. 26, 2017] [retrieved from https://www.ncbi.nlm.nih.gov/protein/NP_057936.1] [3 pages].
NCBI NP_057937.1 "folate receptor alpha precursor [*Homo sapiens*]" published Jun. 26, 2017 [retrieved on Jun. 26, 2017] [retrieved from https://www.ncbi.nlm.nih.gov/protein/NP_057937.1] [3 pages].
IUPAC. "Aerosol." Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. https://doi.org/10.1351/goldbook [1 page].
Dunbar et al., "Dispersion and Characterization of Pharmaceutical Dry Powder Aerosols" 16:7-45 (1998).
Lim & Hudson, "Synthesis and antimicrobial activity of a water-soluble chitosan derivative with a fiber-reactive group." Carbohydr Res. 339(2):313-19 (Jan. 2004).
Mima et al., "Highly deacetylated chitosan and its properties" J. Applied Polymer Science 28(6):1909-1917 (Jun. 1983).
Tatusova & Madden, "BLAST 2 Sequences, a new tool for comparing protein and nucleotide sequences." FEMS Microbiol Lett. 174(2):247-50 (May 1999).
Xiao et al., "Synthesis and characterization of N-(2-hydroxy)propyl-3-trimethyl ammonium chitosan chloride for potential application in gene delivery." Colloids Surf B Biointerfaces 91:168-174 (Mar. 2012).

\* cited by examiner

FORMULATIONS USEFUL IN THE TREATMENT OF PROLIFERATIVE DISEASES AFFECTING THE RESPIRATORY TRACT

INCORPORATION BY CROSS-REFERENCE

This application is a U.S. national phase of International Application No. PCT/EP2014/072281, filed Oct. 16, 2014, which claims priority to European Patent Application No. 13188995.8, filed Oct. 16, 2013, the disclosure of each of which is hereby incorporated by cross-reference in its entirety.

FIELD

The invention is in the medical field, more specifically in the field of treatment of proliferative diseases affecting the respiratory tract, such as tumours or cancers affecting the respiratory tract. The invention allows specific and selective administration of antineoplastic agents to neoplastic cells affecting the respiratory tract, and provides uses, methods and products useful in the treatment of proliferative diseases affecting the respiratory tract.

BACKGROUND

Lung cancer is one of the most frequent cancers in the world and remains the most deadly. According to the World Health Organization (WHO), about 12.7 million of new cases of cancers have been diagnosed and among them about 1.6 million of new cases of lung cancer in 2008, which therefore ranks it as the third most frequent cancer. Moreover, lung cancer is the most deadly in the world because about 1.4 million patients died in 2008 from their lung cancer of the about 7.6 million of deaths due to cancer during the same year according to WHO's statistics.

Lung cancer include two main types, i.e., small cell lung cancer (SCLC) and non-small cell lung cancer (NSCLC), which are named following their cell histology and represent about 15% and about 85% of the primary lung cancers, respectively (Molina et al., *Mayo Clin Proc* 83:584-594, 2008). SCLC is the most aggressive form and a fast-growing type of lung cancer. Their cells are small and grow quickly to create large tumours. These tumours often metastasize rapidly to other parts of the body like the brain, the bones and the liver. NSCLC is the most common type of lung cancer but it usually grows and metastasizes more slowly than SCLC.

In addition to the above proliferative diseases, the lungs are also a common site for metastasis from different organs such as for metastasis from prostate, breast, colorectal, kidney, head, and neck carcinomas as well as from sarcomas and melanomas (Erhunmwunsee et al., *Ann Thorac Surg* 88:2052-2060, 2009).

The available treatments of proliferative diseases of the respiratory tract depend on the stage of the disease and typically consist of surgery, radiotherapy, and/or chemotherapy (Molina et al., supra).

Chemotherapeutic agents are currently administered by oral administration or by intravenous injections, whereby for both administration routes the chemotherapeutic agents are distributed all over the body, i.e., systemically, before reaching the tumour or cancer. Hence, the chemotherapeutic agent inevitably causes severe systemic toxicities to the patient. The lack of selectivity of the chemotherapeutic agents for neoplastic cells such as tumour or cancer cells in comparison with normal cells, will affect rapidly dividing tissues such as bone marrow, gastrointestinal mucosa, skin and gonads to very often induce adverse side effects such as nauseas and vomiting, myelosuppression and alopecia (*Parfitt, Martindale* 32th edition. Pharmaceutical Press, London, 1999). Severity of the adverse effects can be dose-limiting and can induce an interruption of the treatment, for instance when myelosuppression occurs such as for carboplatin, paclitaxel, docetaxel and vinorelbine. Interruption of the treatment is also the case upon nephrotoxicity such as for cisplatin or neurotoxicity such as for paclitaxel. As the toxicity of the chemotherapeutic agents severely limits the delivered dose, the plasmatic concentrations are often not high enough to be therapeutically efficient at the tumour or cancer site. Moreover, due to the interruption of the treatment to allow normal tissue to recover, tumour or cancer cell repopulation occurs in parallel in various organs (Smyth et al., *Informa Healthcare,* pp 81-111, 2008). Furthermore, systemic treatment is also associated with multiple adverse events including damaged veins, infection at the catheter introduction site, or air embolisms via the intravenous line (Jain, *Methods Mol Biol* 437:1-50, 2008).

A therapeutic plateau has been reached today with the different types of treatment and the chemotherapeutics employed for NSCLCs. In fact, the five-year survival rate for NSCLC patients has been about 16% in the United States of America (USA) in the period 1999-2006. This rate is strongly dependent of the stage of the disease with 53%, 24% and 4% for a local, regional or advanced stage, respectively (Howlader et al., *SEER Cancer Statistic Review,* 1975-2008, 2011).

To increase the selectivity of the chemotherapeutic agent for neoplastic cells and to minimise the exposure of normal cells to the chemotherapeutic agent, exploitation of folate receptor (FR)-mediated drug delivery has been recently proposed. Folate or folic acid is required by eukaryotic cells for nucleotide and DNA synthesis. Therefore, folate receptors and many of the folate-related cell cycle genes are highly expressed in rapidly proliferating cells such as tumour or cancer cells probably as a consequence of their increased requirement for folic acid needed for cell proliferation. FR, especially FR alpha or folate receptor 1 (FOLR1), is overexpressed in many cancers such as ovary, lung, kidney, endometrium, breast, brain, colon, and myeloid cells of hematopoetic lineage (Xia and Low, *J Med Chem* 53:6811-6824, 2010). When a medication is formulated with a chemotherapeutic agent, folic acid metabolism can be exploited to carry the non-selective chemotherapeutic agent specifically into the FR-expressing neoplastic cells by linking folate to the chemotherapeutic agent. As the chemotherapeutic agent is released after recognition of the folate by the FR and/or internalization by the FR-expressing neoplastic cells, FR-mediated targeting allows avoiding unwanted effects to FR-negative tissues or low FR-expressing tissues (Xia and Low, supra).

For instance, WO 2011/014821 relates to methods of detecting and assessing functionally active folate receptors on tumours and treatment associated with those tumours. WO 2011/014821 also concerns methods and compositions for treating folate receptor expressing epithelial tumours including ovarian, endometrial, or non-small cell lung cancer tumours with a folate-vinca alkaloid conjugate (generally known as "EC145") in combination with doxorubicin.

The need for further and/or improved formulations for the treatment of proliferative diseases affecting the respiratory tract, such as tumours or cancers affecting the respiratory tract, is self-evident.

SUMMARY

The present inventors have unexpectedly found that pharmaceutical formulations comprising a folate receptor (FR)-targeting antineoplastic substance or composition can be successfully administered by inhalation, and achieve the desired therapeutic effect. This fact can be advantageously exploited in the medical field, particularly in the treatment of proliferative diseases affecting the respiratory tract.

Accordingly, in an aspect the invention provides a pharmaceutical formulation comprising a FR-targeting antineoplastic substance or composition, wherein the pharmaceutical formulation is configured for administration by inhalation.

Preferably, in an aspect the invention provides a pharmaceutical formulation comprising a FR-targeting antineoplastic substance or composition, wherein the pharmaceutical formulation is configured for administration by inhalation, wherein the FR-targeting antineoplastic substance or composition is comprised in a nanoparticle and wherein the nanoparticles are comprised in microparticles A further aspect provides the pharmaceutical formulation as taught herein for use in the treatment of a proliferative disease affecting at least part of the respiratory tract.

A further aspect provides a pharmaceutical formulation comprising an antineoplastic agent and a FR-targeting excipient, for use in the treatment of a proliferative disease affecting at least part of the respiratory tract.

The pharmaceutical formulations embodying the principles of the present invention allow local or specific administration of the FR-targeting antineoplastic substance or composition to the respiratory tract, thereby circumventing the adverse side effects associated with systemic delivery of an antineoplastic substance or composition. The present inventors also found that the present pharmaceutical formulations configured for administration by inhalation selectively target folate receptor-expressing cells such as neoplastic cells leading to higher concentrations of the antineoplastic agent at the tumour or cancer site. Furthermore, the present pharmaceutical formulations may display a desired rate of dissolution once in contact with physiological fluids, thereby conferring controlled liberation of the antineoplastic agent at the tumour or cancer site. Also, the present pharmaceutical formulations may display bioadhesive properties and/or present a long time of retention in the respiratory tract, thereby retaining the pharmaceutical formulations in the respiratory tract. The present pharmaceutical formulations thus confer to the antineoplastic agent an optimal pharmacokinetic behaviour corresponding to a maximization of the time residence in the respiratory tract, while minimizing systemic absorption and elimination of the antineoplastic agent.

Administration of the present pharmaceutical formulations to the respiratory tract by inhalation advantageously allows local delivery of the formulations, thereby maximizing the contribution of the FR-targeting and increasing the selectivity of the treatment of proliferative disease affecting at least part of the respiratory tract. Furthermore, by local administration of the pharmaceutical formulations to the respiratory tract by inhalation, the administered dose of the antineoplastic agent is not diluted in the systemic circulation before reaching the tumour or cancer site, thereby significantly enhancing the therapeutic ratio. Thus, inhalation of the present pharmaceutical formulations allows improving the efficacy of the treatment and also to reduce or even suppress treatment interruptions due to adverse effects, thereby helping to overcome neoplastic cells repopulation.

Administration of the present formulations by inhalation allows direct uptake by neoplastic cells but may also target neoplastic cells through the bloodstream through absorption of the antineoplastic agent in the local circulation irrigating the respiratory tract.

Related aspects hence provide:

Use of the pharmaceutical formulation as taught herein for the manufacture of a medicament for the treatment of a proliferative disease affecting at least part of the respiratory tract;

A method of treating a proliferative disease affecting at least part of the respiratory tract in a subject in need of said treatment comprising the administration of a therapeutically or prophylactically effective amount of the pharmaceutical formulation as taught herein to the subject.

Use of a pharmaceutical formulation comprising an antineoplastic agent and a FR-targeting excipient for the manufacture of a medicament for the treatment of a proliferative disease affecting at least part of the respiratory tract;

A method of treating a proliferative disease affecting at least part of the respiratory tract in a subject in need of said treatment comprising the administration of a therapeutically or prophylactically effective amount of a pharmaceutical formulation comprising an antineoplastic agent and a FR-targeting excipient to the subject.

These and further aspects and preferred embodiments of the invention are described in the following sections and in the appended claims. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. The subject-matter of the appended claims is hereby specifically incorporated in this specification.

The independent and dependent claims set out particular and preferred features of the invention. Features from the dependent claims may be combined with features of the independent or other dependent claims as appropriate.

DESCRIPTION OF EMBODIMENTS

Figure 1:
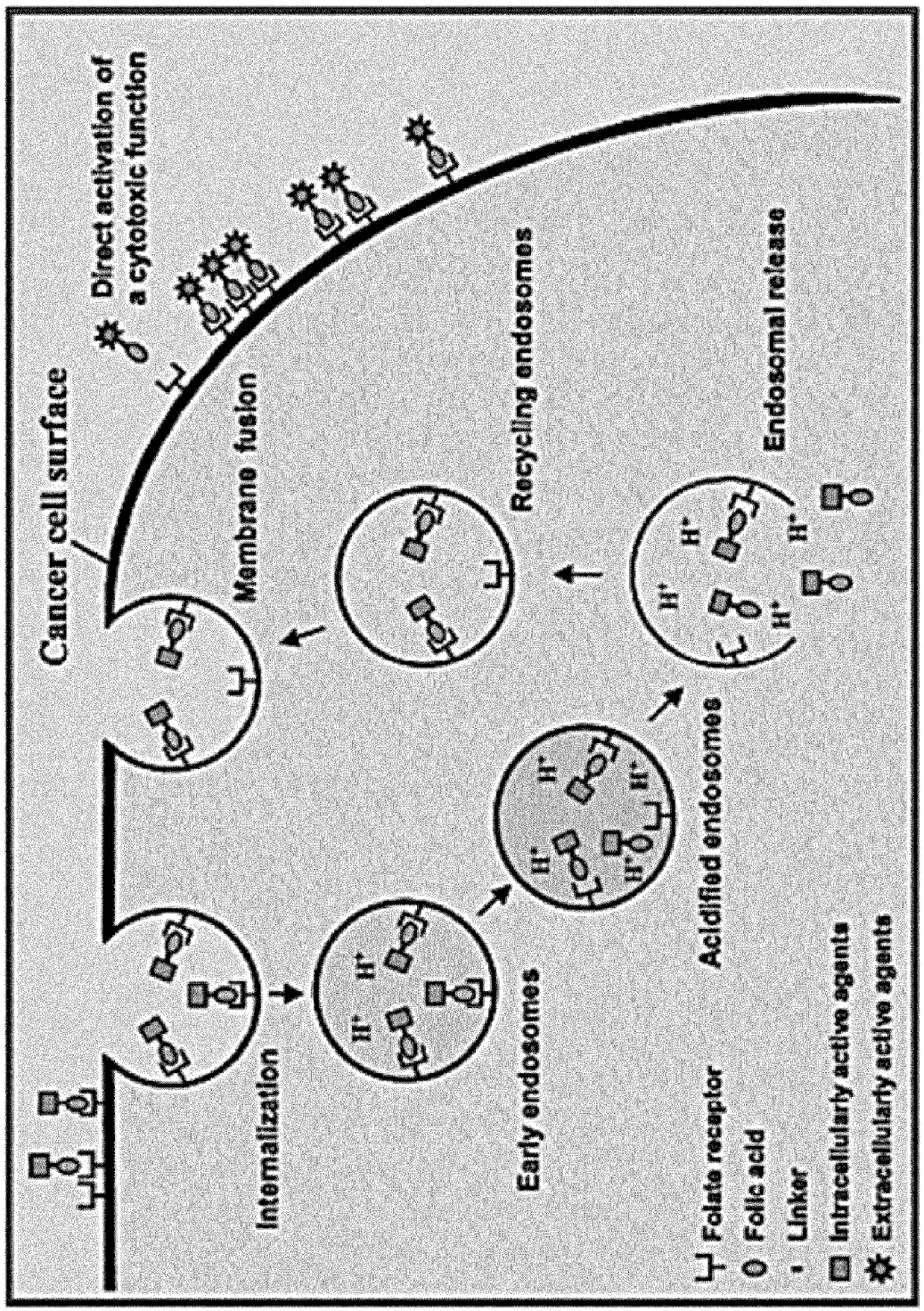
FIG. 1 represents a diagrammatic representation of folate-mediated delivery of therapeutics agents to FR-positive cancer cells (Lu and Low, *Adv Drug Deliv Rev* 54:675-693, 2002).

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

All documents cited in the present specification are hereby incorporated by reference in their entirety. Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

As noted, the present inventors have found that pharmaceutical formulations comprising a FR-targeting antineoplastic substance or composition can be successfully administered by inhalation, thereby selectively and specifically targeting neoplastic cells affecting the respiratory tract, and hence, making the pharmaceutical formulations useful in the treatment of proliferative diseases affecting the respiratory tract such as tumours or cancers affecting the respiratory tract.

Accordingly, in a first aspect, the invention provides a pharmaceutical formulation comprising a FR-targeting antineoplastic substance or composition, wherein the pharmaceutical formulation is configured for administration by inhalation. As mentioned above, the pharmaceutical formulations embodying the principles of the present invention allow local or specific administration of the FR-targeting antineoplastic substance or composition to the respiratory tract, thereby circumventing the adverse side effects associated with systemic delivery of an antineoplastic substance or composition. The present inventors also found that the present pharmaceutical formulations configured for administration by inhalation selectively target folate receptor-expressing cells such as neoplastic cells leading to higher concentrations of the antineoplastic agent at the tumour or cancer site.

The present pharmaceutical formulations may be useful in increasing the sensitivity of tumour cells to other therapy types, for instance to radiation, and also in potentiating or enhancing damage to tumours by the antineoplastic agents, due to the fact that inhalation of the pharmaceutical formulations can allow obtaining higher concentrations of the antineoplastic agent around and inside the tumour site. The term "specificity" of the pharmaceutical formulations, as used herein, refers to the ability of the pharmaceutical formulations to be administered to certain cells, tissues, or organs, and not to certain other cells, tissues, or organs. The pharmaceutical formulations as taught herein are configured for inhalation and hence allow specific administration to cells of the respiratory tract. The specificity of the pharmaceutical formulations as taught herein is in contrast with such prior art formulations which only allow systemic and hence non-specific delivery of pharmaceutical formulations.

The term "selectivity" of the pharmaceutical formulations, as used herein, refers to the ability of the pharmaceutical formulations to bind to, target, or impinge on certain cells and not bind to, target, or impinge on certain other cells. The pharmaceutical formulations as taught herein selectively bind to cells expressing folate receptors and not to other cells.

Formulations disclosed herein are configured for use in medicine, whether or not comprising one or more pharmaceutically acceptable excipients in addition to the other herein recited elements. Accordingly, the terms "pharmaceutical formulation" and "formulation" may be used interchangeably herein. In certain embodiments, the pharmaceutical formulation may comprise a FR-targeting antineoplastic substance or composition. In certain embodiments, the pharmaceutical formulation may comprise a FR-targeting antineoplastic substance or composition, preferably wherein the pharmaceutical formulation is configured for administration by inhalation.

The recitation "FR-targeting", as used herein, refers to the targeting of a folate receptor.

The recitation "FR-targeting antineoplastic substance" refers to a substance or compound comprising an FR-targeting moiety and an antineoplastic agent, wherein the FR-targeting moiety and the antineoplastic agent are covalently associated or bound, i.e. they constitute a substance or compound (e.g. molecule). The FR-targeting moiety and the antineoplastic agent may be covalently associated or bound to each other via (by means of) a direct covalent bond or via (by means of) a linker.

The recitation "FR-targeting antineoplastic composition" refers to a composition comprising an FR-targeting moiety and an antineoplastic agent, wherein the FR-targeting moiety or a substance comprising it (e.g., an excipient) and the antineoplastic agent are non-covalently associated. For instance, the FR-targeting moiety or a substance comprising it (e.g., an excipient) and the antineoplastic agent may be comprised in a nanoparticle.

The recitation "configured for administration by inhalation" as used herein refers to the property of the pharmaceutical formulations as taught herein that allows local or exclusive delivery of the pharmaceutical formulations to the respiratory tract.

Preferred statements (features) and embodiments of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous. Hereto, the present invention is in particular captured by any one or any combination of one or more of the below numbered aspects and statements 1 to 25, with any other statement and/or embodiments.

1. A pharmaceutical formulation comprising a folate receptor (FR)-targeting antineoplastic substance or composition, wherein the pharmaceutical formulation is configured for administration by inhalation.

2. A pharmaceutical formulation comprising a folate receptor (FR)-targeting antineoplastic substance or composition, wherein the pharmaceutical formulation is configured for administration by inhalation, wherein the FR-targeting antineoplastic substance or composition is comprised in a nanoparticle and wherein the nanoparticles are comprised in microparticles.

3. A pharmaceutical formulation comprising a folate receptor (FR)-targeting antineoplastic substance or composition, wherein the pharmaceutical formulation is configured for administration by inhalation, wherein the FR-targeting antineoplastic substance or composition comprises at least one antineoplastic agent and at least one FR-targeting excipient, wherein the FR-targeting excipient is a folate-polysaccharide conjugate comprising at least one folate moiety covalently linked to a polysaccharide or functionally-modified polysaccharide; wherein the polysaccharide or functionally-modified polysaccharide is covalently bound to the folate moiety via a linker, wherein the linker comprises a polyether, ether, amine, polyamine, amino acid, peptide, a polypeptide, a carbohydrate, or a combination of two or more thereof 4. The pharmaceutical formulation according to any one of statements 1 to 3, which is formulated as a dry powder.

5. The pharmaceutical formulation according to any one of statements 1 to 4, wherein the FR-targeting antineoplastic substance or composition is comprised in a nanoparticle.

6. The pharmaceutical formulation according to any one of statements 1 to 5, wherein the FR-targeting antineoplastic substance or composition comprises at least one antineoplastic agent and at least one FR-targeting excipient.

7. The pharmaceutical formulation according to any one of statements 3 to 6, wherein the antineoplastic agent and the FR-targeting excipient are comprised in a nanoparticle, preferably wherein the antineoplastic agent and the FR-targeting excipient are non-covalently associated in the nanoparticle.
8. The pharmaceutical formulation according to any one of statements 1 to 7, wherein the FR-targeting is effected by at least one folate moiety.
9. The pharmaceutical formulation according to any one of statements 3 to 8, wherein the FR-targeting excipient is a folate-polysaccharide conjugate comprising at least one folate moiety covalently linked to a polysaccharide or functionally-modified polysaccharide.
10. The pharmaceutical formulation according to any one of statements 3 to 9, wherein the polysaccharide or functionally-modified polysaccharide is selected from chitosan or functionally-modified chitosan; N-[(2-hydroxy-3- trimethylammonium)propyl] chitosan (HTC) and its salts; N-trimethyl chitosan (TMC) and its salts; N,O-carboxymethyl chitosan (N,O-CMC) and its salts; N-carboxymethyl chitosan (N-CMC) and its salts; N,N-carboxymethyl chitosan (NN-CMC) and its salts; O-carboxymethyl chitosan (O-CMC) and its salts; hydrophobically-modified chitosan (HMC) and its salts; dextran or functionally-modified dextran; hydrophobically-modified dextran (HMD) and its salts; starch or functionally-modified starch; hydroxypropyl starch; amylose or functionally-modified amylose; amylopectin or functionally-modified amylopectin; cellulose or functionally-modified cellulose; methylcellulose and its salts; carboxymethylcellulose and its salts; hydroxyethylcellulose and its salts; ethylcellulose and its salts; hydroxyethylmethylcellulose and its salts; hydroxypropylcellulose and its salts; hypromellose and its salts; hypromellose acetate succinate; hypromellose phthalate; croscarmellose and its salts; chitin; cyclodextrin; dextrate; dextrin;

maltodextrin; pullulan; or guar gum.

11. The pharmaceutical formulation according to any one of statements 3 to 10, wherein the polysaccharide or functionally-modified polysaccharide is covalently bound to the folate moiety via a single bond or via a linker, wherein the linker comprises a polyether, ether, amine, polyamine, amino acid, peptide, a polypeptide, a carbohydrate, or a combination of two or more thereof, preferably wherein the linker comprises or consists essentially of a polyether selected from polyethylene oxide (PEO), polypropylene oxide (PPO), or a block co-polymer of PEO and PPO, more preferably wherein the linker comprises or consists essentially of a PEO.

12. The pharmaceutical formulation according to any one of statements 3 to 11, wherein the FR-targeting excipient is a folate-polysaccharide conjugate comprising at least one unit selected from the group consisting of units of Formula XIb, XIc, XId, and XIe, or a stereoisomer, tautomer, salt, hydrate or solvate thereof, or any subgroup thereof, wherein

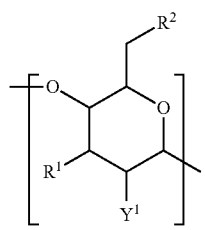

(XIb)

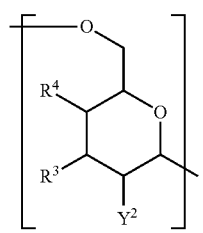

(XIc)

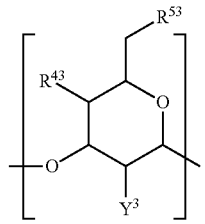

(XId)

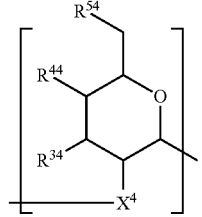

(XIe)

$Y^1$ is $-X^2-X^1-X^3$, or a group selected from $-OR^{10}$, $-N(R^{100})R^{101}$, or $-N^+(R^{100})(R^{101})R^{102}$,
$Y^2$ is $-X^2-X^1-X^3$, or a group selected from $-OR^{20}$, $-N(R^{200})R^{201}$, or $-N^+(R^{200})(R^{201})R^{202}$,
$Y^3$ is $-X^2-X^1-X^3$, or a group selected from $-OR^{30}$, $-N(R^{300})R^{301}$, or $-N^+(R^{300})(R^{301})R^{302}$,
$R^1$ is $-OR^{11}$ or $-X^2-X^1-X^3$,
$R^2$ is $-OR^{21}$ or $-X^2-X^1-X^3$,
$R^3$ is $-OR^{31}$ or $-X^2-X^1-X^3$,
$R^4$ is $-OR^{41}$ or $-X^2-X^1-X^3$,
$R^{34}$ is $-OR^{31}$ or $-X^2-X^1-X^3$,
$R^{43}$ is $-OR^{41}$ or $-X^2-X^1-X^3$,
$R^{44}$ is $-OR^{41}$ or $-X^2-X^1-X^3$,
$R^{53}$ is $-OR^{51}$ or $-X^2-X^1-X^3$,
$R^{54}$ is $-OR^{51}$ or $-X^2-X^1-X^3$,
wherein at least one of $Y^1$, $R^1$, or $R^2$ is $-X^2-X^1-X^3$;
wherein at least one of $Y^2$, $R^3$, or $R^4$ is $-X^2-X^1-X^3$;
wherein at least one of $Y^3$, $R^{43}$, or $R^{53}$ is $-X^2-X^1-X^3$;
wherein at least one of $R^{34}$, $R^{44}$, or $R^{54}$ is $-X^2-X^1-X^3$;
wherein $R^{10}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $-C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$R^{11}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$R^{20}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

R$^{21}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

R$^{30}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

R$^{31}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

R$^{41}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

R$^{51}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

R$^{100}$ is selected from hydrogen, or a group consisting of $C_{1-25}$alkyl, $C_{1-6}$alkylene-N(R$^{111}$)R$^{112}$, $C_{1-6}$alkylene-N$^+$(R$^{111}$)(R$^{112}$)R$^{113}$, $C_{1-25}$alkylcarbonyl, $C_{2-25}$alkenylcarbonyl, $C_{1-6}$alkylene-CO—OR$^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein R$^{111}$ is selected from hydrogen or $C_{1-6}$alkyl, R$^{112}$ is selected from hydrogen or $C_{1-6}$alkyl, R$^{113}$ is selected from hydrogen or $C_{1-6}$alkyl, and R$^{114}$ is selected from hydrogen or $C_{1-6}$alkyl;

R$^{101}$ is selected from hydrogen, or a group consisting of $C_{1-25}$alkyl, $C_{1-6}$alkylene-N(R$^{111}$)R$^{112}$, $C_{1-6}$alkylene-N$^+$(R$^{111}$)(R$^{112}$)R$^{113}$, $C_{1-25}$alkylcarbonyl, $C_{2-25}$alkenylcarbonyl, $C_{1-6}$alkylene-CO—OR$^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein R$^{111}$ is selected from hydrogen or $C_{1-6}$alkyl, R$^{112}$ is selected from hydrogen or $C_{1-6}$alkyl, R$^{113}$ is selected from hydrogen or $C_{1-6}$alkyl, and R$^{114}$ is selected from hydrogen or $C_{1-6}$alkyl;

R$^{102}$ is selected from hydrogen, or a group consisting of $C_{1-25}$alkyl, $C_{1-6}$alkylene-N(R$^{111}$)R$^{112}$, $C_{1-6}$alkylene-N$^+$(R$^{111}$)(R$^{112}$)R$^{113}$, $C_{1-25}$alkylcarbonyl, $C_{2-25}$alkenylcarbonyl, $C_{1-6}$alkylene-CO—OR$^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein R$^{111}$ is selected from hydrogen or $C_{1-6}$alkyl, R$^{112}$ is selected from hydrogen or $C_{1-6}$alkyl, R$^{113}$ is selected from hydrogen or $C_{1-6}$alkyl, and R$^{114}$ is selected from hydrogen or $C_{1-6}$alkyl;

R$^{200}$ is selected from hydrogen, or a group consisting of $C_{1-25}$alkyl, $C_{1-6}$alkylene-N(R$^{211}$)R$^{212}$, $C_{1-6}$alkylene-N$^+$(R$^{211}$)(R$^{212}$)R$^{213}$, $C_{1-25}$alkylcarbonyl, $C_{2-25}$alkenylcarbonyl, $C_{1-6}$alkylene-CO—R$^{214}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein R$^{211}$ is selected from hydrogen or $C_{1-6}$alkyl, R$^{212}$ is selected from hydrogen or $C_{1-6}$alkyl, R$^{213}$ is selected from hydrogen or $C_{1-6}$alkyl, and R$^{214}$ is selected from hydrogen or $C_{1-6}$alkyl;

R$^{201}$ is selected from hydrogen, or a group consisting of $C_{1-25}$alkyl, $C_{1-6}$alkylene-N(R$^{211}$)R$^{212}$, $C_{1-6}$alkylene-N$^+$(R$^{211}$)(R$^{212}$)R$^{213}$, $C_{1-25}$alkylcarbonyl, $C_{2-25}$alkenylcarbonyl, $C_{1-6}$alkylene-CO—R$^{214}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein R$^{211}$ is selected from hydrogen or $C_{1-6}$alkyl, R$^{212}$ is selected from hydrogen or $C_{1-6}$alkyl, $R^{213}$ is selected from hydrogen or $C_{1-6}$alkyl, and $R^{214}$ is selected from hydrogen or $C_{1-6}$alkyl;

$R^{202}$ is selected from hydrogen, or a group consisting of $C_{1-25}$alkyl, $C_{1-6}$alkylene-$N(R^{211})R^{212}$, $C_{1-6}$alkylene-$N^+(R^{211})(R^{212})R^{213}$, $C_{1-25}$alkylcarbonyl, $C_{2-25}$alkenylcarbonyl, $C_{1-6}$alkylene-CO—$R^{214}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{211}$ is selected from hydrogen or $C_{1-6}$alkyl, $R^{212}$ is selected from hydrogen or $C_{1-6}$alkyl, $R^{213}$ is selected from hydrogen or $C_{1-6}$alkyl, and $R^{214}$ is selected from hydrogen or $C_{1-6}$alkyl;

$R^{300}$ is selected from hydrogen, or a group consisting of $C_{1-25}$alkyl, $C_{1-6}$alkylene-$N(R^{211})R^{212}$, $C_{1-6}$alkylene-$N^+(R^{211})(R^{212})R^{213}$, $C_{1-25}$alkylcarbonyl, $C_{2-25}$alkenylcarbonyl, $C_{1-6}$alkylene-CO—$OR^{314}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{311}$ is selected from hydrogen or $C_{1-6}$alkyl, $R^{312}$ is selected from hydrogen or $C_{1-6}$alkyl, $R^{313}$ is selected from hydrogen or $C_{1-6}$alkyl, and $R^{314}$ is selected from hydrogen or $C_{1-6}$alkyl;

$R^{301}$ is selected from hydrogen, or a group consisting of $C_{1-25}$alkyl, $C_{1-6}$alkylene-$N(R^{211})R^{212}$; $C_{1-6}$alkylene-$N^+(R^{211})(R^{212})R^{213}$; $C_{1-25}$alkylcarbonyl, $C_{2-25}$alkenylcarbonyl, $C_{1-6}$alkylene-CO—$OR^{314}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{311}$ is selected from hydrogen or $C_{1-6}$alkyl, $R^{312}$ is selected from hydrogen or $C_{1-6}$alkyl, $R^{313}$ is selected from hydrogen or $C_{1-6}$alkyl, and $R^{314}$ is selected from hydrogen or $C_{1-6}$alkyl;

$R^{302}$ is selected from hydrogen, or a group consisting of $C_{1-25}$alkyl, $C_{1-6}$alkylene-$N(R^{211})R^{212}$, $C_{1-6}$alkylene-$N^+(R^{211})(R^{212})R^{213}$; $C_{1-25}$alkylcarbonyl, $C_{2-25}$alkenylcarbonyl, $C_{1-6}$alkylene-CO—$OR^{314}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{311}$ is selected from hydrogen or $C_{1-6}$alkyl, $R^{312}$ is selected from hydrogen or $C_{1-6}$alkyl, $R^{313}$ is selected from hydrogen or $C_{1-6}$alkyl, and $R^{314}$ is selected from hydrogen or $C_{1-6}$alkyl;

$X^2$ is —O— or —$N(R^{103})$—, wherein $R^{103}$ is selected from hydrogen or $C_{1-6}$alkyl;

$X^1$ is a single bond or a linker comprising a polyether, ether, amine, polyamine, amino acid, peptide, a polypeptide, a carbohydrate, or a combination of two or more thereof, $X^3$ is a folate moiety; preferably $X^3$ is a folate moiety having the structural Formula XII, or a stereoisomer, tautomer, salt, hydrate or solvate thereof, wherein

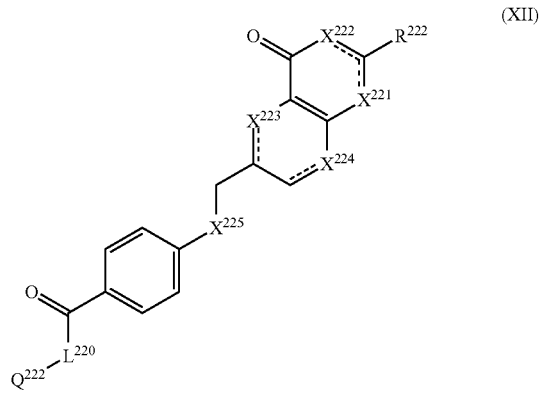

(XII)

$X^{221}$ is selected from N, $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; $L^{220}$ is selected from

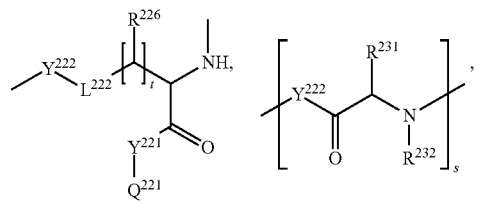

or a group consisting of $C_{1-6}$alkylene, $C_{1-6}$alkylenecarbonyl, —$C_{1-6}$alkylene-$N(R^{227})$—, $C_{2-6}$alkenylene, $C_{2-6}$alkynylene, $C_{3-6}$cycloalkylene, $C_{6-10}$arylene, —(C=O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$ alkynylene, $C_{3-6}$cycloalkylene-(CO)—O—$C_{3-6}$ cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—

(CO)—$C_{3-6}$cycloalkylene, —N($R^{228}$)—, —N($R^{228}$)—(CO)—, and —(CO)—N($R^{228}$)—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —N($R^{229}$)—, or —S—; $Y^{222}$ is selected from a single bond, —O—, —$NR^{229}$—, —N($R^{229}$)—C(=NH)—N($R^{230}$)—, or —S—; $L^{222}$ is a single bond, $C_{6-10}$arylene, or —(C=O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond;

$X^4$ is —O— or —N($R^{403}$)—, wherein $R^{403}$ is selected from hydrogen or $C_{1-6}$alkyl.

13. The pharmaceutical formulation according to any one of statements 4 to 10, wherein the antineoplastic agent is selected from temozolomide, cisplatin, paclitaxel, docetaxel, gemcitabine, vinorelbine, etoposide, irinotecan, cyclophosphamide, doxorubicin, vincristine, or a combination thereof 14. The pharmaceutical formulation according to any one of statements 3 to 13, wherein the nanoparticles are comprised in microparticles.

15. An inhaler comprising the pharmaceutical formulation according to any one of statements 1 to 14, preferably a powder inhaler comprising the pharmaceutical formulation according to any one of statements 1 to 14, more preferably a dry powder inhaler comprising the pharmaceutical formulation according to any one of statements 1 to 14.

16. A pharmaceutical formulation according to any one of statements 1 to 14, for use in the treatment of a proliferative disease affecting at least part of the respiratory tract.

17. A pharmaceutical formulation comprising an antineoplastic agent and a FR-targeting excipient, for use in the treatment of a proliferative disease affecting at least part of the respiratory tract.

18. The pharmaceutical formulation for use according to statement 17, wherein the pharmaceutical formulation is administered by inhalation, preferably by dry powder inhalation 19. The pharmaceutical formulation for use according to any one of statements 14 to 16, wherein the proliferative disease affecting at least part of the respiratory tract is a tumour affecting at least part of the respiratory tract or cancer affecting at least part of the respiratory tract.

20. The pharmaceutical formulation for use according to any one of statements 16 to 19, wherein the proliferative disease affecting at least part of the respiratory tract is small cell lung cancer (SCLC) or non-small cell lung cancer (NSCLC).

21. The pharmaceutical formulation for use according to any one of statements 16 to 19, wherein the proliferative disease affecting at least part of the respiratory tract is a metastatic tumour affecting at least part of the respiratory tract or metastatic cancer affecting at least part of the respiratory tract.

22. A method for preparing the pharmaceutical formulation according to any one of statements 1 to 14, the method comprising the steps of:
(a) preparing in a first solvent a first composition comprising: (i) at least one FR-targeting antineoplastic substance or composition, and (ii) optionally one or more polymeric excipients and/or one or more lipid excipients and/or one or more tensioactive agents, wherein the at least one FR-targeting antineoplastic substance or composition is in solution in the first solvent, and the optional one or more polymeric excipients and/or one or more lipid excipients and/or one or more tensioactive agents are solubilised or dispersed in the first solvent;
(b) preparing in a second solvent a second composition comprising: (i') a FR-targeting excipient, and (ii') optionally one or more polymeric excipients and/or one or more lipid excipients and/or one or more tensioactive agents, wherein the FR-targeting excipient is in solution or in dispersion in the second solvent, and the optional one or more polymeric excipients and/or one or more lipid excipients and/or one or more tensioactive agents are solubilised or dispersed in the second solvent, and wherein the at least one FR-targeting antineoplastic substance or composition is more soluble in the first solvent than in the second solvent;
(c) mixing of the first composition of step (a) and the second composition of step (b) to produce nanoparticles (in the solvent mixture), wherein the nanoparticles comprise the at least one FR-targeting antineoplastic substance or composition.

23. The method according to statement 22, wherein the method comprises the steps of:
(a) preparing in a first solvent a first composition comprising: (i) at least one antineoplastic agent, (ii) at least one FR-targeting excipient, and (iii) optionally one or more polymeric excipients and/or one or more lipid excipients and/or one or more tensioactive agents, wherein the at least one antineoplastic agent and the at least one FR-targeting excipient are in solution in the first solvent, and the optional one or more polymeric excipients and/or one or more lipid excipients and/or one or more tensioactive agents are solubilised or dispersed in the first solvent;
(b) preparing in a second solvent a second composition comprising: (i') a FR-targeting excipient, and (ii') optionally one or more polymeric excipients and/or one or more lipid excipients and/or one or more tensioactive agents, wherein the FR-targeting excipient is in solution or in dispersion in the second solvent, and the optional one or more polymeric excipients and/or one or more lipid excipients and/or one or more tensioactive agents are solubilised or dispersed in the second solvent, and wherein the at least one antineoplastic agent is more soluble in the first solvent than in the second solvent, (c) mixing of the first composition of step (a) and the second composition of step (b) to produce nanoparticles, wherein the at least one antineoplastic agent is at least partly coated or dispersed in the at least one FR-targeting excipient.

24. The method according to statement 22 or 23, for preparing microparticles configured for dry powder inhalation, comprising the steps of:

(a") preparing in a solvent a composition comprising: (i") nanoparticles produced in step (c), (ii") optionally at least one carrier, and (iii") one or more surfactants, wherein the nanoparticles are dispersed in the solvent, the optional carrier is in suspension or solution or dispersed in the solvent, and the one or more surfactants are in solution in the solvent, and (b") drying, preferably spray drying, the composition of step (a") to produce microparticles containing the nanoparticles.

25. The method according to statement 24, wherein the method further comprises dissolving or dispersing the microparticles in an aqueous medium to reconstitute the nanoparticles, wherein the particle size distribution of at least 10% of the reconstituted nanoparticles corresponds to the particle size distribution of the nanoparticles (before they were) comprised in the microparticles.

In certain embodiments, the FR-targeting antineoplastic substance or composition comprises at least one antineoplastic agent and at least one FR-targeting excipient.

In certain embodiments of the products (such as pharmaceutical formulations or FR-targeting excipients), uses, or methods, as taught herein, the FR-targeting may be effected by at least one folate moiety. Such folate moiety advantageously allows that the present pharmaceutical formulations selectively bind to, target, or impinge on cells expressing folate receptors and not bind to, target, or impinge on other cells. In certain embodiments, the FR-targeting antineoplastic substance or composition may comprise a folate moiety. In certain embodiments, the FR-targeting antineoplastic substance or composition may comprise at least one folate moiety. In certain embodiments, the FR-targeting antineoplastic substance or composition may comprise at least one folate moiety connected via a single bond or linker as taught herein (i.e., via $X^1$) to a polysaccharide or functionally-modified polysaccharide as taught herein.

The term "folate moiety" or "folate", as used herein, refers to moieties composed of folic acid, or a derivative thereof (e.g. reduced folic acid), or composed of a subgroup of folic acid (e.g. pteroate moiety), or a derivative thereof (e.g. reduced pteroic acid).

The folate moiety as taught herein may specifically bind a folate receptor. The folate moiety as taught herein may bind a folate receptor with an affinity (dissociation constant or $K_d$) of about $1·10^{-8}$ M or less, such as about $5·10^{-9}$ M or less, or about $1·10^{-9}$ M or less.

The terms "folate" or "folic acid", as used herein, refer to forms of the water-soluble vitamin B9. Folate or folic acid is also known with CAS Number 59-30-3, or as vitamin M, vitamin B9, vitamin $B_e$ (or folacin), pteroyl-L-glutamic acid (i.e., pte-glu), and pteroyl-L-glutamate.

The term "reduced folic acid", as used herein refers to derivatives of folic acid wherein one or more of the functional groups of folic acid are reduced. Non-limiting examples of reduced folic acid are dihydrofolate (i.e., DHF), tetrahydrofolate (i.e., THF), 5-formyl-tetrahydrofolate (i.e., leucovorin), or 5-methyl-tetrahydrofolate (i.e., 5MTHF).

In certain embodiments, the FR-targeting antineoplastic substance or composition may comprise a pteroate moiety.

The term "pteroate moiety" as used herein refers to moieties composed of pteroic acid or pteroic acid derivatives, such as reduced pteroic acid. Non-limiting examples of reduced pteroic acid are dihydro pteroate (i.e., DHP) or tetrahydro pteroate (i.e., THP).

In certain embodiments of the products (such as pharmaceutical formulations FR-targeting antineoplastic substance or composition or FR-targeting excipients) or uses, as taught herein, the folate moiety may have the structural Formula XV, or a stereoisomer, tautomer, salt, hydrate or solvate thereof, wherein

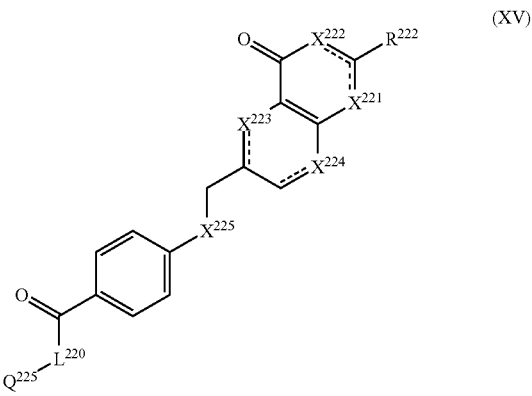

(XV)

$X^{221}$ is selected from N, $NR^{221}$, or O; $X^{222}$ is selected from N, $NR^{221}$ or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —OR$^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halo-substituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; $L^{220}$ is selected from

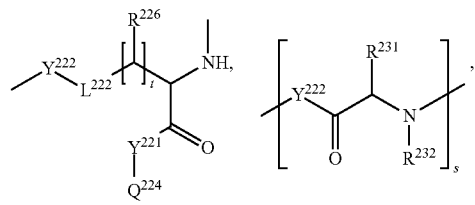

or a group consisting of $C_{1-6}$alkylene, $C_{1-6}$alkylenecarbonyl, $C_{1-6}$alkylene-N(R$^{227}$)—, $C_{2-6}$alkenylene, $C_{2-6}$alkynylene, $C_{3-6}$cycloalkylene, $C_{6-10}$arylene, —(C=O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—(CO)—$C_{3-6}$cycloalkylene, —N($R^{228}$) (CO)—, and —(CO)—N($R^{228}$)—, each group being optionally substituted with one or more substituents each independently selected from hydroxyl or $C_{1-6}$alkyl; wherein the $Y^{222}$ is attached to $Q^{225}$ and —NH— is attached to —(CO)—, or wherein the left side of each group is attached to $Q^{225}$ and the right side of each group is attached to —(CO)—; wherein $Y^{221}$ is selected from a single bond, —O—, —N($R^{229}$)—, or —S—; $Y^{222}$ is selected from a single bond, —O—, —NR$^{229}$—, —N($R^{229}$)—C(=NH)—N($R^{230}$)—, or —S—; $L^{222}$ is a single bond, $C_{6-10}$arylene, or —(C=O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{224}$ is hydrogen or is a single bond connecting the folate moiety to a polysaccharide or functionally-modified polysaccharide as taught herein or to a linker as taught herein (i.e., connecting the folate moiety to $X^1$); $Q^{225}$ is hydrogen or is a single bond connecting the folate moiety to a polysaccharide or functionally-modified polysaccharide as taught herein or to a linker as taught herein (i.e., connecting the folate moiety to $X^1$); wherein at least one of $Q^{224}$ and $Q^{225}$ is a single bond connecting the folate moiety to a polysaccharide or functionally-modified polysaccharide as taught herein or to a linker as taught herein (i.e., connecting the folate moiety to $X^1$); the dotted bond represents a single bond or a double bond.

In certain preferred embodiments, the folate moiety may have the structural Formula XVa, or a stereoisomer, tautomer, salt, hydrate or solvate thereof, wherein $X^{221}$, $X^{222}$, $X^{223}$, $X^{224}$, $X^{225}$, $R^{222}$, $R^{226}$, $L^{222}$, $Y^{221}$, $Y^{222}$, $Q^{224}$, $Q^{225}$ and t have the same meaning as that defined herein above.

In certain preferred embodiments, the folate moiety may have the structural Formula XV or XVa, as taught herein, wherein $X^{221}$ is selected from N, or NR$^{221}$; or O; $X^{222}$ is selected from N, NR$^{221}$, or O; $X^{223}$ is selected from N, NR$^{223}$, or O; $X^{224}$ is selected from N, NR$^{224}$ or O; $X^{225}$ is selected from NR$^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)R$^{225}$, hydrogen, halogen, $C_{1-12}$alkyl, $C_{2-12}$alkenyl, $C_{2-12}$alkynyl, —OR$^{225}$, —CO—R$^{125}$, —CO—O—R$^{225}$, and —CO—N(H)R$^{225}$ wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —N($R^{229}$)—, or —S—; $Y^{222}$ is selected from a single bond, —O—, —N($R^{229}$)—, —N($R^{229}$)—C(=NH)—N($R^{230}$)— or —S—; $L^{222}$ is a single bond, $C_{6-10}$arylene, or —(C=O)—; t is an integer selected, from 1, 2, 3, or 4; $R^{226}$ is hydrogen or $C_{1-6}$alkyl; $R^{229}$ is hydrogen or $C_{1-6}$alkyl; $R^{230}$ is hydrogen or $C_{1-6}$alkyl; $Q^{224}$ is hydrogen or is a single bond connecting the folate moiety to a polysaccharide or functionally-modified polysaccharide as taught herein or to a linker as taught herein (i.e., connecting the folate moiety to $X^1$); $Q^{225}$ is hydrogen or is a single bond connecting the folate moiety to a polysaccharide or functionally-modified polysaccharide as taught herein or to a linker as taught herein (i.e., connecting the folate moiety to $X^1$); wherein at least one of $Q^{224}$ and $Q^{225}$ is a single bond connecting the folate moiety to a polysaccharide or functionally-modified polysaccharide as taught herein or to a linker as taught herein (i.e., connecting the folate moiety to $X^1$); the dotted bond represents a single bond or a double bond.

In certain preferred embodiments, the folate moiety may have the structural Formula XVb, or a stereoisomer, tautomer, salt, hydrate or solvate thereof, wherein

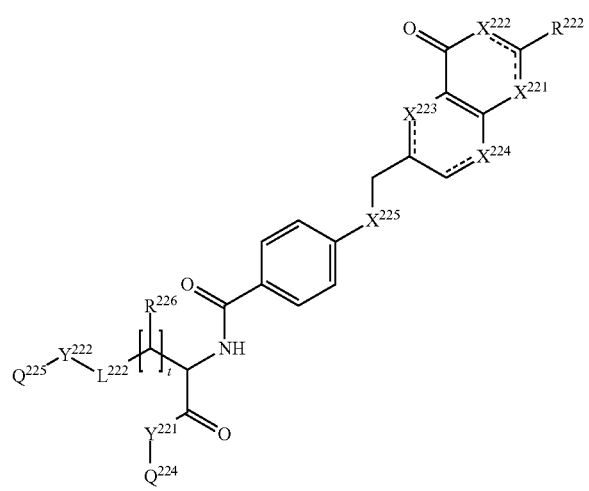

(XVa)

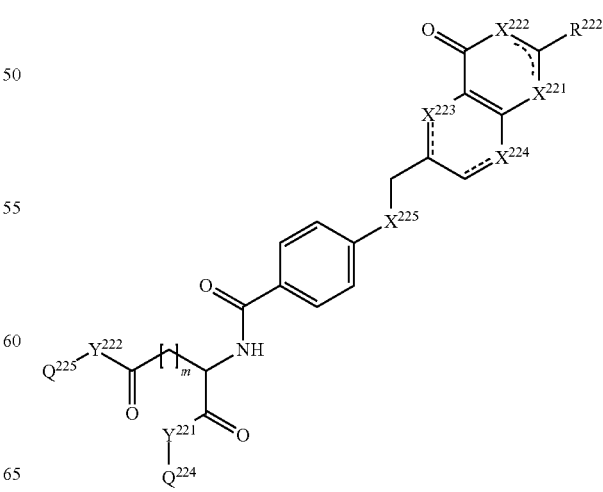

(XVb)

$X^{221}$, $X^{222}$, $X^{223}$, $X^{224}$, $X^{225}$, $R^{222}$, $Y^{221}$, $Y^{222}$, $Q^{224}$, $Q^{225}$ and m have the same meaning as that defined herein above.

In certain preferred embodiments, the folate moiety may have the structural Formula XV, XVa, or XVb, as taught herein, wherein $X^{221}$ is selected from N, $NR^{221}$; or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —$NR^{229}$ or —S; $Y^{222}$ is selected from a single bond, —O—, —$NR^{229}$—, or —S—; m is an integer selected from 1, 2, or 3; $R^{229}$ is hydrogen or $C_{1-6}$alkyl; $Q^{224}$ is hydrogen or is a single bond connecting the folate moiety to a polysaccharide or functionally-modified polysaccharide as taught herein or to a linker as taught herein (i.e., connecting the folate moiety to $X^1$); $Q^{225}$ is hydrogen or is a single bond connecting the folate moiety to a polysaccharide or functionally-modified polysaccharide as taught herein or to a linker as taught herein (i.e., connecting the folate moiety to $X^1$); wherein at least one of $Q^{224}$ and $Q^{225}$ is a single bond connecting the folate moiety to a polysaccharide or functionally-modified polysaccharide as taught herein or to a linker as taught herein (i.e., connecting the folate moiety to $X^1$); the dotted bond represents a single bond or a double bond.

In certain preferred embodiments, the folate moiety may have the structural Formula XV, XVa, or XVb, as taught herein, wherein $X^{221}$ is selected from N or $NR^{221}$; $X^{222}$ is selected from N or $NR^{221}$; $X^{223}$ is selected from N or $NR^{223}$; $X^{224}$ is selected from N or $NR^{224}$; $X^{225}$ is $NR^{224}$, and $R^{221}$, $R^{222}$, $R^{223}$, $R^{224}$, $R^{226}$, $L^{220}$, $L^{222}$, $Y^{221}$, $Y^{222}$, $Q^{224}$, $Q^{225}$, and t have the same meaning as that defined herein above.

In certain preferred embodiments, the folate moiety may have the structural Formula XV, XVa, or XVb, as taught herein, wherein $X^{221}$ is selected from N or NH; $X^{222}$ is selected from N or NH; $X^{223}$ is selected from N or NH; $X^{224}$ is selected from N or NH; $X^{225}$ is NH, and $R^{222}$, $R^{226}$, $L^{220}$, $L^{222}$, $Y^{221}$, $Y^{222}$, $Q^{224}$, $Q^{225}$, and t have the same meaning as that defined herein above.

In certain preferred embodiments, the folate moiety may have the structural Formula XV, XVa, or XVb, as taught herein, wherein $R^{222}$ is selected from the group consisting of —$NHR^{225}$, hydrogen, $C_{1-12}$alkyl, —$OR^{225}$, preferably —$NHR^{125}$, or —$OR^{225}$, wherein $R^{225}$ is selected from hydrogen, halo, $C_{1-12}$alkyl, $C_{2-12}$alkenyl, $C_{2-12}$alkynyl, —OR', —COR', —COOR', or —NHR', wherein R' is H or $C_{1-8}$alkyl, and $X^{221}$, $X^{222}$, $X^{223}$, $X^{224}$, $X^{225}$, $R^{226}$, $L^{220}$, $L^{222}$, $Y^{221}$, $Y^{222}$, $Q^{224}$, $Q^{225}$, and t have the same meaning as that defined herein above.

In certain preferred embodiments, the folate moiety may have the structural Formula XVc, or a stereoisomer, tautomer, salt, hydrate or solvate thereof, wherein

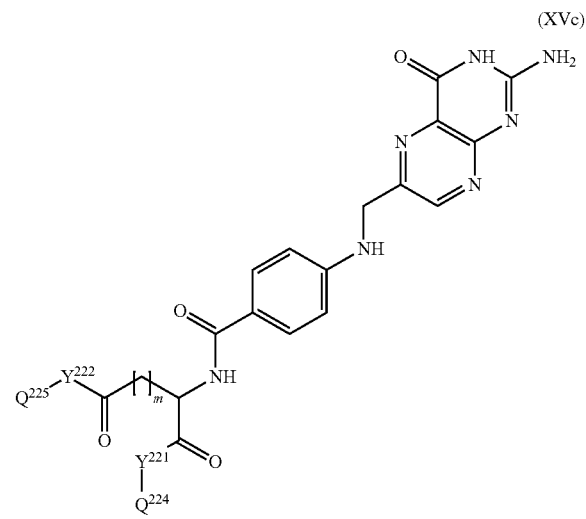

(XVc)

$Y^{221}$, $Y^{222}$, $Q^{224}$, $Q^{225}$, and m have the same meaning as that defined herein above.

In certain preferred embodiments, the folate moiety may have the structural Formula XV, XVa, XVb, or XVc, as taught herein, wherein $Y^{221}$ is selected from a single bond, —O—, —$NR^{229}$— or —S—; $Y^{222}$ is selected from a single bond, —O—, —$NR^{229}$—, or —S—; m is an integer selected from 1, 2, or 3; $R^{229}$ is hydrogen or $C_{1-6}$alkyl; $Q^{224}$ is hydrogen or is a single bond connecting the folate moiety to a polysaccharide or functionally-modified polysaccharide as taught herein or to a linker as taught herein (i.e., connecting the folate moiety to $X^1$); $Q^{225}$ is hydrogen or is a single bond connecting the folate moiety to a polysaccharide or functionally-modified polysaccharide as taught herein or to a linker as taught herein (i.e., connecting the folate moiety to $X^1$); wherein at least one of $Q^{224}$ and $Q^{225}$ is a single bond connecting the folate moiety to a polysaccharide or functionally-modified polysaccharide as taught herein or to a linker as taught herein (i.e., connecting the folate moiety to $X^1$).

In certain preferred embodiments, the folate moiety may have the structural Formula XV, XVa, XVb, or XVc, as taught herein, wherein $Q^{224}$ is hydrogen and $Q^{225}$ is a single bond connecting the folate moiety to a polysaccharide or functionally-modified polysaccharide as taught herein or to a linker as taught herein (i.e., connecting the folate moiety to $X^1$).

In certain preferred embodiments, the folate moiety may have the structural Formula XVd, or a stereoisomer, tautomer, salt, hydrate or solvate thereof, wherein

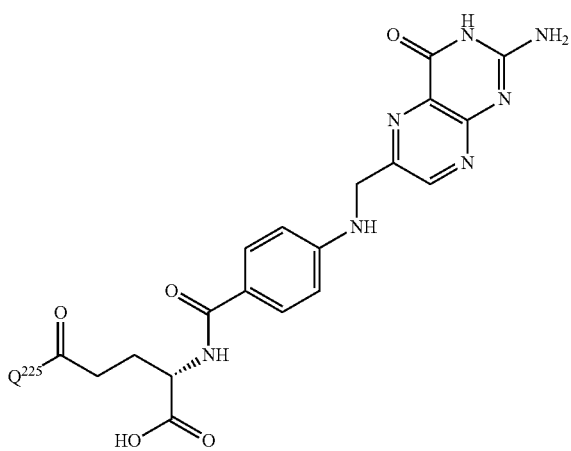

$Q^{225}$ is a single bond connecting the folate moiety to a polysaccharide or functionally-modified polysaccharide as taught herein or to a linker as taught herein (i.e., connecting the folate moiety to $X^1$). In certain embodiments, a salt of the folate moiety may be a hydrochloride, sodium, potassium, calcium, or magnesium salt.

In certain embodiments of the products (such as pharmaceutical formulations or FR-targeting excipients), uses, or methods, as taught herein, the FR-targeting antineoplastic substance or composition may comprise at least one antineoplastic agent and at least one FR-targeting excipient. In certain embodiments, the FR-targeting antineoplastic substance or composition may comprise an antineoplastic agent and a FR-targeting excipient.

The terms "FR-targeting excipient" or "FR-targeting compound" may be used interchangeably herein. In certain embodiments of the products (such as pharmaceutical formulations or FR-targeting excipients), uses, or methods, as taught herein, the FR-targeting excipient may be a folate-polysaccharide conjugate comprising at least one folate moiety covalently linked to a polysaccharide or functionally-modified polysaccharide.

The term "folate-polysaccharide conjugate" as used herein refers to a compound comprising at least a folate moiety and a polysaccharide or functionally-modified polysaccharide, wherein the folate moiety and the polysaccharide or functionally-modified polysaccharide are covalently bound or linked to each other (via at least one single bond or via at least one linker). The term "folate-polysaccharide conjugate" encompasses folate-polysaccharide conjugates and folate-functionally-modified polysaccharide conjugates.

In certain embodiments, FR-targeting excipient may be a folate-polysaccharide conjugate comprising at least one folate moiety covalently linked to a polysaccharide or functionally-modified polysaccharide selected from the group consisting of chitosan or functionally-modified chitosan; N-[(2-hydroxy-3-trimethylammonium)propyl] chitosan (HTC) and its salts; N-trimethyl chitosan (TMC) and its salts; N,O-carboxymethyl chitosan (N,O-CMC) and its salts; N-carboxymethyl chitosan (N-CMC) and its salts; N,N-carboxymethyl chitosan (N,N-CMC) and its salts; O-carboxymethyl chitosan (O-CMC) and its salts; hydrophobically-modified chitosan (HMC) and its salts; dextran or functionally-modified dextran; hydrophobically-modified dextran (HMD) and its salts; starch or functionally-modified starch; hydroxypropyl starch; amylose or functionally-modified amylose; amylopectin or functionally-modified amylopectin; cellulose or functionally-modified cellulose; methylcellulose and its salts; carboxymethylcellulose and its salts; hydroxyethylcellulose and its salts; ethylcellulose and its salts; hydroxyethylmethylcellulose and its salts; hydroxypropylcellulose and its salts; hypromellose and its salts; hypromellose acetate succinate; hypromellose phthalate; croscarmellose and its salts; chitin; cyclodextrin; dextrate; dextrin; maltodextrin; pullulan; and guar gum.

In an embodiment, the FR-targeting excipient may be a folate-polysaccharide conjugate selected from the group consisting of folate-chitosan conjugate or folate-functionally-modified chitosan conjugate; folate-HTC conjugate; folate-TMC conjugate; folate-N,O-CMC conjugate; folate-N—N-CMC conjugate; folate-N,N-CMC conjugate; folate-O-CMC conjugate; folate-HMC conjugate; folate-dextran conjugate or folate-functionally-modified dextran conjugate; folate-HMD conjugate; folate-starch conjugate or folate-functionally-modified starch conjugate; folate-hydroxypropyl starch conjugate; folate-amylose conjugate or folate-functionally-modified amylose conjugate; folate-amylopectin conjugate or folate-functionally-modified amylopectin conjugate; folate-cellulose conjugate or folate-functionally-modified cellulose conjugate; folate-methylcellulose conjugate; folate-carboxymethylcellulose conjugate; folate-hydroxyethylcellulose conjugate; ethylcellulose conjugate; folate-hydroxyethylmethylcellulose conjugate; folate-hydroxypropylcellulose conjugate; folate-hypromellose conjugate; folate-hypromellose acetate succinate conjugate; folate-hypromellose phthalate conjugate; folate-croscarmellose conjugate; folate-chitin conjugate; folate-cyclodextrin conjugate; folate-dextrate conjugate; folate-dextrin conjugate; folate-maltodextrin conjugate; folate-pullulan conjugate; and folate-guar gum conjugate.

In certain embodiments of the products (such as pharmaceutical formulations or FR-targeting excipients), uses, or methods, as taught herein, the FR-targeting excipient may be a folate-polysaccharide conjugate comprising at least one unit selected from the group consisting of units of Formula XIb, XIc, XId, and XIe, or a stereoisomer, tautomer, salt, hydrate or solvate thereof, or any subgroup thereof, wherein

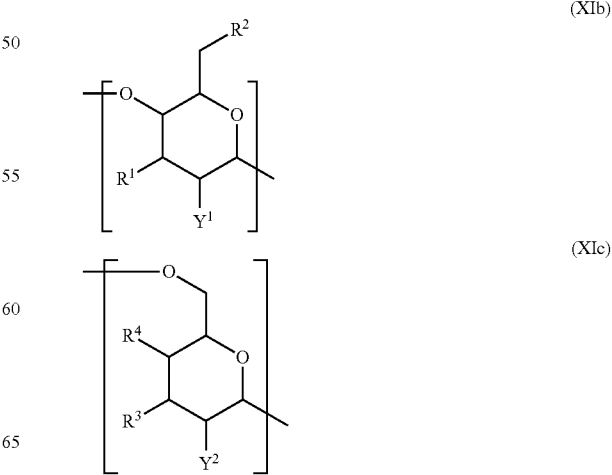

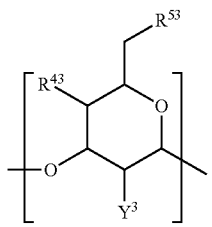

(XId)

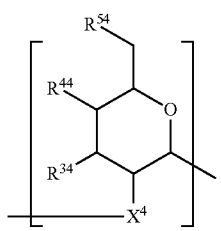

(XIe)

Y$^1$ is —X$^2$—X$^1$—X$^3$, or a group selected from —OR$^{10}$, —N(R$^{100}$)R$^{101}$, or —N$^+$(R$^{100}$)(R$^{101}$)R$^{102}$,
Y$^2$ is —X$^2$—X$^1$—X$^3$, or a group selected from —OR$^{20}$, —N(R$^{200}$)R$^{201}$, or —N$^+$(R$^{200}$)(R$^{201}$)R$^{202}$,
Y$^3$ is —X$^2$—X$^1$—X$^3$, or a group selected from —OR$^{30}$, —N(R$^{300}$)R$^{301}$, or —N$^+$(R$^{300}$)(R$^{301}$)R$^{302}$,
R$^1$ is —OR$^{11}$ or —X$^2$—X$^1$—X$^3$,
R$^2$ is —OR$^{21}$ or —X$^2$—X$^1$—X$^3$,
R$^3$ is —OR$^{31}$ or —X$^2$—X$^1$—X$^3$,
R$^4$ is —OR$^{41}$ or —X$^2$—X$^1$—X$^3$,
R$^{34}$ is —OR$^{31}$ or —X$^2$—X$^1$—X$^3$,
R$^{43}$ is —OR$^{41}$ or —X$^2$—X$^1$—X$^3$,
R$^{44}$ is —OR$^{41}$ or —X$^2$—X$^1$—X$^3$,
R$^{53}$ is —OR$^{51}$ or —X$^2$—X$^1$—X$^3$,
R$^{54}$ is —OR$^{51}$ or —X$^2$—X$^1$—X$^3$,
wherein at least one of Y$^1$, R$^1$, or R$^2$ is —X$^2$—X$^1$—X$^3$;
wherein at least one of Y$^2$, R$^3$, or R$^4$ is —X$^2$—X$^1$—X$^3$;
wherein at least one of Y$^3$, R$^{43}$, or R$^{53}$ is —X$^2$—X$^1$—X$^3$;
wherein at least one of R$^{34}$, R$^{44}$, or R$^{54}$ is —X$^2$—X$^1$—X$^3$;
wherein R$^{10}$ is selected from hydrogen, a mono-, oligo-, or poly-glycosyl moiety, or a group consisting of C$_{1-25}$alkyl, C$_{1-25}$alkylcarbonyl, C$_{2-25}$alkenylcarbonyl, —C$_{1-6}$alkylene-CO—OR$^{12}$, carboxylC$_{1-6}$alkylenecarbonyl, hydroxyC$_{1-6}$alkyl, carboxylC$_{6-12}$arylenecarbonyl, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, or C$_{1-6}$alkoxy, wherein R$^{12}$ is selected from hydrogen or C$_{1-6}$alkyl;

R$^{11}$ is selected from hydrogen, a mono-, oligo-, or poly-glycosyl moiety, or a group consisting of C$_{1-25}$alkyl, C$_{1-25}$alkylcarbonyl, C$_{2-25}$alkenylcarbonyl, C$_{1-6}$alkylene-CO—OR$^{12}$, carboxylC$_{1-6}$alkylenecarbonyl, hydroxyC$_{1-6}$alkyl, carboxylC$_{6-12}$arylenecarbonyl, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, or C$_{1-6}$alkoxy, wherein R$^{12}$ is selected from hydrogen or C$_{1-6}$alkyl;

R$^{20}$ is selected from hydrogen, a mono-, oligo-, or poly-glycosyl moiety, or a group consisting of C$_{1-25}$alkyl, C$_{1-25}$alkylcarbonyl, C$_{2-25}$alkenylcarbonyl, C$_{1-6}$alkylene-CO—OR$^{12}$, carboxylC$_{1-6}$alkylenecarbonyl, hydroxyC$_{1-6}$alkyl, carboxylC$_{6-12}$arylenecarbonyl, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, or C$_{1-6}$alkoxy, wherein R$^{12}$ is selected from hydrogen or C$_{1-6}$alkyl;

R$^{21}$ is selected from hydrogen, a mono-, oligo-, or poly-glycosyl moiety, or a group consisting of C$_{1-25}$alkyl, C$_{1-25}$alkylcarbonyl, C$_{2-25}$alkenylcarbonyl, C$_{1-6}$alkylene-CO—OR$^{12}$, carboxylC$_{1-6}$alkylenecarbonyl, hydroxyC$_{1-6}$alkyl, carboxylC$_{6-12}$arylenecarbonyl, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, or C$_{1-6}$alkoxy, wherein R$^{12}$ is selected from hydrogen or C$_{1-6}$alkyl;

R$^{30}$ is selected from hydrogen, a mono-, oligo-, or poly-glycosyl moiety, or a group consisting of C$_{1-25}$alkyl, C$_{1-25}$alkylcarbonyl, C$_{2-25}$alkenylcarbonyl, C$_{1-6}$alkylene-CO—OR$^{12}$, carboxylC$_{1-6}$alkylenecarbonyl, hydroxyC$_{1-6}$alkyl, carboxylC$_{6-12}$arylenecarbonyl, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, or C$_{1-6}$alkoxy, wherein R$^{12}$ is selected from hydrogen or C$_{1-6}$alkyl;

R$^{31}$ is selected from hydrogen, a mono-, oligo-, or poly-glycosyl moiety, or a group consisting of C$_{1-25}$alkyl, C$_{1-25}$alkylcarbonyl, C$_{2-25}$alkenylcarbonyl, C$_{1-6}$alkylene-CO—OR$^{12}$, carboxylC$_{1-6}$alkylenecarbonyl, hydroxyC$_{1-6}$alkyl, carboxylC$_{6-12}$arylenecarbonyl, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, or C$_{1-6}$alkoxy, wherein R$^{12}$ is selected from hydrogen or C$_{1-6}$alkyl;

R$^{41}$ is selected from hydrogen, a mono-, oligo-, or poly-glycosyl moiety, or a group consisting of C$_{1-25}$alkyl, C$_{1-25}$alkylcarbonyl, C$_{2-25}$alkenylcarbonyl, C$_{1-6}$alkylene-CO—OR$^{12}$, carboxylC$_{1-6}$alkylenecarbonyl, hydroxyC$_{1-6}$alkyl, carboxylC$_{6-12}$arylenecarbonyl, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, or C$_{1-6}$alkoxy, wherein R$^{12}$ is selected from hydrogen or C$_{1-6}$alkyl;

R$^{51}$ is selected from hydrogen, a mono-, oligo-, or poly-glycosyl moiety, or a group consisting of C$_{1-25}$alkyl, C$_{1-25}$alkylcarbonyl, C$_{2-25}$alkenylcarbonyl, C$_{1-6}$alkylene-CO—OR$^{12}$, carboxylC$_{1-6}$alkylenecarbonyl, hydroxyC$_{1-6}$alkyl, carboxylC$_{6-12}$arylenecarbonyl, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, or C$_{1-6}$alkoxy, wherein R$^{12}$ is selected from hydrogen or C$_{1-6}$alkyl;

R$^{100}$ is selected from hydrogen, or a group consisting of C$_{1-25}$alkyl, C$_{1-6}$alkylene-N(R$^{111}$)R$^{112}$, C$_{1-6}$alkylene-N$^+$(R$^{111}$)(R$^{112}$)R$^{113}$, C$_{1-25}$alkylcarbonyl, C$_{2-25}$alkenylcarbonyl, C$_{1-6}$alkylene-CO—OR$^{114}$, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, carboxyl, or C$_{1-6}$alkoxy, wherein R$^{111}$ is selected from hydrogen or C$_{1-6}$alkyl, R$^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl;

$R^{101}$ is selected from hydrogen, or a group consisting of $C_{1-25}$alkyl, $C_{1-6}$alkylene-N$(R^{111})R^{112}$, $C_{1-6}$alkylene-N$^+(R^{111})(R^{112})R^{113}$, $C_{1-25}$alkylcarbonyl, $C_{2-25}$alkenylcarbonyl, $C_{1-6}$alkylene-CO—OR$^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl;

$R^{102}$ is selected from hydrogen, or a group consisting of $C_{1-25}$alkyl, $C_{1-6}$alkylene-N$(R^{111})R^{112}$, $C_{1-6}$alkylene-N$^+(R^{111})(R^{112})R^{113}$, $C_{1-25}$alkylcarbonyl, $C_{2-25}$alkenylcarbonyl, $C_{1-6}$alkylene-CO—OR$^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl;

$R^{200}$ is selected from hydrogen, or a group consisting of $C_{1-25}$alkyl, $C_{1-6}$alkylene-N$(R^{211})R^{212}$, $C_{1-6}$alkylene-N$^+(R^{211})(R^{212})R^{213}$, $C_{1-25}$alkylcarbonyl, $C_{2-25}$alkenylcarbonyl, $C_{1-6}$alkylene-CO—R$^{214}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{211}$ is selected from hydrogen or $C_{1-6}$alkyl, $R^{212}$ is selected from hydrogen or $C_{1-6}$alkyl, $R^{213}$ is selected from hydrogen or $C_{1-6}$alkyl, and $R^{214}$ is selected from hydrogen or $C_{1-6}$alkyl;

$R^{201}$ is selected from hydrogen, or a group consisting of $C_{1-25}$alkyl, $C_{1-6}$alkylene-N$(R^{211})R^{212}$, $C_{1-6}$alkylene-N$^+(R^{211})(R^{212})R^{213}$, $C_{1-25}$alkylcarbonyl, $C_{2-25}$alkenylcarbonyl, $C_{1-6}$alkylene-CO—R$^{214}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{211}$ is selected from hydrogen or $C_{1-6}$alkyl, $R^{212}$ is selected from hydrogen or $C_{1-6}$alkyl, $R^{213}$ is selected from hydrogen or $C_{1-6}$alkyl, and $R^{214}$ is selected from hydrogen or $C_{1-6}$alkyl;

$R^{202}$ is selected from hydrogen, or a group consisting of $C_{1-25}$alkyl, $C_{1-6}$alkylene-N$(R^{211})R^{212}$, $C_{1-6}$alkylene-N$^+(R^{211})(R^{212})R^{213}$, $C_{1-25}$alkylcarbonyl, $C_{2-25}$alkenylcarbonyl, $C_{1-6}$alkylene-CO—R$^{214}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{211}$ is selected from hydrogen or $C_{1-6}$alkyl, $R^{212}$ is selected from hydrogen or $C_{1-6}$alkyl, $R^{213}$ is selected from hydrogen or $C_{1-6}$alkyl, and $R^{214}$ is selected from hydrogen or $C_{1-6}$alkyl;

$R^{300}$ is selected from hydrogen, or a group consisting of $C_{1-25}$alkyl, $C_{1-6}$alkylene-N$(R^{211})R^{212}$, $C_{1-6}$alkylene-N$^+(R^{211})(R^{212})R^{213}$, $C_{1-25}$alkylcarbonyl, $C_{2-25}$alkenylcarbonyl, $C_{1-6}$alkylene-CO—OR$^{314}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{311}$ is selected from hydrogen or $C_{1-6}$alkyl, $R^{312}$ is selected from hydrogen or $C_{1-6}$alkyl, $R^{313}$ is selected from hydrogen or $C_{1-6}$alkyl, and $R^{314}$ is selected from hydrogen or $C_{1-6}$alkyl;

$R^{301}$ is selected from hydrogen, or a group consisting of $C_{1-25}$alkyl, $C_{1-6}$alkylene-N$(R^{211})R^{212}$, $C_{1-6}$alkylene-N$^+(R^{211})(R^{212})R^{213}$, $C_{1-25}$alkylcarbonyl, $C_{2-25}$alkenylcarbonyl, $C_{1-6}$alkylene-CO—OR$^{314}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{311}$ is selected from hydrogen or $C_{1-6}$alkyl, $R^{312}$ is selected from hydrogen or $C_{1-6}$alkyl, $R^{313}$ is selected from hydrogen or $C_{1-6}$alkyl, and $R^{314}$ is selected from hydrogen or $C_{1-6}$alkyl;

$R^{302}$ is selected from hydrogen, or a group consisting of $C_{1-25}$alkyl, $C_{1-6}$alkylene-N$(R^{211})R^{212}$, $C_{1-6}$alkylene-N$^+(R^{211})(R^{212})R^{213}$, $C_{1-25}$alkylcarbonyl, $C_{2-25}$alkenylcarbonyl, $C_{1-6}$alkylene-CO—OR$^{314}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{311}$ is selected from hydrogen or $C_{1-6}$alkyl, $R^{312}$ is selected from hydrogen or $C_{1-6}$alkyl, $R^{313}$ is selected from hydrogen or $C_{1-6}$alkyl, and $R^{314}$ is selected from hydrogen or $C_{1-6}$alkyl;

$X^2$ is —O— or —N$(R^{103})$—, wherein $R^{103}$ is selected from hydrogen or $C_{1-6}$alkyl;

$X^1$ is a single bond or a linker comprising a polyether, ether, amine, polyamine, amino acid, peptide, a polypeptide, a carbohydrate, or a combination of two or more thereof, $X^3$ is a folate moiety; preferably $X^3$ is a folate moiety having the structural Formula XII, or a stereoisomer, tautomer, salt, hydrate or solvate thereof, wherein

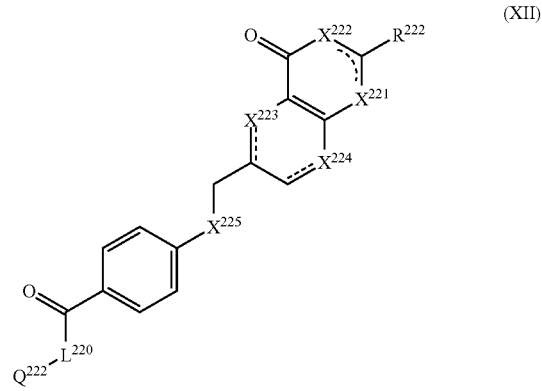

(XII)

$X^{221}$ is selected from N, NR$^{221}$, or O; $X^{222}$ is selected from N, NR$^{221}$, or O; $X^{223}$ is selected from N, NR$^{223}$, or O; $X^{224}$ is selected from N, NR$^{224}$ or O; $X^{2\prime\prime}$ is selected from NR$^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —OR$^{225}$, —CO—R$^{125}$, —CO—O—R$^{225}$, and —CO—N(H)R$^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; $L^{220}$ is selected from

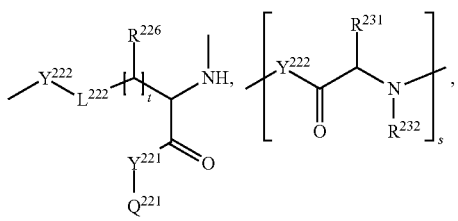

or a group consisting of $C_{1-6}$alkylene, $C_{1-6}$alkylenecarbonyl, $C_{1-6}$alkylene-N(R$^{227}$)—, $C_{2-6}$alkenylene, $C_{2-6}$alkynylene, $C_{3-6}$cycloalkylene, $C_{6-10}$arylene, —(C=O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—(CO)—$C_{3-6}$cycloalkylene, —N(R$^{228}$)—, —N(R$^{228}$)—(CO)—, and —(CO)—N(R$^{228}$)—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —N(R$^{229}$)—, or —S—; $Y^{222}$ is selected from a single bond, —O—, —NR$^{229}$—, —N(R$^{229}$)—C(=NH)—N(R$^{230}$)—, or —S—; $L^{222}$ is a single bond, $C_{6-10}$arylene, or —(C=O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond;

$X^4$ is —O— or —N(R$^{403}$)—, wherein $R^{403}$ is selected from hydrogen or $C_{1-6}$alkyl.

Advantageously, the present inventors have found that the FR-targeting excipients as taught herein allow the formation of nanoparticles with good stability and physical integrity after administration in vivo and at the same time display a desired rate of dissolution once in contact with physiological media. Also, the FR-targeting excipients as taught herein display bioadhesive properties and/or present a long time of retention in the respiratory tract, thereby retaining the present pharmaceutical formulations in the respiratory tract.

Additionally, the present inventors have surprisingly found that the FR-targeting excipients as taught herein are able to interact with the antineoplastic agents (including hydrophilic antineoplastic agents) and these interactions advantageously lead to a better entrapment and/or encapsulation of the antineoplastic agents in the pharmaceutical formulations. Hence, using such FR-targeting excipients allows high drug encapsulation efficiency and drug loading.

The term "unit", as used herein, refers to a monosaccharide unit or functionally-modified monosaccharide unit.

In certain embodiments, the FR-targeting excipients may comprise at least one unit, such as one or more units, of Formula XIb, XIc, XId, or XIe, as taught herein, such as at least two, at least three, at least four, at least five, at least six, at least seven, at least eight, at least nine, at least ten, at least twenty, at least thirty, at least forty, at least fifty, at least sixty, at least seventy, at least eighty, at least ninety, at least 100, at least 200, at least 300, at least 400, at least 500, at least 600, at least 700, at least 800, at least 900, at least 1000, at least 1500, at least 2000, or at least 2500 units of Formula XIb, XIc, XId, or XIe, as taught herein. For example, the polysaccharide or functionally-modified polysaccharide may comprise from about 50 to about 2000, from about 100 to about 1000, or from about 200 to about 500 units of Formula XIb, XIc, XId, or XIe, as taught herein.

In certain embodiments of the products (such as pharmaceutical formulations or FR-targeting excipients) or uses, as taught herein, the FR-targeting excipient may be a folate-polysaccharide conjugate comprising at least one unit of Formula XIb, XIg, and/or XIm, or a stereoisomer, tautomer, salt, hydrate or solvate thereof, or any subgroup thereof, wherein

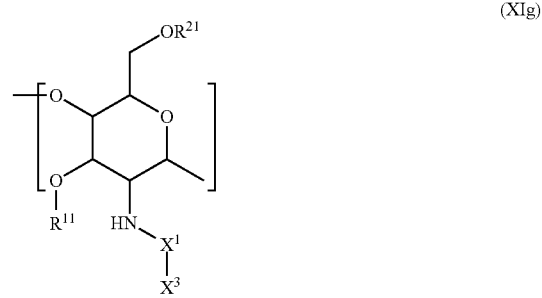

(XIg)

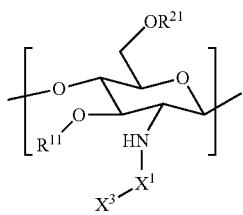

(XIm)

$Y^1$ is —$X^2$—$X^1$—$X^3$, or a group selected from —$OR^{10}$, —$N(R^{100})(R^{101})R^{102}$, or —$N^+(R^{100})(R^{101})R^{102}$, wherein $X^2$ is —O— or —$N(R^{103})$—, wherein $R^{103}$ is selected from hydrogen or $C_{1-6}$alkyl;

$X^1$ is a single bond or a linker comprising a polyether, ether, amine, polyamine, amino acid, peptide, a polypeptide, a carbohydrate, or a combination of two or more thereof;

$X^3$ is a folate moiety; preferably $X^3$ is a folate moiety having the structural Formula XII, as taught herein, wherein $X^{221}$ is selected from N, $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; $L^{220}$ is selected from

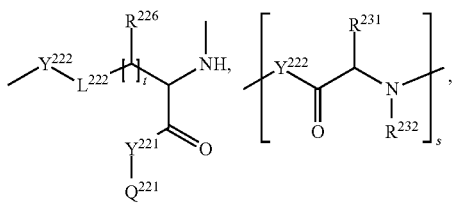

or a group consisting of $C_{1-6}$alkylene, $C_{1-6}$alkylenecarbonyl, $C_{1-6}$alkylene-$N(R^{227})$, $C_{2-6}$alkenylene, $C_{2-6}$alkynylene, $C_{3-6}$cycloalkylene, $C_{6-10}$arylene, —(C=O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—(CO)—$C_{3-6}$cycloalkylene, —$N(R^{228})$—, —$N(R^{228})$—(CO)—, and —(CO)—N$(R^{228})$—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —$N(R^{229})$—, or —S—; $Y^{222}$ is selected from a single bond, —O—, —$NR^{229}$—, —$N(R^{229})$—C(=NH) or —S—; $L^{222}$ is a single bond, $C_{6-10}$arylene, or —(C=O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; $R^{10}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, —$C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$R^{100}$ is selected from hydrogen, or a group consisting of $C_{1-25}$alkyl, $C_{1-6}$alkylene-$N(R^{111})R^{112}$, $C_{1-6}$alkylene-$N^+(R^{111})(R^{112})R^{113}$, $C_{1-25}$alkylcarbonyl, $C_{2-25}$alkenylcarbonyl, $C_{1-6}$alkylene-CO—$OR^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl;

$R^{101}$ is selected from hydrogen, or a group consisting of $C_{1-25}$alkyl, $C_{1-6}$alkylene-$N(R^{111})R^{112}$, $C_{1-6}$alkylene-$N^+(R^{111})(R^{112})R^{113}$, $C_{1-25}$alkylcarbonyl, $C_{2-25}$alkenylcarbonyl, $C_{1-6}$alkylene-CO—$OR^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl;

$R^{102}$ is selected from hydrogen, or a group consisting of $C_{1-25}$alkyl, $C_{1-6}$alkylene-$N(R^{111})R^{112}$, $C_{1-6}$alkylene-$N^+(R^{111})(R^{112})R^{113}$, $C_{1-25}$alkylcarbonyl, $C_{2-25}$alkenylcarbonyl, $C_{1-6}$alkylene-CO—$OR^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl;

$R^1$ is —$OR^{11}$ or —$X^2$—$X^1$—$X^3$, wherein $R^{11}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$X^2$, $X^1$, and $X^3$ have the same meaning as that defined herein;

$R^2$ is —$OR^{21}$ or —$X^2$—$X^1$—$X^3$, wherein $R^{21}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$X^2$, $X^1$, and $X^3$ have the same meaning as that defined herein;

wherein at least one of $Y^1$, $R^1$, or $R^2$ is —$X^2$—$X^1$—$X^3$.

In certain embodiments of the products (such as pharmaceutical formulations or FR-targeting excipients) or uses, as taught herein, the FR-targeting excipient may be a folate-polysaccharide conjugate comprising at least one unit of Formula XIc, XIh, XIj, XIk, XIn, XIp, and/or XIq, or a stereoisomer, tautomer, salt, hydrate or solvate thereof, or any subgroup thereof, wherein (XIh)

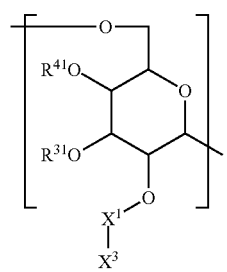

(XIj)

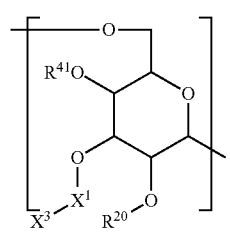

-continued (XIk)

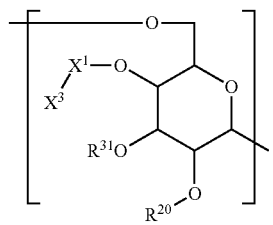

(XIn)

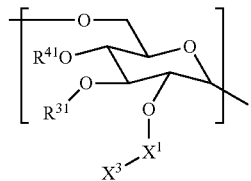

(XIp)

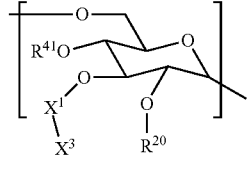

(XIq)

$Y^2$ is —$X^2$—$X^1$—$X^3$, or a group selected from —$OR^{20}$, —$N(R^{200})R^{201}$, or —$N^+(R^{20})(R^{201})R^{202}$, wherein $X^2$ is —O— or —$N(R^{103})$—, wherein $R^{103}$ is selected from hydrogen or $C_{1-6}$alkyl;

$X^1$ is a single bond or a linker comprising a polyether, ether, amine, polyamine, amino acid, peptide, a polypeptide, a carbohydrate, or a combination of two or more thereof;

$X^3$ is a folate moiety; preferably $X^3$ is a folate moiety having the structural Formula XII, as taught herein, wherein $X^{221}$ is selected from N, $NR^{221}$; or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; $L^{220}$ is selected from

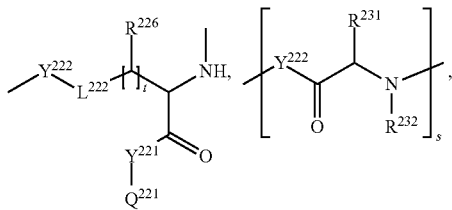

or a group consisting of $C_{1-6}$alkylene, $C_{1-6}$alkylenecarbonyl, —$C_{1-6}$alkylene-N($R^{227}$)—, $C_{2-6}$alkenylene, $C_{2-6}$alkynylene, $C_{3-6}$cycloalkylene, $C_{6-10}$arylene, —(C=O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—(CO)—$C_{3-6}$cycloalkylene, —N($R^{228}$)—, —N($R^{228}$)—(CO)—, and —(CO)—N($R^{228}$)—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —N($R^{229}$)—, or —S—; $Y^{222}$ is selected from a single bond, —O—, —N$R^{229}$—, —N($R^{229}$)—C(=NH) or —S—; $L^{222}$ is a single bond, $C_{6-10}$arylene, or —(C=O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond;

$R^{20}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$R^{200}$ is selected from hydrogen, or a group consisting of $C_{1-25}$alkyl, $C_{1-6}$alkylene-N($R^{211}$)$R^{212}$, $C_{1-6}$alkylene-N$^+$($R^{211}$)($R^{212}$)$R^{213}$, $C_{1-25}$alkylcarbonyl, $C_{2-25}$alkenylcarbonyl, $C_{1-6}$alkylene-CO—$OR^{214}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{211}$ is selected from hydrogen or $C_{1-6}$alkyl, $R^{212}$ is selected from hydrogen or $C_{1-6}$alkyl, $R^{213}$ is selected from hydrogen or $C_{1-6}$alkyl, and $R^{214}$ is selected from hydrogen or $C_{1-6}$alkyl;

$R^{201}$ is selected from hydrogen, or a group consisting of $C_{1-25}$alkyl, $C_{1-6}$alkylene-N($R^{211}$)$R^{212}$, $C_{1-6}$alkylene-N$^+$($R^{211}$)($R^{212}$)$R^{213}$, $C_{1-25}$alkylcarbonyl, $C_{2-25}$alkenylcarbonyl, $C_{1-6}$alkylene-CO—$R^{214}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{211}$ is selected from hydrogen or $C_{1-6}$alkyl, $R^{212}$ is selected from hydrogen or $C_{1-6}$alkyl, $R^{213}$ is selected from hydrogen or $C_{1-6}$alkyl, and $R^{214}$ is selected from hydrogen or $C_{1-6}$alkyl;

$R^{202}$ is selected from hydrogen, or a group consisting of $C_{1-25}$alkyl, $C_{1-6}$alkylene-N($R^{211}$)$R^{212}$, $C_{1-6}$alkylene-N$^+$($R^{211}$)($R^{212}$)$R^{213}$, $C_{1-25}$alkylcarbonyl, $C_{2-25}$alkenylcarbonyl, $C_{1-6}$alkylene-CO—$R^{214}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{211}$ is selected from hydrogen or $C_{1-6}$alkyl, $R^{212}$ is selected from hydrogen or $C_{1-6}$alkyl, $R^{213}$ is selected from hydrogen or $C_{1-6}$alkyl, and $R^{214}$ is selected from hydrogen or $C_{1-6}$alkyl;

$R^3$ is —$OR^{31}$ or —$X^2$—$X^1$—$X^3$, wherein
$R^{31}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$X^2$, $X^1$, and $X^3$ have the same meaning as that defined herein;

$R^4$ is —$OR^{41}$ or —$X^2$—$X^1$—$X^3$, wherein
$R^{41}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$X^2$, $X^1$, and $X^3$ have the same meaning as that defined herein;

wherein at least one of $Y^2$, $R^3$, or $R^4$ is —$X^2$—$X^1$—$X^3$.

In certain embodiments of the products (such as pharmaceutical formulations or FR-targeting excipients) or uses, as taught herein, the FR-targeting excipient may be a folate-polysaccharide conjugate comprising at least one unit of Formula XId as taught herein, or any subgroup thereof, wherein $Y^3$ is —$X^2$—$X^1$—$X^3$, or a group selected from —$OR^{30}$, —$N(R^{300})R^{301}$, or —$N^+(R^{30})(R^{301})R^{302}$ wherein
$X^2$ is —O— or —$N(R^{103})$—, wherein $R^{103}$ is selected from hydrogen or $C_{1-6}$alkyl;
$X^1$ is a single bond or a linker comprising a polyether, ether, amine, polyamine, amino acid, peptide, a polypeptide, a carbohydrate, or a combination of two or more thereof;
$X^3$ is a folate moiety; preferably $X^3$ is a folate moiety having the structural Formula XII, as taught herein, wherein $X^{221}$ is selected from N, $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —$N(H)R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; $L^{220}$ is selected from

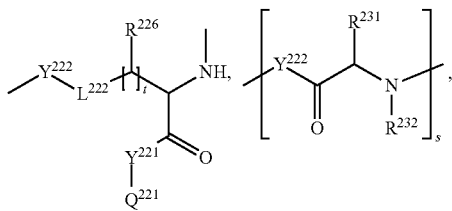

or a group consisting of $C_{1-6}$alkylene, $C_{1-6}$alkylenecarbonyl, —$C_{1-6}$alkylene-$N(R^{227})$—, $C_{2-6}$alkenylene, $C_{2-6}$alkynylene, $C_{3-6}$cycloalkylene, $C_{6-10}$arylene, —(C=O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—(CO)—$C_{3-6}$cycloalkylene, —$N(R^{228})$—, —$N(R^{228})$—(CO)—, and —(CO)—N$(R^{228})$—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —$N(R^{229})$— or —S—; $Y^{222}$ is selected from a single bond, —O—, —$NR^{229}$—, —$N(R^{229})$—C(=NH)—$N(R^{230}$—, or —S—; $L^{222}$ is a single bond, $C_{6-10}$arylene, or —(C=O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond;

$R^{30}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$R^{300}$ is selected from hydrogen, or a group consisting of $C_{1-25}$alkyl, $C_{1-6}$alkylene-$N(R^{211})R^{212}$, $C_{1-6}$alkylene-$N^+(R^{211})(R^{212})R^{213}$, $C_{1-25}$alkylcarbonyl, $C_{2-25}$alkenylcarbonyl, $C_{1-6}$alkylene-CO—$OR^{314}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{311}$ is selected from hydrogen or $C_{1-6}$alkyl, $R^{312}$ is selected from hydrogen or $C_{1-6}$alkyl, $R^{313}$ is selected from hydrogen or $C_{1-6}$alkyl, and $R^{314}$ is selected from hydrogen or $C_{1-6}$alkyl;

$R^{301}$ is selected from hydrogen, or a group consisting of $C_{1-25}$alkyl, $C_{1-6}$alkylene-$N(R^{211})R^{212}$, $C_{1-6}$alkylene-$N^+(R^{211})(R^{212})R^{213}$, $C_{1-25}$alkylcarbonyl, $C_{2-25}$alkenylcarbonyl, $C_{1-6}$alkylene-CO—$OR^{314}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{311}$ is selected from hydrogen or $C_{1-6}$alkyl, $R^{312}$ is selected from hydrogen or $C_{1-6}$alkyl, $R^{313}$ is selected from hydrogen or $C_{1-6}$alkyl, and $R^{314}$ is selected from hydrogen or $C_{1-6}$alkyl;

$R^{302}$ is selected from hydrogen, or a group consisting of $C_{1-25}$alkyl, $C_{1-6}$alkylene-$N(R^{211})R^{212}$, $C_{1-6}$alkylene-$N^+(R^{211})(R^{212})R^{213}$, $C_{1-25}$alkylcarbonyl, $C_{2-25}$alkenylcarbonyl, $C_{1-6}$alkylene-CO—$OR^{314}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{311}$ is selected from hydrogen or $C_{1-6}$alkyl, $R^{312}$ is selected from hydrogen or $C_{1-6}$alkyl, $R^{313}$ is selected from hydrogen or $C_{1-6}$alkyl, and $R^{314}$ is selected from hydrogen or $C_{1-6}$alkyl;

$R^{43}$ is —$OR^{41}$ or —$X^2$—$X^1$—$X^3$, wherein
$R^{41}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$X^2$, $X^1$, and $X^3$ have the same meaning as that defined herein;

$R^{53}$ is —$OR^{51}$ or —$X^2$—$X^1$—$X^3$, wherein
$R^{51}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$X^2$, $X^1$, and $X^3$ have the same meaning as that defined herein;

wherein at least one of $Y^3$, $R^{43}$, or $R^{53}$ is —$X^2$—$X^1$—$X^3$.

In certain embodiments of the products (such as pharmaceutical formulations or FR-targeting excipients) or uses, as taught herein, the FR-targeting excipient may be a folate-polysaccharide conjugate comprising at least one unit of Formula XIe as taught herein, or any subgroup thereof, wherein $X^4$ is —O— or —$N(R^{403})$—, wherein $R^{403}$ is selected from hydrogen or $C_{1-6}$alkyl;

$R^{34}$ is —$OR^{31}$ or —$X^2$—$X^1$—$X^3$, wherein
$R^{31}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$X^2$ is —O— or —$N(R^{103})$—, wherein $R^{103}$ is selected from hydrogen or $C_{1-6}$alkyl;

$X^1$ is a single bond or a linker comprising a polyether, ether, amine, polyamine, amino acid, peptide, a polypeptide, a carbohydrate, or a combination of two or more thereof;

$X^3$ is a folate moiety; preferably $X^3$ is a folate moiety having the structural Formula XII, as taught herein, wherein $X^{221}$ is selected from N, $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H) $R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; $L^{220}$ is selected from

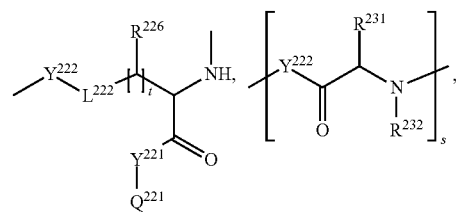

or a group consisting of $C_{1-6}$alkylene, $C_{1-6}$alkylenecarbonyl, —$C_{1-6}$alkylene-$N(R^{227})$—, $C_{2-6}$alkenylene, $C_{2-6}$alkynylene, $C_{3-6}$cycloalkylene, $C_{6-10}$arylene, —(C=O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—(CO)—$C_{3-6}$cycloalkylene, —$N(R^{228})$—, —$N(R^{228})$—(CO)—, and —(CO)—N$(R^{228})$—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —$N(R^{229})$—, or —S—; $Y^{222}$ is selected from a single bond, —O—, —$NR^{229}$—, —$N(R^{229})$—C(=NH)—$N(R^{230})$—, or —S—; $L^{222}$ is a single bond, $C_{6-10}$arylene, or —(C=O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond;

$R^{44}$ is —$OR^{41}$ or —$X^2$—$X^1$—$X^3$, wherein
$R^{41}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

X$^2$, X$^1$, and X$^3$ have the same meaning as that defined herein;

R$^{54}$ is —OR$^{51}$ or —X$^2$—X$^1$—X$^3$, wherein

R$^{51}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

X$^2$, X$^1$, and X$^3$ have the same meaning as that defined herein;

wherein at least one of R$^{34}$, R$^{44}$, or R$^{54}$ is —X$^2$—X$^1$—X$^3$.

In certain embodiments, the FR-targeting excipient may be a folate-polysaccharide conjugate comprising at least one unit of Formula XIb, XIc, XId, XIe, XIg, XIh, XIj, XIk, XIm, XIn, XIp, and/or XIq, as taught herein, or any subgroup thereof, wherein Y$^1$, Y$^2$, Y$^3$, X$^4$, R$^1$, R$^2$, R$^3$, R$^4$, R$^{11}$, R$^{20}$, R$^{21}$, R$^{31}$, R$^{34}$, R$^{41}$, R$^{43}$, R$^{53}$, R$^{54}$, X$^1$, and X$^3$ have the same meaning as defined herein.

In certain embodiments, the FR-targeting excipient may be a folate-polysaccharide conjugate comprising one or more units of Formula XIb, XIc, XId, XIe, XIg, XIh, XIj, XIk, XIm, XIn, XIp, or XIq, as taught herein, or any subgroup thereof, wherein Y$^1$, Y$^2$, Y$^3$, X$^4$, R$^1$, R$^2$, R$^3$, R$^4$, R$^{11}$, R$^{20}$, R$^{21}$, R$^{31}$, R$^{34}$, R$^{41}$, R$^{43}$, R$^{53}$, R$^{54}$, X$^1$, and X$^3$ have the same meaning as defined herein.

In certain embodiments, the FR-targeting excipients may comprise at least one unit, such as one or more units, of Formula XIb, XIc, XId, XIe, XIg, XIh, XIj, XIk, XIm, XIn, XIp, or XIq, as taught herein, such as at least two, at least three, at least four, at least five, at least six, at least seven, at least eight, at least nine, at least ten, at least twenty, at least thirty, at least forty, at least fifty, at least sixty, at least seventy, at least eighty, at least ninety, at least 100, at least 200, at least 300, at least 400, at least 500, at least 600, at least 700, at least 800, at least 900, at least 1000, at least 1500, at least 2000, or at least 2500 units of Formula XIb, XIc, XId, XIe, XIg, XIh, XIj, XIk, XIm, XIn, XIp, or XIq, as taught herein. For example, the polysaccharide or functionally-modified polysaccharide may comprise from about 50 to about 2000, from about 100 to about 1000, or from about 200 to about 500 units of Formula XIb, XIc, XId, XIe, XIg, XIh, XIj, XIk, XIm, XIn, XIp, or XIq, as taught herein.

In certain embodiments, the FR-targeting excipient may be a folate-polysaccharide conjugate comprising at least one unit of Formula XIg, XIh, XIj, and/or XIk, as taught herein, or any subgroup thereof, wherein R$^{11}$, R$^{20}$, R$^{21}$, R$^{31}$, R$^{41}$, X$^1$, and X$^3$ have the same meaning as that defined herein.

In certain embodiments, the FR-targeting excipient may be a folate-polysaccharide conjugate comprising at least one unit selected from the group consisting of units of Formula XIg, XIh, XIj, and XIk, as taught herein, or any subgroup thereof. In certain embodiments, the FR-targeting excipient may be a folate-polysaccharide conjugate comprising one or more units of Formula XIg, XIh, XIj, or XIk, as taught herein, or any subgroup thereof.

In certain embodiments, the FR-targeting excipient may be a folate-polysaccharide conjugate comprising at least one unit of Formula XIm, XIn, XIp, and/or XIq, as taught herein, or any subgroup thereof, wherein R$^{11}$, R$^{20}$, R$^{21}$, R$^{31}$, R$^{41}$, X$^1$, and X$^3$ have the same meaning as that defined herein.

In certain embodiments, the FR-targeting excipient may be a folate-polysaccharide conjugate comprising at least one unit selected from the group consisting of units of Formula XIm, XIn, XIp, and XIq, as taught herein, or any subgroup thereof. In certain embodiments, the FR-targeting excipient may be a folate-polysaccharide conjugate comprising one or more units of Formula XIm, XIn, XIp, or XIq, as taught herein, or any subgroup thereof.

In certain embodiments of the products (such as pharmaceutical formulations or FR-targeting excipients) or uses, as taught herein, the FR-targeting excipient may be a folate-polysaccharide conjugate comprising at least one unit selected from the group consisting of units of Formula XIb, XIc, XId, XIe, XIg, XIh, XIj, XIk, XIm, XIn, XIp, and XIq, as taught herein, or any subgroup thereof, wherein Y$^1$ is —X$^2$—X$^1$—X$^3$, or a group selected from —OR$^{10}$, —N(R$^{100}$)R$^{101}$, or —N$^+$(R$^{100}$)(R$^{101}$)R$^{102}$, Y$^2$ is —X$^2$—X$^1$—X$^3$, or a group selected from —OR$^{20}$, —N(R$^{200}$)R$^{201}$, or —N$^+$(R$^{200}$)(R$^{201}$)R$^{202}$, Y$^3$ is —X$^2$—X$^1$—X$^3$, or a group selected from —OR$^{30}$, —N(R$^{300}$)R$^{201}$, or —N$^+$(R$^{300}$)(R$^{301}$)R$^{302}$, R$^1$ is —OR$^{11}$ or —X$^2$—X$^1$—X$^3$,
R$^2$ is —OR$^{21}$ or —X$^2$—X$^1$—X$^3$,
R$^3$ is —OR$^{31}$ or —X$^2$—X$^1$—X$^3$,
R$^4$ is —OR$^{41}$ or —X$^2$—X$^1$—X$^3$,
R$^{34}$ is —OR$^{31}$ or —X$^2$—X$^1$—X$^3$,
R$^{43}$ is —OR$^{41}$ or —X$^2$—X$^1$—X$^3$,
R$^{44}$ is —OR$^{41}$ or —X$^2$—X$^1$—X$^3$,
R$^{53}$ is —OR$^{51}$ or —X$^2$—X$^1$—X$^3$,
R$^{54}$ is —OR$^{51}$ or —X$^2$—X$^1$—X$^3$, wherein at least one of Y$^1$, R$^1$, or R$^2$ is —X$^2$—X$^1$—X$^3$;
wherein at least one of Y$^2$, R$^3$, or R$^4$ is —X$^2$—X$^1$—X$^3$;
wherein at least one of Y$^3$, R$^{43}$, or R$^{53}$ is —X$^2$—X$^1$—X$^3$;
wherein at least one of R$^{34}$, R$^{44}$, or R$^{54}$ is —X$^2$—X$^1$—X$^3$;
wherein R$^{10}$, R$^{11}$, R$^{20}$, R$^{21}$, R$^{30}$, R$^{31}$, R$^{41}$, R$^{51}$ are each independently selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, —$C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl; preferably R$^{10}$, R$^{11}$, R$^{20}$, R$^{21}$, R$^{30}$, R$^{31}$, R$^{41}$, R$^{51}$ are each independently selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCO—OR$^{12}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein R$^{12}$ is selected from hydrogen or $C_{1-4}$alkyl; preferably R$^{10}$, R$^{11}$, R$^{20}$, R$^{21}$, R$^{30}$, R$^{31}$, R$^{41}$, R$^{51}$ are each independently selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxyC$_{1-3}$alkyl, C$_{2-3}$alkenyl, and C$_{2-3}$alkynyl, each group being optionally substituted with one or more substituents each independently selected from hydroxyl, halogen, C$_{1-3}$alkyl, or C$_{1-3}$alkoxy; preferably R$^{10}$, R$^{11}$, R$^{20}$, R$^{21}$, R$^{30}$, R$^{31}$, R$^{41}$, R$^{51}$, are each independently selected from hydrogen, or a group consisting of C$_{1-3}$alkyl, C$_{1-25}$alkylcarbonyl, and C$_{13-25}$alkenylcarbonyl; preferably R$^{10}$, R$^{11}$, R$^{20}$, R$^{21}$, R$^{30}$, R$^{31}$, R$^{41}$, R$^{51}$ are each independently selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

R$^{100}$, R$^{101}$, R$^{102}$, R$^{200}$, R$^{201}$, R$^{202}$, R$^{300}$, R$^{301}$, R$^{302}$ are each independently selected from hydrogen, or a group consisting of C$_{1-25}$alkyl, C$_{1-6}$alkylene-N(R$^{111}$)R$^{112}$, C$_{1-6}$alkylene-N$^+$(R$^{111}$)(R$^{112}$)R$^{113}$, C$_{1-25}$alkylcarbonyl, C$_{2-25}$alkenylcarbonyl, C$_{1-6}$alkylene-CO—OR$^{114}$, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, carboxyl, or C$_{1-6}$alkoxy, wherein R$^{111}$ is selected from hydrogen or C$_{1-6}$alkyl, R$^{112}$ is selected from hydrogen or C$_{1-6}$alkyl, R$^{113}$ is selected from hydrogen or C$_{1-6}$alkyl, and R$^{114}$ is selected from hydrogen or C$_{1-6}$alkyl; preferably R$^{100}$, R$^{101}$, R$^{102}$, R$^{200}$, R$^{201}$, R$^{202}$, R$^{300}$, R$^{301}$, R$^{302}$ are each independently selected from hydrogen, or a group consisting of C$_{1-6}$alkyl, C$_{1-4}$alkylene-N(R$^{111}$)R$^{112}$, C$_{1-4}$alkylene-N$^+$(R$^{111}$)(R$^{112}$)R$^{113}$, C$_{1-25}$alkylcarbonyl, C$_{3-25}$alkenylcarbonyl, C$_{1-4}$alkylene-CO—OR$^{114}$, C$_{2-4}$alkenyl, and C$_{2-4}$alkynyl, each group being optionally substituted with one or more substituents each independently selected from hydroxyl, halogen, C$_{1-4}$alkyl, or C$_{1-4}$alkoxy, wherein R$^{111}$ is selected from hydrogen or C$_{1-4}$alkyl, R$^{112}$ is selected from hydrogen or C$_{1-4}$alkyl, R$^{113}$ is selected from hydrogen or C$_{1-4}$alkyl, and R$^{114}$ is selected from hydrogen or C$_{1-4}$alkyl; preferably R$^{100}$, R$^{101}$, R$^{102}$, R$^{200}$, R$^{201}$, R$^{202}$, R$^{300}$, R$^{301}$, R$^{302}$ are each independently selected from hydrogen, or a group consisting of C$_{1-4}$alkyl, C$_{1-3}$alkylene-N(R$^{111}$)R$^{112}$, C$_{1-3}$alkylene-N$^+$(R$^{111}$)(R$^{112}$)R$^{113}$, C$_{1-25}$alkylcarbonyl, C$_{5-23}$alkenylcarbonyl, C$_{1-3}$alkylene-CO—OR$^{114}$, C$_{2-3}$alkenyl, and C$_{2-3}$alkynyl, each group being optionally substituted with one or more substituents each independently selected from hydroxyl, halogen, C$_{1-3}$alkyl, or C$_{1-3}$alkoxy, wherein R$^{111}$ is selected from hydrogen or C$_{1-3}$alkyl, R$^{112}$ is selected from hydrogen or C$_{1-3}$alkyl, R$^{113}$ is selected from hydrogen or C$_{1-3}$alkyl, and R$^{114}$ is selected from hydrogen or C$_{1-3}$alkyl; preferably R$^{100}$, R$^{101}$, R$^{102}$, R$^{200}$, R$^{201}$, R$^{202}$, R$^{300}$, R$^{301}$, R$^{302}$ are each independently selected from hydrogen, or a group consisting of C$_{1-3}$alkyl, C$_{1-3}$alkylene-N(R$^{111}$)R$^{112}$, C$_{1-3}$alkylene-N$^+$(R$^{111}$)(R$^{112}$)R$^{113}$, C$_{1-25}$alkylcarbonyl, C$_{13-21}$alkenylcarbonyl, and C$_{1-3}$alkylene-CO—OR$^{114}$, each group being optionally substituted with one or more substituents each independently selected from hydroxyl, halogen, C$_{1-3}$alkyl, or C$_{1-3}$alkoxy, wherein R$^{111}$ is selected from hydrogen or C$_{1-3}$alkyl, R$^{112}$ is selected from hydrogen or C$_{1-3}$alkyl, R$^{113}$ is selected from hydrogen or C$_{1-3}$alkyl, and R$^{114}$ is selected from hydrogen or C$_{1-3}$alkyl; preferably R$^{100}$, R$^{101}$, R$^{102}$, R$^{200}$, R$^{201}$, R$^{202}$, R$^{300}$, R$^{301}$, R$^{302}$ are each independently selected from hydrogen, or a group consisting of methyl, ethyl, n-propyl, i-propyl, methylene-N(R$^{111}$)R$^{112}$, ethylene-N(R$^{111}$)R$^{112}$, n-propylene-N(R$^{111}$)R$^{112}$, methylene-N$^+$(R$^{111}$)(R$^{112}$)R$^{113}$, ethylene-N$^+$(R$^{111}$)(R$^{112}$)R$^{113}$, n-propylene-N$^+$(R$^{111}$)(R$^{112}$)R$^{113}$, methylene-CO—OR$^{114}$, ethylene-CO—OR$^{114}$, n-propylene-CO—OR$^{114}$, C$_{1-25}$alkylcarbonyl, and, C$_{13-21}$alkenylcarbonyl, each group being optionally substituted with one or more substituents each independently selected from hydroxyl, halogen, methyl, or ethyl, wherein R$^{111}$ is selected from hydrogen, methyl, or ethyl, R$^{112}$ is selected from hydrogen, methyl, or ethyl, R$^{113}$ is selected from hydrogen, methyl, or ethyl, and R$^{114}$ is selected from hydrogen, methyl, or ethyl; preferably R$^{100}$, R$^{101}$, R$^{102}$, R$^{200}$, R$^{201}$, R$^{202}$, R$^{300}$, R$^{301}$, R$^{302}$ are each independently selected from) hydrogen, or a group consisting of methyl, ethyl, n-propyl, i-propyl, methylene-N$^+$(R$^{111}$)(R$^{112}$)R$^{113}$, ethylene-N$^+$(R$^{111}$)(R$^{112}$)R$^{113}$, n-propylene-N$^+$(R$^{111}$)(R$^{112}$)R$^{113}$, methylene-CO—OR$^{114}$ ethylene-CO—OR$^{114}$, n-propylene-CO—OR$^{114}$, C$_{1-25}$alkylcarbonyl, and, C$_{13-21}$alkenylcarbonyl, each group being optionally substituted with one or more substituents each independently selected from hydroxyl or methyl, wherein R$^{111}$ is selected from hydrogen or methyl, R$^{112}$ is selected from hydrogen or methyl, R$^{113}$ is selected from hydrogen or methyl, and R$^{114}$ is selected from hydrogen or methyl; preferably R$^{100}$, R$^{101}$, R$^{102}$, R$^{200}$, R$^{201}$, R$^{202}$, R$^{300}$, R$^{301}$, R$^{302}$ are each independently selected from hydrogen, or a group consisting of methyl, ethyl, n-propyl, i-propyl, 2-hydroxy-propyleneN$^+$(CH$_3$)$_3$, methylene-CO—OH, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the nitrogen to which it is bound a caprylic amide moiety), n-nonylcarbonyl (e.g. which may form together with the nitrogen to which it is bound a capric amide moiety), n-undecylcarbonyl (e.g. which may form together with the nitrogen to which it is bound a lauric amide moiety), n-tridecylcarbonyl (e.g. which may form together with the nitrogen to which it is bound a myristic amide moiety), n-pentadecylcarbonyl (e.g. which may form together with the nitrogen to which it is bound a palmitic amide moiety), n-heptadecylcarbonyl (e.g. which may form together with the nitrogen to which it is bound a stearic amide moiety), n-nonadecylcarbonyl (e.g. which may form together with the nitrogen to which it is bound an arachidic amide moiety), n-henicosylcarbonyl (e.g. which may form together with the nitrogen to which it is bound a behenic amide moiety), n-tricosylcarbonyl (e.g. which may form together with the nitrogen to which it is bound a lignoceric amide moiety), n-pentacosylcarbonyl (e.g. which may form together with the nitrogen to which it is bound a cerotic amide moiety), n-tridecenylcarbonyl (e.g. which may form together with the nitrogen to which it is bound a myristoleic amide), n-pentadecenylcarbonyl (e.g. which may form together with the nitrogen to which it is bound a palmitoleic amide moiety or sapienic amide moiety), n-heptadecenylcarbonyl (e.g. which may form together with the nitrogen to which it is bound an oleic amide moiety, elaidic amide moiety, vaccenic amide moiety, linoleic amide moiety, linoelaidic amide moiety, or α-linolenic amide moiety), n-nonadecenylcarbonyl (e.g. which may form together with the nitrogen to which it is bound an arachidonic amide moiety or eicosapentaenoic amide moiety), or n-henicosenylcarbonyl (e.g. which may form together with the nitrogen to which it is bound an erucic amide moiety or docosahexaenoic amide moiety);

$X^2$ is —O— or —N($R^{103}$)—, wherein $R^{103}$ is selected from hydrogen or $C_{1-6}$alkyl;

$X^1$ is a single bond or a linker comprising a polyether, ether, amine, polyamine, amino acid, peptide, a polypeptide, a carbohydrate, or a combination of two or more thereof, preferably $X^1$ is a single bond or a linker comprising a poly($C_{1-6}$alkyleneoxide), $C_{1-6}$alkyleneoxide, amine, poly (iminoC$_{1-6}$alkylene), amino acid, peptide, polypeptide, monosaccharide, or polysaccharide, preferably $X^1$ is a single bond or a linker of Formula X, $$-A^1-L^1-A^2- \qquad (X)$$

wherein the left side of the linker of Formula X is attached to $X^2$ and the right side thereof is attached to $X^3$; wherein $A^1$ is selected from a group consisting of —CO—, —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-6}$alkylene optionally substituted with one or more substituents selected from a group consisting of hydroxyl, $C_{1-6}$alkyl and $C_{1-6}$alkoxy; $R^{16}$ and $R^{17}$ are each independently selected from hydrogen or $C_{1-6}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-4}$alkylene optionally substituted with one or more substituents selected from a group consisting of hydroxyl, $C_{1-4}$alkyl and $C_{1-4}$alkoxy; $R^{16}$ and $R^{17}$ are each independently selected from hydrogen or $C_{1-4}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-3}$alkylene optionally substituted with one or more substituents selected from a group consisting of hydroxyl and $C_{1-3}$alkyl; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$ is methylene, ethylene, n-propylene; $L^{15}$, $L^{16}$, $L^{17}$, and $L^{18}$ are each independently methylene or ethylene; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;

$L^1$ is a poly($C_{1-6}$alkyleneoxide); preferably $L^1$ is selected from a polyethylene oxide (PEO), a polypropylene oxide (PPO), or a block copolymer of PEO and PPO; preferably $L^1$ is a polyethylene oxide having the Formula —(CH$_2$—CH$_2$—O)$_q$— or —(O—CH$_2$—CH$_2$)$_q$—, wherein q is an integer selected from 20 to 120; preferably $L^1$ is a polyethylene oxide having the Formula —(CH$_2$—CH$_2$—O)$_q$— or —(O—CH$_2$—CH$_2$)$_q$—, wherein q is an integer selected from 40 to 110; preferably $L^1$ is a polyethylene oxide having the Formula —(CH$_2$—CH$_2$—O)$_q$— or —(O—CH$_2$—CH$_2$)$_q$—, wherein q is an integer selected from 60 to 90;

$A^2$ is a single bond or is selected from a group consisting of —N($R^{18}$)—, —O—, -$L^{19}$-N($R^{19}$)—, and -$L^{20}$-O—, wherein the left side of each group is attached to $L^1$ and the right side thereof is attached to $X^3$, wherein $L^{19}$ and $L^{20}$ are each independently $C_{1-6}$alkylene being optionally substituted with one or more substituents selected from a group consisting of hydroxyl, $C_{1-6}$alkyl, and $C_{1-6}$alkoxy, $R^{18}$ and $R^{19}$ are each independently selected from hydrogen or $C_{1-6}$alkyl; preferably $A^2$ is a single bond or is selected from a group consisting of —N($R^{18}$)—, —O—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-4}$alkylene being optionally substituted with one or more substituents selected from a group consisting of hydroxyl, $C_{1-4}$alkyl, and $C_{1-4}$alkoxy, $R^{18}$ and $R^{19}$ are each independently selected from hydrogen or $C_{1-4}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-3}$alkylene being optionally substituted with one or more substituents selected from a group consisting of hydroxyl and $C_{1-3}$alkyl, $R^{18}$ and $R^{19}$ are each independently selected from hydrogen or $C_{1-3}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently methylene or ethylene; $R^{18}$ and $R^{19}$ are each independently selected from hydrogen or $C_{1-3}$alkyl; preferably $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;

$X^3$ is a folate moiety; preferably $X^3$ is a folate moiety having the structural Formula XII, as taught herein, wherein $X^{221}$ is selected from N, $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C═O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C═O), —OR', —COR', and halosubstituted —COR', wherein R' is H or $C_{1-8}$alkyl; $L^{220}$ is selected from

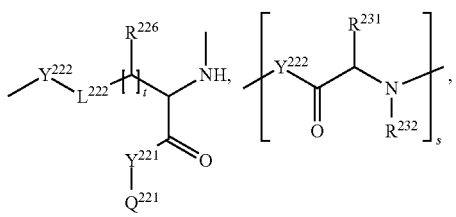

or a group consisting of $C_{1-6}$alkylene, $C_{1-6}$alkylenecarbonyl, —$C_{1-6}$alkylene-N($R^{227}$)—, $C_{2-6}$alkenylene, $C_{2-6}$alkynylene, $C_{3-6}$cycloalkylene, $C_{6-10}$arylene, —(C═O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—(CO)—$C_{3-6}$ cycloalkylene, —N($R^{228}$)—, —N($R^{228}$)—(CO)—, and —(CO)—N($R^{228}$)—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —N($R^{229}$)—, or —S—; $Y^{222}$ is selected from a single bond, —O—, —$NR^{229}$—, —N($R^{229}$)—C(═NH)—N($R^{230}$)—, or —S—; $L^{222}$ is a single bond, $C_{6-10}$arylene, or —(C═O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIa, or a stereoisomer, tautomer, salt, hydrate or solvate thereof, wherein

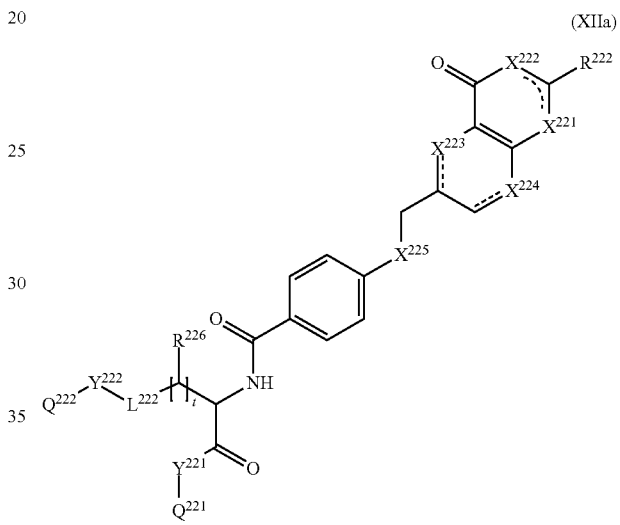

(XIIa)

$X^{221}, X^{222}, X^{223}, X^{224}, X^{225}, R^{222}, R^{226}, L^{222}, Y^{221}, Y^{222}, Q^{221}, Q^{222}$ and t have the same meaning as that defined herein above; preferably $X^3$ is a folate moiety having the structural Formula XII or XIIa, as taught herein, wherein $X^{221}$ is selected from N, or $NR^{221}$; or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C═O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C═O), —OR', —COR', and halosubstituted —COR', wherein R' is H or $C_{1-8}$alkyl; wherein $Y^{221}$ is selected from a single bond, —O—, —N($R^{229}$)—, or —S—; $Y^{222}$ is selected from a single bond —O—, —N($R^{229}$)—, —N($R^{229}$)—C—

(=NH)—N($R^{230}$)—, or —S—; $L^{222}$ is a single bond, $C_{6-10}$arylene, or —(C=O)—; t is an integer selected from 1, 2, 3, or 4; $R^{226}$ is hydrogen or $C_{1-6}$alkyl; $R^{229}$ is hydrogen or $C_{1-6}$alkyl; $R^{230}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIb, or a stereoisomer, tautomer, salt, hydrate or solvate thereof, wherein

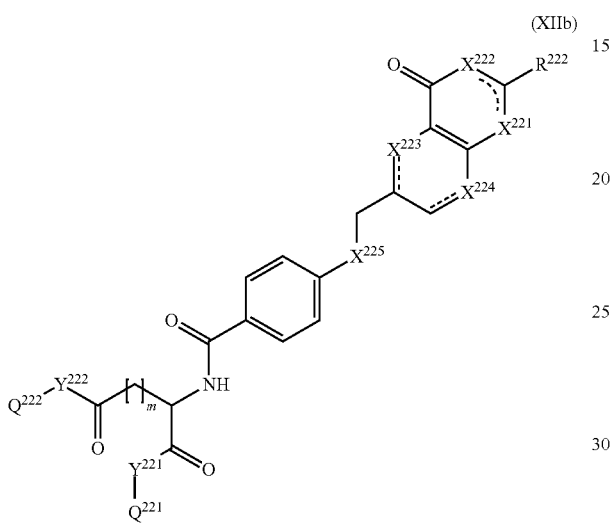

(XIIb)

$X^{221}$, $X^{222}$, $X^{223}$, $X^{224}$, $X^{225}$, $R^{222}$, $Y^{221}$, $Y^{222}$, $Q^{221}$, $Q^{222}$ and m have the same meaning as that defined herein above; preferably $X^3$ is a folate moiety having the structural Formula XII, XIIa, or XIIb, as taught herein, wherein $X^{221}$ is selected from N, $NR^{221}$; or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —$NR^{229}$— or —S—; $Y^{222}$ is selected from a single bond, —O—, —$NR^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XII, XIIa, or XIIb, as taught herein, wherein $X^{221}$ is selected from N or $NR^{221}$; $X^{222}$ is selected from N or $NR^{221}$; $X^{223}$ is selected from N or $NR^{223}$; $X^{224}$ is selected from N or $NR^{224}$; $X^{225}$ is $NR^{224}$, and $R^{221}$, $R^{222}$, $R^{223}$, $R^{224}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $X^{221}$ is selected from N or NH; $X^{222}$ is selected from N or NH; $X^{223}$ is selected from N or NH; $X^{224}$ is selected from N or NH; $X^{225}$ is NH, and $R^{222}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $R^{222}$ is selected from the group consisting of —$NHR^{225}$, hydrogen, $C_{1-12}$alkyl, —$OR^{225}$, preferably —$NHR^{125}$, or —$OR^{225}$, wherein $R^{225}$ is selected from hydrogen, halo, $C_{1-12}$alkyl, $C_{2-12}$alkenyl, $C_{2-12}$alkynyl, —OR', —COR', —COOR', or —NHR', wherein R' is H or $C_{1-8}$alkyl, and $X^{221}$, $X^{222}$, $X^{223}$, $X^{224}$, $X^{225}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XIIc, or a stereoisomer, tautomer, salt, hydrate or solvate thereof, wherein

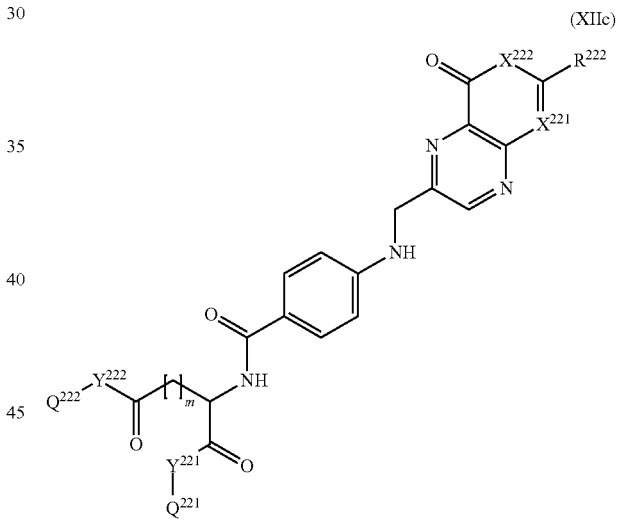

(XIIc)

$Y^{221}$, $Y^{222}$, $Q^{221}$, $Q^{222}$, and m have the same meaning as that defined herein above; preferably $X^3$ is a folate moiety having the structural Formula XII, XIIa, XIIb, or XIIc, as taught herein, wherein $Y^{221}$ is selected from a single bond, —O—, —$NR^{229}$ or —S—; $Y^{222}$ is selected from a single bond, —O—, —$NR^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; preferably $X^3$ is a folate moiety having the structural Formula XII, XIIa, XIIb, or XIIc, as taught herein, wherein $Q^{221}$ is hydrogen and $Q^{222}$ is a single bond connected to $X^1$; preferably $X^3$ is a folate moiety having the structural Formula XIId, or a stereoisomer, tautomer, salt, hydrate or solvate thereof, wherein (XIId)

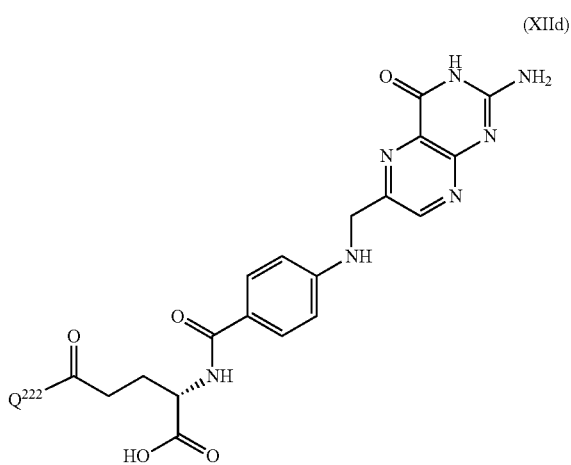

$Q^{222}$ is a single bond connected to $X^1$;
$X^4$ is —O— or —N($R^{403}$)—, wherein $R^{403}$ is selected from hydrogen or $C_{1-6}$alkyl.

In certain preferred embodiments of the products (such as pharmaceutical formulations or FR-targeting excipients) or uses, as taught herein, the FR-targeting excipient may be a folate-polysaccharide conjugate comprising at least one unit of Formula XIb, XIc, XId, XIe, XIg, XIh, XIj, XIk, XIm, XIn, XIp, or XIq, as taught herein, or any subgroup thereof, wherein $R^{11}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{11}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxyl$C_{1-4}$ alkylenecarbonyl, hydroxy$C_{1-4}$alkyl, carboxyl $C_{6-10}$ arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{11}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$ alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{11}$ is selected from hydrogen, or a group consisting of $C_{1-3}$alkyl, $C_{1-25}$alkylcarbonyl, and $C_{13-25}$alkenylcarbonyl; preferably $R^{11}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{21}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

preferably $R^{21}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkylene COOR$^{12}$, carboxyl$C_{1-4}$alkylenecarbonyl, hydroxy$C_{1-4}$ alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{21}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$ alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{21}$ is selected from hydrogen, or a group consisting of $C_{1-3}$alkyl, $C_{1-25}$alkylcarbonyl, and $C_{13-25}$alkenylcarbonyl; preferably $R^{21}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{31}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{31}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxyl$C_{1-4}$ alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{31}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$ alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{31}$ is selected from hydrogen, a mono-, oligo-, or poly-glycosyl moiety, or a group consisting of $C_{1-3}$alkyl, $C_{1-25}$alkylcarbonyl, and $C_{13-25}$alkenylcarbonyl; preferably $R^{31}$ is selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{41}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{41}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxyl$C_{1-4}$ alkylenecarbonyl, hydroxy$C_{1-4}$alkyl, carboxyl $C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{41}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$ alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{41}$ is selected from hydrogen, a mono-, oligo-, or poly-glycosyl moiety, or a group consisting of $C_{1-3}$alkyl, $C_{1-25}$alkylcarbonyl, and $C_{13-25}$alkenylcarbonyl; preferably $R^{41}$ is selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{20}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene $COOR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{20}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxyl$C_{1-4}$ alkylenecarbonyl, hydroxy$C_{1-4}$alkyl, carboxyl $C_{6-10}$ arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{20}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$ alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{20}$ is selected from hydrogen, a mono-, oligo-, or poly-glycosyl moiety, or a group consisting of $C_{1-3}$alkyl, $C_{1-25}$alkylcarbonyl, and $C_{13-25}$alkenylcarbonyl; preferably $R^{20}$ is selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$X^1$ is a single bond or a linker comprising a polyether, ether, amine, polyamine, amino acid, peptide, a polypeptide, a carbohydrate, or a combination of two or more thereof, preferably $X^1$ is a single bond or a linker comprising a poly($C_{1-6}$alkyleneoxide), $C_{1-6}$alkyleneoxide, amine, poly (imino$C_{1-6}$alkylene), amino acid, peptide, polypeptide, monosaccharide, or polysaccharide, preferably $X^1$ is a single bond or a linker of Formula X, as taught herein, wherein the left side of the linker of Formula X is attached to $X^2$ and the right side thereof is attached to $X^3$; wherein $A^1$ is selected from a group consisting of —CO—, —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-6}$alkylene optionally substituted with one or more substituents selected from a group consisting of hydroxyl, $C_{1-6}$alkyl and $C_{1-6}$alkoxy; $R^{16}$ and $R^{17}$ are each independently selected from hydrogen or $C_{1-6}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N ($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-4}$alkylene optionally substituted with one or more substituents selected from a group consisting of hydroxyl, $C_{1-4}$alkyl and $C_{1-4}$alkoxy; $R^{16}$ and $R^{17}$ are each independently selected from hydrogen or $C_{1-4}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-3}$alkylene optionally substituted with one or more substituents selected from a group consisting of hydroxyl and $C_{1-3}$alkyl; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$ is methylene, ethylene, n-propylene; $L^{15}$, $L^{16}$, $L^{17}$, and $L^{18}$ are each independently methylene or ethylene; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene; $L^1$ is a poly($C_{1-6}$alkyleneoxide); preferably $L^1$ is selected from a polyethylene oxide (PEO), a polypropylene oxide (PPO), or a block copolymer of PEO and PPO; preferably $L^1$ is a polyethylene oxide having the Formula —$(CH_2-CH_2-O)_q$— or —$(O-CH_2-CH_2)_q$—, wherein q is an integer selected from 20 to 120; preferably $L^1$ is a polyethylene oxide having the Formula —$(CH_2-CH_2-O)_q$— or —$(O-CH_2-CH_2)_q$—, wherein q is an integer selected from 40 to 110; preferably $L^1$ is a polyethylene oxide having the Formula —$(CH_2-CH_2-O)_q$— or —$(O-CH_2-CH_2)_q$—, wherein q is an integer selected from 60 to 90; $A^2$ is a single bond or is selected from a group consisting of —N($R^{18}$)—, —O—, -$L^{19}$-N($R^{19}$)—, and -$L^{20}$-O—, wherein the left side of each group is attached to $L^1$ and the right side thereof is attached to $X^3$, wherein $L^{19}$ and $L^{20}$ are each independently $C_{1-6}$alkylene being optionally substituted with one or more substituents selected from a group consisting of hydroxyl, $C_{1-6}$alkyl, and $C_{1-6}$alkoxy, $R^{18}$ and $R^{19}$ are each independently selected from hydrogen or $C_{1-6}$alkyl; preferably $A^2$ is a single bond or is selected from a group consisting of —N($R^{18}$)—, —O—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-4}$alkylene being optionally substituted with one or more substituents selected from a group consisting of hydroxyl, $C_{1-4}$alkyl, and $C_{1-4}$alkoxy, $R^{18}$ and $R^{19}$ are each independently selected from hydrogen or $C_{1-4}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-3}$alkylene being optionally substituted with one or more substituents selected from a group consisting of hydroxyl and $C_{1-3}$alkyl, $R^{18}$ and $R^{19}$ are each independently selected from hydrogen or $C_{1-3}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently methylene or ethylene; $R^{18}$ and $R^{19}$ are each independently selected from hydrogen or $C_{1-3}$alkyl; preferably $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;

$X^3$ is a folate moiety; preferably $X^3$ is a folate moiety having the structural Formula XII, as taught herein, wherein $X^{221}$ is selected from N, $NR^{221}$; or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C═O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C═O), —OR', —COR', and halosubstituted —COR', wherein R' is H or $C_{1-8}$alkyl; $L^{220}$ is selected from

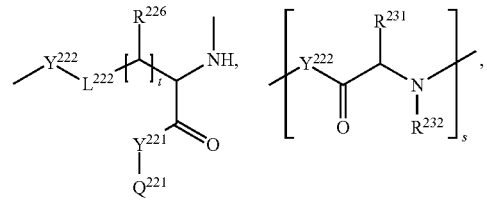

or a group consisting of $C_{1-6}$alkylene, $C_{1-6}$alkylenecarbonyl, —$C_{1-6}$alkylene-N($R^{227}$)—, $C_{2-6}$alkenylene, $C_{2-6}$alkynylene, $C_{3-6}$cycloalkylene, $C_{6-10}$arylene, —(C═O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—(CO)—$C_{3-6}$cycloalkylene, —N($R^{228}$)—, —N($R^{228}$)—(CO)—, and —(CO)—N($R^{228}$)—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —N($R^{229}$)—, or —S—; $Y^{222}$ is selected from a single bond, —O—, —$NR^{229}$—, —N($R^{229}$)—C(═NH)—N($R^{230}$)—, or —S—; $L^{222}$ is a single bond, $C_{6-10}$arylene, or —(C═O)—; t is an integer, selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIa, as taught herein, wherein $X^{221}$, $X^{222}$, $X^{223}$, $X^{224}$, $X^{225}$, $R^{222}$, $R^{226}$, $L^{222}$, $Y^{221}$, $Y^{222}$, $Q^{221}$, $Q^{222}$ and t have the same meaning as that defined herein above; preferably $X^3$ is a folate moiety having the structural Formula XII or XIIa, as taught herein, wherein $X^{221}$ is selected from N, or $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —OR$^{225}$, —CO—R$^{125}$, —CO—O—R$^{225}$, and —CO—N(H)R$^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —N($R^{229}$)—, or —S—; $Y^{222}$ is selected from a single bond, —O—, —N($R^{229}$)—, —N($R^{229}$)—C(=NH)—N($R^{230}$)—, or —S—; $L^{222}$ is a single bond, $C_{6-10}$arylene, or —(C=O)—; t is an integer selected from 1, 2, 3, or 4; $R^{226}$ is hydrogen or $C_{1-6}$alkyl; $R^{229}$ is hydrogen or $C_{1-6}$alkyl; $R^{230}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIb, as taught herein, wherein $X^{221}$, $X^{222}$, $X^{223}$, $X^{224}$, $X^{225}$, $R^{222}$, $Y^{221}$, $Y^{222}$, $Q^{221}$, $Q^{222}$ and m have the same meaning as that defined herein above; preferably $X^3$ is a folate moiety having the structural Formula XII, XIIa, or XIIb, as taught herein, wherein $X^{221}$ is selected from N, $NR^{221}$; or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —OR$^{225}$, —CO—R$^{125}$, —CO—O—R$^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —NR$^{229}$— or —S—; $Y^{222}$ is selected from a single bond, —O—, —NR$^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XII, XIIa, or XIIb, as taught herein, wherein $X^{221}$ is selected from N or $NR^{221}$; $X^{222}$ is selected from N or $NR^{221}$; $X^{223}$ is selected from N or $NR^{223}$; $X^{224}$ is selected from N or $NR^{224}$; $X^{225}$ is $NR^{224}$, and $R^{221}$, $R^{222}$, $R^{223}$, $R^{224}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $X^{221}$ is selected from N or NH; $X^{222}$ is selected from N or NH; $X^{223}$ is selected from N or NH; $X^{224}$ is selected from N or NH; $X^{225}$ is NH, and $R^{222}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $R^{222}$ is selected from the group consisting of —NHR$^{225}$, hydrogen, $C_{1-12}$alkyl, —OR$^{225}$, preferably —NHR$^{125}$, or —OR$^{225}$, wherein $R^{225}$ is selected from hydrogen, halo, $C_{1-12}$alkyl, $C_{2-12}$alkenyl, $C_{2-12}$alkynyl, —OR', —COR', —COOR', or —NHR', wherein R' is H or $C_{1-8}$alkyl, and $X^{221}$, $X^{222}$, $X^{223}$, $X^{224}$, $X^{225}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XIIc, as taught herein, wherein $Y^{221}$, $Y^{222}$, $Q^{221}$, $Q^{222}$ and m have the same meaning as that defined herein above; preferably $X^3$ is a folate moiety having the structural Formula XII, XIIa, XIIb, or XIIc, as taught herein, wherein $Y^{221}$ is selected from a single bond, —O—, —NR$^{229}$— or —S—; $Y^{222}$ is selected from a single bond, —O—, —NR$^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; preferably $X^3$ is a folate moiety having the structural Formula XII, XIIa, XIIb, or XIIc, as taught herein, wherein $Q^{221}$ is hydrogen and $Q^{222}$ is a single bond connected to $X^1$; preferably $X^3$ is a folate moiety having the structural Formula XIId, as taught herein, wherein $Q^{222}$ is a single bond connected to $X^1$.

In certain preferred embodiments, the FR-targeting excipient may be a folate-polysaccharide conjugate comprising at least one unit of Formula XIb, XIg, or XIm, as taught herein, or any subgroup thereof, wherein $Y^1$ is —$X^2$—$X^1$—$X^3$, or a group selected from —OR$^{10}$, —N($R^{100}$)$R^{101}$, or —N$^+$($R^{100}$)($R^{101}$)$R^{102}$, preferably $Y^1$ is —$X^1$—$X^2$—$X^3$; wherein $X^2$ is —O— or —N($R^{103}$)—, wherein $R^{103}$ is selected from hydrogen or $C_{1-6}$alkyl, preferably $X^2$ is —N($R^{103}$)—, wherein $R^{103}$ is selected from hydrogen or $C_{1-6}$alkyl, preferably $X^2$ is —NH—;

$X^1$ is a single bond or a linker comprising a polyether, ether, amine, polyamine, amino acid, peptide, a polypeptide, a carbohydrate, or a combination of two or more thereof, preferably $X^1$ is a single bond or a linker comprising a poly($C_{1-6}$alkyleneoxide), $C_{1-6}$alkyleneoxide, amine, poly(imino$C_{1-6}$alkylene), amino acid, peptide, polypeptide, monosaccharide, or polysaccharide, preferably $X^1$ is a single bond or a linker of Formula X, as taught herein, wherein the left side of the linker of Formula X is attached to $X^2$ and the right side thereof is attached to $X^3$; wherein $A^1$ is selected from a group consisting of —CO—, —CO-L$^{14}$-O—, —CO-L$^{15}$-CO—O—, —CO-L$^{16}$-

CO—N($R^{16}$)-$L^{17}$-, and —CO-$L^{18}$-CO—N($R^{17}$)—, wherein the right side of each group is attached to 17, $L^1$ and the left side thereof is attached to $X^2$, wherein $L^{14}$, $L^{15}$, $L^{16}$, $L^{17}$, and $L^{18}$ are each independently $C_{1-6}$alkylene optionally substituted with one or more substituents selected from a group consisting of hydroxyl, $C_{1-6}$alkyl and $C_{1-6}$alkoxy; $R^{16}$ and $R^{17}$ are each independently selected from hydrogen or $C_{1-6}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-4}$alkylene optionally substituted with one or more substituents selected from a group consisting of hydroxyl, $C_{1-4}$alkyl and $C_{1-4}$alkoxy; $R^{16}$ and $R^{17}$ are each independently selected from hydrogen or $C_{1-4}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-3}$alkylene optionally substituted with one or more substituents selected from a group consisting of hydroxyl and $C_{1-3}$alkyl; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$ is methylene, ethylene, n-propylene; $L^{15}$, $L^{16}$, $L^{17}$, and $L^{18}$ are each independently methylene or ethylene; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;

$L^1$ is a poly($C_{1-6}$alkyleneoxide); preferably $L^1$ is selected from a polyethylene oxide (PEO), a polypropylene oxide (PPO), or a block copolymer of PEO and PPO; preferably $L^1$ is a polyethylene oxide having the Formula —$(CH_2—CH_2—O)_q$— or —$(O—CH_2—CH_2)_q$—, wherein q is an integer selected from 20 to 120; preferably $L^1$ is a polyethylene oxide having the Formula —$(CH_2—CH_2—O)_q$— or —$(O—CH_2—CH_2)_q$—, wherein q is an integer selected from 40 to 110; preferably $L^1$ is a polyethylene oxide having the Formula —$(CH_2—CH_2—O)_q$— or —$(O—CH_2—CH_2)_q$—, wherein q is an integer selected from 60 to 90;

$A^2$ is a single bond or is selected from a group consisting of —N($R^{18}$)—, —O—, -$L^{19}$-N($R^{19}$)—, and -$L^{20}$-O—, wherein the left side of each group is attached to $L^1$ and the right side thereof is attached to $X^3$, wherein $L^{19}$ and $L^{20}$ are each independently $C_{1-6}$alkylene being optionally substituted with one or more substituents selected from a group consisting of hydroxyl, $C_{1-6}$alkyl, and $C_{1-6}$alkoxy; $R^{18}$ and $R^{19}$ are each independently selected from hydrogen or $C_{1-6}$alkyl; preferably $A^2$ is a single bond or is selected from a group consisting of —N($R^{18}$)—, —O—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-4}$alkylene being optionally substituted with one or more substituents selected from a group consisting of hydroxyl, $C_{1-4}$alkyl, and $C_{1-4}$alkoxy, $R^{18}$ and $R^{19}$ are each independently selected from hydrogen or $C_{1-4}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-3}$alkylene being optionally substituted with one or more substituents selected from a group consisting of hydroxyl and $C_{1-3}$alkyl, $R^{18}$ and $R^{19}$ are each independently selected from hydrogen or $C_{1-3}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently methylene or ethylene; $R^{18}$ and $R^{19}$ are each independently selected from hydrogen or $C_{1-3}$alkyl; preferably $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;

$X^3$ is a folate moiety; preferably $X^3$ is a folate moiety having the structural Formula XII, as taught herein, wherein $X^{221}$ is selected from N, $NR^{221}$; or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; $L^{220}$ is selected from

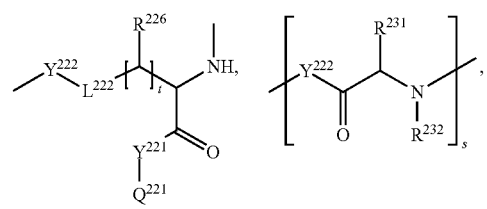

or a group consisting of $C_{1-6}$alkylene, $C_{1-6}$alkylenecarbonyl, —$C_{1-6}$alkylene-N($R^{227}$)—, $C_{2-6}$alkenylene, $C_{2-6}$alkynylene, $C_{3-6}$cycloalkylene, $C_{6-10}$arylene, —(C=O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—(CO)—$C_{3-6}$cycloalkylene, —N($R^{228}$)—, —N($R^{228}$)—(CO)—, and —(CO)—N($R^{228}$)—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —N($R^{229}$)—, or —S—; $Y^{222}$ is selected from a single bond, —O—, —N$R^{229}$—, —N($R^{229}$)—C(=NH)—N($R^{230}$)—, or —S—; $L^{222}$ is a single bond, $C_{6-10}$arylene, or —(C=O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIa, as taught herein, wherein $X^{221}$, $X^{222}$, $X^{223}$, $X^{224}$, $X^{225}$, $R^{222}$, $R^{226}$, $L^{222}$, $Y^{221}$, $Y^{222}$, $Q^{221}$, $Q^{222}$ and t have the same meaning as that defined herein above; preferably $X^3$ is a folate moiety having the structural Formula XII or XIIa, as taught herein, wherein $X^{221}$ is selected from N, or $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —O$R^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —N($R^{229}$)—, or —S—; $Y^{222}$ is selected from a single bond, —O—, —N($R^{229}$)—, —N($R^{229}$)—C(=NH)—N($R^{230}$)—, or —S—; $L^{222}$ is a single bond, $C_{6-10}$arylene, or —(C=O)—; t is an integer selected from 1, 2, 3, or 4; $R^{226}$ is hydrogen or $C_{1-6}$alkyl; $R^{229}$ is hydrogen or $C_{1-6}$alkyl; $R^{230}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIb, as taught herein, wherein $X^{221}$, $X^{222}$, $X^{223}$, $X^{224}$, $X^{225}$, $R^{222}$, $Y^{221}$, $Y^{222}$, $Q^{221}$, $Q^{222}$ and m have the same meaning as that defined herein above; preferably $X^3$ is a folate moiety having the structural Formula XII, XIIa, or XIIb, as taught herein, wherein $X^{221}$ is selected from N, $NR^{221}$ or O; $X^{222}$ is selected from N, $NR^{221}$ or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —O$R^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —N$R^{229}$— or —S—; $Y^{222}$ is selected from a single bond, —O—, —N$R^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XII, XIIa, or XIIb, as taught herein, wherein $X^{221}$ is selected from N or $NR^{221}$; $X^{222}$ is selected from N or $NR^{221}$; $X^{223}$ is selected from N or $NR^{223}$; $X^{224}$ is selected from N or $NR^{224}$; $X^{225}$ is $NR^{224}$, and $R^{221}$, $R^{222}$, $R^{223}$, $R^{224}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $X^{221}$ is selected from N or NH; $X^{222}$ is selected from N or NH; $X^{223}$ is selected from N or NH; $X^{224}$ is selected from N or NH; $X^{225}$ is NH, and $R^{222}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $R^{222}$ is selected from the group consisting of —NH$R^{225}$, hydrogen, $C_{1-12}$alkyl, —O$R^{225}$, preferably —NH$R^{125}$, or —O$R^{225}$, wherein $R^{225}$ is selected from hydrogen, halo, $C_{1-12}$alkyl, $C_{2-12}$alkenyl, $C_{2-12}$alkynyl, —OR', —COR', —COOR', or —NHR', wherein R' is H or $C_{1-8}$alkyl, and $X^{221}$, $X^{222}$, $X^{223}$, $X^{224}$, $X^{225}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XIIc, as taught herein, wherein $Y^{221}$, $Y^{222}$, $Q^{221}$, $Q^{222}$, and m have the same meaning as that defined herein above; preferably $X^3$ is a folate moiety having the structural Formula XII, XIIa, XIIb, or XIIc, as taught herein, wherein $Y^{221}$ is selected from a single bond, —O—, —N$R^{229}$— or —S—; $Y^{222}$ is selected from a single bond, —O—, —N$R^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; preferably $X^3$ is a folate moiety having the structural Formula XII, XIIa, XIIb, or XIIc, as taught herein, wherein $Q^{221}$ is hydrogen and $Q^{222}$ is a single bond connected to $X^1$; preferably $X^3$ is a folate moiety having the structural Formula XIId, as taught herein, wherein $Q^{222}$ is a single bond connected to $X^1$;

$R^{10}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{10}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCO—OR$^{12}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{10}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{10}$ is selected from hydrogen, or a group consisting of $C_{1-3}$alkyl, $C_{1-25}$alkylcarbonyl, and $C_{13-25}$alkenylcarbonyl; preferably $R^{10}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);)

$R^{100}$ is selected from hydrogen, or a group consisting of $C_{1-25}$alkyl, $C_{1-6}$alkylene-N(R$^{111}$)R$^{112}$, $C_{1-6}$alkylene-N$^+$(R$^{111}$)(R$^{112}$)R$^{113}$, $C_{1-25}$alkylcarbonyl, $C_{2-25}$alkenylcarbonyl, $C_{1-6}$alkylene-COOR$^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl;

$R^{101}$ is selected from hydrogen, or a group consisting of $C_{1-25}$alkyl, $C_{1-6}$alkylene-N(R$^{111}$)R$^{112}$, $C_{1-6}$alkylene-N$^+$(R$^{111}$)(R$^{112}$)R$^{113}$, $C_{1-25}$alkylcarbonyl, $C_{2-25}$alkenylcarbonyl, $C_{1-6}$alkylene-COOR$^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl;

$R^{102}$ is selected from hydrogen, or a group consisting of $C_{1-25}$alkyl, $C_{1-6}$alkylene-N(R$^{111}$)R$^{112}$, $C_{1-6}$alkylene-N$^+$(R$^{111}$)(R$^{112}$)R$^{113}$, $C_{1-25}$alkylcarbonyl, $C_{2-25}$alkenylcarbonyl, $C_{1-6}$alkylene-CO—OR$^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl;

$R^1$ is —OR$^{11}$ or —X$^2$—X$^1$—X$^3$, wherein $R^{11}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{11}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{11}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{11}$ is selected from hydrogen, or a group consisting of $C_{1-3}$alkyl, $C_{1-25}$alkylcarbonyl, and $C_{13-25}$alkenylcarbonyl; preferably $R^{11}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$X^2$, $X^1$, and $X^3$ have the same meaning as that defined herein;

$R^2$ is $-OR^{21}$ or $-X^2-X^1-X^3$, wherein $R^{21}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{21}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{21}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{21}$ is selected from hydrogen, or a group consisting of $C_{1-3}$alkyl, $C_{1-25}$alkylcarbonyl, and $C_{13-25}$alkenylcarbonyl; preferably $R^{21}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$X^2$, $X^1$, and $X^3$ have the same meaning as that defined herein;

wherein at least one of, such as one, two, or three of, $Y^1$, $R^1$, or $R^2$ is $-X^2-X^1-X^3$.

In certain preferred embodiments, the FR-targeting excipient may be a folate-polysaccharide conjugate comprising at least one unit of Formula XIb, XIg, or XIm, as taught herein, or any subgroup thereof, wherein $Y^1$ is $-X^2-X^1-X^3$, wherein $X^2$ is —O— or —N($R^{103}$)—, wherein $R^{103}$ is selected from hydrogen or $C_{1-6}$alkyl;

$X^1$ is a single bond or a linker comprising a poly($C_{1-6}$alkyleneoxide), $C_{1-6}$alkyleneoxide, amine, poly(imino$C_{1-6}$alkylene), amino acid, peptide, polypeptide, monosaccharide, or polysaccharide, preferably $X^1$ is a single bond or a linker of Formula X, as taught herein, wherein the left side of the linker of Formula X is attached to $X^2$ and the right side thereof is attached to $X^3$; wherein $A^1$ is selected from a group consisting of —CO—, —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-6}$alkylene optionally substituted with one or more substituents selected from a group consisting of hydroxyl, $C_{1-6}$alkyl and $C_{1-6}$alkoxy; $R^{16}$ and $R^{17}$ are each independently selected from hydrogen or $C_{1-6}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-4}$alkylene optionally substituted with one or more substituents selected from a group consisting of hydroxyl, $C_{1-4}$alkyl and $C_{1-4}$alkoxy; $R^{16}$ and $R^{17}$ are each independently selected from hydrogen or $C_{1-4}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-3}$alkylene optionally substituted with one or more substituents selected from a group consisting of hydroxyl and $C_{1-3}$alkyl; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$ is methylene, ethylene, n-propylene; $L^{15}$, $L^{16}$, $L^{17}$, and $L^{18}$ are each independently methylene or ethylene; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;

$L^1$ is a poly($C_{1-6}$alkyleneoxide); preferably $L^1$ is selected from a polyethylene oxide (PEO), a polypropylene oxide (PPO), or a block copolymer of PEO and PPO; preferably $L^1$ is a polyethylene oxide having the Formula —($CH_2$—$CH_2$—O)$_q$— or —(O—$CH_2$—$CH_2$)$_q$—, wherein q is an integer selected from 20 to 120; preferably $L^1$ is a polyethylene oxide having the Formula —($CH_2$—$CH_2$—O)$_q$— or —(O—$CH_2$—$CH_2$)$_q$—, wherein q is an integer selected from 40 to 110; preferably $L^1$ is a polyethylene oxide having the Formula —($CH_2$—$CH_2$—O)$_q$— or —(O—$CH_2$—$CH_2$)$_q$—, wherein q is an integer selected from 60 to 90;

$A^2$ is a single bond or is selected from a group consisting of —N($R^{18}$)—, —O—, -$L^{19}$-N($R^{19}$)—, and -$L^{20}$-O—, wherein the left side of each group is attached to $L^1$ and the right side thereof is attached to $X^3$, wherein $L^{19}$ and $L^{20}$ are each independently $C_{1-6}$alkylene being optionally substituted with one or more substituents selected from a group consisting of hydroxyl, $C_{1-6}$alkyl, and $C_{1-6}$alkoxy, $R^{18}$ and $R^{19}$ are each independently selected from hydrogen or $C_{1-6}$alkyl; preferably $A^2$ is a single bond or is selected from a group consisting of —N($R^{18}$)—, —O—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-4}$alkylene being optionally substituted with one or more substituents selected from a group consisting of hydroxyl, $C_{1-4}$alkyl, and $C_{1-4}$alkoxy, $R^{18}$ and $R^{19}$ are each independently selected from hydrogen or $C_{1-4}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-3}$alkylene being optionally substituted with one or more substituents selected from a group consisting of hydroxyl and $C_{1-3}$alkyl, $R^{18}$ and $R^{19}$ are each independently selected from hydrogen or $C_{1-3}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently methylene or ethylene; $R^{18}$ and $R^{19}$ are each independently selected from hydrogen or $C_{1-3}$alkyl; preferably $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;

$X^3$ is a folate moiety having the structural Formula XII, as taught herein, wherein $X^{221}$ is selected from N, $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; $L^{220}$ is selected from

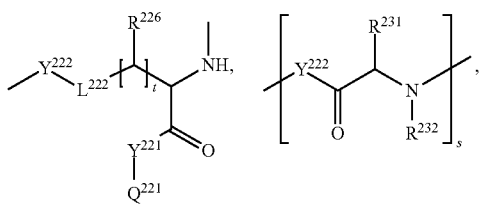

or a group consisting of $C_{1-6}$alkylene, $C_{1-6}$alkylenecarbonyl, —$C_{1-6}$alkylene-$N(R^{227})$—, $C_{2-6}$alkenylene, $C_{2-6}$alkynylene, $C_{3-6}$cycloalkylene, $C_{6-10}$arylene, —(C=O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—(CO)—$C_{3-6}$cycloalkylene, —$N(R^{228})$—, —$N(R^{228})$—(CO)—, and —(CO)—N($R^{228}$)—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —$N(R^{229})$—, or —S—; $Y^{222}$ is selected from a single bond, —O—, —$NR^{229}$—, —$N(R^{229})$—C(=NH)—$N(R^{230})$—, or —S—; $L^{222}$ is a single bond, $C_{6-10}$arylene, or —(C=O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIa, as taught herein, wherein $X^{221}$, $X^{222}$, $X^{223}$, $X^{224}$, $X^{225}$, $R^{222}$, $R^{226}$, $L^{222}$, $Y^{221}$, $Y^{222}$, $Q^{221}$, $Q^{222}$ and t have the same meaning as that defined herein above; preferably $X^3$ is a folate moiety having the structural Formula XII or XIIa, as taught herein, wherein $X^{221}$ is selected from N, or $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —$N(R^{229})$—, or —S—; $Y^{222}$ is selected from a single bond, —O—, —$N(R^{229})$—, —$N(R^{229})$—C(=NH)—$N(R^{230})$—, or —S—; $L^{222}$ is a single bond, $C_{6-10}$arylene, or —(C=O)—; t is an integer selected from 1, 2, 3, or 4; $R^{226}$ is hydrogen or $C_{1-6}$alkyl; $R^{229}$ is hydrogen or $C_{1-6}$alkyl; $R^{230}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XII, XIIa, or XIIb, as taught herein, wherein $X^{221}$, $X^{222}$, $X^{223}$, $X^{224}$, $X^{225}$, $R^{222}$, $Y^{221}$, $Y^{222}$, $Q^{221}$, $Q^{222}$ and m have the same meaning as that defined herein above; preferably $X^3$ is a folate moiety having the structural Formula XII, XIIa, or XIIb, as taught herein, wherein $X^{221}$ is selected from N, $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —$NR^{229}$— or —S—; $Y^{222}$ is selected from a single bond, —O—, —$NR^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XII, XIIa, or XIIb, as taught herein, wherein $X^{221}$ is selected from N or $NR^{221}$; $X^{222}$ is selected from N or $NR^{221}$; $X^{223}$ is selected from N or $NR^{223}$; $X^{224}$ is selected from N or $NR^{224}$; $X^{225}$ is $NR^{224}$, and $R^{221}$, $R^{222}$, $R^{223}$, $R^{224}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $X^{221}$ is selected from N or NH; $X^{222}$ is selected from N or NH; $X^{223}$ is selected from N or NH; $X^{224}$ is selected from N or NH; $X^{225}$ is NH, and $R^{222}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $R^{222}$ is selected from the group consisting of —$NHR^{225}$, hydrogen, $C_{1-12}$alkyl, —$OR^{225}$, preferably —$NHR^{125}$, or —$OR^{225}$, wherein $R^{225}$ is selected from hydrogen, halo, $C_{1-12}$alkyl, $C_{2-12}$alkenyl, $C_{2-12}$alkynyl, —OR', —COR', —COOR', or —NHR', wherein R' is H or $C_{1-8}$alkyl, and $X^{221}$, $X^{222}$, $X^{223}$, $X^{224}$, $X^{225}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XIIc, as taught herein, wherein $Y^{221}$, $Y^{222}$, $Q^{221}$, $Q^{222}$, and m have the same meaning as that defined herein above; preferably $X^3$ is a folate moiety having the structural Formula XII, XIIa, XIIb, or XIIc, $Y^{222}$ is as taught herein, wherein $Y^{221}$ is selected from a single bond, —O—, —NR$^{229}$— or —S—; selected from a single bond, —O—, —NR$^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; preferably $X^3$ is a folate moiety having the structural Formula XII, XIIa, XIIb, or XIIc, as taught herein, wherein $Q^{221}$ is hydrogen and $Q^{222}$ is a single bond connected to $X^1$; preferably $X^3$ is a folate moiety having the structural Formula XIId, as taught herein, wherein $Q^{222}$ is a single bond connected to $X^1$;

$R^1$ is —OR$^{11}$, wherein $R^{11}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$R^2$ is —OR$^{21}$, wherein $R^{21}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl.

In certain embodiments, the FR-targeting excipient may be a folate-polysaccharide conjugate comprising at least one unit of Formula XIb, XIg, or XIm, as taught herein, or any subgroup thereof, wherein $Y^1$ is —X$^2$—X$^1$—X$^3$, wherein $X^2$ is —N(R$^{103}$)—, wherein $R^{103}$ is selected from hydrogen or $C_{1-6}$alkyl;

$X^1$ is a single bond or a linker of Formula X, as taught herein, wherein the left side of the linker of Formula X is attached to $X^2$ and the right side thereof is attached to $X^3$; wherein $A^1$ is selected from a group consisting of —CO-L$^{14}$-O—, —CO-L$^{15}$-CO—O—, —CO-L$^{16}$-CO—N(R$^{16}$)-L$^{17}$-, and —CO-L$^{18}$-CO—N(R$^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-4}$alkylene optionally substituted with one or more substituents selected from a group consisting of hydroxyl, $C_{1-4}$alkyl and $C_{1-4}$alkoxy; $R^{16}$ and $R^{17}$ are each independently selected from hydrogen or $C_{1-4}$alkyl; preferably $A^1$ is selected from a group consisting of —CO-L$^{14}$-O—, —CO-L$^{15}$-CO—O—, —CO-L$^{16}$-CO—N(R$^{16}$)-L$^{17}$-, and —CO-L$^{18}$-CO—N(R$^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-3}$alkylene optionally substituted with one or more substituents selected from a group consisting of hydroxyl and $C_{1-3}$alkyl; $R^{16}$ and $R^{17}$ are each independently selected from hydrogen or $C_{1-3}$alkyl; preferably $A^1$ is selected from a group consisting of —CO-L$^{14}$-O—, —CO-L$^{15}$-CO—O—, —CO-L$^{16}$-CO—N(R$^{16}$)-L$^{17}$-, and —CO-L$^{18}$-CO—N(R$^{17}$)—, wherein the right side of each group is attached to $L^1$ and the left side thereof is attached to $X^2$, wherein $L^{14}$ is methylene, ethylene, n-propylene; $L^{15}$, $L^{16}$, $L^{17}$, and $L^{18}$ are each independently methylene or ethylene; $R^{16}$ and $R^{17}$ are each independently selected from hydrogen or $C_{1-3}$alkyl; preferably $A^1$ is selected from a group consisting of —CO-L$^{14}$-O—, —CO-L$^{15}$-CO—O—, —CO-L$^{16}$-CO—NH-L$^{17}$-, and —CO-L$^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;

$L^1$ is selected from a polyethylene oxide (PEO), a polypropylene oxide (PPO), or a block copolymer of PEO and PPO; preferably $L^1$ is a polyethylene oxide having the Formula —(CH$_2$—CH$_2$—O)$_q$— or —(O—CH$_2$—CH$_2$)$_q$—, wherein q is an integer selected from 20 to 120; preferably $L^1$ is a polyethylene oxide having the Formula —(CH$_2$—CH$_2$—O)$_q$— or —(O—CH$_2$—CH$_2$)$_q$—, wherein q is an integer selected from 40 to 110; preferably $L^1$ is a polyethylene oxide having the Formula —(CH$_2$—CH$_2$—O)$_q$— or —(O—CH$_2$—CH$_2$)$_q$—, wherein q is an integer selected from 60 to 90;

$A^2$ is a single bond or is selected from a group consisting of —N(R$^{18}$)—, —O—, -L$^{19}$-N(R$^{19}$)—, or -L$^{20}$O—, wherein the left side of each group is attached to $L^1$ and the right side thereof is attached to $X^3$, wherein $L^{19}$ and $L^{20}$ are each independently $C_{1-4}$alkylene being optionally substituted with one or more substituents selected from a group consisting of hydroxyl, $C_{1-4}$alkyl, and $C_{1-4}$alkoxy, $R^{18}$ and $R^{19}$ are each independently selected from hydrogen or $C_{1-4}$alkyl; preferably $A^2$ is a single bond or is selected from a group consisting of —N(R$^{18}$)—, -L$^{19}$-N(R$^{19}$)—, or -L$^{20}$O—, wherein the left side of each group is attached to $L^1$ and the right side thereof is attached to $X^3$, wherein $L^{19}$ and $L^{20}$ are each independently $C_{1-3}$alkylene being optionally substituted with one or more substituents selected from a group consisting of hydroxyl and $C_{1-3}$alkyl, $R^{18}$ and $R^{19}$ are each independently selected from hydrogen or $C_{1-3}$alkyl; preferably $A^2$ is a single bond or is selected from a group consisting of —N(R$^{18}$)—, -L$^{19}$-N(R$^{19}$)—, or -L$^{20}$O—, wherein the left side of each group is attached to $L^1$ and the right side thereof is attached to $X^3$, wherein $L^{19}$ and $L^{20}$ are each independently methylene or ethylene; $R^{18}$ and $R^{19}$ are each independently selected from hydrogen or $C_{1-3}$alkyl; preferably $A^2$ is a single bond or is selected from a group consisting of —N(H)—, -L$^{19}$-N(H)—, or -L$^{20}$O—, wherein the left side of each group is attached to $L^1$ and the right side thereof is attached to $X^3$, wherein $L^{19}$ and $L^{20}$ are each independently ethylene;

$X^3$ is a folate moiety having the structural Formula XIIa, as taught herein, wherein $X^{221}$, $X^{222}$, $X^{223}$, $X^{224}$, $X^{225}$, $R^{222}$, $R^{226}$, $L^{222}$, $Y^{221}$, $Y^{222}$, $Q^{221}$, $Q^{222}$ and t have the same meaning as that defined herein above; preferably $X^3$ is a folate moiety having the structural Formula XII or XIIa, as taught herein, wherein $X^{221}$ is selected from N, or $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —OR$^{225}$, —CO—R$^{125}$, —CO—O—R$^{225}$, and —CO—N(H)R$^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —N(R$^{229}$)—, or —S—; $Y^{222}$ is selected from a single bond, —O—, —N(R$^{229}$)—, —N(R$^{229}$)—C(=NH)—N(R$^{230}$)—, or —S—; $L^{222}$ is a single bond, $C_{6-10}$arylene, or —(C=O)—; t is an integer selected from 1, 2, 3, or 4; $R^{226}$ is hydrogen or $C_{1-6}$alkyl; $R^{229}$ is hydrogen or $C_{1-6}$alkyl; $R^{230}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIb, as taught herein, wherein $X^{221}$, $X^{222}$, $X^{223}$, $X^{224}$, $X^{225}$, $R^{222}$, $Y^{221}$, $Y^{222}$, $Q^{221}$, $Q^{222}$ and m have the same meaning as that defined herein above; preferably $X^3$ is a folate moiety having the structural Formula XII, XIIa, or XIIb, as taught herein, wherein $X^{221}$ is selected from N, $NR^{221}$, or O; $X^{222}$ is selected from N, $NR^{221}$ or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)R$^{225}$, hydrogen, halogen, $C_{1-12}$alkyl, $C_{2-12}$alkenyl, $C_{2-12}$alkynyl, —OR$^{225}$, —CO—R$^{125}$, —CO—O—R$^{225}$, and —CO—N(H)R$^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —NR$^{229}$— or —S—; $Y^{222}$ is selected from a single bond, —O—, —NR$^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XII, XIIa, or XIIb, as taught herein, wherein $X^{221}$ is selected from N or $NR^{221}$; $X^{222}$ is selected from N or $NR^{221}$; $X^{223}$ is selected from N or $NR^{223}$; $X^{224}$ is selected from N or $NR^{224}$; $X^{225}$ is $NR^{224}$, and $R^{221}$, $R^{222}$, $R^{223}$, $R^{224}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $X^{221}$ is selected from N or NH; $X^{222}$ is selected from N or NH; $X^{223}$ is selected from N or NH; $X^{224}$ is selected from N or NH; $X^{225}$ is NH, and $R^{222}$, $R^{226}$, $L^{220}$, $L^{222}$, $Y^{221}$, $Y^{222}$, $Q^{221}$, $Q^{222}$ selected from N or NH; $X^{224}$ and t have the same meaning as that defined herein above; preferably $X^3$ is a folate moiety having the structural Formula XII, XIIa, or XIIb, as taught herein, wherein $R^{222}$ is selected from the group consisting of —NHR$^{225}$, hydrogen, $C_{1-12}$alkyl, —OR$^{225}$, preferably —NHR$^{125}$, or —OR$^{225}$, wherein $R^{225}$ is selected from hydrogen, halo, $C_{1-12}$alkyl, $C_{2-12}$alkenyl, $C_{2-12}$alkynyl, —OR', —COR', —COOR', or —NHR', wherein R' is H or $C_{1-8}$alkyl, and $X^{221}$, $X^{222}$, $X^{223}$, $X^{224}$, $X^{225}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XIIc, as taught herein, wherein $Y^{221}$, $Y^{222}$, $Q^{221}$, $Q^{222}$, and m have the same meaning as that defined herein above; preferably $X^3$ is a folate moiety having the structural Formula XII, XIIa, XIIb, or XIIc, as taught herein, wherein $Y^{221}$ is selected from a single bond, —O—, —NR$^{229}$ or —S—; $Y^{222}$ is selected from a single bond, —O—, —NR$^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; preferably $X^3$ is a folate moiety having the structural Formula XII, XIIa, XIIb, or XIIc, as taught herein, wherein $Q^{221}$ is hydrogen and $Q^{222}$ is a single bond connected to $X^1$; preferably $X^3$ is a folate moiety having the structural Formula XIId, as taught herein, wherein $Q^{222}$ is a single bond connected to $X^1$;

$R^1$ is —OR$^{11}$, wherein $R^{11}$ is selected from hydrogen, a mono-, oligo-, or polyglycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxyl$C_{1-4}$alkylenecarbonyl, hydroxy$C_{1-4}$alkyl, carboxyl$C_{640}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl;

$R^2$ is —OR$^{21}$, wherein $R^{21}$ is selected from hydrogen, a mono-, oligo-, or polyglycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxyl$C_{1-4}$alkylenecarbonyl, hydroxy$C_{1-4}$alkyl, carboxyl$C_{640}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl.

In certain embodiments, the FR-targeting excipient may be a folate-polysaccharide conjugate comprising at least one unit of Formula XIb, XIg, or XIm, as taught herein, or any subgroup thereof, wherein $Y^1$ is —$X^2$—$X^1$—$X^3$, wherein $X^2$ is —NH—;

$X^1$ is a linker of Formula X, as taught herein, wherein the left side of the linker of Formula X is attached to $X^2$ and the right side thereof is attached to $X^3$; wherein $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-3}$alkylene optionally substituted with one or more substituents selected from a group consisting of hydroxyl and $C_{1-3}$alkyl; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$ is methylene, ethylene, n-propylene; $L^{15}$, $L^{16}$, $L^{17}$, and $L^{18}$ are each independently methylene or ethylene; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;

$L^1$ is a polyethylene oxide having the Formula —(CH$_2$—CH$_2$—O)$_q$— or —(O—CH$_2$—CH$_2$)$_q$—, wherein q is an integer selected from 20 to 120; preferably $L^1$ is a polyethylene oxide having the Formula —(CH$_2$—CH$_2$—O)$_q$— or —(O—CH$_2$—CH$_2$)$_q$—, wherein q is an integer selected from 40 to 110; preferably $L^1$ is a polyethylene oxide having the Formula —(CH$_2$—CH$_2$—O)$_q$— or —(O—CH$_2$—CH$_2$)$_q$—, wherein q is an integer selected from 60 to 90;

$A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-3}$alkylene being optionally substituted with one or more substituents selected from a group consisting of hydroxyl and $C_{1-3}$alkyl, $R^{18}$ and $R^{19}$ are each independently selected from hydrogen or $C_{1-3}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently methylene or ethylene; $R^{18}$ and $R^{19}$ are each independently selected from hydrogen or $C_{1-3}$alkyl; preferably $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;

$X^3$ is a folate moiety having the structural Formula XIIb, as taught herein, wherein $X^{221}$, $X^{222}$, $X^{223}$, $X^{224}$, $X^{225}$, $R^{222}$, $Y^{221}$, $Y^{222}$, $Q^{221}$, $Q^{222}$ and m have the same meaning as that defined herein above; preferably $X^3$ is a folate moiety having the structural Formula XII, XIIa, or XIIb, as taught herein, wherein $X^{221}$ is selected from N, NR$^{221}$; or O; $X^{222}$ is selected from N, NR$^{221}$, or O; $X^{223}$ is selected from N, NR$^{223}$, or O; $X^{224}$ is selected from N, NR$^{224}$ or O; $X^{225}$ is selected from NR$^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)R$^{225}$, hydrogen, halogen, $C_{1-12}$alkyl, $C_{2-12}$alkenyl, $C_{2-12}$alkynyl, —OR$^{225}$, —CO—R$^{125}$, —CO—O—R$^{225}$, and —CO—N(H)R$^{225}$, wherein R$^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —NR$^{229}$— or —S—; $Y^{222}$ is selected from a single bond, —O—, —NR$^{229}$—, or —S—; m is an integer selected from 1, 2, or 3; R$^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XII, XIIa, or XIIb, as taught herein, wherein $X^{221}$ is selected from N or NR$^{221}$; $X^{222}$ is selected from N or NR$^{221}$; $X^{223}$ is selected from N or NR$^{223}$; $X^{224}$ is selected from N or NR$^{224}$; $X^{225}$ is NR$^{224}$, and R$^{221}$, R$^{222}$, R$^{223}$, R$^{224}$, R$^{226}$, L$^{220}$, L$^{222}$, Y$^{221}$, Y$^{222}$, Q$^{221}$, Q$^{222}$ and t have the same meaning as that defined herein above; preferably $X^3$ is a folate moiety having the structural Formula XII, XIIa, or XIIb, as taught herein, wherein $X^{221}$ is selected from N or NH; $X^{222}$ is selected from N or NH; $X^{223}$ is selected from N or NH; $X^{224}$ is selected from N or NH; $X^{225}$ is NH, and R$^{222}$, R$^{226}$, L$^{220}$, L$^{222}$, Y$^{221}$, Y$^{222}$, Q$^{221}$, Q$^{222}$ and t have the same meaning as that defined herein above; preferably $X^3$ is a folate moiety having the structural Formula XII, XIIa, or XIIb, as taught herein, wherein R$^{222}$ is selected from the group consisting of —NHR$^{225}$, hydrogen, $C_{1-12}$alkyl, —OR$^{225}$, preferably —NHR$^{125}$, or —OR$^{225}$, wherein R$^{225}$ is selected from hydrogen, halo, $C_{1-12}$alkyl, $C_{2-12}$alkenyl, $C_{2-12}$alkynyl, —OR', —COR', —COOR', or —NHR', wherein R' is H or $C_{1-8}$alkyl, and $X^{221}$, $X^{222}$, $X^{223}$, $X^{224}$, $X^{225}$, R$^{226}$, L$^{220}$, L$^{222}$, Y$^{221}$, Y$^{222}$, Q$^{221}$, Q$^{222}$ and t have the same meaning as that defined herein above; preferably $X^3$ is a folate moiety having the structural Formula XIIc, as taught herein, wherein Y$^{221}$, Y$^{222}$, Q$^{221}$, Q$^{222}$, and m have the same meaning as that defined herein above; preferably $X^3$ is a folate moiety having the structural Formula XII, XIIa, XIIb, or XIIc, as taught herein, wherein Y$^{221}$ is selected from a single bond, —O—, —NR$^{229}$— or —S—; Y$^{222}$ is selected from a single bond, —O—, —NR$^{229}$—, or —S—; m is an integer selected from 1, 2, or 3; R$^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; preferably $X^3$ is a folate moiety having the structural Formula XII, XIIa, XIIb, or XIIc, as taught herein, wherein $Q^{221}$ is hydrogen and $Q^{222}$ is a single bond connected to $X^1$; preferably $X^3$ is a folate moiety having the structural Formula XIId, as taught herein, wherein $Q^{222}$ is a single bond connected to $X^1$;

$R^1$ is —$OR^{11}$, wherein $R^{11}$ is selected from hydrogen, a mono-, oligo-, or polyglycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy;

$R^2$ is —$OR^{21}$, wherein $R^{21}$ is selected from hydrogen, a mono-, oligo-, or polyglycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy.

In certain embodiments, the FR-targeting excipient may be a folate-polysaccharide conjugate comprising at least one unit of Formula XIb, XIg, or XIm, as taught herein, or any subgroup thereof, wherein $Y^1$ is —$X^2$—$X^1$—$X^3$, wherein $X^2$ is —NH—;

$X^1$ is a linker of Formula X, as taught herein, wherein the left side of the linker of Formula X is attached to $X^2$ and the right side thereof is attached to $X^3$; wherein $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$ is methylene, ethylene, n-propylene; $L^{15}$, $L^{16}$, $L^{17}$, and $L^{18}$ are each independently methylene or ethylene; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;

$L^1$ is a polyethylene oxide having the Formula —$(CH_2$—$CH_2$—$O)_q$— or —$(O$—$CH_2$—$CH_2)_q$—, wherein q is an integer selected from 40 to 110; preferably $L^1$ is a polyethylene oxide having the Formula —$(CH_2$—$CH_2$—$O)_q$— or —$(O$—$CH_2$—$CH_2)_q$—, wherein q is an integer selected from 60 to 90;

$A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently methylene or ethylene; $R^{18}$ and $R^{19}$ are each independently selected from hydrogen or $C_{1-3}$alkyl; preferably $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;

$X^3$ is a folate moiety having the structural Formula XIIc, as taught herein, wherein $Y^{221}$, $Y^{222}$, $Q^{221}$, $Q^{222}$, and m have the same meaning as that defined herein above; preferably $X^3$ is a folate moiety having the structural Formula XII, XIIa, XIIb, or XIIc, as taught herein, wherein $Y^{221}$ is selected from a single bond, —O—, —$NR^{229}$— or —S—; $Y^{222}$ is selected from a single bond, —O—, —$NR^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; preferably $X^3$ is a folate moiety having the structural Formula XII, XIIa, XIIb, or XIIc, as taught herein, wherein $Q^{221}$ is hydrogen and $Q^{222}$ is a single bond connected to $X^1$; preferably $X^3$ is a folate moiety having the structural Formula XIId, as taught herein, wherein $Q^{222}$ is a single bond connected to $X^1$;

$R^1$ is —$OR^{11}$, wherein $R^{11}$ is selected from hydrogen, or a group consisting of $C_{1-3}$alkyl, $C_{1-25}$alkylcarbonyl, and $C_{13-25}$alkenylcarbonyl;

$R^2$ is —$OR^{21}$, wherein $R^{21}$ is selected from hydrogen, or a group consisting of $C_{1-3}$alkyl, $C_{1-25}$alkylcarbonyl, and $C_{13-25}$alkenylcarbonyl.

In certain embodiments, the FR-targeting excipient may be a folate-polysaccharide conjugate comprising at least one unit of Formula XIb, XIg, or XIm, as taught herein, or any subgroup thereof, wherein $Y^1$ is —$X^2$—$X^1$—$X^3$, wherein $X^2$ is —NH—;

$X^1$ is a linker of Formula X, as taught herein, wherein the left side of the linker of Formula X is attached to $X^2$ and the right side thereof is attached to $X^3$; wherein $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;

$L^1$ is a polyethylene oxide having the Formula —$(CH_2$—$CH_2$—$O)_q$— or —$(O$—$CH_2$—$CH_2)_q$—, wherein q is an integer selected from 60 to 90;

$A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;

$X^3$ is a folate moiety having the structural Formula XIId, as taught herein, wherein $Q^{222}$ is a single bond connected to $X^1$;

$R^1$ is —$OR^{11}$, wherein $R^{11}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^2$ is $-OR^{21}$, wherein $R^{21}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety).

In certain embodiments, the FR-targeting excipient may be a folate-polysaccharide conjugate comprising at least one unit of Formula XIc, XIh, XIj, XIk, XIn, XIp, or XIq, as taught herein, or any subgroup thereof, wherein $Y^2$ is $-X^2-X^1-X^3$, or a group selected from $-OR^{20}$, $-N(R^{200})R^{201}$, or $-N^+(R^{20})(R^{201})R^{202}$, preferably $Y^2$ is $-X^2-X^1-X^3$, or $-OR^{20}$, wherein $X^2$ is $-O-$ or $-N(R^{103})-$, wherein $R^{103}$ is selected from hydrogen or $C_{1-6}$alkyl, preferably $X^2$ is $-O-$;

$X^1$ is a single bond or a linker comprising a polyether, ether, amine, polyamine, amino acid, peptide, a polypeptide, a carbohydrate, or a combination of two or more thereof, preferably $X^1$ is a single bond or a linker comprising a poly($C_{1-6}$alkyleneoxide), $C_{1-6}$alkyleneoxide, amine, poly(imino$C_{1-6}$alkylene), amino acid, peptide, polypeptide, monosaccharide, or polysaccharide, preferably $X^1$ is a single bond or a linker of Formula X, as taught herein, wherein the left side of the linker of Formula X is attached to $X^2$ and the right side thereof is attached to $X^3$; wherein $A^1$ is selected from a group consisting of $-CO-$, $-CO-L^{14}-O-$, $-CO-L^{15}-CO-O-$, $-CO-L^{16}-CO-N(R^{16})-L^{17}-$, and $-CO-L^{18}-CO-N(R^{17})-$, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-6}$alkylene optionally substituted with one or more substituents selected from a group consisting of hydroxyl, $C_{1-6}$alkyl and $C_{1-6}$alkoxy; $R^{16}$ and $R^{17}$ are each independently selected from hydrogen or $C_{1-6}$alkyl; preferably $A^1$ is selected from a group consisting of $-CO-L^{14}-O-$, $-CO-L^{15}-CO-O-$, $-CO-L^{16}-CO-N(R^{16})-L^{17}-$, and $-CO-L^{18}-CO-N(R^{17})-$, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-4}$alkylene optionally substituted with one or more substituents selected from a group consisting of hydroxyl, $C_{1-4}$alkyl and $C_{1-4}$alkoxy; $R^{16}$ and $R^{17}$ are each independently selected from hydrogen or $C_{1-4}$alkyl; preferably $A^1$ is selected from a group consisting of $-CO-L^{14}-O-$, $-CO-L^{15}-CO-O-$, $-CO-L^{16}-CO-N(R^{16})-L^{17}-$, and $-CO-L^{18}-CO-N(R^{17})-$, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-3}$alkylene optionally substituted with one or more substituents selected from a group consisting of hydroxyl and $C_{1-3}$alkyl; $R^{16}$ and $R^{17}$ are each independently selected from hydrogen or $C_{1-3}$alkyl; preferably $A^1$ is selected from a group consisting of $-CO-L^{14}-O-$, $-CO-L^{15}-CO-O-$, $-CO-L^{16}-CO-N(R^{16})-L^{17}-$, and $-CO-L^{18}-CO-N(R^{17})-$, wherein the right side of each group is attached to $L^1$ and the left side thereof is attached to $X^2$, wherein $L^{14}$ is methylene, ethylene, n-propylene; $L^{15}$, $L^{16}$, $L^{17}$, and $L^{18}$ are each independently methylene or ethylene; $R^{16}$ and $R^{17}$ are each independently selected from hydrogen or $C_{1-3}$alkyl; preferably $A^1$ is selected from a group consisting of $-CO-L^{14}-O-$, $-CO-L^{15}-CO-O-$, $-CO-L^{16}-CO-NH-L^{17}-$, and $-CO-L^{18}-CO-NH-$, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;

$L^1$ is a poly($C_{1-6}$alkyleneoxide); preferably $L^1$ is selected from a polyethylene oxide (PEO), a polypropylene oxide (PPO), or a block copolymer of PEO and PPO; preferably $L^1$ is a polyethylene oxide having the Formula —($CH_2$—$CH_2$—O)$_q$— or —(O—$CH_2$—$CH_2$)$_q$—, wherein q is an integer selected from 20 to 120; preferably $L^1$ is a polyethylene oxide having the Formula —($CH_2$—$CH_2$—O)$_q$— or —(O—$CH_2$—$CH_2$)$_q$—, wherein q is an integer selected from 40 to 110; preferably $L^1$ is a polyethylene oxide having the Formula —($CH_2$—$CH_2$—O)$_q$— or —(O—$CH_2$—$CH_2$)$_q$—, wherein q is an integer selected from 60 to 90;

$A^2$ is a single bond or is selected from a group consisting of —N($R^{18}$)—, —O—, -$L^{19}$-N($R^{19}$)—, and -$L^{20}$-O—, wherein the left side of each group is attached to $L^1$ and the right side thereof is attached to $X^3$, wherein $L^{19}$ and $L^{20}$ are each independently $C_{1-6}$alkylene being optionally substituted with one or more substituents selected from a group consisting of hydroxyl, $C_{1-6}$alkyl, and $C_{1-6}$alkoxy, $R^{18}$ and $R^{19}$ are each independently selected from hydrogen or $C_{1-6}$alkyl; preferably $A^2$ is a single bond or is selected from a group consisting of —N($R^{18}$)—, —O—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-4}$alkylene being optionally substituted with one or more substituents selected from a group consisting of hydroxyl, $C_{1-4}$alkyl, and $C_{1-4}$alkoxy, $R^{18}$ and $R^{19}$ are each independently selected from hydrogen or $C_{1-4}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-3}$alkylene being optionally substituted with one or more substituents selected from a group consisting of hydroxyl and $C_{1-3}$alkyl, $R^{18}$ and $R^{19}$ are each independently selected from hydrogen or $C_{1-3}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently methylene or ethylene; $R^{18}$ and $R^{19}$ are each independently selected from hydrogen or $C_{1-3}$alkyl; preferably $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;

$X^3$ is a folate moiety; preferably $X^3$ is a folate moiety having the structural Formula XII, as taught herein, wherein $X^{221}$ is selected from N, $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —OR$^{225}$, —CO—$R^{125}$, —CO—O—$R^{225}$, and —CO—N(H)—

$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; $L^{220}$ is selected from

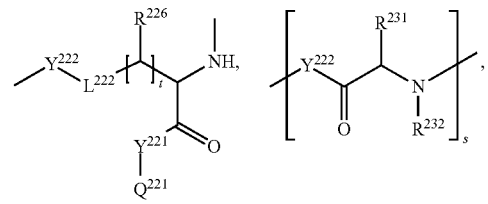

or a group consisting of $C_{1-6}$alkylene, $C_{1-6}$alkylenecarbonyl, —$C_{1-6}$alkylene-N($R^{227}$)—, $C_{2-6}$alkenylene, $C_{2-6}$alkynylene, $C_{3-6}$cycloalkylene, $C_{6-10}$arylene, —(C=O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—(CO)—$C_{3-6}$cycloalkylene, —N($R^{228}$)—, —N($R^{228}$)—(CO)—, and —(CO)—N($R^{228}$)—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —N($R^{229}$)—, or —S—; $Y^{222}$ is selected from a single bond, —O—, —$NR^{229}$—, —N($R^{229}$)—(=NH)—N($R^{230}$)—, or —S—; $L^{222}$ is a single bond, $C_{6-10}$arylene, or —(C=O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIa, as taught herein, wherein $X^{221}$, $X^{222}$, $X^{223}$, $X^{224}$, $X^{225}$, $R^{222}$, $R^{226}$, $L^{222}$, $Y^{221}$, $Y^{222}$, $Q^{221}$, $Q^{222}$ and t have the same meaning as that defined herein above; preferably $X^3$ is a folate moiety having the structural Formula XII or XIIa, as taught herein, wherein $X^{221}$ is selected from N, or $NR^{221}$; or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —N($R^{229}$)—, or —S—; $Y^{222}$ is selected from a single bond, —O—, —N($R^{229}$)—, —N($R^{229}$)—C(=NH)—N($R^{230}$)—, or —S—; $L^{222}$ is a single bond, $C_{6-10}$arylene, or —(C=O)—; t is an integer selected from 1, 2, 3, or 4; $R^{226}$ is hydrogen or $C_{1-6}$alkyl; $R^{229}$ is hydrogen or $C_{1-6}$alkyl; $R^{230}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIb, as taught herein, wherein $X^{221}$, $X^{222}$, $X^{223}$, $X^{224}$, $X^{225}$, $R^{222}$, $Y^{221}$, $Y^{222}$, $Q^{221}$, $Q^{222}$ and m have the same meaning as that defined herein above; preferably $X^3$ is a folate moiety having the structural Formula XII, XIIa, or XIIb, as taught herein, wherein $X^{221}$ is selected from N, $NR^{221}$, or O; $X^{222}$ is selected from N, $NR^{221}$ or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —$NR^{229}$— or —S—; $Y^{222}$ is selected from a single bond, —O—, —$NR^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XII, XIIa, or XIIb, as taught herein, wherein $X^{221}$ is selected from N or $NR^{221}$; $X^{222}$ is selected from N or $NR^{221}$; $X^{223}$ is selected from N or $NR^{223}$; $X^{224}$ is selected from N or $NR^{224}$; $X^{225}$ is $NR^{224}$, and $R^{221}$, $R^{222}$, $R^{223}$, $R^{224}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $X^{221}$ is selected from N or NH; $X^{222}$ is selected from N or NH; $X^{223}$ is selected from N or NH; $X^{224}$ is selected from N or NH; $X^{225}$ is NH, and $R^{222}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $R^{222}$ is selected from the group consisting of —$NHR^{225}$, hydrogen, $C_{1-12}$alkyl, —$OR^{225}$, preferably —$NHR^{125}$, or —$OR^{225}$, wherein $R^{225}$ is selected from hydrogen, halo, $C_{1-12}$alkyl, $C_{2-12}$alkenyl, $C_{2-12}$alkynyl, —OR', —COR', —COOR', or —NHR', wherein R' is H or $C_{1-8}$alkyl, and $X^{221}$, $X^{222}$, $X^{223}$, $X^{224}$, $X^{225}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XIIc, as taught herein, wherein $Y^{221}$, $Y^{222}$, $Q^{221}$, $Q^{222}$, and m have the same meaning as that defined herein above; preferably $X^3$ is a folate moiety having the structural Formula XII, XIIa, XIIb, or XIIc, as taught herein, wherein $Y^{221}$ is selected from a single bond, —O—, —$NR^{229}$—, or —S—; $Y^{222}$ is selected from a single bond, —O—, —$NR^{229}$ or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; preferably $X^3$ is a folate moiety having the structural Formula XII, XIIa, XIIb, or XIIc, as taught herein, wherein $Q^{221}$ is hydrogen and $Q^{222}$ is a single bond connected to $X^1$; preferably $X^3$ is a folate moiety having the structural Formula XIId, as taught herein, wherein $Q^{222}$ is a single bond connected to $X^1$;

$R^{20}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkyleneCOO$R^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{20}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCOO$R^{12}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{20}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxylC$_{1-3}$alkylenecarbonyl, hydroxyC$_{1-3}$alkyl, C$_{2-3}$alkenyl, and C$_{2-3}$alkynyl, each group being optionally substituted with one or more substituents each independently selected from hydroxyl, halogen, C$_{1-3}$alkyl, or C$_{1-3}$alkoxy; preferably R$^{20}$ is selected from hydrogen, a mono-, oligo-, or poly-glycosyl moiety, or a group consisting of C$_{1-3}$alkyl, C$_{1-25}$alkylcarbonyl, and C$_{13-25}$alkenylcarbonyl; preferably R$^{20}$ is selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);)

R$^{200}$ is selected from hydrogen, or a group consisting of C$_{1-25}$alkyl, C$_{1-6}$alkylene-N(R$^{211}$)R$^{212}$, C$_{1-6}$alkylene-N$^+$(R$^{211}$)(R$^{212}$)R$^{213}$, C$_{1-25}$alkylcarbonyl, C$_{2-25}$alkenylcarbonyl, C$_{1-6}$alkylene-COOR$^{214}$, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, carboxyl, or C$_{1-6}$alkoxy, wherein R$^{211}$ is selected from hydrogen or C$_{1-6}$alkyl, R$^{212}$ is selected from hydrogen or C$_{1-6}$alkyl, R$^{213}$ is selected from hydrogen or C$_{1-6}$alkyl, and R$^{214}$ is selected from hydrogen or C$_{1-6}$alkyl;

R$^{201}$ is selected from hydrogen, or a group consisting of C$_{1-25}$alkyl, C$_{1-6}$alkylene-N(R$^{211}$)R$^{212}$, C$_{1-6}$alkylene-N$^+$(R$^{211}$)(R$^{212}$)R$^{213}$, C$_{1-25}$alkylcarbonyl, C$_{2-25}$alkenylcarbonyl, C$_{1-6}$alkylene-CO—R$^{214}$, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, carboxyl, or C$_{1-6}$alkoxy, wherein R$^{211}$ is selected from hydrogen or C$_{1-6}$alkyl, R$^{212}$ is selected from hydrogen or C$_{1-6}$alkyl, R$^{213}$ is selected from hydrogen or C$_{1-6}$alkyl, and R$^{214}$ is selected from hydrogen or C$_{1-6}$alkyl;

R$^{202}$ is selected from hydrogen, or a group consisting of C$_{1-25}$alkyl, C$_{1-6}$alkylene-N(R$^{211}$)R$^{212}$, C$_{1-6}$alkylene-N$^+$(R$^{211}$)(R$^{212}$)R$^{213}$, C$_{1-25}$alkylcarbonyl, C$_{2-25}$alkenylcarbonyl, C$_{1-6}$alkylene-CO—R$^{214}$, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, carboxyl, or C$_{1-6}$alkoxy, wherein R$^{211}$ is selected from hydrogen or C$_{1-6}$alkyl, R$^{212}$ is selected from hydrogen or C$_{1-6}$alkyl, R$^{213}$ is selected from hydrogen or C$_{1-6}$alkyl, and R$^{214}$ is selected from hydrogen or C$_{1-6}$alkyl;

R$^3$ is —OR$^{31}$ or —X$^2$—X$^1$—X$^3$, wherein
R$^{31}$ is selected from hydrogen, a mono-, oligo-, or poly-glycosyl moiety, or a group consisting of C$_{1-25}$alkyl, C$_{1-25}$alkylcarbonyl, C$_{2-25}$alkenylcarbonyl, C$_{1-6}$alkyleneCOOR$^{12}$, carboxylC$_{1-6}$alkylenecarbonyl, hydroxyC$_{1-6}$alkyl, carboxylC$_{6-12}$arylenecarbonyl, C$_{2-6}$alkenyl, C$_{2-6}$alkynyl, C$_{3-6}$cycloalkyl, and C$_{6-10}$aryl, each group being optionally substituted with one or more substituents each independently selected from hydroxyl, halogen, C$_{1-6}$alkyl, or C$_{1-6}$alkoxy, wherein R$^{12}$ is selected from hydrogen or C$_{1-6}$alkyl; preferably R$^{31}$ is selected from hydrogen, a mono-, oligo-, or poly-glycosyl moiety, or a group consisting of C$_{1-4}$alkyl, C$_{1-25}$alkylcarbonyl, C$_{3-25}$alkenylcarbonyl, C$_{1-4}$alkyleneCOOR$^{12}$, carboxylC$_{1-4}$alkylenecarbonyl, hydroxyC$_{1-4}$alkyl, carboxylC$_{6-10}$arylenecarbonyl, C$_{2-4}$alkenyl, and C$_{2-4}$alkynyl, each group being optionally substituted with one or more substituents each independently selected from hydroxyl, halogen, C$_{1-4}$alkyl, or C$_{1-4}$alkoxy, wherein R$^{12}$ is selected from hydrogen or C$_{1-4}$alkyl; preferably R$^{31}$ is selected from hydrogen, a mono-, oligo-, or poly-glycosyl moiety, or a group consisting of C$_{1-4}$alkyl, C$_{1-25}$alkylcarbonyl, C$_{5-25}$alkenylcarbonyl, C$_{1-3}$alkyleneCOOH, carboxylC$_{1-3}$alkylenecarbonyl, hydroxyC$_{1-3}$alkyl, C$_{2-3}$alkenyl, and C$_{2-3}$alkynyl, each group being optionally substituted with one or more substituents each independently selected from hydroxyl, halogen, C$_{1-3}$alkyl, or C$_{1-3}$alkoxy; preferably R$^{31}$ is selected from hydrogen, a mono-, oligo-, or poly-glycosyl moiety, or a group consisting of C$_{1-3}$alkyl, C$_{1-25}$alkylcarbonyl, and C$_{13-25}$alkenylcarbonyl; preferably R$^{31}$ is selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$X^2$, $X^1$, and $X^3$ have the same meaning as that defined herein;

$R^4$ is —$OR^{41}$ or —$X^2$—$X^1$—$X^3$, wherein $R^{41}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{41}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{41}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{41}$ is selected from hydrogen, a mono-, oligo-, or poly-glycosyl moiety, or a group consisting of $C_{1-3}$alkyl, $C_{1-25}$alkylcarbonyl, and $C_{13-25}$alkenylcarbonyl; preferably $R^{41}$ is selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$X^2$, $X^1$, and $X^3$ have the same meaning as that defined herein;

wherein at least one of, such as one, two, or three of, $Y^2$, $R^3$, or $R^4$ is —$X^2$—$X^1$—$X^3$.

In certain embodiments, the FR-targeting excipient may be a folate-polysaccharide conjugate comprising at least one unit of Formula XIc, XIh, XIj, XIk, XIn, XIp, or XIq, as taught herein, or any subgroup thereof, wherein $Y^2$ is —$X^2$—$X^1$—$X^3$, or —$OR^{20}$, wherein $X^2$ is —O— or —N($R^{103}$)—, wherein $R^{103}$ is selected from hydrogen or $C_{1-6}$alkyl;

$X^1$ is a single bond or a linker comprising a poly($C_{1-6}$ alkyleneoxide), $C_{1-6}$alkyleneoxide, amine, poly(imino$C_{1-6}$alkylene), amino acid, peptide, polypeptide, monosaccharide, or polysaccharide, preferably $X^1$ is a single bond or a linker of Formula X, as taught herein, wherein the left side of the linker of Formula X is attached to $X^2$ and the right side thereof is attached to $X^3$; wherein $A^1$ is selected from a group consisting of —CO—, —CO-L$^{14}$-O—, —CO-L$^{15}$-CO—O—, —CO-L$^{16}$-CO—N(R$^{16}$)-L$^{17}$-, and —CO-L$^{18}$-CO—N(R$^{17}$)—, wherein the right side of each group is attached to L$^1$ and the left side thereof is attached to $X^2$, wherein L$^{14}$, L$^{15}$, L$^{16}$, L$^{17}$, and L$^{18}$ are each independently $C_{1-6}$alkylene optionally substituted with one or more substituents selected from a group consisting of hydroxyl, $C_{1-6}$alkyl and $C_{1-6}$alkoxy; R$^{16}$ and R$^{17}$ are each independently selected from hydrogen or $C_{1-6}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-4}$alkylene optionally substituted with one or more substituents selected from a group consisting of hydroxyl, $C_{1-4}$alkyl and $C_{1-4}$alkoxy; $R^{16}$ and $R^{17}$ are each independently selected from hydrogen or $C_{1-4}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-3}$alkylene optionally substituted with one or more substituents selected from a group consisting of hydroxyl and $C_{1-3}$alkyl; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$ is methylene, ethylene, n-propylene; $L^{15}$, $L^{16}$, $L^{17}$, and $L^{18}$ are each independently methylene or ethylene; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;

$L^1$ is a poly($C_{1-6}$alkyleneoxide); preferably $L^1$ is selected from a polyethylene oxide (PEO), a polypropylene oxide (PPO), or a block copolymer of PEO and PPO; preferably $L^1$ is a polyethylene oxide having the Formula —($CH_2$—$CH_2$—O)$_q$— or —(O—$CH_2$—$CH_2$)$_q$—, wherein q is an integer selected from 20 to 120; preferably $L^1$ is a polyethylene oxide having the Formula —($CH_2$—$CH_2$—O)$_q$— or —(O—$CH_2$—$CH_2$)$_q$—, wherein q is an integer selected from 40 to 110; preferably $L^1$ is a polyethylene oxide having the Formula —($CH_2$—$CH_2$—O)$_q$— or —(O—$CH_2$—$CH_2$)$_q$—, wherein q is an integer selected from 60 to 90;

$A^2$ is a single bond or is selected from a group consisting of —N($R^{18}$)—, —O—, -$L^{19}$-N($R^{19}$)—, and -$L^{20}$-O—, wherein the left side of each group is attached to $L^1$ and the right side thereof is attached to $X^3$, wherein $L^{19}$ and $L^{20}$ are each independently $C_{1-6}$alkylene being optionally substituted with one or more substituents selected from a group consisting of hydroxyl, $C_{1-6}$alkyl, and $C_{1-6}$alkoxy, $R^{18}$ and $R^{19}$ are each independently selected from hydrogen or $C_{1-6}$alkyl; preferably $A^2$ is a single bond or is selected from a group consisting of —N($R^{18}$)—, —O—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-4}$alkylene being optionally substituted with one or more substituents selected from a group consisting of hydroxyl, $C_{1-4}$alkyl, and $C_{1-4}$alkoxy, $R^{18}$ and $R^{19}$ are each independently selected from hydrogen or $C_{1-4}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-3}$alkylene being optionally substituted with one or more substituents selected from a group consisting of hydroxyl and $C_{1-3}$alkyl, $R^{18}$ and $R^{19}$ are each independently selected from hydrogen or $C_{1-3}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently methylene or ethylene; $R^{18}$ and $R^{19}$ are each independently selected from hydrogen or $C_{1-3}$alkyl; preferably $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;

$X^3$ is a folate moiety having the structural Formula XII, as taught herein, wherein $X^{221}$ is selected from N, $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —OR$^{225}$, —CO—R$^{125}$, —CO—O—R$^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; $L^{220}$ is selected from

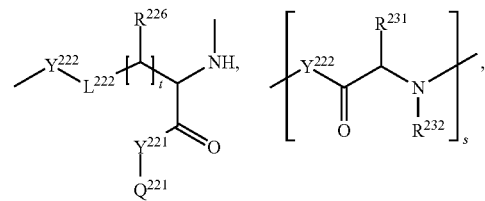

or a group consisting of $C_{1-6}$alkylene, $C_{1-6}$alkylenecarbonyl, —$C_{1-6}$alkylene-N($R^{227}$)—, $C_{2-6}$alkenylene, $C_{2-6}$alkynylene, $C_{3-6}$cycloalkylene, $C_{6-10}$arylene, —(C=O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene- O—(CO)—$C_{2-6}$alkynylene, $C_{3-6}$cycloalkylene-O—(CO)—$C_{3-6}$cycloalkylene, —N($R^{228}$)—, —N($R^{228}$)—(CO)—, and —(CO)—N($R^{228}$)—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —N($R^{229}$)—, or —S—; $Y^{222}$ is selected from a single bond, —O—, —N$R^{229}$—, —N($R^{229}$)—C(=NH)—N($R^{230}$)—, or —S—; $L^{222}$ is a single bond, $C_{6-10}$arylene, or —(C=O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIa, as taught herein, wherein $X^{221}$, $X^{222}$, $X^{223}$, $X^{224}$, $X^{225}$, $R^{222}$, $R^{226}$, $L^{222}$, $Y^{221}$, $Y^{222}$, $Q^{221}$, $Q^{222}$ and t have the same meaning as that defined herein above; preferably $X^3$ is a folate moiety having the structural Formula XII or XIIa, as taught herein, wherein $X^{221}$ is selected from N, or N$R^{221}$, or O; $X^{222}$ is selected from N, N$R^{221}$, or O; $X^{223}$ is selected from N, N$R^{223}$, or O; $X^{224}$ is selected from N, N$R^{224}$ or O; $X^{225}$ is selected from N$R^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —OR$^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —N($R^{229}$)—, or —S—; $Y^{222}$ is selected from a single bond, —O—, —N($R^{229}$)—, —N($R^{229}$)—C(=NH)—N($R^{230}$)—, or —S—; $L^{222}$ is a single bond, $C_{6-10}$arylene, or —(C=O)—; t is an integer selected from 1, 2, 3, or 4; $R^{226}$ is hydrogen or $C_{1-6}$alkyl; $R^{229}$ is hydrogen or $C_{1-6}$alkyl; $R^{230}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIb, as taught herein, wherein $X^{221}$, $X^{222}$, $X^{223}$, $X^{224}$, $X^{225}$, $R^{222}$, $Y^{221}$, $Y^{222}$, $Q^{221}$, $Q^{222}$ and m have the same meaning as that defined herein above; preferably $X^3$ is a folate moiety having the structural Formula XII, XIIa, or XIIb, as taught herein, wherein $X^{221}$ is selected from N, N$R^{221}$, or O; $X^{222}$ is selected from N, N$R^{221}$, or O; $X^{223}$ is selected from N, N$R^{223}$, or O; $X^{224}$ is selected from N, N$R^{224}$ or O; $X^{225}$ is selected from N$R^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —OR$^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —N$R^{229}$—, or —S—; $Y^{222}$ is selected from a single bond, —O—, —N$R^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XII, XIIa, or XIIb, as taught herein, wherein $X^{221}$ is selected from N or N$R^{221}$; $X^{222}$ is selected from N or N$R^{221}$; $X^{223}$ is selected from N or N$R^{223}$; $X^{224}$ is selected from N or N$R^{224}$; $X^{225}$ is N$R^{224}$, and $R^{221}$, $R^{222}$, $R^{223}$, $R^{224}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $X^{221}$ is selected from N or NH; $X^{222}$ is selected from N or NH; $X^{223}$ is selected from N or NH; $X^{224}$ is selected from N or NH; $X^{225}$ is NH and $R^{222}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $R^{222}$ is selected from the group consisting of —NH$R^{225}$, hydrogen, $C_{1-12}$alkyl, —OR$^{225}$, preferably —NH$R^{125}$, or —OR$^{225}$, wherein $R^{225}$ is selected from hydrogen, halo, $C_{1-12}$alkyl, $C_{2-12}$alkenyl, $C_{2-12}$alkynyl, —OR', —COR', —COOR', or —NHR', wherein R' is H or $C_{1-8}$alkyl, and $X^{221}$, $X^{222}$, $X^{223}$, $X^{224}$, $X^{225}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XIIc, as taught herein, wherein $Y^{221}$, $Y^{222}$, $Q^{221}$, $Q^{222}$, and m have the same meaning as that defined herein above; preferably $X^3$ is a folate moiety having the structural Formula XII, XIIa, XIIb, or XIIc, as taught herein, wherein $Y^{221}$ is selected from a single bond, —O—, —N$R^{229}$—, or —S—; $Y^{222}$ is selected from a single bond, —O—, —N$R^{229}$—, or —S—; m is an integer selected from 1, 2, or 3; $R^{229}$ is hydrogen or $C_{1-6}$alkyl; $Q^{221}$ is hydrogen or is a single bond connected to $X^1$;

$Q^{222}$ is hydrogen or is a single bond connected to $X^1$; wherein at least one of $Q^{221}$ and $Q^{222}$ is a single bond connected to $X^1$; preferably $X^3$ is a folate moiety having the structural Formula XII, XIIa, XIIb, or XIIc, as taught herein, wherein $Q^{221}$ is hydrogen and $Q^{222}$ is a single bond connected to $X^1$; preferably $X^3$ is a folate moiety having the structural Formula XIId, as taught herein, wherein $Q^{222}$ is a single bond connected to $X^1$;

$R^{20}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$R^3$ is —OR$^{31}$ or —X$^2$—X$^1$—X$^3$, wherein $R^{31}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$X^2$, $X^1$, and $X^3$ have the same meaning as that defined herein;

$R^4$ is —OR$^{41}$ or —X$^2$—X$^1$—X$^3$, wherein $R^{41}$ is selected from hydrogen, a mono-, oligo-, or polyglycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$X^2$, $X^1$, and $X^3$ have the same meaning as that defined herein;

wherein at least one of $Y^2$, $R^3$, or $R^4$ is —X$^2$—X$^1$—X$^3$.

In certain embodiments, the FR-targeting excipient may be a folate-polysaccharide conjugate comprising at least one unit of Formula XIc, XIh, XIj, XIk, XIn, XIp, or XIq, as taught herein, or any subgroup thereof, wherein $Y^2$ is —X$^2$—X$^1$—X$^3$, or —OR$^{20}$, wherein $X^2$ is —O—;

$X^1$ is a single bond or a linker of Formula X, as taught herein, wherein the left side of the linker of Formula X is attached to $X^2$ and the right side thereof is attached to $X^3$; wherein $A^1$ is selected from a group consisting of —CO-L$^{14}$-O—, —CO-L$^{15}$-CO—O—, —CO-L$^{16}$-CO—N(R$^{16}$)-L$^{17}$-, and —CO-L$^{18}$-CO—N(R$^{17}$)—, wherein the right side of each group is attached to L$^1$ and the left side thereof is attached to X$^2$, wherein L$^{14}$, L$^{15}$, L$^{16}$, L$^{17}$, and L$^{18}$ are each independently $C_{1-4}$alkylene optionally substituted with one or more substituents selected from a group consisting of hydroxyl, $C_{1-4}$alkyl and $C_{1-4}$alkoxy; R$^{16}$ and R$^{17}$ are each independently selected from hydrogen or $C_{1-4}$alkyl; preferably A$^1$ is selected from a group consisting of —CO-L$^{14}$-O—, —CO-L$^{15}$-CO—O—, —CO-L$^{16}$-CO—N(R$^{16}$)-L$^{17}$-, and —CO-L$^{18}$-CO—N(R$^{17}$)—, wherein the right side of each group is attached to L$^1$ and the left side thereof is attached to X$^2$, wherein L$^{14}$, L$^{15}$, L$^{16}$, L$^{17}$, and L$^{18}$ are each independently $C_{1-3}$alkylene optionally substituted with one or more substituents selected from a group consisting of hydroxyl and $C_{1-3}$alkyl; R$^{16}$ and R$^{17}$ are each independently selected from hydrogen or $C_{1-3}$alkyl; preferably A$^1$ is selected from a group consisting of —CO-L$^{14}$-O—, —CO-L$^{15}$-CO—O—, —CO-L$^{16}$-CO—N(R$^{16}$)-L$^{17}$-, and —CO-L$^{18}$-CO—N(R$^{17}$)—, wherein the right side of each group is attached to L$^1$ and the left side thereof is attached to X$^2$, wherein L$^{14}$ is methylene, ethylene, n-propylene; L$^{15}$, L$^{16}$, L$^{17}$, and L$^{18}$ are each independently methylene or ethylene; R$^{16}$ and R$^{17}$ are each independently selected from hydrogen or $C_{1-3}$alkyl; preferably A$^1$ is selected from a group consisting of —CO-L$^{14}$-O—, —CO-L$^{15}$-CO—O—, —CO-L$^{16}$-CO—NH-L$^{17}$-, and —CO-L$^{18}$-CO—NH—, wherein the right side of each group is attached to L$^1$ and the left side thereof is attached to X$^2$, wherein L$^{14}$ is n-propylene; L$^{15}$, L$^{16}$, L$^{17}$, and L$^{18}$ are each independently ethylene;

L$^1$ is selected from a polyethylene oxide (PEO), a polypropylene oxide (PPO), or a block copolymer of PEO and PPO; preferably L$^1$ is a polyethylene oxide having the Formula —(CH$_2$—CH$_2$—O)$_q$— or —(O—CH$_2$—CH$_2$)$_q$—, wherein q is an integer selected from 20 to 120; preferably L$^1$ is a polyethylene oxide having the Formula —(CH$_2$—CH$_2$—O)$_q$— or —(O—CH$_2$—CH$_2$)$_q$—, wherein q is an integer selected from 40 to 110; preferably L$^1$ is a polyethylene oxide having the Formula —(CH$_2$—CH$_2$—O)$_q$— or —(O—CH$_2$—CH$_2$)$_q$—, wherein q is an integer selected from 60 to 90;

A$^2$ is a single bond or is selected from a group consisting of —N(R$^{18}$)—, —O—, -L$^{19}$-N(R$^{19}$)—, or -L$^{20}$O—, wherein the left side of each group is attached to L$^1$ and the right side thereof is attached to X$^3$, wherein L$^{19}$ and L$^{20}$ are each independently $C_{1-4}$alkylene being optionally substituted with one or more substituents selected from a group consisting of hydroxyl, $C_{1-4}$alkyl, and $C_{1-4}$alkoxy, R$^{18}$ and R$^{19}$ are each independently selected from hydrogen or $C_{1-4}$alkyl; preferably A$^2$ is a single bond or is selected from a group consisting of —N(R$^{18}$)—, -L$^{19}$-N(R$^{19}$)—, or -L$^{20}$O—, wherein the left side of each group is attached to L$^1$ and the right side thereof is attached to X$^3$, wherein L$^{19}$ and L$^{20}$ are each independently $C_{1-3}$alkylene being optionally substituted with one or more substituents selected from a group consisting of hydroxyl and $C_{1-3}$alkyl, R$^{18}$ and R$^{19}$ are each independently selected from hydrogen or $C_{1-3}$alkyl; preferably A$^2$ is a single bond or is selected from a group consisting of —N(R$^{18}$)—, -L$^{19}$-N(R$^{19}$)—, or -L$^{20}$O—, wherein the left side of each group is attached to L$^1$ and the right side thereof is attached to X$^3$, wherein L$^{19}$ and L$^{20}$ are each independently methylene or ethylene; R$^{18}$ and R$^{19}$ are each independently selected from hydrogen or $C_{1-3}$alkyl; preferably A$^2$ is a single bond or is selected from a group consisting of —N(H)—, -L$^{19}$-N(H)—, or -L$^{20}$O—, wherein the left side of each group is attached to $L^1$ and the right side thereof is attached to $X^3$, wherein $L^{19}$ and $L^{20}$ are each independently ethylene;

$X^3$ is a folate moiety having the structural Formula XIIa, as taught herein, wherein $X^{221}$, $X^{222}$, $X^{223}$, $X^{224}$, $X^{225}$, $R^{222}$, $R^{226}$, $L^{222}$, $Y^{221}$, $Y^{222}$, $Q^{221}$, $Q^{222}$ and t have the same meaning as that defined herein above; preferably $X^3$ is a folate moiety having the structural Formula XII or XIIa, as taught herein, wherein $X^{221}$ is selected from N, or $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —OR$^{225}$, —CO—R$^{125}$, —CO—O—R$^{225}$, and —CO—N(H)R$^{225}$, wherein R$^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —N(R$^{229}$)—, or —S—; $Y^{222}$ is selected from a single bond, —O—, —N(R$^{229}$)—, —N(R$^{229}$)—C(=NH)—N(R$^{230}$)—, or —S—; $L^{222}$ is a single bond, $C_{6-10}$arylene, or —(C=O)—; t is an integer selected from 1, 2, 3, or 4; $R^{226}$ is hydrogen or $C_{1-6}$alkyl; $R^{229}$ is hydrogen or $C_{1-6}$alkyl; $R^{230}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XIIb, as taught herein, wherein $X^{221}$, $X^{222}$, $X^{223}$, $X^{224}$, $X^{225}$, $R^{222}$, $Y^{221}$, $Y^{222}$, $Q^{221}$, $Q^{222}$ and m have the same meaning as that defined herein above; preferably $X^3$ is a folate moiety having the structural Formula XII, XIIa, or XIIb, as taught herein, wherein $X^{221}$ is selected from N, $NR^{221}$, or O; $X^{222}$ is selected from N, $NR^{221}$ or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)R$^{225}$, hydrogen, halogen, $C_{1-12}$alkyl, $C_{2-12}$alkenyl, $C_{2-12}$alkynyl, —OR$^{225}$, —CO—R$^{125}$, —CO—O—R$^{225}$, and —CO—N(H)R$^{225}$, wherein R$^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —NR$^{229}$— or —S—; $Y^{222}$ is selected from a single bond, —O—, —NR$^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XII, XIIa, or XIIb, as taught herein, wherein $X^{221}$ is selected from N or $NR^{221}$; $X^{222}$ is selected from N or $NR^{221}$; $X^{223}$ is selected from N or $NR^{223}$; $X^{224}$ is selected from N or $NR^{224}$; $X^{225}$ is $NR^{224}$, and $R^{221}$, $R^{222}$, $R^{223}$, $R^{224}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $X^{221}$ is selected from N or NH; $X^{222}$ is selected from N or NH; $X^{223}$ is selected from N or NH; $X^{224}$ is selected from N or NH; $X^{225}$ is NH, and $R^{222}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $R^{222}$ is selected from the group consisting of —NHR$^{225}$, hydrogen, $C_{1-12}$alkyl, —OR$^{225}$, preferably —NHR$^{125}$, or —OR$^{225}$, wherein R$^{225}$ is selected from hydrogen, halo, $C_{1-12}$alkyl, $C_{2-12}$alkenyl, $C_{2-12}$alkynyl, —OR', —COR', —COOR', or —NHR', wherein R' is H or $C_{1-8}$alkyl, and $X^{221}$, $X^{222}$, $X^{223}$, $X^{224}$, $X^{225}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XIIc, as taught herein, wherein $Y^{221}$, $Y^{222}$, $Q^{221}$, $Q^{222}$, and m have the same meaning as that defined herein above; preferably $X^3$ is a folate moiety having the structural Formula XII, XIIa, XIIb, or XIIc, as taught herein, wherein $Y^{221}$ is selected from a single bond, —O—, —NR$^{229}$—, or —S—; $Y^{222}$ is selected from a single bond, —O—, —NR$^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; preferably $X^3$ is a folate moiety having the structural Formula XII, XIIa, XIIb, or XIIc, as taught herein, wherein $Q^{221}$ is hydrogen and $Q^{222}$ is a single bond connected to $X^1$; preferably $X^3$ is a folate moiety having the structural Formula XIId, as taught herein, wherein $Q^{222}$ is a single bond connected to $X^1$;

$R^{20}$ is selected from hydrogen, a mono-, oligo-, or polyglycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxylC$_{1-4}$alkylenecarbonyl, hydroxyC$_{1-4}$alkyl, carboxylC$_{640}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl;

$R^3$ is —OR$^{31}$ or —X$^2$—X$^1$—X$^3$, wherein
$R^{31}$ is selected from hydrogen, a mono-, oligo-, or polyglycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxylC$_{1-4}$alkylenecarbonyl, hydroxyC$_{1-4}$alkyl, carboxylC$_{640}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl;

$X^2$, $X^1$, and $X^3$ have the same meaning as that defined herein;

$R^4$ is —$OR^{41}$ or —$X^2$—$X^1$—$X^3$, wherein $R^{41}$ is selected from hydrogen, a mono-, oligo-, or polyglycosyl moiety, or a group consisting of $C_{1-6}$alkyl, $C_{1-25}$alkylcarbonyl, $C_{3-25}$alkenylcarbonyl, $C_{1-4}$alkyleneCOO$R^{12}$, carboxyl$C_{1-4}$alkylenecarbonyl, hydroxy$C_{1-4}$alkyl, carboxyl$C_{6-40}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl;

$X^2$, $X^1$, and $X^3$ have the same meaning as that defined herein;

wherein at least one of $Y^2$, $R^3$, or $R^4$ is —$X^2$—$X^1$—$X^3$.

In certain embodiments, the FR-targeting excipient may be a folate-polysaccharide conjugate comprising at least one unit of Formula XIc, XIh, XIj, XIk, XIn, XIp, or XIq, as taught herein, or any subgroup thereof, wherein $Y^2$ is —$X^2$—$X^1$—$X^3$, or —$OR^{20}$, wherein $X^2$ is —O—;

$X^1$ is a linker of Formula X, as taught herein, wherein the left side of the linker of Formula X is attached to $X^2$ and the right side thereof is attached to $X^3$; wherein $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$, $L^{15}$, $L^{16}$, $L^{17}$, and $L^{18}$ are each independently $C_{1-3}$alkylene optionally substituted with one or more substituents selected from a group consisting of hydroxyl and $C_{1-3}$alkyl; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$ is methylene, ethylene, n-propylene; $L^{15}$, $L^{16}$, $L^{17}$, and $L^{18}$ are each independently methylene or ethylene; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;

$L^1$ is a polyethylene oxide having the Formula —(CH$_2$—CH$_2$—O)$_q$— or —(O—CH$_2$—CH$_2$)$_q$—, wherein q is an integer selected from 20 to 120; preferably $L^1$ is a polyethylene oxide having the Formula —(CH$_2$—CH$_2$—O)$_q$— or —(O—CH$_2$—CH$_2$)$_q$—, wherein q is an integer selected from 40 to 110; preferably $L^1$ is a polyethylene oxide having the Formula —(CH$_2$—CH$_2$—O)$_q$— or —(O—CH$_2$—CH$_2$)$_q$—, wherein q is an integer selected from 60 to 90;

$A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently $C_{1-3}$alkylene being optionally substituted with one or more substituents selected from a group consisting of hydroxyl and $C_{1-3}$alkyl, $R^{18}$ and $R^{19}$ are each independently selected from hydrogen or $C_{1-3}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently methylene or ethylene; $R^{18}$ and $R^{19}$ are each independently selected from hydrogen or $C_{1-3}$alkyl; preferably $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;

$X^3$ is a folate moiety having the structural Formula XIIb, as taught herein, wherein $X^{221}$, $X^{222}$, $X^{223}$, $X^{224}$, $X^{225}$, $R^{222}$, $Y^{221}$, $Y^{222}$, $Q^{221}$, $Q^{222}$ and m have the same meaning as that defined herein above; preferably $X^3$ is a folate moiety having the structural Formula XII, XIIa, or XIIb, as taught herein, wherein $X^{221}$ is selected from N, N$R^{221}$, or O; $X^{222}$ is selected from N, N$R^{221}$, or O; $X^{223}$ is selected from N, N$R^{223}$, or O; $X^{224}$ is selected from N, N$R^{224}$ or O; $X^{2"}$ is selected from N$R^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —O$R^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; wherein $Y^{221}$ is selected from a single bond, —O—, —N$R^{229}$—, or —S—; $Y^{222}$ is selected from a single bond, —O—, —N$R^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond; preferably $X^3$ is a folate moiety having the structural Formula XII, XIIa, or XIIb, as taught herein, wherein $X^{221}$ is selected from N or N$R^{221}$; $X^{222}$ is selected from N or N$R^{221}$; $X^{223}$ is selected from N or NR is selected from N or N$R^{223}$; $X^{224}$ is selected from N or N$R^{224}$; $X^{222}$ is N$R^{224}$, and $R^{221}$, $R^{222}$, $R^{223}$, $R^{224}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $X^{221}$ is selected from N or NH; $X^{222}$ is selected from N or NH; $X^{223}$ is selected from N or NH; $X^{224}$ is selected from N or NH; $X^{225}$ is NH, and $R^{222}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XII, XIIa, or XIIb, as taught herein, wherein $R^{222}$ is selected from the group consisting of —$NHR^{225}$, hydrogen, $C_{1-12}$alkyl, —$OR^{225}$, preferably —$NHR^{125}$, or —$OR^{225}$, wherein $R^{225}$ is selected from hydrogen, halo, $C_{1-12}$alkyl, $C_{2-12}$alkenyl, $C_{2-12}$alkynyl, —OR', —COR', —COOR', or —NHR', wherein R' is H or $C_{1-8}$alkyl, and $X^{221}$, $X^{222}$, $X^{223}$, $X^{224}$, $X^{225}$, $R^{226}$, $L^{220}$, $L^{222}$, $Y^{221}$, $Y^{222}$, $Q^{221}$, $Q^{222}$ and t have the same meaning as that defined herein above; preferably $X^3$ is a folate moiety having the structural Formula XIIc, as taught herein, wherein $Y^{221}$, $Y^{222}$, $Q^{221}$, $Q^{222}$, and m have the same meaning as that defined herein above; preferably $X^3$ is a folate moiety having the structural Formula XII, XIIa, XIIb, or XIIc, as taught herein, wherein $Y^{221}$ is selected from a single bond, —O—, —$NR^{229}$—, or —S—; $Y^{222}$ is selected from a single bond, —O—, —$NR^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; preferably $X^3$ is a folate moiety having the structural Formula XII, XIIa, XIIb, or XIIc, as taught herein, wherein $Q^{221}$ is hydrogen and $Q^{222}$ is a single bond connected to $X^1$; preferably $X^3$ is a folate moiety having the structural Formula XIId, as taught herein, wherein $Q^{222}$ is a single bond connected to $X^1$; $R^{20}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy;

$R^3$ is —$OR^{31}$ or —$X^2$—$X^1$—$X^3$, wherein
$R^{31}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy;
$X^2$, $X^1$, and $X^3$ have the same meaning as that defined herein;

$R^4$ is —$OR^{41}$ or —$X^2$—$X^1$—$X^3$, wherein
$R^{41}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy;
$X^2$, $X^1$, and $X^3$ have the same meaning as that defined herein;

wherein at least one of $Y^2$, $R^3$, or $R^4$ is —$X^2$—$X^1$—$X^3$.

In certain embodiments, the FR-targeting excipient may be a folate-polysaccharide conjugate comprising at least one unit of XIc, XIh, XIj, XIk, XIn, XIp, or XIq, as taught herein, or any subgroup thereof, wherein
$Y^2$ is —$X^2$—$X^1$—$X^3$, or —$OR^{20}$, wherein
$X^2$ is —O—;
$X^1$ is a linker of Formula X, as taught herein, wherein the left side of the linker of Formula X is attached to $X^2$ and the right side thereof is attached to $X^3$; wherein $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is attached to $X^2$, wherein $L^{14}$ is methylene, ethylene, n-propylene; $L^{15}$, $L^{16}$, $L^{17}$, and $L^{18}$ are each independently methylene or ethylene; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;

$L^1$ is a polyethylene oxide having the Formula —($CH_2$—$CH_2$—O)$_q$— or —(O—$CH_2$—$CH_2$)$_q$—, wherein q is an integer selected from 40 to 110; preferably $L^1$ is a polyethylene oxide having the Formula —($CH_2$—$CH_2$—O)$_q$— or —(O—$CH_2$—$CH_2$)$_q$—, wherein q is an integer selected from 60 to 90;

$A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is attached to $X^3$, wherein $L^{19}$ and $L^{20}$ are each independently methylene or ethylene; $R^{18}$ and $R^{19}$ are each independently selected from hydrogen or $C_{1-3}$alkyl; preferably $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;

$X^3$ is a folate moiety having the structural Formula XIIc, as taught herein, wherein $Y^{221}$, $Y^{222}$, $Q^{221}$, $Q^{222}$, and m have the same meaning as that defined herein above; preferably $X^3$ is a folate moiety having the structural Formula XII, XIIa, XIIb, or XIIc, as taught herein, wherein $Y^{221}$ is selected from a single bond, —O—, —$NR^{229}$—, or —S—; $Y^{222}$ is selected from a single bond, —O—, —$NR^{229}$—, or —S—; m is an integer selected from 1, 2, or 3; $R^{229}$ is hydrogen or $C_{1-6}$alkyl; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; preferably $X^3$ is a folate moiety having the structural Formula XII, XIIa, XIIb, or XIIc, as taught herein, wherein $Q^{221}$ is hydrogen and $Q^{222}$ is a single bond connected to $X^1$; preferably $X^3$ is a folate moiety having the structural Formula XIId, as taught herein, wherein $Q^{222}$ is a single bond connected to $X^1$;

$R^{20}$ is selected from hydrogen, a mono-, oligo-, or poly-glycosyl moiety, or a group consisting of $C_{1-3}$alkyl, $C_{1-25}$alkylcarbonyl, and $C_{13-25}$alkenylcarbonyl;

$R^3$ is —$OR^{31}$ or —$X^2$—$X^1$—$X^3$, wherein
$R^{31}$ is selected from hydrogen, a mono-, oligo-, or poly-glycosyl moiety, or a group consisting of $C_{1-3}$alkyl, $C_{1-25}$alkylcarbonyl, and $C_{13-25}$alkenylcarbonyl;
$X^2$, $X^1$, and $X^3$ have the same meaning as that defined herein;

$R^4$ is —$OR^{41}$ or —$X^2$—$X^1$—$X^3$, wherein
$R^{41}$ is selected from hydrogen, a mono-, oligo-, or poly-glycosyl moiety, or a group consisting of $C_{1-3}$alkyl, $C_{1-25}$alkylcarbonyl, and $C_{13-25}$alkenylcarbonyl;
$X^2$, $X^1$, and $X^3$ have the same meaning as that defined herein;

wherein at least one of $Y^2$, $R^3$, or $R^4$ is —$X^2$—$X^1$—$X^3$.

In certain embodiments, the FR-targeting excipient may be a folate-polysaccharide conjugate comprising at least one unit of Formula XIc, XIh, XIj, XIk, XIn, XIp, or XIq, as taught herein, or any subgroup thereof, wherein $Y^2$ is —$X^2$—$X^1$—$X^3$, or —$OR^{20}$, wherein
  $X^2$ is —O—;
  $X^1$ is a linker of Formula X, as taught herein, wherein the left side of the linker of Formula X is attached to $X^2$ and the right side thereof is attached to $X^3$; wherein
    $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;
    $L^1$ is a polyethylene oxide having the Formula —($CH_2$—$CH_2$—O$)_q$— or —(O—$CH_2$—$CH_2)_q$—, wherein q is an integer selected from 60 to 90;
    $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;
  $X^3$ is a folate moiety having the structural Formula XIId, as taught herein, wherein $Q^{222}$ is a single bond connected to $X^1$;
  $R^{20}$ is selected from hydrogen, a mono-, oligo-, or polyglycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^3$ is —$OR^{31}$ or —$X^2$—$X^1$—$X^3$, wherein
  $R^{31}$ is selected from hydrogen, a mono-, oligo-, or polyglycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^4$ is —$OR^{41}$ or —$X^2$—$X^1$—$X^3$, wherein
  $R^{41}$ is selected from hydrogen, a mono-, oligo-, or polyglycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

wherein at least one of $Y^2$, $R^3$, or $R^4$ is $-X^2-X^1-X^3$.

In certain embodiments of the products (such as pharmaceutical formulations or FR-targeting excipients) or uses, as taught herein, the FR-targeting excipient may comprise at least one unit of Formula XIb, XIc, XId, XIe, XIg, XIh, XIj, XIk, XIm, XIn, XIp, and/or XIq, as taught herein, or any subgroup thereof, and at least one unit of Formula V, a stereoisomer, salt, hydrate or solvate thereof, wherein

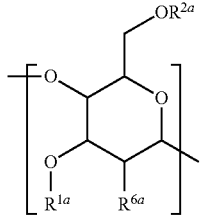

(V)

$Y^1$, $R^1$, $R^2$, $Y^2$, $R^3$, $R^4$, $Y^3$, $R^{43}$, $R^{53}$, $X^4$, $R^{44}$, $R^{54}$, $R^{11}$, $R^{21}$, $R^{31}$, $R^{41}$, $R^{20}$, $X^1$, and $X^3$ have the same meaning as that defined herein above;

$R^{1a}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $-C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{1a}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCO—OR$^{12}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{1a}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{1a}$ is selected from hydrogen, or a group consisting of $C_{1-3}$alkyl, $C_{1-25}$alkylcarbonyl, and $C_{13-25}$ alkenylcarbonyl; preferably $R^{1a}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{2a}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $-C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{2a}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCO—OR$^{12}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{2a}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{2a}$ is selected from hydrogen, or a group consisting of $C_{1-3}$alkyl, $C_{1-25}$alkylcarbonyl, and $C_{13-25}$alkenylcarbonyl; preferably $R^{2a}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{6a}$ is selected from amino, ammonium, —$NHR^{8a}$, —$NR^{8a}R^{9a}$, or —$N^+R^{8a}R^{9a}R^{10a}$, wherein $R^{8a}$ is selected from a group consisting of $C_{1-25}$alkyl, $C_{1-6}$alkylene-$N(R^{111})R^{112}$, $C_{1-6}$alkylene-$N^+(R^{111})(R^{112})R^{113}$, $C_{1-25}$alkylcarbonyl, $C_{2-25}$alkenylcarbonyl, $C_{1-6}$alkylene-CO—$OR^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl; preferably $R^{8a}$ is selected from a group consisting of $C_{1-6}$alkyl, $C_{1-4}$alkylene-$N(R^{111})R^{112}$, $C_{1-4}$alkylene-$N^+(R^{111})(R^{112})R^{113}$, $C_{1-25}$alkylcarbonyl, $C_{3-25}$alkenylcarbonyl, $C_{1-4}$alkylene-CO—$OR^{114}$, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{111}$ is selected from hydrogen or $C_{1-4}$alkyl, $R^{112}$ is selected from hydrogen or $C_{1-4}$alkyl, $R^{113}$ is selected from hydrogen or $C_{1-4}$alkyl, and $R^{114}$ is selected from hydrogen or $C_{1-4}$alkyl; preferably lea is selected from a group consisting of $C_{1-4}$alkyl, $C_{1-3}$alkylene-$N(R^{111})R^{112}$, $C_{1-3}$alkylene-$N^+(R^{111})(R^{112})R^{113}$, $C_{1-25}$alkylcarbonyl, $C_{5-23}$alkenylcarbonyl, $C_{1-3}$alkyleneCO—$OR^{114}$, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy, wherein $R^{111}$ is selected from hydrogen or $C_{1-3}$alkyl, $R^{112}$ is selected from hydrogen or $C_{1-3}$alkyl, $R^{113}$ is selected from hydrogen or $C_{1-3}$alkyl, and $R^{114}$ is selected from hydrogen or $C_{1-3}$alkyl; preferably lea is selected from a group consisting of $C_{1-3}$alkyl, $C_{1-3}$alkylene-$N(R^{111})R^{112}$, $C_{1-3}$alkylene-$N^+(R^{111})(R^{112})R^{113}$, $C_{1-25}$alkylcarbonyl, $C_{13-21}$alkenylcarbonyl, and $C_{1-3}$alkyleneCO—$OR^{114}$, each group being optionally substituted with one or more substituents each independently selected from hydroxyl, halogen, $C_{1-3}$alkyl, or $C_{1-3}$alkoxy, wherein $R^{111}$ is selected from hydrogen or $C_{1-3}$alkyl, $R^{112}$ is selected from hydrogen or $C_{1-3}$alkyl, $R^{113}$ is selected from hydrogen or $C_{1-3}$alkyl, and $R^{114}$ is selected from hydrogen or $C_{1-3}$alkyl; preferably lea is selected from a group consisting of methyl, ethyl, n-propyl, i-propyl, methylene-$N^+(R^{111})R^{112}$, ethylene-$N(R^{111})R^{112}$, n-propylene-$N(R^{111})R^{112}$, methylene-$N^+(R^{111})(R^{112})R^{113}$, ethylene-$N^+(R^{111})(R^{112})R^{113}$, n-propylene-$N^+(R^{111})(R^{112})R^{113}$, methylene-CO—$OR^{114}$, ethylene-CO—$OR^{114}$, n-propylene-CO—$OR^{114}$, $C_{1-25}$alkylcarbonyl, and, $C_{13-21}$alkenylcarbonyl, each group being optionally substituted with one or more substituents each independently selected from hydroxyl, halogen, methyl, or ethyl, wherein $R^{111}$ is selected from hydrogen, methyl, or ethyl, $R^{112}$ is selected from hydrogen, methyl, or ethyl, $R^{113}$ is selected from hydrogen, methyl, or ethyl, and $R^{114}$ is selected from hydrogen, methyl, or ethyl; preferably $R^{8a}$ is selected from a group consisting of methyl, ethyl, n-propyl, i-propyl, methylene-$N^+(R^{111})(R^{112})R^{113}$ ethylene-$N^+(R^{111})(R^{112})R^{113}$, n-propylene-$N^+(R^{111})(R^{112})R^{113}$, methylene-CO—$OR^{114}$, ethylene-CO—$OR^{114}$ n-propylene-CO—$OR^{114}$, $C_{1-25}$alkylcarbonyl, and, $C_{13-21}$alkenylcarbonyl, each group being optionally substituted with one or more substituents each independently selected from hydroxyl or methyl, wherein $R^{111}$ is selected from hydrogen or methyl, $R^{112}$ is selected from hydrogen or methyl, $R^{113}$ is selected from hydrogen or methyl, and $R^{114}$ is selected from hydrogen or methyl; preferably lea is selected from a group consisting of methyl, ethyl, n-propyl, i-propyl, 2-hydroxypropylene-$N^+(CH_3)_3$, methylene-CO—OH, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the nitrogen to which it is bound a caprylic amide moiety), n-nonylcarbonyl (e.g. which may form together with the nitrogen to which it is bound a capric amide moiety), n-undecylcarbonyl (e.g. which may form together with the nitrogen to which it is bound a lauric amide moiety), n-tridecylcarbonyl (e.g. which may form together with the nitrogen to which it is bound a myristic amide moiety), n-pentadecylcarbonyl (e.g. which may form together with the nitrogen to which it is bound a palmitic amide moiety), n-heptadecylcarbonyl (e.g. which may form together with the nitrogen to which it is bound a stearic amide moiety), n-nonadecylcarbonyl (e.g. which may form together with the nitrogen to which it is bound an arachidic amide moiety), n-henicosylcarbonyl (e.g. which may form together with the nitrogen to which it is bound a behenic amide moiety), n-tricosylcarbonyl (e.g. which may form together with the nitrogen to which it is bound a lignoceric amide moiety), n-pentacosylcarbonyl (e.g. which may form together with the nitrogen to which it is bound a cerotic amide moiety), n-tridecenylcarbonyl (e.g. which may form together with the nitrogen to which it is bound a myristoleic amide), n-pentadecenylcarbonyl (e.g. which may form together with the nitrogen to which it is bound a palmitoleic amide moiety or sapienic amide moiety), n-heptadecenylcarbonyl (e.g. which may form together with the nitrogen to which it is bound an oleic amide moiety, elaidic amide moiety, vaccenic amide moiety, linoleic amide moiety, linoelaidic amide moiety, or α-linolenic amide moiety), n-nonadecenylcarbonyl (e.g. which may form together with the nitrogen to which it is bound an arachidonic amide moiety or eicosapentaenoic amide moiety), or n-henicosenylcarbonyl (e.g. which may form together with the nitrogen to which it is bound an erucic amide moiety or docosahexaenoic amide moiety);

$R^{9a}$ is selected from a group consisting of $C_{1-25}$alkyl, $C_{1-6}$alkylene-N($R^{111}$)$R^{112}$, $C_{1-6}$alkylene-N$^+$($R^{111}$)($R^{112}$)$R^{113}$, $C_{1-25}$alkylcarbonyl, $C_{2-25}$alkenylcarbonyl, $C_{1-6}$alkylene-CO—O$R^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl; preferably $R^{9a}$ is selected from a group consisting of $C_{1-6}$alkyl, $C_{1-4}$alkylene-N($R^{111}$)$R^{112}$, $C_{1-4}$alkylene-N$^+$($R^{111}$)($R^{112}$)$R^{113}$, $C_{1-25}$alkylcarbonyl, $C_{3-25}$alkenylcarbonyl, $C_{1-4}$alkylene-CO—O$R^{114}$, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{111}$ is selected from hydrogen or $C_{1-4}$alkyl, $R^{112}$ is selected from hydrogen or $C_{1-4}$alkyl, $R^{113}$ is selected from hydrogen or $C_{1-4}$alkyl, and $R^{114}$ is selected from hydrogen or $C_{1-4}$alkyl; preferably $R^{9a}$ is selected from a group consisting of $C_{1-4}$alkyl, $C_{1-3}$alkylene-N($R^{111}$)$R^{112}$, $C_{1-3}$alkylene-N$^+$($R^{111}$)($R^{112}$)$R^{113}$, $C_{1-25}$alkylcarbonyl, $C_{5-23}$alkenylcarbonyl, $C_{1-3}$alkylene-CO—O$R^{114}$, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy, wherein $R^{111}$ is selected from hydrogen or $C_{1-3}$alkyl, $R^{112}$ is selected from hydrogen or $C_{1-3}$alkyl, $R^{113}$ is selected from hydrogen or $C_{1-3}$alkyl, and $R^{114}$ is selected from hydrogen or $C_{1-3}$alkyl; preferably $R^{9a}$ is selected from a group consisting of $C_{1-3}$alkyl, $C_{1-3}$alkylene-N($R^{111}$)$R^{112}$, $C_{1-3}$alkylene-N$^+$($R^{111}$)($R^{112}$)$R^{113}$, $C_{1-25}$alkylcarbonyl, $C_{13-21}$alkenylcarbonyl, and $C_{1-3}$alkylene-CO—O$R^{114}$, each group being optionally substituted with one or more substituents each independently selected from hydroxyl, halogen, $C_{1-3}$alkyl, or $C_{1-3}$alkoxy, wherein $R^{111}$ is selected from hydrogen or $C_{1-3}$alkyl, $R^{112}$ is selected from hydrogen or $C_{1-3}$alkyl, $R^{113}$ is selected from hydrogen or $C_{1-3}$alkyl, and $R^{114}$ is selected from hydrogen or $C_{1-3}$alkyl; preferably $R^{9a}$ is selected from a group consisting of methyl, ethyl, n-propyl, i-propyl, methylene-N($R^{111}$)$R^{112}$, ethylene-N($R^{111}$)$R^{112}$, n-propylene-N($R^{111}$)$R^{112}$, methylene-N$^+$($R^{111}$)($R^{112}$)$R^{113}$, ethylene-N$^+$($R^{111}$)($R^{112}$)$R^{113}$, n-propylene-N$^+$($R^{111}$)($R^{112}$)$R^{113}$, methylene-CO—O$R^{114}$, ethylene-CO—O$R^{114}$, n-propylene-CO—O$R^{114}$, $C_{1-25}$alkylcarbonyl, and, $C_{13-21}$alkenylcarbonyl, each group being optionally substituted with one or more substituents each independently selected from hydroxyl, halogen, methyl, or ethyl, wherein $R^{111}$ is selected from hydrogen, methyl, or ethyl, $R^{112}$ is selected from hydrogen, methyl, or ethyl, $R^{113}$ is selected from hydrogen, methyl, or ethyl, and $R^{114}$ is selected from hydrogen, methyl, or ethyl; preferably $R^{9a}$ is selected from a group consisting of methyl, ethyl, n-propyl, i-propyl, methylene-N$^+$($R^{111}$)($R^{112}$)$R^{113}$ ethylene-N$^+$($R^{111}$)($R^{112}$)$R^{113}$, n-propylene-N$^+$($R^{111}$)($R^{112}$) $R^{113}$, methylene-CO—O$R^{114}$, ethylene-CO—O$R^{114}$, n-propylene-CO—O$R^{114}$, $C_{1-25}$alkylcarbonyl, and, $C_{13-21}$alkenylcarbonyl, each group being optionally substituted with one or more substituents each independently selected from hydroxyl or methyl, wherein $R^{111}$ is selected from hydrogen or methyl, $R^{112}$ is selected from hydrogen or methyl, $R^{113}$ is selected from hydrogen or methyl, and $R^{114}$ is selected from hydrogen or methyl; preferably $R^{9a}$ is selected from a group consisting of methyl, ethyl, n-propyl, i-propyl, 2-hydroxypropylene-N$^+$(CH$_3$)$_3$, methylene-CO—OH, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the nitrogen to which it is bound a caprylic amide moiety), n-nonylcarbonyl (e.g. which may form together with the nitrogen to which it is bound a capric amide moiety), n-undecylcarbonyl (e.g. which may form together with the nitrogen to which it is bound a lauric amide moiety), n-tridecylcarbonyl (e.g. which may form together with the nitrogen to which it is bound a myristic amide moiety), n-pentadecylcarbonyl (e.g. which may form together with the nitrogen to which it is bound a palmitic amide moiety), n-heptadecylcarbonyl (e.g. which may form together with the nitrogen to which it is bound a stearic amide moiety), n-nonadecylcarbonyl (e.g. which may form together with the nitrogen to which it is bound an arachidic amide moiety), n-henicosylcarbonyl (e.g. which may form together with the nitrogen to which it is bound a behenic amide moiety), n-tricosylcarbonyl (e.g. which may form together with the nitrogen to which it is bound a lignoceric amide moiety), n-pentacosylcarbonyl (e.g. which may form together with the nitrogen to which it is bound a cerotic amide moiety), n-tridecenylcarbonyl (e.g. which may form together with the nitrogen to which it is bound a myristoleic amide), n-pentadecenylcarbonyl (e.g. which may form together with the nitrogen to which it is bound a palmitoleic amide moiety or sapienic amide moiety), n-heptadecenylcarbonyl (e.g. which may form together with the nitrogen to which it is bound an oleic amide moiety, elaidic amide moiety, vaccenic amide moiety, linoleic amide moiety, linoelaidic amide moiety, or α-linolenic amide moiety), n-nonadecenylcarbonyl (e.g. which may form together with the nitrogen to which it is bound an arachidonic amide moiety or eicosapentaenoic amide moiety), or n-henicosenylcarbonyl (e.g. which may form together with the nitrogen to which it is bound an erucic amide moiety or docosahexaenoic amide moiety); $R^{10a}$ is selected from a group consisting of $C_{1-25}$alkyl, $C_{1-6}$alkylene-N($R^{111}$)$R^{112}$, $C_{1-6}$alkylene-N$^+$($R^{111}$)($R^{112}$)$R^{113}$, $C_{1-25}$alkylcarbonyl, $C_{2-25}$alkenylcarbonyl, $C_{1-6}$alkylene-CO—O$R^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl; preferably $R^{10a}$ is selected from a group consisting of $C_{1-6}$alkyl, $C_{1-4}$alkylene-N($R^{111}$)$R^{112}$, $C_{1-4}$alkylene-N$^+$($R^{111}$)($R^{112}$)$R^{113}$, $C_{1-25}$alkylcarbonyl, $C_{3-25}$alkenylcarbonyl, $C_{1-4}$alkylene-CO—O$R^{114}$, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{111}$ is selected from hydrogen or $C_{1-4}$alkyl, $R^{112}$ is selected from hydrogen or $C_{1-4}$alkyl, $R^{113}$ is selected from hydrogen or $C_{1-4}$alkyl, and $R^{114}$ is selected from hydrogen or $C_{1-4}$alkyl; preferably $R^{111}$ is selected from a group consisting of $C_{1-4}$alkyl, $C_{1-3}$alkylene-$N(R^{111})R^{112}$, $C_{1-3}$alkylene-$N^+(R^{111})(R^{112})R^{113}$, $C_{1-25}$alkylcarbonyl, $C_{5-23}$alkenylcarbonyl, $C_{1-3}$alkylene-CO—$OR^{114}$, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy, wherein $R^{111}$ is selected from hydrogen or $C_{1-3}$alkyl, $R^{112}$ is selected from hydrogen or $C_{1-3}$alkyl, $R^{113}$ is selected from hydrogen or $C_{1-3}$alkyl, and $R^{114}$ is selected from hydrogen or $C_{1-3}$alkyl; preferably $R^{10a}$ is selected from a group consisting of $C_{1-3}$alkyl, $C_{1-3}$alkylene-$N(R^{111})R^{112}$, $C_{1-3}$alkylene-$N^+(R^{111})(R^{112})R^{113}$, $C_{1-25}$alkylcarbonyl, $C_{13-21}$alkenylcarbonyl, and $C_{1-3}$alkylene-CO—$OR^{114}$, each group being optionally substituted with one or more substituents each independently selected from hydroxyl, halogen, $C_{1-3}$alkyl, or $C_{1-3}$alkoxy, wherein $R^{111}$ is selected from hydrogen or $C_{1-3}$alkyl, $R^{112}$ is selected from hydrogen or $C_{1-3}$alkyl, $R^{113}$ is selected from hydrogen or $C_{1-3}$alkyl, and $R^{114}$ is selected from hydrogen or $C_{1-3}$alkyl; preferably $R^{10a}$ is selected from a group consisting of methyl, ethyl, n-propyl, i-propyl, methylene-$N(R^{111})R^{112}$, ethylene-$N(R^{111})R^{112}$, n-propylene-$N(R^{111})R^{112}$, methylene-$N^+(R^{111})(R^{112})R^{113}$, ethylene-$N^+(R^{111})(R^{112})R^{113}$, n-propylene-$N^+(R^{111})(R^{112})R^{113}$, methylene-CO—$OR^{114}$, ethylene-CO—$OR^{114}$, n-propylene-CO—$OR^{114}$, $C_{1-25}$alkylcarbonyl, and, $C_{13-21}$alkenylcarbonyl, each group being optionally substituted with one or more substituents each independently selected from hydroxyl, halogen, methyl, or ethyl, wherein $R^{111}$ is selected from hydrogen, methyl, or ethyl, $R^{112}$ is selected from hydrogen, methyl, or ethyl, $R^{113}$ is selected from hydrogen, methyl, or ethyl, and $R^{114}$ is selected from hydrogen, methyl, or ethyl; preferably $R^{10a}$ is selected from a group consisting of methyl, ethyl, n-propyl, i-propyl, methylene-$N^+(R^{111})(R^{112})R^{113}$ ethylene-$N^+(R^{111})(R^{112})R^{113}$, n-propylene-$N^+(R^{111})(R^{112})R^{113}$, methylene-CO—$OR^{114}$, ethylene-CO—$OR^{114}$ n-propylene-CO—$OR^{114}$, $C_{1-25}$alkylcarbonyl, and, $C_{13-21}$alkenylcarbonyl, each group being optionally substituted with one or more substituents each independently selected from hydroxyl or methyl, wherein $R^{111}$ is selected from hydrogen or methyl, $R^{112}$ is selected from hydrogen or methyl, $R^{113}$ is selected from hydrogen or methyl, and $R^{114}$ is selected from hydrogen or methyl; preferably $R^{10a}$ is selected from a group consisting of methyl, ethyl, n-propyl, i-propyl, 2-hydroxy-propylene-$N^+(CH_3)_3$, methylene-CO—OH, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the nitrogen to which it is bound a caprylic amide moiety), n-nonylcarbonyl (e.g. which may form together with the nitrogen to which it is bound a capric amide moiety), n-undecylcarbonyl (e.g. which may form together with the nitrogen to which it is bound a lauric amide moiety), n-tridecylcarbonyl (e.g. which may form together with the nitrogen to which it is bound a myristic amide moiety), n-pentadecylcarbonyl (e.g. which may form together with the nitrogen to which it is bound a palmitic amide moiety), n-heptadecylcarbonyl (e.g. which may form together with the nitrogen to which it is bound a stearic amide moiety), n-nonadecylcarbonyl (e.g. which may form together with the nitrogen to which it is bound an arachidic amide moiety), n-henicosylcarbonyl (e.g. which may form together with the nitrogen to which it is bound a behenic amide moiety), n-tricosylcarbonyl (e.g. which may form together with the nitrogen to which it is bound a lignoceric amide moiety), n-pentacosylcarbonyl (e.g. which may form together with the nitrogen to which it is bound a cerotic amide moiety), n-tridecenylcarbonyl (e.g. which may form together with the nitrogen to which it is bound a myristoleic amide), n-pentadecenylcarbonyl (e.g. which may form together with the nitrogen to which it is bound a palmitoleic amide moiety or sapienic amide moiety), n-heptadecenylcarbonyl (e.g. which may form together with the nitrogen to which it is bound an oleic amide moiety, elaidic amide moiety, vaccenic amide moiety, linoleic amide moiety, linoelaidic amide moiety, or α-linolenic amide moiety), n-nonadecenylcarbonyl (e.g. which may form together with the nitrogen to which it is bound an arachidonic amide moiety or eicosapentaenoic amide moiety), or n-henicosenylcarbonyl (e.g. which may form together with the nitrogen to which it is bound an erucic amide moiety or docosahexaenoic amide moiety).

In certain embodiments, the FR-targeting excipient may comprise at least one unit of Formula XIb, XIc, XId, XIe, XIg, XIh, XIj, XIk, XIm, XIn, XIp, and/or XIq, as taught herein, or any subgroup thereof, and $R^1$, $R^2$, $Y^2$, $R^3$, $R^4$, $Y^3$, $R^{43}$, $R^{53}$, $X^4$, $R^{44}$, $R^{54}$, at least one unit of Formula V, as taught herein, wherein $Y^1$, $R^{11}$, $R^{21}$, $R^{31}$, $R^{41}$, $R^{20}$, $X^1$, and $X^3$ have the same meaning as that defined herein above;

$R^{1a}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{2a}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety); $R^{6a}$ is selected from amino, ammonium, —$NHR^{8a}$, —$NR^{8a}R^{9a}$, or —$N^+R^{8a}R^{9a}R^{10a}$, wherein $R^{8a}$, $R^{9a}$, and $R^{10a}$ are each independently selected from a group consisting of methyl, ethyl, n-propyl, i-propyl, 2-hydroxy-propylene-$N^+(CH_3)_3$, methylene-CO—OH, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the nitrogen to which it is bound a caprylic amide moiety), n-nonylcarbonyl (e.g. which may form together with the nitrogen to which it is bound a capric amide moiety), n-undecylcarbonyl (e.g. which may form together with the nitrogen to which it is bound a lauric amide moiety), n-tridecylcarbonyl (e.g. which may form together with the nitrogen to which it is bound a myristic amide moiety), n-pentadecylcarbonyl (e.g. which may form together with the nitrogen to which it is bound a palmitic amide moiety), n-heptadecylcarbonyl (e.g. which may form together with the nitrogen to which it is bound a stearic amide moiety), n-nonadecylcarbonyl (e.g. which may form together with the nitrogen to which it is bound an arachidic amide moiety), n-henicosylcarbonyl (e.g. which may form together with the nitrogen to which it is bound a behenic amide moiety), n-tricosylcarbonyl (e.g. which may form together with the nitrogen to which it is bound a lignoceric amide moiety), n-pentacosylcarbonyl (e.g. which may form together with the nitrogen to which it is bound a cerotic amide moiety), n-tridecenylcarbonyl (e.g. which may form together with the nitrogen to which it is bound a myristoleic amide), n-pentadecenylcarbonyl (e.g. which may form together with the nitrogen to which it is bound a palmitoleic amide moiety or sapienic amide moiety), n-heptadecenylcarbonyl (e.g. which may form together with the nitrogen to which it is bound an oleic amide moiety, elaidic amide moiety, vaccenic amide moiety, linoleic amide moiety, linoelaidic amide moiety, or oi-linolenic amide moiety), n-nonadecenylcarbonyl (e.g. which may form together with the nitrogen to which it is bound an arachidonic amide moiety or eicosapentaenoic amide moiety), or n-henicosenylcarbonyl (e.g. which may form together with the nitrogen to which it is bound an erucic amide moiety or docosahexaenoic amide moiety).

In certain embodiments of the products (such as pharmaceutical formulations or FR-targeting excipients) or uses, as taught herein, the FR-targeting excipient may comprise at least one unit of Formula XIb, XIc, XId, XIe, XIg, XIh, XIj, XIk, XIm, XIn, XIp, and/or XIq, as taught herein, or any subgroup thereof, and at least one unit of Formula IX, or a stereoisomer, salt, hydrate or solvate thereof, wherein

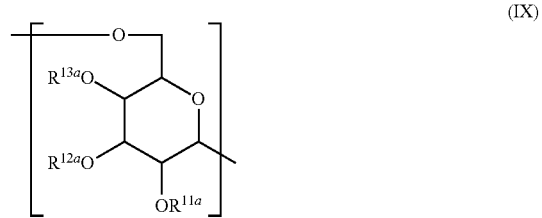

(IX)

$Y^1$, $R^1$, $R^2$, $Y^2$, $R^3$, $R^4$, $Y^3$, $R^{43}$, $R^{53}$, $X^4$, $R^{44}$, $R^{54}$, $R^{11}$, $R^{21}$, $R^{31}$, $R^{41}$, $R^{20}$, $X^1$, and $X^3$ have the same meaning as that defined herein above;

$R^{11a}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene COOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{11a}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{11a}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{11a}$ is selected from hydrogen, a mono-, oligo-, or poly-glycosyl moiety, or a group consisting of $C_{1-3}$alkyl, $C_{1-25}$alkylcarbonyl, and $C_{13-25}$alkenylcarbonyl; preferably $R^{11a}$ is selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g.

which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{12a}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{12a}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{12a}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{12a}$ is selected from hydrogen, a mono-, oligo-, or poly-glycosyl moiety, or a group consisting of $C_{1-3}$alkyl, $C_{1-25}$alkylcarbonyl, and $C_{13-25}$alkenylcarbonyl; preferably $R^{12a}$ is selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{13a}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkyleneCOOR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl; preferably $R^{13a}$ is selected from hydrogen, a mono-, oligo-, or poly-glycosyl moiety, or a group consisting of $C_{1-6}$alkyl, $C_{1-25}$alkylcarbonyl, $C_{3-25}$alkenylcarbonyl, $C_{1-4}$alkyleneCOOR$^{12}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{12}$ is selected from hydrogen or $C_{1-4}$alkyl; preferably $R^{13a}$ is selected from hydrogen, a mono-, oligo-, or poly-glycosyl moiety, or a group consisting of $C_{1-4}$alkyl, $C_{1-25}$alkylcarbonyl, $C_{5-25}$alkenylcarbonyl, $C_{1-3}$alkyleneCOOH, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy; preferably $R^{13a}$ is selected from hydrogen, a mono-, oligo-, or poly-glycosyl moiety, or a group consisting of $C_{1-3}$alkyl, $C_{1-25}$alkylcarbonyl, and $C_{13-25}$alkenylcarbonyl; preferably $R^{13a}$ is selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g.

which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety).

In certain embodiments, the FR-targeting excipient may comprise at least one unit of Formula XIb, XIc, XId, XIe, XIg, XIh, XIj, XIk, XIm, XIn, XIp, and/or XIq, as taught herein, or any subgroup thereof, and $R^1$, $R^2$, $Y^2$, $R^3$, $R^4$, $Y^3$, $R^{43}$, $R^{53}$, $X^4$, $R^{44}$, $R^{54}$, at least one unit of Formula IX, as taught herein, wherein $Y^1$, $R^{11}$, $R^{21}$, $R^{31}$, $R^{41}$, $R^{20}$, $X^1$, and $X^3$ have the same meaning as that defined herein above; $R^{11a}$, $R^{12a}$, and $R^{13a}$ are each independently selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety).

In certain preferred embodiments of the products (such as pharmaceutical formulations or FR-targeting excipients) or uses, as taught herein, the FR-targeting excipient may comprise at least one unit of Formula XIb, XIc, XId, XIe, XIg, XIh, XIj, XIk, XIm, XIn, XIp, or XIq, as taught herein, or any subgroup thereof, (preferably at least one unit of Formula XIb, XIg, or XIm as taught herein, or any subgroup thereof), and at least one unit of Formula Va, or a salt, hydrate or solvate thereof, wherein

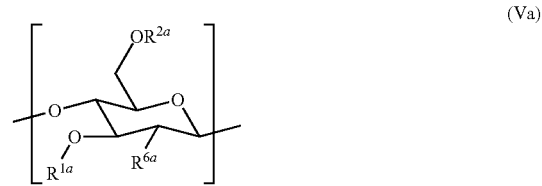

(Va)

$Y^1$, $R^1$, $R^2$, $Y^2$, $R^3$, $R^4$, $Y^3$, $R^{43}$, $R^{53}$, $X^4$, $R^{44}$, $R^{54}$, $R^{11}$, $R^{21}$, $R^{31}$, $R^{41}$, $R^{20}$, $X^1$, $X^3$, $R^{1a}$, $R^{2a}$, and $R^{6a}$ have the same meaning as that defined herein.

In certain preferred embodiments of the products (such as pharmaceutical formulations or FR-targeting excipients) or uses, as taught herein, the FR-targeting excipient may comprise at least one unit of Formula XIb, XIc, XId, XIe, XIg, XIh, XIj, XIk, XIm, XIn, XIp, or XIq, as taught herein, or any subgroup thereof, (preferably at least one unit of Formula XIb, XIg, or XIm as taught herein, or any subgroup thereof), and at least one unit of Formula VIa, VIIa, and/or VIIIa, a salt, hydrate or solvate thereof, wherein

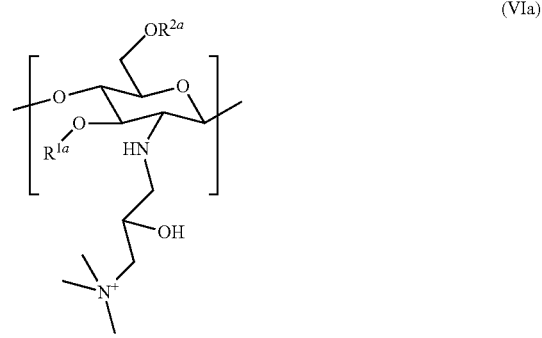

(VIa)

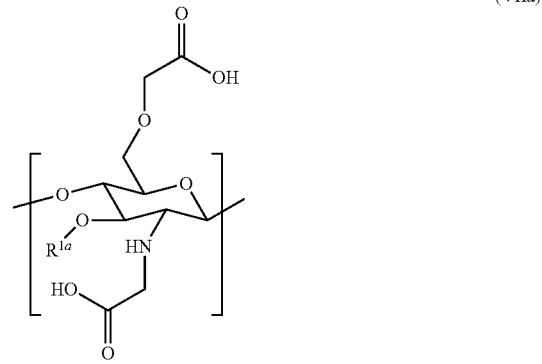

(VIIa)

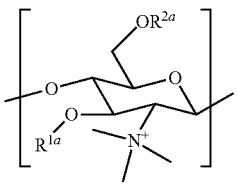

(VIIIa)

$Y^1$, $R^1$, $R^2$, $Y^2$, $R^3$, $R^4$, $Y^3$, $R^{43}$, $R^{53}$, $X^4$, $R^{44}$, $R^{54}$, $R^{11}$, $R^{21}$, $R^{31}$, $R^{41}$, $R^{20}$, $X^1$, $X^3$, $R^{1a}$ and $R^{2a}$ have the same meaning as that defined herein.

In certain preferred embodiments, the FR-targeting excipient may comprise at least one unit of Formula XIb, XIg, or XIm, as taught herein, or any subgroup thereof, (preferably at least one unit of Formula XIm as taught herein, or any subgroup thereof), and at least one unit of Formula Va, VIa, VIIa, or VIIIa, as taught herein, wherein $Y^1$, $R^1$, $R^2$, $R^{11}$, $R^{21}$, $X^1$, $X^3$, $R^{1a}$, $R^{2a}$ and $R^{6a}$ have the same meaning as that defined herein.

In certain embodiments, the FR-targeting excipient may be a folate-polysaccharide conjugate comprising at least one unit of Formula XIb, XIg, or XIm, as taught herein, or any subgroup thereof, (preferably at least one unit of Formula XIm as taught herein, or any subgroup thereof), and at least one unit of Formula Va, VIa, VIIa, or VIIIa, as taught herein, wherein $Y^1$ is —$X^2$—$X^1$—$X^3$, wherein
   $X^2$ is —NH—;
   $X^1$ is a linker of Formula X, as taught herein, wherein the left side of the linker of Formula X is attached to $X^2$ and the right side thereof is attached to $X^3$; wherein
      $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;
      $L^1$ is a polyethylene oxide having the Formula —(CH$_2$—CH$_2$—O)$_q$— or —(O—CH$_2$—CH$_2$)$_q$—, wherein q is an integer selected from 60 to 90;
      $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;
   $X^3$ is a folate moiety having the structural Formula XIId, as taught herein, wherein $Q^{222}$ is a single bond connected to $X^1$;

$R^1$ is —$OR^{11}$, wherein $R^{11}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^2$ is —$OR^{21}$, wherein $R^{21}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{1a}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{2a}$ is selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{6a}$ is selected from amino, ammonium, $-NHR^{8a}$, $-NR^{8a}R^{9a}$, or $-N^+R^{8a}R^{9a}R^{10a}$, wherein $R^{8a}$, $R^{9a}$, and $R^{10a}$ are each independently selected from a group consisting of methyl, ethyl, n-propyl, i-propyl, 2-hydroxypropylene-$N^+(CH_3)_3$, methylene-CO—OH, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the nitrogen to which it is bound a caprylic amide moiety), n-nonylcarbonyl (e.g. which may form together with the nitrogen to which it is bound a capric amide moiety), n-undecylcarbonyl (e.g. which may form together with the nitrogen to which it is bound a lauric amide moiety), n-tridecylcarbonyl (e.g. which may form together with the nitrogen to which it is bound a myristic amide moiety), n-pentadecylcarbonyl (e.g. which may form together with the nitrogen to which it is bound a palmitic amide moiety), n-heptadecylcarbonyl (e.g. which may form together with the nitrogen to which it is bound a stearic amide moiety), n-nonadecylcarbonyl (e.g. which may form together with the nitrogen to which it is bound an arachidic amide moiety), n-henicosylcarbonyl (e.g. which may form together with the nitrogen to which it is bound a behenic amide moiety), n-tricosylcarbonyl (e.g. which may form together with the nitrogen to which it is bound a lignoceric amide moiety), n-pentacosylcarbonyl (e.g. which may form together with the nitrogen to which it is bound a cerotic amide moiety), n-tridecenylcarbonyl (e.g. which may form together with the nitrogen to which it is bound a myristoleic amide), n-pentadecenylcarbonyl (e.g. which may form together with the nitrogen to which it is bound a palmitoleic amide moiety or sapienic amide moiety), n-heptadecenylcarbonyl (e.g. which may form together with the nitrogen to which it is bound an oleic amide moiety, elaidic amide moiety, vaccenic amide moiety, linoleic amide moiety, linoelaidic amide moiety, or oi-linolenic amide moiety), n-nonadecenylcarbonyl (e.g. which may form together with the nitrogen to which it is bound an arachidonic amide moiety or eicosapentaenoic amide moiety), or n-henicosenylcarbonyl (e.g. which may form together with the nitrogen to which it is bound an erucic amide moiety or docosahexaenoic amide moiety).

In certain preferred embodiments of the products (such as pharmaceutical formulations or FR-targeting excipients) or uses, as taught herein, the FR-targeting excipient may comprise at least one unit of Formula XIb, XIc, XId, XIe, XIg, XIh, XIj, XIk, XIm, XIn, XIp, or XIq, as taught herein, or any subgroup thereof, (preferably at least one unit of Formula XIn, XIp, and/or XIq, as taught herein, or any subgroup thereof), and at least one unit of Formula IXa, a salt, hydrate or solvate thereof, wherein

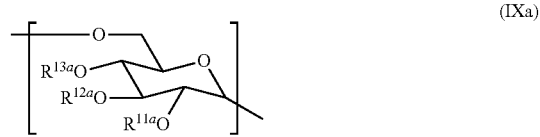

(IXa)

$Y^1$, $R^1$, $R^2$, $Y^2$, $R^3$, $R^4$, $Y^3$, $R^{43}$, $R^{53}$, $X^4$, $R^{44}$, $R^{54}$, $R^{11}$, $R^{21}$, $R^{31}$, $R^{41}$, $R^{20}$, $X^1$, $X^3$, $R^{11a}$, $R^{12a}$ and $R^{13a}$ have the same meaning as that defined herein.

In certain preferred embodiments, the FR-targeting excipient may comprise at least one unit of Formula XIc, XIh, XIj, XIk, XIn, XIp, or XIq, as taught herein, or any subgroup thereof, (preferably at least one unit of Formula XIn, XIp, and/or XIq, as taught herein, or any subgroup thereof), and at least one unit of Formula IXa, as taught herein, wherein $Y^2$, $R^3$, $R^4$, $R^{31}$, $R^{41}$, $R^{20}$, $X^1$, $X^3$, $R^{11a}$, $R^{12a}$, and $R^{13a}$ have the same meaning as that defined herein.

In certain preferred embodiments, the FR-targeting excipient may comprise at least one unit of Formula XIc, XIh, XIj, XIk, XIn, XIp, or XIq, as taught herein, or any subgroup thereof, (preferably at least one unit of Formula XIn, XIp, and/or XIq, as taught herein, or any subgroup thereof), and at least one unit of Formula IXa, as taught herein, wherein $Y^2$ is —$X^2$—$X^1$—$X^3$, or —$OR^{20}$,
$R^3$ is —$OR^{31}$ or —$X^2$—$X^1$—$X^3$,
$R^4$ is —$OR^{41}$ or —$X^2$—$X^1$—$X^3$,
wherein at least one of $Y^2$, $R^3$, or $R^4$ is —$X^2$—$X^1$—$X^3$;
wherein
$X^2$ is —O—;
$X^1$ is a linker of Formula X, as taught herein, wherein the left side of the linker of Formula X is attached to $X^2$ and the right side thereof is attached to $X^3$; wherein
   $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is attached to $X^2$, wherein $L^{14}$ is n-propylene; $L^{15}$, $L^{16}$, $L^{17}$, and $L^{18}$ are each independently ethylene;
   $L^1$ is a polyethylene oxide having the Formula —(CH$_2$—CH$_2$—O)$_q$— or —(O—CH$_2$—CH$_2$)$_q$—, wherein
   q is an integer selected from 60 to 90;
   $A^2$ is a single bond or is selected from a group consisting of —N(H)—, -$L^{19}$-N(H)—, or -$L^{20}$O—, wherein the left side of each group is attached to $L^1$ and the right side thereof is attached to $X^3$, wherein $L^{19}$ and $L^{20}$ are each independently ethylene;
$X^3$ is a folate moiety having the structural Formula XIId, as taught herein, wherein $Q^{222}$ is a single bond connected to $X^1$;
$R^{20}$ is selected from hydrogen, a mono-, oligo-, or polyglycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);
$R^{31}$ is selected from hydrogen, a mono-, oligo-, or polyglycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);
$R^{41}$ is selected from hydrogen, a mono-, oligo-, or polyglycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety);

$R^{11a}$, $R^{12a}$, and $R^{13a}$ are each independently selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic ester moiety), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety).

Such FR-targeting excipients advantageously allow interaction between the polysaccharide or functionally-modified polysaccharide as taught herein and the antineoplastic agents as taught herein (including hydrophilic antineoplastic agents as taught herein) and these interactions advantageously lead to a better entrapment and/or encapsulation of the antineoplastic agents as taught herein (including hydrophilic antineoplastic agents as taught herein) in the pharmaceutical formulations.

In certain embodiments, the FR-targeting excipient may comprise the folate moiety as taught herein. In certain embodiments, the FR-targeting excipient may comprise the folate moiety as taught herein covalently linked to a polysaccharide or functionally-modified polysaccharide.

The term "polysaccharide" generally refers to a polymer or macromolecule consisting of monosaccharide units joined together by glycosidic bonds. Polysaccharides may be linear or branched. The term "polysaccharide or functionally-modified polysaccharide" as used herein encompasses polysaccharides or functionally-modified polysaccharides containing a substantial proportion of amino sugar residues.

The terms "polysaccharide" and "polysaccharide moiety" may be used interchangeably herein.

The terms "functionally-modified polysaccharide" and "functionally-modified polysaccharide moiety" may be used interchangeably herein.

The polysaccharide or functionally-modified polysaccharide as taught herein may comprise from about 20 to about 5000 monosaccharide units, such as from about 30 to about 4000 monosaccharide units, from about 40 to about 3000 monosaccharide units, or from about 40 to about 2500 monosaccharide units. The term "functionally-modified polysaccharide" as used herein refers to a polysaccharide wherein one or more of the functional groups are chemically modified, such as for example in order to alter one or more of the chemical or physical properties of the polysaccharide.

The functionally-modified polysaccharide may comprise a polysaccharide wherein one or more functional groups such as hydroxyl groups (e.g. in glucose units or galactose units) or amine groups (e.g. in glucosamine units or galactosamine units) of one or more monosaccharide units are functionally modified.

The functionally-modified polysaccharide may comprise a polysaccharide wherein one or more functional groups such as hydroxyl groups (e.g. in glucose units or galactose units) or amine groups (e.g. in glucosamine units or galactosamine units) of one or more monosaccharide units are modified to alter, such as increase or decrease, the hydrophobicity of the polysaccharide.

The functionally-modified polysaccharide may comprise a polysaccharide wherein one or more functional groups such as hydroxyl groups (e.g. in glucose units or galactose units) or amine groups (e.g. in glucosamine units or galactosamine units) of one or more monosaccharide units are modified to increase the hydrophobicity of the polysaccharide.

The functional modification may comprise modifying one or more functional groups, such as hydroxyl groups (e.g. in glucose units or galactose units), amine groups (e.g. in glucosamine units or galactosamine units), or hydroxyl groups and amine groups (e.g. in glucosamine units or galactosamine units), of one or more monosaccharide units of the polysaccharide to alter, such as increase or decrease, the hydrophobicity of the polysaccharide. The functional modification may comprise modifying one or more functional groups, such as hydroxyl groups (e.g. in glucose units or galactose units) and/or amine groups (e.g. in glucosamine units or galactosamine units), of one or more monosaccharide units of the polysaccharide to increase the hydrophobicity of the polysaccharide.

The term "hydrophobicity" generally refers to the physical property of a molecule to be repelled from a mass of water.

In certain embodiments, the functionally-modified polysaccharide may be a hydrophobically-modified polysaccharide.

The recitation "hydrophobically-modified polysaccharide" as used herein refers to a polysaccharide wherein one or more functional groups are modified to increase the hydrophobicity of the polysaccharide. The hydrophobicity of a polysaccharide may be appreciated by the determination of the graft ratio of the (hydrophobic) functional groups on the polysaccharide chains (such as by the determination of the fatty acid graft ratio as defined herein), by the wettability of the polysaccharide powder, or by the ability to dissolve in aqueous media.

The functionally-modified polysaccharide may comprise a polysaccharide wherein one or more functional groups such as hydroxyl groups (e.g. in glucose units or galactose units) and/or amine groups (e.g. in glucosamine units or galactosamine units) of one or more monosaccharide units are modified with a saturated or unsaturated fatty acid (e.g., esterification of a hydroxyl group and/or an amidation of an amino group) to alter, such as increase or decrease, the hydrophobicity of the polysaccharide.

The functionally-modified polysaccharide may comprise a polysaccharide wherein the hydrogen atom of a hydroxyl group or one or more hydrogen atoms of an amine group of one or more monosaccharide units of the polysaccharide are replaced by a group consisting of $C_{1-25}$alkyl, $C_{1-6}$alkylene-$N(R^{111})R^{112}$, $C_{1-6}$alkylene-$N^+(R^{111})(R^{112})R^{113}$, $C_{1-25}$alkylcarbonyl, $C_{2-25}$alkenylcarbonyl, $C_{1-6}$alkylene-CO—$OR^{114}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl; preferably a group consisting of $C_{1-6}$alkyl, $C_{1-4}$alkylene-$N(R^{111})R^{112}$, $C_{1-4}$alkylene-$N^+(R^{111})(R^{112})R^{113}$, $C_{1-25}$alkylcarbonyl, $C_{3-25}$alkenylcarbonyl, $C_{1-4}$alkylene-CO—$OR^{114}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{111}$ is selected from hydrogen or $C_{1-4}$alkyl, $R^{112}$ is selected from hydrogen or $C_{1-4}$alkyl, $R^{113}$ is selected from hydrogen or $C_{1-4}$alkyl, and $R^{114}$ is selected from hydrogen or $C_{1-4}$alkyl; preferably a group consisting of $C_{1-4}$alkyl, $C_{1-3}$alkylene-$N(R^{111})R^{112}$, $C_{1-3}$alkylene-$N^+(R^{111})(R^{112})R^{113}$, $C_{1-25}$alkylcarbonyl, $C_{5-25}$alkenylcarbonyl, $C_{1-3}$alkylene-CO—$OR^{114}$, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy, wherein $R^{111}$ is selected from hydrogen or $C_{1-3}$alkyl, $R^{112}$ is selected from hydrogen or $C_{1-3}$alkyl, $R^{113}$ is selected from hydrogen or $C_{1-3}$alkyl, and $R^{114}$ is selected from hydrogen or $C_{1-3}$alkyl; preferably a group consisting of $C_{1-3}$alkyl, $C_{1-3}$alkylene-$N(R^{111})R^{112}$, $C_{1-3}$alkylene-$N^+(R^{111})(R^{112})R^{113}$, $C_{1-25}$alkylcarbonyl, $C_{13-25}$alkenylcarbonyl, and $C_{1-3}$alkylene-CO—$OR^{114}$, each group being optionally substituted with one or more substituents each independently selected from hydroxyl, halogen, $C_{1-3}$alkyl, or $C_{1-3}$alkoxy, wherein $R^{111}$ is selected from hydrogen or $C_{1-3}$alkyl, $R^{112}$ is selected from hydrogen or $C_{1-3}$alkyl, $R^{113}$ is selected from hydrogen or $C_{1-3}$alkyl, and $R^{114}$ is selected from hydrogen or $C_{1-3}$alkyl; preferably a group consisting of methyl, ethyl, n-propyl, i-propyl, methylene-$N(R^{111})R^{112}$, ethylene-$N(R^{111})R^{112}$, n-propylene-$N(R^{111})R^{112}$, methylene-$N^+(R^{111})(R^{112})R^{113}$, ethylene-$N^+(R^{111})(R^{112})R^{113}$, n-propylene-$N^+(R^{111})(R^{112})R^{113}$, methyleneCO—$OR^{114}$, ethyleneCO—$OR^{114}$, n-propyleneCO—$OR^{114}$, $C_{1-25}$alkylcarbonyl, and, $C_{13-25}$alkenylcarbonyl, each group being optionally substituted with one or more substituents each independently selected from hydroxyl, halogen, methyl, or ethyl, wherein $R^{111}$ is selected from hydrogen, methyl, or ethyl, $R^{112}$ is selected from hydrogen, methyl, or ethyl, $R^{113}$ is selected from hydrogen, methyl, or ethyl, and $R^{114}$ is selected from hydrogen, methyl, or ethyl; preferably a group consisting of methyl, ethyl, n-propyl, i-propyl, methylene-$N^+(R^{111})(R^{112})R^{113}$, ethylene-$N^+(R^{111})(R^{112})R^{113}$, n-propylene-$N^+(R^{111})(R^{112})R^{113}$, methylene-CO—$OR^{114}$, ethylene-CO—$OR^{114}$, n-propylene-CO—$OR^{114}$, $C_{1-25}$alkylcarbonyl, and, $C_{13-25}$alkenylcarbonyl, each group being optionally substituted with one or more substituents each independently selected from hydroxyl or methyl, wherein $R^{111}$ is selected from hydrogen or methyl, $R^{112}$ is selected from hydrogen or methyl, $R^{113}$ is selected from hydrogen or methyl, and $R^{114}$ is selected from hydrogen or methyl; preferably a group consisting of methyl, ethyl, n-propyl, i-propyl, 2-hydroxy-propylene-$N^+(CH_3)_3$, methylene-CO—OH, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety, or which may form together with the nitrogen to which it is bound a caprylic amide moiety), n-nonylcarbonyl (e.g. which may form together with the oxygen to which it is bound a capric ester moiety, or which may form together with the nitrogen to which it is bound a capric amide moiety), n-undecylcarbonyl (e.g. which may form together with the oxygen to which it is bound a lauric ester moiety, or which may form together with the nitrogen to which it is bound a lauric amide moiety), n-tridecylcarbonyl (e.g. which may form together with the oxygen to which it is bound a myristic ester moiety, or which may form together with the nitrogen to which it is bound a myristic amide moiety), n-pentadecylcarbonyl (e.g. which may form together with the oxygen to which it is bound a palmitic ester moiety, or which may form together with the nitrogen to which it is bound a palmitic amide moiety), n-heptadecylcarbonyl (e.g. which may form together with the oxygen to which it is bound a stearic ester moiety, or which may form together with the nitrogen to which it is bound a stearic amide moiety), n-nonadecylcarbonyl (e.g. which may form together with the oxygen to which it is bound an arachidic ester moiety, or which may form together with the nitrogen to which it is bound an arachidic amide moiety), n-henicosylcarbonyl (e.g. which may form together with the oxygen to which it is bound a behenic ester moiety, or which may form together with the nitrogen to which it is bound a behenic amide moiety), n-tricosylcarbonyl (e.g. which may form together with the oxygen to which it is bound a lignoceric ester moiety, or which may form together with the nitrogen to which it is bound a lignoceric amide moiety), n-pentacosylcarbonyl (e.g. which may form together with the oxygen to which it is bound a cerotic ester moiety, or which may form together with the nitrogen to which it is bound a cerotic amide moiety), n-tridecenylcarbonyl (e.g. which may form together with the oxygen to which it is bound a myristoleic ester moiety, or which may form together with the nitrogen to which it is bound a myristoleic amide moiety), n-pentadecenylcarbonyl (e.g. which may form together with the oxygen to which it is bound a palmitoleic ester moiety or sapienic ester moiety, or which may form together with the nitrogen to which it is bound a palmitoleic amide moiety or sapienic amide moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety, or which may form together with the nitrogen to which it is bound an oleic amide moiety, elaidic amide moiety, vaccenic amide moiety, linoleic amide moiety, linoelaidic amide moiety, or α-linolenic amide moiety), n-nonadecenylcarbonyl (e.g. which may form together with the oxygen to which it is bound an arachidonic ester moiety or eicosapentaenoic ester moiety, or which may form together with the nitrogen to which it is bound an arachidonic amide moiety or eicosapentaenoic amide moiety), or n-henicosenylcarbonyl (e.g. which may form together with the oxygen to which it is bound an erucic ester moiety or docosahexaenoic ester moiety, or which may form together with the nitrogen to which it is bound an erucic amide moiety or docosahexaenoic amide moiety) to alter, such as increase or decrease, the hydrophobicity of the polysaccharide.

The functional modification may comprise modifying one or more functional groups, such as one or more hydroxyl groups or one or more amine groups, of one or more monosaccharide units of the polysaccharide with a saturated or unsaturated fatty acid (e.g., esterification of a hydroxyl group or an amidation of an amino group), or replacing the hydrogen atom of a hydroxyl group or one or more hydrogen atoms of an amine group of one or more monosaccharide units of the polysaccharide by a group consisting of a group consisting of $C_{1-25}$alkyl, $C_{1-6}$alkylene-N($R^{111}$)$R^{112}$, $C_{1-6}$alkylene-N$^+$($R^{111}$)($R^{112}$)$R^{113}$, $C_{1-25}$alkylcarbonyl, $C_{2-25}$alkenylcarbonyl, $C_{1-6}$alkylene-CO—O$R^{114}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{111}$ is selected from hydrogen or $C_{1-6}$alkyl, $R^{112}$ is selected from hydrogen or $C_{1-6}$alkyl, $R^{113}$ is selected from hydrogen or $C_{1-6}$alkyl, and $R^{114}$ is selected from hydrogen or $C_{1-6}$alkyl; preferably a group consisting of $C_{1-6}$alkyl, $C_{1-4}$alkylene-N($R^{111}$)$R^{112}$, $C_{1-4}$alkylene-N$^+$($R^{111}$)($R^{112}$)$R^{113}$, $C_{1-25}$alkylcarbonyl, $C_{3-25}$alkenylcarbonyl, $C_{1-4}$alkylene-CO—O$R^{114}$, carboxyl$C_{1-4}$alkylenecarbonyl, hydroxy$C_{1-4}$alkyl, carboxyl$C_{6-10}$arylenecarbonyl, $C_{2-4}$alkenyl, and $C_{2-4}$alkynyl, each group being optionally substituted with one or more substituents each independently selected from hydroxyl, halogen, $C_{1-4}$alkyl, or $C_{1-4}$alkoxy, wherein $R^{111}$ is selected from hydrogen or $C_{1-4}$alkyl, $R^{112}$ is selected from hydrogen or $C_{1-4}$alkyl, $R^{113}$ is selected from hydrogen or $C_{1-4}$alkyl, and $R^{114}$ is selected from hydrogen or $C_{1-4}$alkyl; preferably a group consisting of $C_{1-4}$alkyl, $C_{1-3}$alkylene-N($R^{111}$)$R^{112}$, $C_{1-3}$alkylene-N$^+$($R^{111}$)($R^{112}$)$R^{113}$, $C_{1-25}$alkylcarbonyl, $C_{5-25}$alkenylcarbonyl, $C_{1-3}$alkylene-CO—O$R^{114}$, carboxyl$C_{1-3}$alkylenecarbonyl, hydroxy$C_{1-3}$alkyl, $C_{2-3}$alkenyl, and $C_{2-3}$alkynyl, each group being optionally substituted with one or more substituents each independently selected from hydroxyl, halogen, $C_{1-3}$alkyl, or $C_{1-3}$alkoxy, wherein $R^{111}$ is selected from hydrogen or $C_{1-3}$alkyl, $R^{112}$ is selected from hydrogen or $C_{1-3}$alkyl, $R^{113}$ is selected from hydrogen or $C_{1-3}$alkyl, and $R^{114}$ is selected from hydrogen or $C_{1-3}$alkyl; preferably a group consisting of $C_{1-3}$alkyl $C_{1-3}$alkylene-N($R^{111}$)$R^{112}$, $C_{1-3}$alkylene-N$^+$($R^{111}$)($R^{112}$)$R^{113}$, $C_{1-25}$alkylcarbonyl, $C_{13-25}$alkenylcarbonyl, and $C_{1-3}$alkyleneCO—O$R^{114}$, each group being optionally substituted with one or more substituents each independently selected from hydroxyl, halogen, $C_{1-3}$alkyl, or $C_{1-3}$alkoxy, wherein $R^{111}$ is selected from hydrogen or $C_{1-3}$alkyl, $R^{112}$ is selected from hydrogen or $C_{1-3}$alkyl, $R^{113}$ is selected from hydrogen or $C_{1-3}$alkyl, and $R^{114}$ is selected from hydrogen or $C_{1-3}$alkyl; preferably a group consisting of methyl, ethyl, n-propyl, i-propyl, methylene-N($R^{111}$)$R^{112}$, ethylene-N($R^{111}$)$R^{112}$, n-propylene-N($R^{111}$)$R^{112}$, methylene-N$^+$($R^{111}$)($R^{112}$)$R^{113}$, ethylene-N$^+$($R^{111}$)($R^{112}$)$R^{113}$, n-propylene-N$^+$($R^{111}$)($R^{112}$)$R^{113}$, methylene-CO—O$R^{114}$, ethylene-CO—O$R^{114}$, n-propylene-CO—O$R^{114}$, $C_{1-25}$alkylcarbonyl, and, $C_{13-25}$alkenylcarbonyl, each group being optionally substituted with one or more substituents each independently selected from hydroxyl, halogen, methyl, or ethyl, wherein $R^{111}$ is selected from hydrogen, methyl, or ethyl, $R^{112}$ is selected from hydrogen, methyl, or ethyl, $R^{113}$ is selected from hydrogen, methyl, or ethyl, and $R^{114}$ is selected from hydrogen, methyl, or ethyl; preferably a group consisting of methyl, ethyl, n-propyl, i-propyl, methylene-N$^+$($R^{111}$)($R^{112}$)$R^{113}$, ethylene-N$^+$($R^{111}$)($R^{112}$)$R^{113}$, n-propylene-N$^+$($R^{111}$)($R^{112}$)$R^{113}$, methylene-CO—O$R^{114}$, ethylene-CO—O$R^{114}$, n-propylene-CO—O$R^{114}$, $C_{1-25}$alkylcarbonyl, and, $C_{13-25}$alkenylcarbonyl, each group being optionally substituted with one or more substituents each independently selected from hydroxyl or methyl, wherein $R^{111}$ is selected from hydrogen or methyl, $R^{112}$ is selected from hydrogen or methyl, $R^{113}$ is selected from hydrogen or methyl, and $R^{114}$ is selected from hydrogen or methyl; preferably a group consisting of methyl, ethyl, n-propyl, i-propyl, 2-hydroxy-propylene-N$^+$($CH_3$)$_3$, methylene-CO—OH, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety, or which may form together with the nitrogen to which it is bound a caprylic amide moiety), n-nonylcarbonyl (e.g. which may form together with the oxygen to which it is bound a capric ester moiety, or which may form together with the nitrogen to which it is bound a capric amide moiety), n-undecylcarbonyl (e.g. which may form together with the oxygen to which it is bound a lauric ester moiety, or which may form together with the nitrogen to which it is bound a lauric amide moiety), n-tridecylcarbonyl (e.g. which may form together with the oxygen to which it is bound a myristic ester moiety, or which may form together with the nitrogen to which it is bound a myristic amide moiety), n-pentadecylcarbonyl (e.g. which may form together with the oxygen to which it is bound a palmitic ester moiety, or which may form together with the nitrogen to which it is bound a palmitic amide moiety), n-heptadecylcarbonyl (e.g. which may form together with the oxygen to which it is bound a stearic ester moiety, or which may form together with the nitrogen to which it is bound a stearic amide moiety), n-nonadecylcarbonyl (e.g. which may form together with the oxygen to which it is bound an arachidic ester moiety, or which may form together with the nitrogen to which it is bound an arachidic amide moiety), n-henicosylcarbonyl (e.g. which may form together with the oxygen to which it is bound a behenic ester moiety, or which may form together with the nitrogen to which it is bound a behenic amide moiety), n-tricosylcarbonyl (e.g. which may form together with the oxygen to which it is bound a lignoceric ester moiety, or which may form together with the nitrogen to which it is bound a lignoceric amide moiety), n-pentacosylcarbonyl (e.g. which may form together with the oxygen to which it is bound a cerotic ester moiety, or which may form together with the nitrogen to which it is bound a cerotic amide moiety), n-tridecenylcarbonyl (e.g. which may form together with the oxygen to which it is bound a myristoleic ester moiety, or which may form together with the nitrogen to which it is bound a myristoleic amide moiety), n-pentadecenylcarbonyl (e.g. which may form together with the oxygen to which it is bound a palmitoleic ester moiety or sapienic ester moiety, or which may form together with the nitrogen to which it is bound a palmitoleic amide moiety or sapienic amide moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety, or which may form together with the nitrogen to which it is bound an oleic amide moiety, elaidic amide moiety, vaccenic amide moiety, linoleic amide moiety, linoelaidic amide moiety, or oi-linolenic amide moiety), n-nonadecenylcarbonyl (e.g. which may form together with the oxygen to which it is bound an arachidonic ester moiety or eicosapentaenoic ester moiety, or which may form together with the nitrogen to which it is bound an arachidonic amide moiety or eicosapentaenoic amide moiety), or n-henicosenylcarbonyl (e.g. which may form together with the oxygen to which it is bound an erucic ester moiety or docosahexaenoic ester moiety, or which may form together with the nitrogen to which it is bound an erucic amide moiety or docosahexaenoic amide moiety); to increase the hydrophobicity of the polysaccharide.

In certain embodiments, the proportion of functional modification of a functionally-modified polysaccharide may be from about 1% to about 100%. For instance, the proportion of functional modification of a functionally-modified polysaccharide may be from about 1% to about 80%, from about 5% to about 70%, from about 10% to about 60%, or from about 15% to about 50%. For instance, the proportion of functional modification of a functionally-modified polysaccharide may be at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 30%, at least about 50%, at least about 70%, or at least about 90%.

The recitation "proportion of functional modification" or "degree of functional modification" of a compound (i.e., functionally-modified polysaccharide in a folate-polysaccharide conjugate), as used herein, refers to the relative abundance of a functionally-modified functional group (such as hydroxyl group and/or amine group) in the compound (i.e., functionally-modified polysaccharide) divided by the relative abundance of the functional groups (i e, unmodified and functionally-modified functional groups) in the compound (i.e., functionally-modified polysaccharide), suitably expressed as a percentage. The proportion of functional modification corresponds to the percentage of functional groups of the functionally-modified polysaccharide which are functionally modified. The proportion of functional modification may be measured by $^1$H-NMR.

In certain embodiments, the fatty acid graft ratio (FA-GR) of a FR-targeting excipient may be at least about 1%. For example, the FA-GR of a FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%. For example, the FA-GR of a FR-targeting excipient may be ranging from about 1 to about 100%, from about 1% to about 80%, from about 5% to about 70%, from about 10% to about 60%, or from about 15% to about 50%.

The recitation "fatty acid graft ratio" or "FA-GR" of a compound (i.e., FR-targeting excipient), as used herein, refers to the relative abundance of a fatty acid in the compound (i.e., FR-targeting excipient) divided by the relative abundance of functional groups (i e, unmodified and functionally-modified functional groups) of a polysaccharide (i.e., functionally-modified polysaccharide) in the compound (i.e., FR-targeting excipient), suitably expressed as a percentage. The FA-GR corresponds to the percentage of functional groups of the functionally-modified polysaccharide which are linked to a fatty acid. The fatty acid-graft ratio (FA-GR) may be determined by $^1$H NMR (for example in DMSO-d6 at 293 K). The fatty acid graft ratio may be determined by $^1$H NMR and calculated using a suitable equation. For example, the fatty acid graft ratio of HMD may be calculated using equation (2):

$$FA-GR(\%) = 100 \times \frac{[(CH_3)FA]}{9 \times [(CHO)GLC]} \qquad (2)$$

wherein "[(CH$_3$)FA]" is the integral of proton peak of the fatty acid at 0.85 ppm (CH$_3$CH$_2$) and "[(CHO)GLC]" is the integral of the peak of glucose monomer at 4.68 ppm (CHO), "9" is the number of H$^+$ in CH$_3$ (i.e., 3) multiplied by the number of hydroxyl group per glucose unit (i.e., 3).

In certain embodiments, the polysaccharide or functionally-modified polysaccharide may have a molecular weight ranging from about 1 kDa to about 500 kDa. For instance, the polysaccharide or functionally-modified polysaccharide may have a molecular weight ranging from about 5 kDa to about 500 kDa, from about 10 kDa to about 450 kDa, from about 50 kDa to about 400 kDa, from about 90 kDa to about 310 kDa, or from about 100 kDa to about 300 kDa. For instance, the polysaccharide or functionally-modified polysaccharide may have a molecular weight of at least about 1 kDa, at least about 5 kDa, at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 150 kDa, at least about 200 kDa, at least about 250 kDa, or at least about 300 kDa.

The terms "molecular weight" or "molecular mass", as used herein, refer to the mass of a molecule. The molecular mass can be measured directly using mass spectrometry.

In certain embodiments of the products (such as pharmaceutical formulations or FR-targeting excipients), uses, or methods, as taught herein, the polysaccharide or functionally-modified polysaccharide may be selected from chitosan or functionally-modified chitosan; N-[(2-hydroxy-3-trimethylammonium)propyl] chitosan (HTC) and its salts (such as chloride, acetate, glutamate, or lactate salts) for example HTCC (i.e., chloride salt); N-trimethyl chitosan (TMC) and its salts (such as chloride, acetate, glutamate, or lactate salts); N,O-carboxymethyl chitosan (N,O-CMC) and its salts (such as chloride, acetate, glutamate, or lactate salts); N-carboxymethyl chitosan (N-CMC) and its salts (such as chloride, acetate, glutamate, or lactate salts); N,N-carboxymethyl chitosan (NN-CMC) and its salts (such as chloride, acetate, glutamate, or lactate salts); O-carboxymethyl chitosan (O-CMC) and its salts (such as chloride, acetate, glutamate, or lactate salts); hydrophobically-modified chitosan (HMC) and its salts (such as chloride, acetate, glutamate, or lactate salts); dextran or functionally-modified dextran; hydrophobically-modified dextran (HMD) and its salts (such as chloride, acetate, glutamate, or lactate salts); starch or functionally-modified starch; hydroxypropyl starch; amylose or functionally-modified amylose; amylopectin or functionally-modified amylopectin; cellulose or functionally-modified cellulose; methylcellulose and its salts (such as acetate or acetate phthalate salts); carboxymethylcellulose and its salts (such as acetate or acetate phthalate salts); hydroxyethylcellulose and its salts (such as acetate or acetate phthalate salts); ethylcellulose and its salts (such as acetate or acetate phthalate salts); hydroxyethylmethylcellulose and its salts (such as acetate or acetate phthalate salts); hydroxypropylcellulose and its salts (such as acetate or acetate phthalate salts); hypromellose and its salts (such as acetate or acetate phthalate salts); hypromellose acetate succinate; hypromellose phthalate; croscarmellose and its salts (such as acetate or acetate phthalate salts); chitin; cyclodextrin; dextrate; dextrin; maltodextrin; pullulan; or guar gum. In certain embodiments of the products (such as pharmaceutical formulations or FR-targeting excipients) or uses, as taught herein, the polysaccharide or functionally-modified polysaccharide may be selected from chitosan or functionally-modified chitosan; HTC and its salts (such as chloride, acetate, glutamate, or lactate salts) for example HTCC (i.e. chloride salt); TMC and its salts (such as chloride, acetate, glutamate, or lactate salts); N,O-CMC and its salts (such as chloride, acetate, glutamate, or lactate salts); N-CMC and its salts (such as chloride, acetate, glutamate, or lactate salts); N,N-CMC and its salts (such as chloride, acetate, glutamate, or lactate salts); O-CMC and its salts (such as chloride, acetate, glutamate, or lactate salts); HMC and its salts (such as chloride, acetate, glutamate, or lactate salts); dextran or functionally-modified dextran; and HMD and its salts (such as chloride, acetate, glutamate, or lactate salts).

In certain embodiments of the products (such as pharmaceutical formulations or FR-targeting excipients) or uses, as taught herein, the polysaccharide or functionally-modified polysaccharide may be selected from the group consisting of chitosan; HTCC; HTC and its acetate, glutamate, or lactate salts; TMC and its chloride, acetate, glutamate, or lactate salts; N,O-CMC and its chloride, acetate, glutamate, or lactate salts; N-CMC and its chloride, acetate, glutamate, or lactate salts; N,N-CMC and its chloride, acetate, glutamate, or lactate salts; O-CMC and its chloride, acetate, glutamate, or lactate salts; HMC and its chloride, acetate, glutamate, or lactate salts; dextran; and HMD and its chloride, acetate, glutamate, or lactate salts.

Advantageously, the present inventors have found that such polysaccharides or functionally-modified polysaccharides, in particular hydrophobically-modified polysaccharides, allow the formation of nanoparticles with good stability and physical integrity after administration in vivo and at the same time display a desired rate of dissolution once in contact with physiological media. Also, the polysaccharides or functionally-modified polysaccharides, in particular hydrophobically-modified polysaccharides, as taught herein, display bioadhesive properties and/or present a long time of retention in the respiratory tract retaining the present pharmaceutical formulations in the respiratory tract.

Additionally, the present inventors have surprisingly found that the polysaccharides or functionally-modified polysaccharides are able to interact with the antineoplastic agents (including hydrophilic antineoplastic agents) and these interactions advantageously lead to a better entrapment and/or encapsulation of the antineoplastic agents in the pharmaceutical formulations. Hence, using such polysaccharides or functionally-modified polysaccharides allows high drug encapsulation efficiency and drug loading.

The term "chitosan" generally refers to a linear polysaccharide composed of randomly distributed β-(1,4)-linked D-glucosamine (deacetylated unit) and N-acetyl-D-glucosamine (acetylated unit).

In certain embodiments, the chitosan may have a molecular weight ranging from about 1 kDa to about 500 kDa. For instance, the chitosan may have a molecular weight ranging from about 5 kDa to about 500 kDa, from about 10 kDa to about 450 kDa, from about 50 kDa to about 400 kDa, from about 90 kDa to about 310 kDa, or from about 100 kDa to about 300 kDa. For instance, the chitosan may have a molecular weight ranging of at least about 1 kDa, at least about 5 kDa, at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 150 kDa, at least about 200 kDa, at least about 250 kDa, or at least about 300 kDa.

The term "HTCC" or "N-[(2-hydroxy-3-trimethylammonium)propyl] chitosan chloride" as used herein refers to functionally-modified chitosan, wherein one or more D-glucosamine and/or N-acetyl-D-glucosamine units are modified to, replaced by, or substituted by a functionally-modified monosaccharide unit having the structural Formula XIII.

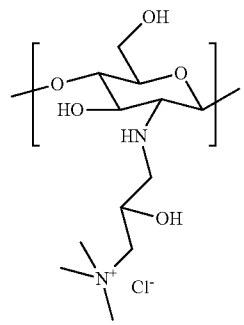

(XIII)

The proportion of substitution of HTCC may be from about 1% to about 100%. For instance, the proportion of substitution of HTCC may be from about 5% to about 99%, from about 10% to about 90%, from about 15% to about 80%, from about 20% to about 70%, from about 25% to about 60%, or from about 30% to about 50%. Preferably, the proportion of substitution of HTCC is from about 20% to about 40%. For instance, the proportion of substitution of HTCC may be at least about 1%, at least about 10%, at least about 20%, at least about 30%, at least about 50%, at least about 70%, or at least about 90%. The proportion of substitution of HTCC may be measured by $^1$H-NMR.

The recitation "proportion of substitution" or "degree of substitution" of a compound (i.e., functionally-modified polysaccharide in a folate-polysaccharide conjugate), as used herein, refers to the relative abundance of a functionally-modified monosaccharide unit in the compound (i.e., functionally-modified polysaccharide) divided by the relative abundance of the monosaccharide units (i e, unmodified and functionally-modified monosaccharide units) in the compound (i.e., functionally-modified polysaccharide), suitably expressed as a percentage. The proportion of substitution corresponds to the percentage of monosaccharide units of the functionally-modified polysaccharide which are substituted by a functionally-modified monosaccharide unit. The proportion of substitution may be measured by $^1$H-NMR.

The degree of acetylation of HTCC may be from about 1% to about 100%. For instance, the degree of acetylation of HTCC may be from about 5% to about 99%, from about 10% to about 90%, from about 15% to about 80%, from about 20% to about 70%, from about 25% to about 60%, or from about 30% to about 50%. Preferably, the degree of acetylation of HTCC may be from about 10% to about 30%, such as about 20%. The degree of acetylation may be measured by $^1$H-NMR, as known in the art.

In certain embodiments, the HTCC may have a molecular weight ranging from about 1 kDa to about 500 kDa. For instance, the HTCC may have a molecular weight ranging from about 5 kDa to about 500 kDa, from about 10 kDa to about 450 kDa, from about 50 kDa to about 400 kDa, from about 90 kDa to about 310 kDa, or from about 100 kDa to about 300 kDa. For instance, the HTCC may have a molecular weight ranging of at least about 1 kDa, at least about 5 kDa, at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 150 kDa, at least about 200 kDa, at least about 250 kDa, or at least about 300 kDa. By means of example, the HTCC may have a molecular weight ranging from about 50 kDa to about 150 kDa, such as from about 70 kDa to about 120 kDa, for example about 80 kDa, about 90 kDa, about 100 kDa, or about 110 kDa.

Exemplary non-limiting methods for the preparation of HTCC are described hereunder. For instance, HTCC is prepared by a modified method of Lim and Hudson (*Carbohydr. Res.*, 339, 313, 2004) as disclosed in Xiao et al. (*Colloids and Surfaces B: Biointerfaces* 91 168-174, 2012). In the modified method, 3 g of chitosan powder is suspended in 30 mL of deionized water. Chitosan can be obtained by highly deacetylating chitin following a known method (Mima et al., *J. Appl. Polym. Sci.* 28, 2003). In brief, chitin can be prepared from shells of the crab, *Chionoecetes oplio*. The shells are cut into pieces with the longest side of <2-5 cm only to facilitate treatment in a reaction beaker. The shell pieces are cleansed from proteins and lipids by treatment for 3 h in 1N NaOH solution at about 80° C. and washing in water. They are then digested for 12 h in 1N HCl solution at room temperature. The alkali and acid treatments are repeated twice. The chitin is decolorized by refluxing in acetone. The obtained product is snow-white and the ash content is <0.17%. In brief, chitosan can be prepared from chitin as follows. The chitin is treated for 1 (or 2) h in 47% NaOH solution in a Ni crucible at 110° C. (or 600 C) under nitrogen atmosphere, without making the sample pieces smaller. The chitosan product obtained by the alkali treatment is washed in water at about 80° C. to neutrality, the deacetylation being about 80% or less by the first treatment. The chitosan after being washed in water is treated again in the alkaline solution for further deacetylation. The alkali treatment and washing in water are repeated two or more times to obtain chitosan products which are 90-95% deacetylated. For even further deacetylation, threadlike chitosan is prepared by pouring a 1.5-2% chitosan aqueous solution containing 2% acetic acid in a small stream into a large amount of 1N NaOH solution. The threadlike chitosan is then subjected to alkali treatment. The mixture of chitosan powder in deionized water is stirred for 30 min prior to dropwise addition of Glycidyl trimethylammonium chloride (GTMAC) with continuous stirring. GTMAC can be obtained from Fluka (Buchs, Switzerland). The weight ratio of GTMAC to chitosan can be changed from 0.6:1 to 1.8:1 to produce HTCC with a degree of quaternization (DQ) (as measured by conductometric titration and data are quoted as mean±S.D, n=3) of 12.4%±1.2%, 28.1%±3.7%, 43.7%±2.5V, respectively. The reaction mixture is stirred at 85° C. for 6 h. After being precipitated and washed by hot alcohol, the product is collected by filtration. The collected polymer is dissolved in distilled water and dialyzed (MWCO=3500) against distilled water for 5 days and can be lyophilized.

As an exemplary alternative, the original method of Lim and Hudson describes that HTCC is prepared by a modified method of Lang et al. (U.S. Pat. No. 4,921,949, 1990). In brief, deacetylated chitosan (6 g, 37.0 mmol) is dispersed in distilled water (60 mL) at 85° C. GTMAC (21.3 mL, 111 mmol, purchased from Fluka Chemical Co.) is added in three portions (7.1 mL each) at 2-h intervals. After 10 h of reaction, the clear and yellowish reaction solution is poured into cold acetone (200 mL) while stirring and kept in the refrigerator overnight. The next day, acetone is decanted and the remaining gel-like product is dissolved in MeOH (100 mL). The solution is precipitated in 4:1 acetone-ethanol (250 mL). The white product is collected by filtration and further purified by washing with hot EtOH using a Soxhlet extractor for 24 h. The final product is dried at 70° C. overnight. In the method of Lim and Hudson, Chitosan (from crab shells) as a ground form with a low molecular weight can be purchased from Korea Chitosan Co., Ltd. For deacetylation of chitosan, chitosan (20 g) is dispersed in 200 mL of 10% (w/w) NaOH solution containing NaBH4 (2 g) as an antioxidant. After 5 h of stirring at 110° C., the mixture is filtered over a glass filter and washed with distilled water until neutral to pH paper. The chitosan is further washed with MeOH and acetone and dried at 70° C. under vacuum overnight.

As another exemplary alternative, HTCC is prepared by the method of Lang et al. (U.S. Pat. No. 4,921,949, 1990).

HTCC may be denotes as CAS 106602-18-0.

The term "TMC", "N-trimethyl chitosan", or "N,N,N-trimethyl chitosan" as used herein refers to functionally-modified chitosan wherein one or more D-glucosamine and/or N-acetyl-D-glucosamine units are modified to, replaced by, or substituted by a functionally-modified monosaccharide unit having the structural Formula XIV.

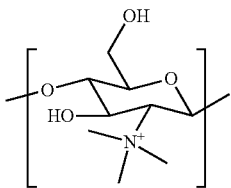
(XIV)

The proportion of substitution of TMC may be from about 1% to about 100%. For instance, the proportion of substitution of TMC may be from about 5% to about 99%, from about 10% to about 90%, from about 15% to about 80%, from about 20% to about 70%, from about 25% to about 60%, or from about 30% to about 50%. For instance, the proportion of substitution of TMC may be at least about 1%, at least about 10%, at least about 20%, at least about 30%, at least about 50%, at least about 70%, or at least about 90%. The proportion of substitution of TMC may be measured by $^1$H-NMR.

In certain embodiments, the TMC may have a molecular weight ranging from about 1 kDa to about 500 kDa. For instance, the TMC may have a molecular weight ranging from about 5 kDa to about 500 kDa, from about 10 kDa to about 450 kDa, from about 50 kDa to about 400 kDa, from about 90 kDa to about 310 kDa, or from about 100 kDa to about 300 kDa. For instance, the TMC may have a molecular weight ranging of at least about 1 kDa, at least about 5 kDa, at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 150 kDa, at least about 200 kDa, at least about 250 kDa, or at least about 300 kDa.

The term "N,O-CMC" or "N,O-carboxymethyl chitosan" as used herein refers to functionally-modified chitosan wherein one or more D-glucosamine and/or N-acetyl-D-glucosamine units are modified to, replaced by, or substituted by a functionally-modified monosaccharide unit having the structural Formula XVI.

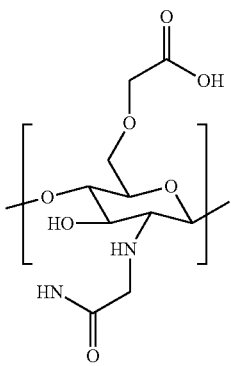
(XVI)

The proportion of substitution of N,O-CMC may be from about 1% to about 100%. For instance, the proportion of substitution of N,O-CMC may be from about 5% to about 99%, from about 10% to about 90%, from about 15% to about 80%, from about 20% to about 70%, from about 25% to about 60%, or from about 30% to about 50%. For instance, the proportion of substitution of N,O-CMC may be at least about 1%, at least about 10%, at least about 20%, at least about 30%, at least about 50%, at least about 70%, or at least about 90%. The proportion of substitution of N,O-CMC may be measured by $^1$H-NMR.

In certain embodiments, the N,O-CMC may have a molecular weight ranging from about 1 kDa to about 500 kDa. For instance, the N,O-CMC may have a molecular weight ranging from about 5 kDa to about 500 kDa, from about 10 kDa to about 450 kDa, from about 50 kDa to about 400 kDa, from about 90 kDa to about 310 kDa, or from about 100 kDa to about 300 kDa. For instance, the N,O-CMC may have a molecular weight ranging of at least about 1 kDa, at least about 5 kDa, at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 150 kDa, at least about 200 kDa, at least about 250 kDa, or at least about 300 kDa.

The term "N-CMC" or "N-carboxymethyl chitosan" as used herein refers to functionally-modified chitosan wherein one or more D-glucosamine and/or N-acetyl-D-glucosamine units are modified to, replaced by, or substituted by a functionally-modified monosaccharide unit having the structural Formula XVII.

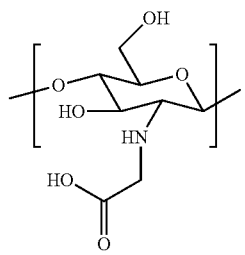
(XVII)

The proportion of substitution of N-CMC may be from about 1% to about 100%. For instance, the proportion of substitution of N-CMC may be from about 5% to about 99%, from about 10% to about 90%, from about 15% to about 80%, from about 20% to about 70%, from about 25% to about 60%, or from about 30% to about 50%. For instance, the proportion of substitution of N-CMC may be at least about 1%, at least about 10%, at least about 20%, at least about 30%, at least about 50%, at least about 70%, or at least about 90%. The proportion of substitution of N-CMC may be measured by $^1$H-NMR.

In certain embodiments, the N-CMC may have a molecular weight ranging from about 1 kDa to about 500 kDa. For instance, the N-CMC may have a molecular weight ranging from about 5 kDa to about 500 kDa, from about 10 kDa to about 450 kDa, from about 50 kDa to about 400 kDa, from about 90 kDa to about 310 kDa, or from about 100 kDa to about 300 kDa. For instance, the N-CMC may have a molecular weight ranging of at least about 1 kDa, at least about 5 kDa, at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 150 kDa, at least about 200 kDa, at least about 250 kDa, or at least about 300 kDa.

The term "N,N-CMC" or "N,N-carboxymethyl chitosan" as used herein refers to functionally-modified chitosan wherein one or more D-glucosamine units and/or N-acetyl-D-glucosamine units are modified to, replaced by, or substituted by a functionally-modified monosaccharide unit having the structural Formula XVIII.

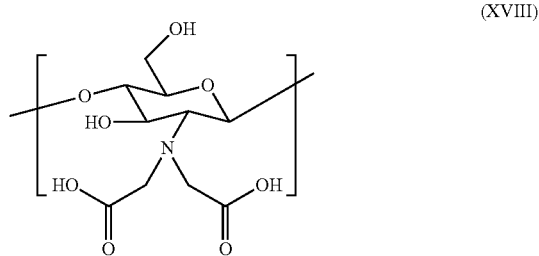

(XVIII)

The proportion of substitution of N,N-CMC may be from about 1% to about 100%. For instance, the proportion of substitution of N,N-CMC may be from about 5% to about 99%, from about 10% to about 90%, from about 15% to about 80%, from about 20% to about 70%, from about 25% to about 60%, or from about 30% to about 50%. For instance, the proportion of substitution of N,N-CMC may be at least about 1%, at least about 10%, at least about 20%, at least about 30%, at least about 50%, at least about 70%, or at least about 90%. The proportion of substitution of N,N-CMC may be measured by $^1$H-NMR.

In certain embodiments, the N,N-CMC may have a molecular weight ranging from about 1 kDa to about 500 kDa. For instance, the N,N-CMC may have a molecular weight ranging from about 5 kDa to about 500 kDa, from about 10 kDa to about 450 kDa, from about 50 kDa to about 400 kDa, from about 90 kDa to about 310 kDa, or from about 100 kDa to about 300 kDa. For instance, the N,N-CMC may have a molecular weight ranging of at least about 1 kDa, at least about 5 kDa, at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 150 kDa, at least about 200 kDa, at least about 250 kDa, or at least about 300 kDa.

The term "O-CMC" or "O-carboxymethyl chitosan" as used herein refers to functionally-modified chitosan wherein one or more D-glucosamine and/or N-acetyl-D-glucosamine units are modified to, replaced by, or substituted by a functionally-modified monosaccharide unit having the structural Formula XIX.

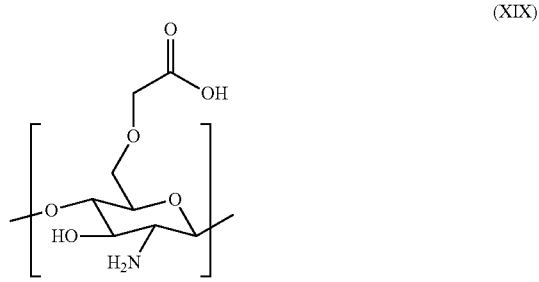

(XIX)

The proportion of substitution of O-CMC may be from about 1% to about 100%. For instance, the proportion of substitution of O-CMC may be from about 5% to about 99%, from about 10% to about 90%, from about 15% to about 80%, from about 20% to about 70%, from about 25% to about 60%, or from about 30% to about 50%. For instance, the proportion of substitution of O-CMC may be at least about 1%, at least about 10%, at least about 20%, at least about 30%, at least about 50%, at least about 70%, or at least about 90%. The proportion of substitution of O-CMC may be measured by $^1$H-NMR. In certain embodiments, the O-CMC may have a molecular weight ranging from about 1 kDa to about 500 kDa. For instance, the O-CMC may have a molecular weight ranging from about 5 kDa to about 500 kDa, from about 10 kDa to about 450 kDa, from about 50 kDa to about 400 kDa, from about 90 kDa to about 310 kDa, or from about 100 kDa to about 300 kDa. For instance, the O-CMC may have a molecular weight ranging of at least about 1 kDa, at least about 5 kDa, at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 150 kDa, at least about 200 kDa, at least about 250 kDa, or at least about 300 kDa.

The term "HMC" or "hydrophobically-modified chitosan" as used herein refers to functionally-modified chitosan wherein one or more functional groups, preferably the amine group, of one or more D-glucosamine units are modified (e.g., amidation) with a saturated or unsaturated fatty acid as defined herein.

In certain embodiments, the HMC may have a molecular weight ranging from about 1 kDa to about 500 kDa. For instance, the HMC may have a molecular weight ranging from about 5 kDa to about 500 kDa, from about 10 kDa to about 450 kDa, from about 50 kDa to about 400 kDa, from about 90 kDa to about 310 kDa, or from about 100 kDa to about 300 kDa. For instance, the HMC may have a molecular weight ranging of at least about 1 kDa, at least about 5 kDa, at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 150 kDa, at least about 200 kDa, at least about 250 kDa, or at least about 300 kDa.

In certain embodiments, the fatty acid graft ratio (FA-GR) as defined herein of the HMC may be at least about 1%. For example, the FA-GR as defined herein of the HMC may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%. For example, the FA-GR as defined herein of the HMC may be ranging from about 1% to about 100%, from about 1% to about 80%, from about 5% to about 70%, from about 10% to about 60%, or from about 15% to about 50%.

The term "dextran" as used herein refers to a branched polysaccharide composed of D-glucose units linked by α-glycosidic bonds. Generally, class 1 dextrans contain a backbone of α-(1,6)-linked D-glucopyranosyl units modified with small side chains of D-glucose branches with α-(1,2), α-(1,3), and α-(1,4)-linkage. Class 2 dextrans (or alternans) contain a backbone structure of alternating α-(1,3) and α-(1,6)-linked D-glucopyranosyl units with α-(1,3)-linked branches. Class 3 dextrans (or mutans) have a backbone structure of consecutive α-(1,3)-linked D-glucopyranosyl units with α-(1,6)-linked branches.

In certain embodiments, the dextran may have a molecular weight ranging from about 1 kDa to about 500 kDa. For instance, the dextran may have a molecular weight ranging from about 5 kDa to about 500 kDa, from about 10 kDa to about 450 kDa, from about 50 kDa to about 400 kDa, from about 90 kDa to about 310 kDa, or from about 100 kDa to about 300 kDa. For instance, the dextran may have a molecular weight ranging of at least about 1 kDa, at least about 5 kDa, at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 150 kDa, at least about 200 kDa, at least about 250 kDa, or at least about 300 kDa.

The term "HMD" or "hydrophobically-modified dextran" as used herein refers to functionally-modified dextran, wherein one or more hydroxyl groups of one or more D-glucose units are modified (i.e., esterified) with a saturated or unsaturated fatty acid as defined herein.

In certain embodiments, the fatty acid graft ratio (FA-GR) as defined herein of the HMD may be at least about 1%. For example, the FA-GR as defined herein of the HMD may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%. For example, the FA-GR as defined herein of the HMD may be ranging from about 1% to about 100%, from about 1% to about 80%, from about 5% to about 70%, from about 10% to about 60%, or from about 15% to about 50%.

In certain embodiments, the HMD may have a molecular weight ranging from about 1 kDa to about 500 kDa. For instance, the HMD may have a molecular weight ranging from about 5 kDa to about 500 kDa, from about 10 kDa to about 450 kDa, from about 50 kDa to about 400 kDa, from about 90 kDa to about 310 kDa, or from about 100 kDa to about 300 kDa. For instance, the HMD may have a molecular weight ranging of at least about 1 kDa, at least about 5 kDa, at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 150 kDa, at least about 200 kDa, at least about 250 kDa, or at least about 300 kDa.

In certain embodiments of the products (such as pharmaceutical formulations or FR-targeting excipients) or uses, as taught herein, the polysaccharide or functionally-modified polysaccharide may comprise at least one unit of Formula Ia, Ib, Ic, IIa, IIb, IIc, IIIa, IIIb, IIIc, IVa, IVb, and/or IVc, or a stereoisomer, tautomer, salt, hydrate or solvate thereof, or any subgroup thereof, wherein

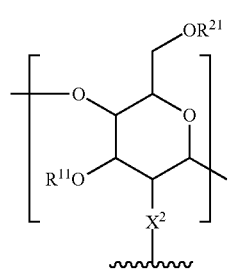

(Ia)

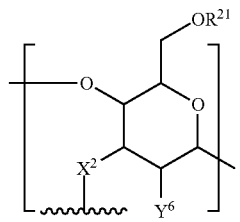

(Ib)

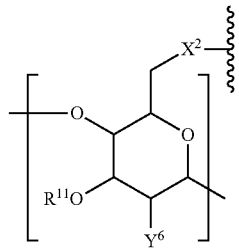

(Ic)

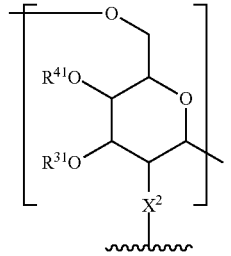

(IIa)

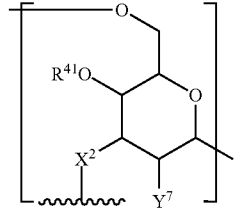

(IIb)

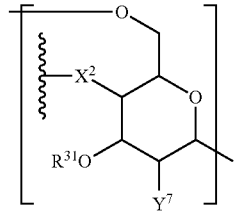

(IIc)

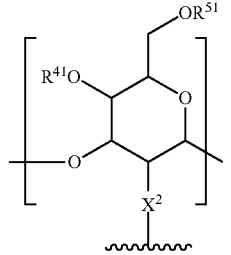

(IIIa)

143
-continued

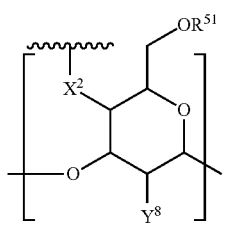
(IIIb)

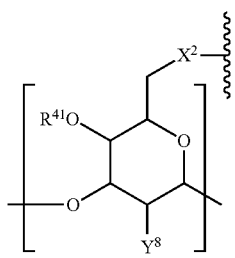
(IIIc)

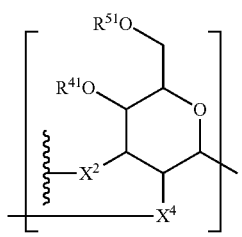
(IVa)

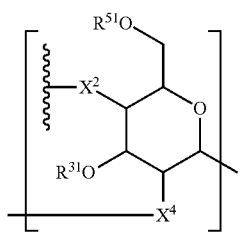
(IVb)

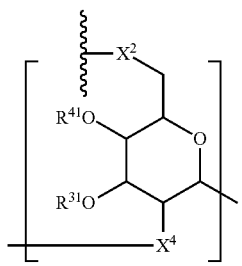
(IVc)

$Y^6$ is a group selected from —$OR^{10}$, —$N(R^{100})R^{101}$, or —$N^+(R^{100})(R^{101})R^{102}$, $Y^7$ is group selected from —$OR^{20}$, —$N(R^{200})R^{201}$, or —$N^+(R^{200})(R^{201})R^{202}$, $Y^8$ is a group selected from —$OR^{30}$, —$N(R^{300})R^{301}$, or —$N^+(R^{300})(R^{301})R^{302}$, $R^{10}$, $R^{11}$, $R^{20}$, $R^{21}$, $R^{30}$, $R^{31}$, $R^{41}$, $R^{51}$, $R^{100}$, $R^{101}$, $R^{102}$, $R^{200}$, $R^{201}$, $R^{202}$, $R^{300}$, $R^{301}$, $R^{302}$, $X^2$, $X^3$ and $X^4$ have the same meaning as that defined herein; and represents a covalent bond linking or connecting the polysaccharide or functionally-modified polysaccharide to a folate moiety as taught herein or to a linker as taught herein (i.e., connecting the polysaccharide or functionally-modified polysaccharide to —$X^1$—$X^3$).

Advantageously, the present inventors have found that the polysaccharides or functionally-modified polysaccharides as taught herein allow the formation of nanoparticles with good stability and physical integrity after administration in vivo and at the same time display a desired rate of dissolution once in contact with physiological media. Also, the polysaccharides or functionally-modified polysaccharides as taught herein, display bioadhesive properties and/or present a long time of retention in the respiratory tract, thereby retaining the present pharmaceutical formulations in the respiratory tract.

Additionally, the present inventors have surprisingly found that the polysaccharides or functionally-modified polysaccharides as taught herein are able to interact with the antineoplastic agents (including hydrophilic antineoplastic agents) and these interactions advantageously lead to a better entrapment and/or encapsulation of the antineoplastic agents in the pharmaceutical formulations. Hence, using such polysaccharides or functionally-modified polysaccharides allows high drug encapsulation efficiency and drug loading.

In certain preferred embodiments of the products (such as pharmaceutical formulations or FR-targeting excipients) or uses, as taught herein, the polysaccharide or functionally-modified polysaccharide may comprising at least one unit of Formula Ia1, IIa1, IIb1, IIc1, Ia2, IIa2, IIb2, and/or IIc2, or a stereoisomer, tautomer, salt, hydrate or solvate thereof, or any subgroup thereof, wherein

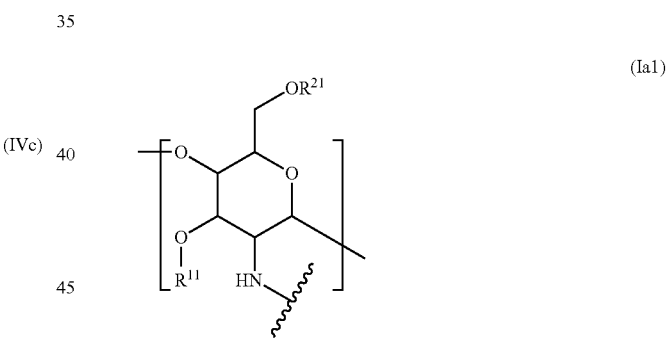
(Ia1)

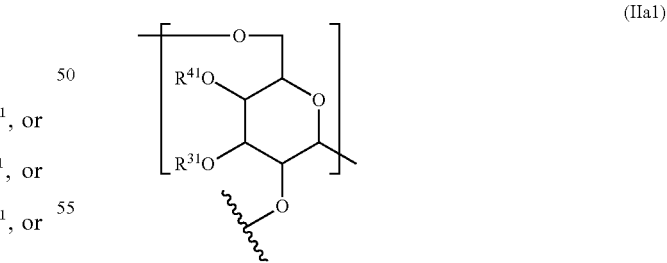
(IIa1)

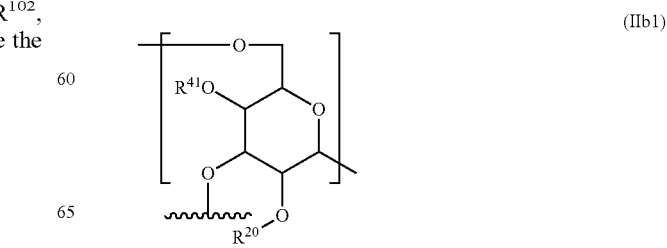
(IIb1)

145

-continued

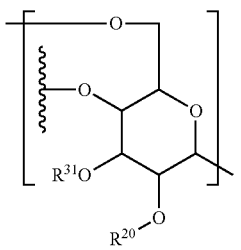
(IIc1)

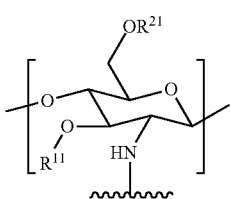
(Ia2)

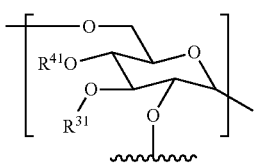
(IIa2)

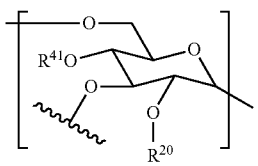
(IIb2)

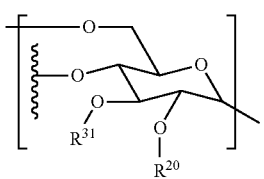
(IIc2)

$R^{11}$, $R^{20}$, $R^{21}$, $R^{31}$, and $R^{41}$ have the same meaning as that defined herein; and

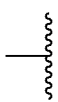

represents a covalent bond linking or connecting the polysaccharide or functionally-modified polysaccharide to a folate moiety as taught herein or to a linker as taught herein (i.e., connecting the polysaccharide or functionally-modified polysaccharide to —$X^1$—$X^3$).

The term "unit", as used herein, refers to a monosaccharide or functionally-modified monosaccharide.

The term "monosaccharide" (as opposed to oligosaccharide or polysaccharide) generally refers to a single unit without glycosidic connection to other such units.

It is to be understood that each unit of a formula as taught herein may be independently selected from the group consisting of the units of said formula as taught herein.

In certain embodiments, the polysaccharide or functionally-modified polysaccharide may comprise at least one, such as one or more, units of Formula Ia, Ib, Ic, IIa, IIb, IIc, IIIa, IIIb, IIIc, IVa, IVb, IVc, Ia1, IIa1, IIb1, IIc1, Ia2, IIa2,

146

IIb2, and/or IIc2, as taught herein, such as at least two, at least three, at least four, at least five, at least six, at least seven, at least eight, at least nine, at least ten, at least twenty, at least thirty, at least forty, at least fifty, at least sixty, at least seventy, at least eighty, at least ninety, at least 100, at least 200, at least 300, at least 400, at least 500, at least 600, at least 700, at least 800, at least 900, at least 1000, at least 1500, at least 2000, or at least 2500 units of Formula Ia, Ib, Ic, IIa, IIb, IIc, IIIa, IIIb, IIIc, IVa, IVb, IVc, Ia1, IIa1, IIb1, IIc1, Ia2, IIa2, IIb2, and/or IIc2, as taught herein. For example, the polysaccharide or functionally-modified polysaccharide may comprise from about 50 to about 2000, from about 100 to about 1000, or from about 200 to about 500 units of Formula Ia, Ib, Ic, IIa, IIb, IIc, IIIa, IIIb, IIIc, IVa, IVb, IVc, Ia1, IIa1, IIb1, IIc1, Ia2, IIa2, IIb2, and/or IIc2, as taught herein.

In certain embodiments, the one or more units of Formula Ia, Ib, Ic, IIa, IIb, IIc, IIIa, IIIb, IIIc, IVa, IVb, IVc, Ia1, IIa1, IIb1, IIc1, Ia2, IIa2, IIb2, and/or IIc2, as taught herein, may be randomly distributed in the polysaccharide or functionally-modified polysaccharide.

The terms "randomly distributed" or "randomly positioned" as used herein refers to the position of each unit (i.e., monosaccharide unit or functionally-modified monosaccharide unit) in the polysaccharide or functionally modified polysaccharide, wherein the position of each unit is independent from the position of each other unit.

In certain embodiments, the polysaccharide or functionally-modified polysaccharide may comprise at least one unit of Formula Ia, Ib, Ic, IIa, IIb, IIc, IIIa, IIIb, IIIc, IVa, IVb, IVc, Ia1, IIa1, IIb1, IIc1, Ia2, IIa2, IIb2, and/or IIc2, as taught herein, wherein $R^{11}$, $R^{20}$, $R^{21}$, $R^{31}$, and $R^{41}$ are each independently selected from hydrogen, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic acid), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety), and the fatty acid graft ratio (FA-GR) as defined herein of the functionally-modified polysaccharide may be at least about 1%, for example the FA-GR as defined herein of the functionally-modified polysaccharide may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the FA-GR as defined herein of the functionally-modified polysaccharide may be ranging from about 1% to about 100%, from about 1% to about 80%, from about 5% to about 70%, from about 10% to about 60%, or from about 15% to about 50%.

In certain embodiments, the polysaccharide or functionally-modified polysaccharide may comprise at least one unit of Formula Ia, Ib, Ic, IIa, IIb, IIc, IIIa, IIIb, IIIc, IVa, IVb, IVc, Ia1, IIa1, IIb1, IIc1, IIa2, IIa2, IIb2, and/or IIc2, as taught herein, and at least one unit of Formula V, as taught herein, wherein $Y^6, Y^7, Y^8, R^{10}, R^{11}, R^{20}, R^{21}, R^{30}, R^{31}, R^{41}, R^{51}, R^{100}, R^{101}, R^{102}, R^{200}, R^{201}, R^{202}, R^{300}, R^{301}, R^{302}, X^2, X^4$,

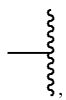

$R^{1a}, R^{2a}$, and $R^{6a}$ have the same meaning as that defined herein.

In certain embodiments, the polysaccharide or functionally-modified polysaccharide may comprise at least one unit of Formula Ia, Ib, Ic, IIa, IIb, IIc, IIIa, IIIb, IIIc, IVa, IVb, IVc, Ia1, IIa1, IIb1, IIc1, IIa2, IIa2, IIb2, and/or IIc2, as taught herein, and at least one unit of Formula IX, as taught herein, wherein $Y^6, Y^7, R^8, R^{10}, R^{11}, R^{20}, R^{21}, R^{30}, R^{31}, R^{41}, R^{51}, R^{100}, R^{101}, R^{102}, R^{200}, R^{201}, R^{202}, R^{300}, R^{301}, R^{302}, X^2, X^4$,

$R^{11a}, R^{12a}$, and $R^{13a}$ have the same meaning as that defined herein.

In certain embodiments, the polysaccharide or functionally-modified polysaccharide may comprise, consist essentially of, or consist of randomly distributed units of Formula Ia, Ib, Ic, IIa, IIb, IIc, IIIa, IIIb, IIIc, IVa, IVb, IVc, Ia1, IIa1, IIb1, and/or IIc1, as taught herein, and of Formula V and/or IX, as taught herein.

In certain embodiments, the polysaccharide or functionally-modified polysaccharide may comprise, consist essentially of, or consist of randomly distributed units of Formula Ia, Ib, Ic, IIa, IIb, IIc, IIIa, IIIb, IIIc, IVa, IVb, IVc, Ia1, IIa1, IIb1, and/or IIc1, as taught herein, and of Formula V and/or IX, as taught herein, wherein the units are linked by a glycosidic bonds.

In certain embodiments, the polysaccharide or functionally-modified polysaccharide may comprise, consist essentially of, or consist of randomly distributed units of Formula Ia, Ib, Ic, IIa, IIb, IIc, IIIa, IIIb, IIIc, IVa, IVb, IVc, Ia1, IIa1, IIb1, and/or IIc1, as taught herein, and of Formula V and/or IX, as taught herein, wherein the units are linked by α-(1,2), α-(1,3), α-(1,4), and/or α-(1,6) glycosidic bonds.

In certain embodiments, the polysaccharide or functionally-modified polysaccharide may comprise, consist essentially of, or consist of randomly distributed units of Formula Ia, Ib, Ic, IIa, IIb, IIc, IIIa, IIIb, IIIc, IVa, IVb, IVc, Ia1, IIa1, IIb1, and/or IIc1, as taught herein, and of Formula V and/or IX, as taught herein, wherein the units are linked by β glycosidic bonds.

In certain embodiments, the polysaccharide or functionally-modified polysaccharide may comprise, consist essentially of, or consist of randomly distributed units of Formula Ia, Ib, Ic, IIa, IIb, IIc, IIIa, IIIb, IIIc, IVa, IVb, IVc, Ia1, IIa1, IIb1, and/or IIc1, as taught herein, and of Formula V and/or IX, as taught herein, wherein the units are linked by β-(1,2), β-(1,3), β-(1,4), and/or β-(1,6) glycosidic bonds.

In certain embodiments, the polysaccharide or functionally-modified polysaccharide may comprise, consist essentially of, or consist of randomly distributed units of Formula Ia, Ib, Ic, IIa, IIb, IIc, IIIa, IIIb, IIIc, IVa, IVb, IVc, Ia1, IIa1, IIb1, and/or IIc1, as taught herein, and of Formula V and/or IX, as taught herein, wherein the units are linked by a glycosidic bonds and/or β glycosidic bonds.

In certain embodiments, the polysaccharide or functionally-modified polysaccharide may comprise, consist essentially of, or consist of randomly distributed units of Formula Ia, Ib, Ic, IIa, IIb, IIc, IIIa, IIIb, IIIc, IVa, IVb, IVc, Ia1, IIa1, IIb1, and/or IIc1, as taught herein, and of Formula V and/or IX, as taught herein, wherein the units are linked by α-(1,2), α-(1,3), α-(1,4), α-(1,6), β-(1,2), β-(1,3), β-(1,4), and/or β-(1,6) glycosidic bonds.

The term "glycosidic bond" generally refers to the bond between the hemiacetal or hemiketal hydroxyl group of a monosaccharide, oligosaccharide, or polysaccharide and a hydroxyl group of a second compound (i.e., a monosaccharide, oligosaccharide, or polysaccharide) (and accompanied by elimination of water).

The term "a glycosidic bond" or "alpha glycosidic bond" refers to a glycosidic bond wherein the hydroxyl group attached to the anomeric carbon and the —CH$_2$OH group attached to the other carbon next to the ether have a cis configuration.

The term "β glycosidic bond" or "beta glycosidic bond" refers to refers to a glycosidic bond wherein the hydroxyl group attached to the anomeric carbon and the —CH$_2$OH group attached to the other carbon next to the ether have a trans configuration.

In certain preferred embodiments, the polysaccharide or functionally-modified polysaccharide may comprise, consist of, or essentially consist of randomly distributed units of Formula Ia, Ib, Ic, IIa, IIb, IIc, IIIa, IIIb, IIIc, IVa, IVb, IVc, Ia1, IIa1, IIb1, IIc1, Ia2, IIa2, IIb2, and/or IIc2, as taught herein, or any subgroup thereof, (preferably of Formula Ia, Ia1, or Ia2 as taught herein, or any subgroup thereof), and of Formula Va, VIa, VIIa, and/or VIIIa, as taught herein, wherein $Y^6, Y^7, Y^8, R^{10}, R^{11}, R^{20}, R^{21}, R^{30}, R^{31}, R^{41}, R^{51}, R^{100}, R^{101}, R^{102}, R^{200}, R^{201}, R^{202}, R^{300}, R^{301}, R^{302}, X^2, X^4$,

$R^{1a}$, $R^{2a}$, and $R^{6a}$ have the same meaning as that defined herein.

In certain preferred embodiments, the polysaccharide or functionally-modified polysaccharide may comprise consist of, or essentially consist of randomly distributed units of Formula Ia, Ia1, or Ia2, as taught herein, or any subgroup thereof, (preferably of Formula Ia2 as taught herein, or any subgroup thereof), and of Formula Va, VIa, VIIa, and/or VIIIa, as taught herein, wherein the units are linked by 13-(1,4) glycosidic bonds; and $R^{20}$, $R^{21}$, $R^{30}$, $R^{31}$, $R^{41}$,

$R^{1a}$, $R^{2a}$, and $R^{6a}$ have the same meaning as that defined herein.

In certain preferred embodiments, the unit of Formula Va is a D-glucosamine moiety.

In certain preferred embodiments, the unit of Formula Va is an N-acetyl-D-glucosamine moiety.

In certain preferred embodiments, the polysaccharide or functionally-modified polysaccharide may comprise, consist of, or essentially consist of randomly distributed units of Formula Ia2, as taught herein, and of Formula Va, VIa, VIIa, and/or VIIIa, as taught herein, wherein the units are linked by β-(1,4) glycosidic bonds; $R^{11}$, it $R^{1a}$, and $R^{2a}$, and

have the same meaning as that defined herein;

$R^{6a}$ is selected from amino, ammonium, —$NHR^{8a}$, —$NR^{8a}R^{9a}$, or —$N^+R^{8a}R^{9a}R^{10a}$, wherein $R^{8a}$, $R^{9a}$, and $R^{10a}$ are each independently selected from a group consisting of methyl, ethyl, n-propyl, i-propyl, 2-hydroxy-propylene-$N^+(CH_3)_3$, methylene-CO—OH, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the nitrogen to which it is bound a caprylic amide moiety), n-nonylcarbonyl (e.g. which may form together with the nitrogen to which it is bound a capric amide moiety), n-undecylcarbonyl (e.g. which may form together with the nitrogen to which it is bound a lauric amide moiety), n-tridecylcarbonyl (e.g. which may form together with the nitrogen to which it is bound a myristic amide moiety), n-pentadecylcarbonyl (e.g. which may form together with the nitrogen to which it is bound a palmitic amide moiety), n-heptadecylcarbonyl (e.g. which may form together with the nitrogen to which it is bound a stearic amide moiety), n-nonadecylcarbonyl (e.g. which may form together with the nitrogen to which it is bound an arachidic amide moiety), n-henicosylcarbonyl (e.g. which may form together with the nitrogen to which it is bound a behenic amide moiety), n-tricosylcarbonyl (e.g. which may form together with the nitrogen to which it is bound a lignoceric amide moiety), n-pentacosylcarbonyl (e.g. which may form together with the nitrogen to which it is bound a cerotic amide moiety), n-tridecenylcarbonyl (e.g. which may form together with the nitrogen to which it is bound a myristoleic amide), n-pentadecenylcarbonyl (e.g. which may form together with the nitrogen to which it is bound a palmitoleic amide moiety or sapienic amide moiety), n-heptadecenylcarbonyl (e.g. which may form together with the nitrogen to which it is bound an oleic amide moiety, elaidic amide moiety, vaccenic amide moiety, linoleic amide moiety, linoelaidic amide moiety, or α-linolenic amide moiety), n-nonadecenylcarbonyl (e.g. which may form together with the nitrogen to which it is bound an arachidonic amide moiety or eicosapentaenoic amide moiety), or n-henicosenylcarbonyl (e.g. which may form together with the nitrogen to which it is bound an erucic amide moiety or docosahexaenoic amide moiety).

In certain preferred embodiments, the polysaccharide or functionally-modified polysaccharide may comprise, consist of, or essentially consist of randomly distributed units of Formula Ia2, as taught herein, and of Formula Va, as taught herein, wherein the units are linked by β-(1,4) glycosidic bonds; $R^{11}$, $R^{21}$, $R^{1a}$, and $R^{2a}$, and

have the same meaning as that defined herein;

$R^{6a}$ is selected from amino, ammonium, —$NHR^{8a}$, —$NR^{8a}R^{9a}$, or —$N^+R^{8a}R^{9a}R^{10a}$, wherein $R^{8a}$, $R^{9a}$, and $R^{10a}$ are each independently selected from a group consisting of methyl, ethyl, n-propyl, i-propyl, 2-hydroxy-propylene-$N^+(CH_3)_3$, methylene-CO—OH, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the nitrogen to which it is bound a caprylic amide moiety), n-nonylcarbonyl (e.g. which may form together with the nitrogen to which it is bound a capric amide moiety), n-undecylcarbonyl (e.g. which may form together with the nitrogen to which it is bound a lauric amide moiety), n-tridecylcarbonyl (e.g. which may form together with the nitrogen to which it is bound a myristic amide moiety), n-pentadecylcarbonyl (e.g. which may form together with the nitrogen to which it is bound a palmitic amide moiety), n-heptadecylcarbonyl (e.g. which may form together with the nitrogen to which it is bound a stearic amide moiety), n-nonadecylcarbonyl (e.g. which may form together with the nitrogen to which it is bound an arachidic amide moiety), n-henicosylcarbonyl (e.g. which may form together with the nitrogen to which it is bound a behenic amide moiety), n-tricosylcarbonyl (e.g. which may form together with the nitrogen to which it is bound a lignoceric amide moiety), n-pentacosylcarbonyl (e.g. which may form together with the nitrogen to which it is bound a cerotic amide moiety), n-tridecenylcarbonyl (e.g. which may form together with the nitrogen to which it is bound a myristoleic amide), n-pentadecenylcarbonyl (e.g. which may form together with the nitrogen to which it is bound a palmitoleic amide moiety or sapienic amide moiety), n-heptadecenylcarbonyl (e.g. which may form together with the nitrogen to which it is bound an oleic amide moiety, elaidic amide moiety, vaccenic amide moiety, linoleic amide moiety, linoelaidic amide moiety, or α-linolenic amide moiety), n-nonadecenylcarbonyl (e.g. which may form together with the nitrogen to which it is bound an arachidonic amide moiety or eicosapentaenoic amide moiety), or n-henicosenylcarbonyl (e.g. which may form together with the nitrogen to which it is bound an erucic amide moiety or docosahexaenoic amide moiety); and the fatty acid graft ratio (FA-GR) as defined herein of the functionally-modified polysaccharide may be at least about 1%, for example the FA-GR as defined herein of the functionally-modified polysaccharide may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the FA-GR as defined herein of the functionally-modified polysaccharide may be ranging from about 1% to about 100%, from about 1% to about 80%, from about 5% to about 70%, from about 10% to about 60%, or from about 15% to about 50%.

In certain preferred embodiments, the polysaccharide or functionally-modified polysaccharide may comprise, consist of, or essentially consist of randomly distributed units of Formula Ia2, as taught herein, and of Formula VIa, VIIa, and/or VIIIa, as taught herein wherein $R^{11}$, $R^{21}$,

$R^{1a}$, and $R^{2a}$ have the same meaning as that defined herein.

In certain preferred embodiments, the polysaccharide or functionally-modified polysaccharide may comprise, consist of, or essentially consist of randomly distributed units of Formula Ia2, as taught herein, and of Formula VIa, VIIa, and/or VIIIa, as taught herein, wherein the units are linked by β-(1,4) glycosidic bonds, wherein $R^{11}$, $R^{21}$,

$R^{1a}$, and $R^{2a}$ have the same meaning as that defined herein.

In certain preferred embodiments, the polysaccharide or functionally-modified polysaccharide may comprise, consist of, or essentially consist of randomly distributed units of Formula Ia, Ib, Ic, IIa, IIb, IIc, IIIa, IIIb, IIIc, IVa, IVb, IVc, Ia1, IIa1, IIb1, IIc1, Ia2, IIa2, IIb2, and/or IIc2, as taught herein, or any subgroup thereof, (preferably of Formula IIa, IIb, IIc, IIa1, IIb1, IIc1, IIa2, IIb2, and/or IIc2, as taught herein, or any subgroup thereof), and of Formula IXa, as taught herein, wherein $Y^6$, $Y^7$, $Y^8$, $R^{10}$, $R^{11}$, $R^{20}$, $R^{21}$, $R^{30}$, $R^{31}$, $R^{41}$, $R^{51}$, $R^{100}$, $R^{101}$, $R^{102}$, $R^{200}$, $R^{201}$, $R^{202}$, $R^{300}$, $R^{301}$, $R^{302}$, $X^2$, $X^4$,

$R^{11a}$, $R^{12a}$, and $R^{13a}$ have the same meaning as that defined herein.

In certain preferred embodiments, the polysaccharide or functionally-modified polysaccharide may comprise, consist of, or essentially consist of randomly distributed units of Formula IIa, IIb, IIc, IIa1, IIb1, IIc1, IIa2, IIb2, and/or IIc2, as taught herein, or any subgroup thereof, (preferably of Formula IIa2, IIb2, and/or IIc2, as taught herein, or any subgroup thereof), and of Formula IXa, as taught herein, wherein the units are linked by α-(1,6) glycosidic bonds and branched by α-(1,2), α-(1,3), and/or α-(1,4) glycosidic bonds, preferably branched by α-(1,3) glycosidic bonds, and wherein $Y^6$, $Y^7$, $Y^8$, $R^{10}$, $R^{11}$, $R^{20}$, $R^{21}$, $R^{30}$, $R^{31}$, $R^{41}$, $R^{51}$, $R^{100}$, $R^{101}$, $R^{102}$, $R^{200}$, $R^{201}$, $R^{202}$, $R^{300}$, $R^{301}$, $R^{302}$, $X^2$, $X^4$,

$R^{11a}$, $R^{12a}$, and $R^{13a}$ have the same meaning as that defined herein.

In certain preferred embodiments, the polysaccharide or functionally-modified polysaccharide may comprise, consist of, or essentially consist of randomly distributed units of Formula IIa, IIb, IIc, IIa1, IIb1, IIc1, IIa2, IIb2, and/or IIc2, as taught herein, or any subgroup thereof, (preferably of Formula IIa2, IIb2, and/or IIc2, as taught herein, or any subgroup thereof), and at least one unit of Formula IXa, as taught herein, wherein $R^{20}$, $R^{31}$, $R^{41}$, $R^{11a}$, $R^{12a}$, and $R^{13a}$ are each independently selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic acid), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety).

In certain preferred embodiments, the polysaccharide or functionally-modified polysaccharide may comprise, consist of, or essentially consist of randomly distributed units of Formula IIa, IIb, IIc, IIa1, IIb1, IIc1, IIa2, IIb2, and/or IIc2, as taught herein, or any subgroup thereof, (preferably of Formula IIa2, IIb2, and/or IIc2, as taught herein, or any subgroup thereof), and at least one unit of Formula IXa, as taught herein, wherein $R^{20}$, $R^{31}$, $R^{41}$, $R^{11a}$, $R^{12a}$, and $R^{13a}$ are each independently selected from hydrogen, a mono-, oligo-, or poly-glycosyl moiety, or a group consisting of methyl, ethyl, methylcarbonyl, ethylcarbonyl, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic acid), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety), and the fatty acid graft ratio (FA-GR) as defined herein of the functionally-modified polysaccharide may be at least about 1%, for example the FA-GR as defined herein of the functionally-modified polysaccharide may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the FA-GR as defined herein of the functionally-modified polysaccharide may be ranging from about 1% to about 100%, from about 1% to about 80%, from about 5% to about 70%, from about 10% to about 60%, or from about 15% to about 50%.

In certain preferred embodiments, the polysaccharide or functionally-modified polysaccharide may comprise, consist of, or essentially consist of randomly distributed units of Formula IIa2, IIb2, and/or IIc2, as taught herein, and at least one unit of Formula IXa, as taught herein, wherein $R^{20}$, $R^{31}$, $R^{41}$, $R^{11a}$, $R^{12a}$, and $R^{13a}$ are each independently selected from hydrogen, a mono-, oligo-, or poly-glycosyl moiety, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic acid), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or oi-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety).

In certain preferred embodiments, the polysaccharide or functionally-modified polysaccharide may comprise, consist of, or essentially consist of randomly distributed units of Formula IIa2, IIb2, and/or IIc2, as taught herein, and at least one unit of Formula IXa, as taught herein, wherein $R^{20}$, $R^{31}$, $R^{41}$, $R^{11a}$, $R^{12a}$, and $R^{13a}$ are each independently selected from hydrogen, a mono-, oligo-, or poly-glycosyl moiety, n-propylcarbonyl, i-propylcarbonyl, n-butylcarbonyl, i-butylcarbonyl, t-butylcarbonyl, n-pentylcarbonyl, n-hexylcarbonyl, n-heptylcarbonyl (e.g. which may form together with the oxygen to which it is bound a caprylic ester moiety), n-nonylcarbonyl (e.g. which may form together with the oxygen to which it is bound a capric ester moiety), n-undecylcarbonyl (e.g. which may form together with the oxygen to which it is bound a lauric ester moiety), n-tridecylcarbonyl (e.g. which may form together with the oxygen to which it is bound a myristic ester moiety), n-pentadecylcarbonyl (e.g. which may form together with the oxygen to which it is bound a palmitic ester moiety), n-heptadecylcarbonyl (e.g. which may form together with the oxygen to which it is bound a stearic ester moiety), n-nonadecylcarbonyl (e.g. which may form together with the oxygen to which it is bound an arachidic ester moiety), n-henicosylcarbonyl (e.g. which may form together with the oxygen to which it is bound a behenic ester moiety), n-tricosylcarbonyl (e.g. which may form together with the oxygen to which it is bound a lignoceric ester moiety), n-pentacosylcarbonyl (e.g. which may form together with the oxygen to which it is bound a cerotic ester moiety), n-tridecenylcarbonyl (e.g. which may form together with the oxygen to which it is bound a myristoleic acid), n-pentadecenylcarbonyl (e.g. which may form together with the oxygen to which it is bound a palmitoleic ester moiety or sapienic ester moiety), n-heptadecenylcarbonyl (e.g. which may form together with the oxygen to which it is bound an oleic ester moiety, elaidic ester moiety, vaccenic ester moiety, linoleic ester moiety, linoelaidic ester moiety, or α-linolenic ester moiety), n-nonadecenylcarbonyl (e.g. which may form together with the oxygen to which it is bound an arachidonic ester moiety or eicosapentaenoic ester moiety), or n-henicosenylcarbonyl (e.g. which may form together with the oxygen to which it is bound an erucic ester moiety or docosahexaenoic ester moiety, and the fatty acid graft ratio (FA-GR) as defined herein of the functionally-modified polysaccharide may be at least about 1%, for example the FA-GR as defined herein of the functionally-modified polysaccharide may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the FA-GR as defined herein of the functionally-modified polysaccharide may be ranging from about 1% to about 100%, from about 1% to about 80%, from about 5% to about 70%, from about 10% to about 60%, or from about 15% to about 50%.

In certain preferred embodiments of the products (such as pharmaceutical formulations or FR-targeting excipients) or uses, as taught herein, the polysaccharide or functionally-modified polysaccharide may comprise, consist of, or essentially consist of at least one unit of Formula Ia, Ib, Ic, IIa, IIb, IIc, IIIa, IIIb, IIIc, IVa, IVb, IVc, Ia1, IIa1, IIb1, IIc1, Ia2, IIa2, IIb2, and/or IIc2, as taught herein, and at least one unit of Formula V, Va, VIa, VIIa, VIIIa, IX, and/or IXa, as taught herein.

In certain preferred embodiments, the polysaccharide or functionally-modified polysaccharide may comprise, consist of, or essentially consist of randomly distributed units of Formula Ia, Ib, Ic, IIa, IIb, IIc, IIIa, IIIb, IIIc, IVa, IVb, IVc, Ia1, IIa1, IIb1, IIc1, Ia2, IIa2, IIb2, and/or IIc2, as taught herein, and of Formula V, Va, VIa, VIIa, VIIIa, IX, and/or IXa, as taught herein.

In certain embodiments, the polysaccharide or functionally-modified polysaccharide may comprise at least one, such as one or more, units of Formula Ia, Ib, Ic, IIa, IIb, IIc, IIIa, IIIb, IIIc, IVa, IVb, IVc, Ia1, IIa1, IIb1, IIc1, Ia2, IIa2, IIb2, and/or IIc2, as taught herein, such as at least two, at least three, at least four, at least five, at least six, at least seven, at least eight, at least nine, at least ten, at least twenty, at least thirty, at least forty, at least fifty, at least sixty, at least seventy, at least eighty, at least ninety, at least 100, at least 200, at least 300, at least 400, at least 500, at least 600, at least 700, at least 800, at least 900, at least 1000, at least 1500, at least 2000, or at least 2500 units of Formula Ia, Ib, Ic, IIa, IIb, IIc, IIIa, IIIb, IIIc, IVa, IVb, IVc, Ia1, IIa1, IIb1, IIc1, Ia2, IIa2, IIb2, and/or IIc2, as taught herein, and at least one, such as one or more, units of Formula V, Va, VIa, VIIa, VIIIa, IX, and/or IXa, as taught herein, such as at least two, at least three, at least four, at least five, at least six, at least seven, at least eight, at least nine, at least ten, at least twenty, at least thirty, at least forty, at least fifty, at least sixty, at least seventy, at least eighty, at least ninety, at least 100, at least 200, at least 300, at least 400, at least 500, at least 600, at least 700, at least 800, at least 900, at least 1000, at least 1500, at least 2000, or at least 2500 units of Formula V, Va, VIa, VIIa, VIIIa, IX, and/or IXa, as taught herein. For example, the polysaccharide or functionally-modified polysaccharide may comprise from about 50 to about 2000, from about 100 to about 1000, or from about 200 to about 500 units of Formula Ia, Ib, Ic, IIa, IIb, IIc, IIIa, IIIb, IIIc, IVa, IVb, IVc, Ia1, IIa1, IIb1, IIc1, Ia2, IIa2, IIb2, and/or IIc2, as taught herein and from about 50 to about 2000, from about 100 to about 1000, or from about 200 to about 500 units of Formula V, Va, VIa, VIIa, VIIIa, IX, and/or IXa, as taught herein.

In certain embodiments of the products (such as pharmaceutical formulations or FR-targeting excipients), uses, or methods, as taught herein, the polysaccharide or functionally-modified polysaccharide may be covalently bound to the folate moiety via a single bond (i.e., covalent bond) or via a linker, wherein the linker comprises a polyether, ether, amine, polyamine, amino acid, peptide, a polypeptide, a carbohydrate, or a combination of two or more thereof.

The use of a linker spatially extends the folate moiety from the polysaccharide or functionally-modified polysaccharide (which may be comprised in the nanoparticle core), thereby enhancing the flexibility of the folate moiety and assuring optimal interaction between the folate moiety and targeted folate receptor.

Furthermore, the use of a linker can increase at least partially the solubility of the folate moiety in an aqueous medium, thereby increasing the interaction between the folate moiety and the folate receptor. Advantageously, the use of the linker may also increase the tolerance of the polysaccharide or functionally-modified polysaccharide by the cells.

The term "polyether" generally refers to a class of organic compounds that contain more than one ether group (i.e., an oxygen atom connected to two alkyl or aryl groups). Non-limiting examples of polyether to be used as a linker are polyethylene oxide (PEO) (i.e., linked polyethylene glycol (PEG) units), polypropylene oxide (PPO), or a block co-polymer of PEO and PPO.

The term "polyamine" generally refers to a class of organic compounds that contain more than one amine group (i.e., a nitrogen atom connected to two or three alkyl or aryl groups). Non-limiting examples of polyamine to be used as a linker are polyethylene imine (PEI), polypropylene imine (PPI), or a block co-polymer of PEI and PPI.

The term "carbohydrate" generally refers to an organic compound comprising only carbon, hydrogen, and oxygen. Non-limiting examples of carbohydrates to be used as a linker are monosaccharides or polysaccharides.

In certain embodiments, the linker may comprise or consist essentially of a polyether, ether, amine, polyamine, amino acid, peptide, a polypeptide, a carbohydrate, or a combination of two or more thereof.

In certain embodiments, the linker may comprise or consist essentially of a poly($C_{1-6}$alkyleneoxide), $C_{1-6}$alkyleneoxide, amine, poly(imino$C_{1-6}$alkylene), amino acid, peptide, polypeptide, monosaccharide, or polysaccharide.

In certain embodiments of the products (such as pharmaceutical formulations or FR-targeting excipients) or uses, as taught herein, the linker may comprise or consist essentially of a polyether selected from PEO, PPO, or a block co-polymer of PEO and PPO. In certain embodiments, the linker may comprise or consist essentially of a PEO.

In certain embodiments, the linker may comprise or consist essentially of a polyethylene oxide, and the polyethylene oxide graft ratio (PEO-GR or GR) of the FR-targeting excipients may be at least about 1%. For example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%. For example, the GR of the FR-targeting excipient may be ranging from about 1% to about 100%, from about 1% to about 80%, from about 5% to about 70%, from about 10% to about 60%, or from about 15% to about 50%.

The recitation "graft ratio", "GR", "polyethylene oxide graft ratio", "PEO-GR", or "PEG-GR" of a compound (i.e., FR-targeting excipient), as used herein, refers to the relative abundance of PEO (i.e., polyethylene oxide) in the compound (i.e., FR-targeting excipient) divided by the relative abundance of monosaccharide units of a polysaccharide (i.e., polysaccharide or functionally-modified polysaccharide) in the compound (i.e., FR-targeting excipient), suitably expressed as a percentage. The GR corresponds to the percentage of monosaccharide units of the polysaccharide or functionally-modified polysaccharide which are linked to a polyethylene oxide chain.

The graft ratio may be determined by $^1$H NMR (for example at 293 K in $D_2O$). The graft ratio may be determined by $^1$H NMR and calculated using a suitable equation.

For example, the graft ratio of PEO on HTCC may be calculated using equation (1):

$$GR(\%) = \frac{[PEG] \times DQ \times 9}{nH^+PEG \times [N^+(CH_3)_3]} \quad (1)$$

wherein "[PEG]" is the integral of proton peak of PEO at 3.7 ppm ($CH_2O$), "DQ" is the degree of quaternization or degree of substitution of HTCC (expressed in %); "9" is the number of $H^+$ in $N^+(CH_3)_3$; "$nH^+PEG$" is the number of protons of the PEO chain according to the molecular weight of the PEO; and "[$N^+(CH_3)_3$]" is the integral of the peak at 3.3 ppm ($N^+(CH_3)_3$) In equation (1), the ratio [PEG]/$nH^+PEG$ is the relative abundance of PEO in the compound. For the relative abundance of the glucosamine units of HTCC in the compound, it is not possible to determine one specific peak for the glucosamine unit. So, the peak of $N^+(CH_3)_3$ may be chosen and, as the degree of quaternization (DQ) or degree of substitution of a HTCC is known, it is possible to extrapolate the relative abundance of the glucosamine units.

For example, the graft ratio of PEO on HMD may be calculated equation (4):

$$GR(\%) = \frac{12 \times [PEG] \times [SU - GR]}{nH^+PEG \times [(CH_2CH_2)SU]} \quad (4)$$

wherein "12" is the number of $H^+$ in $CH_2CH_2$ (i.e., 4) multiplied by the number of hydroxyl group per glucose unit (i.e., 3), "[PEG]" is the integral of proton peak of PEO at 3.7 ppm ($CH_2O$), "[SU-GR]" is the SU-graft ratio (expressed in %) of HMD-COOH, "$nH^+PEG$" is the number of proton per PEO chain according to the molecular weight of PEG, and "[$(CH_2CH_2)SU$]" is the integral of protons peaks of succinate at 2.51 and 2.71 ppm ($CH_2CH_2$).

In equation (4), [PEG]/$nH^+PEG$ is the relative abundance of PEO in the compound. For the relative abundance of the glucose units of HMD in the compound the succinate peaks at 2.51 and 2.71 ppm may be chosen and, as the [SU-GR] can be determined, it is possible to extrapolate the relative abundance of the glucose units.

In certain embodiments, the GR may provide an estimation of the folate graft ratio of a compound (i.e., FR-targeting excipient). As the percentage of PEO which binds to folate can be experimentally determined, the determination of the PEO-GR allows the determination of the folate graft ratio. For example, when about 90% of PEO binds to folate, the determination of the PEO-GR allows the determination of the folate graft ratio (which is about 90% of the PEO-GR).

In certain embodiments, the linker may comprise or consist essentially of a polyethylene oxide having the Formula —$(CH_2—CH_2—O)_q$— or —$(O—CH_2—CH_2)_q$—, wherein q is an integer selected from 20 to 120. For example, q is an integer selected from 40 to 110, from 50 to 100, or from 60 to 90.

Such polyethylene oxide chain lengths allow optimal distance between the folate moiety and the polysaccharide or functionally-modified polysaccharide, such as when polysaccharide or functionally-modified polysaccharide is comprised in a nanoparticle, between the folate moiety and the nanoparticle surface.

In certain embodiments, the linker may comprise or consist essentially of a polyethylene oxide having an average molecular weight ranging from about 500 Da to about 7500 Da. For example, the linker may comprise or consist essentially of a polyethylene oxide having an average molecular weight ranging from about 1000 Da to about 5000 Da, or from about 2000 Da to about 4000 Da. For example, the linker may comprise or consist essentially of a polyethylene oxide having an average molecular weight of at least about 500 Da, at least about 1000 Da, at least about 1500 Da, at least about 2000 Da, at least about 2500 Da, at least about 3000 Da, at least about 3500 Da, or at least about 4000 Da.

In certain embodiments of the products (such as pharmaceutical formulations or FR-targeting excipients) or uses, as taught herein the linker may have the Formula X,

$$-A^1-L^1-A^2- \quad (X)$$

wherein the left side of the linker of Formula X is connected to a polysaccharide or functionally-modified polysaccharide as taught herein (i.e., connected to $X^2$) and the right side of the linker of Formula X is connected to a folate moiety as taught herein (i.e., connected to $X^3$); wherein $A^1$ is selected from a group consisting of —CO—, —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached or connected to $L^1$ and the left side thereof is connected to a polysaccharide or functionally-modified polysaccharide as taught herein (i.e., connected to $X^2$), wherein $L^{14}$, $L^{15}$, $L^{16}$, $L^{17}$, and $L^{18}$ are each independently $C_{1-6}$alkylene optionally substituted with one or more substituents selected from a group consisting of hydroxyl, $C_{1-6}$alkyl and $C_{1-6}$alkoxy; $R^{16}$ and $R^{17}$ are each independently selected from hydrogen or $C_{1-6}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is connected to a polysaccharide or functionally-modified polysaccharide as taught herein (i.e., connected to $X^2$), wherein $L^{14}$, $L^{15}$, $L^{16}$, $L^{17}$, and $L^{18}$ are each independently $C_{1-4}$alkylene optionally substituted with one or more substituents selected from a group consisting of hydroxyl, $C_{1-4}$alkyl and $C_{1-4}$alkoxy; $R^{16}$ and $R^{17}$ are each independently selected from hydrogen or $C_{1-4}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N($R^{17}$)—, wherein the right side of each group is attached to $L^1$ and the left side thereof is connected to a polysaccharide or functionally-modified polysaccharide as taught herein (i.e., connected to $X^2$), wherein $L^{14}$, $L^{15}$, $L^{16}$, $L^{17}$, and $L^{18}$ are each independently $C_{1-3}$alkylene optionally substituted with one or more substituents selected from a group consisting of hydroxyl and $C_{1-3}$alkyl; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—N($R^{16}$)-$L^{17}$-, and —CO-$L^{18}$-CO—N ($R^{17}$)—, wherein the right side of each group is attached to $L^1$ and the left side thereof is connected to a polysaccharide or functionally-modified polysaccharide as taught herein (i.e. connected to $X^2$), wherein L is methylene, ethylene n-propylene; $L^{15}$, $L^{16}$, $L^{17}$ and $L^{18}$ are each independently methylene or ethylene; $R^{16}$ and $R^{17}$ are each independently selected from hydrogen or $C_{1-3}$alkyl; preferably $A^1$ is selected from a group consisting of —CO-$L^{14}$-O—, —CO-$L^{15}$-CO—O—, —CO-$L^{16}$-CO—NH-$L^{17}$-, and —CO-$L^{18}$-CO—NH—, wherein the right side of each group is attached to $L^1$ and the left side thereof is connected to a polysaccharide or functionally-modified polysaccharide as taught herein (i.e., connected to $X^2$), wherein $L^{14}$ is n-propylene; $L^{15}$, $L^{16}$, $L^{17}$, and $L^{18}$ are each independently ethylene;

$L^1$ is a poly($C_{1-6}$alkyleneoxide); preferably $L^1$ is selected from a polyethylene oxide (PEO), a polypropylene oxide (PPO), or a block copolymer of PEO and PPO; preferably $L^1$ is a polyethylene oxide having the Formula —($CH_2$—$CH_2$—O)$_q$— or —(O—$CH_2$—$CH_2$)$_q$—, wherein q is an integer selected from 20 to 120; preferably $L^1$ is a polyethylene oxide having the Formula —($CH_2$—$CH_2$—O)$_q$— or —(O—$CH_2$—$CH_2$)$_q$—, wherein q is an integer selected from 40 to 110; preferably $L^1$ is a polyethylene oxide having the Formula —($CH_2$—$CH_2$—O)$_q$— or —(O—$CH_2$—$CH_2$)$_q$—, wherein q is an integer selected from 60 to 90;

$A^2$ is a single bond or is selected from a group consisting of —N($R^{18}$)—, —O—, -$L^{19}$-N($R^{19}$)—, and -$L^{20}$-O—, wherein the left side of each group is attached to $L^1$ and the right side thereof is connected to a folate moiety as taught herein (i.e., connected to $X^3$), wherein $L^{19}$ and $L^{20}$ are each independently $C_{1-6}$alkylene being optionally substituted with one or more substituents selected from a group consisting of hydroxyl, $C_{1-6}$alkyl, and $C_{1-6}$alkoxy, $R^{18}$ and $R^{19}$ are each independently selected from hydrogen or $C_{1-6}$alkyl; preferably $A^2$ is a single bond or is selected from a group consisting of —N($R^{18}$)—, —O—, -$L^{19}$-N($R^{19}$)—, or -$L^{20}$O—, wherein the left side of each group is attached to $L^1$ and the right side thereof is connected to a folate moiety as taught herein (i.e., connected to $X^3$), wherein $L^{19}$ and $L^{20}$ are each independently $C_{1-4}$alkylene being optionally substituted with one or more substituents selected from a group consisting of hydroxyl, $C_{1-4}$alkyl, and $C_{1-4}$alkoxy, $R^{18}$ and $R^{19}$ are each independently selected from hydrogen or $C_{1-4}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is connected to a folate moiety as taught herein (i.e., connected to $X^3$), wherein $L^{19}$ and $L^{20}$ are each independently $C_{1-3}$alkylene being optionally substituted with one or more substituents selected from a group consisting of hydroxyl and $C_{1-3}$alkyl, $R^{18}$ and $R^{19}$ are each independently selected from hydrogen or $C_{1-3}$alkyl; preferably $A^2$ is a single bond or is selected from a group consisting of —N($R^{18}$)—, -$L^{19}$-N($R^{19}$)—, or -$L^{20}$O—, wherein the left side of each group is attached to $L^1$ and the right side thereof is connected to a folate moiety as taught herein (i.e., connected to $X^3$), wherein $L^{19}$ and $L^{20}$ are each independently methylene or ethylene; $R^{18}$ and $R^{19}$ are each independently selected from hydrogen or $C_{1-3}$alkyl; preferably $A^2$ is a single bond or is selected from a group consisting of —N(H)—, -$L^{19}$-N(H)—, or -$L^{20}$O—, wherein the left side of each group is attached to $L^1$ and the right side thereof is connected to a folate moiety as taught herein (i.e., connected to $X^3$), wherein $L^{19}$ and $L^{20}$ are each independently ethylene.

In certain embodiments, the linker may have the Formula X as taught herein, wherein $A^1$ and $A^2$ have the same meaning as that defined herein, $L^1$ is a polyethylene oxide, and the polyethylene oxide graft ratio (PEO-GR or GR) of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%.

In certain embodiments, the linker may have the Formula X as taught herein, wherein $L^1$ and $A^2$ have the same meaning as that defined herein, $A^1$ comprises —CO($CH_2$)$_2$CO— (i.e., succinate moiety) (i.e., $A^1$ is —CO($CH_2$)$_2$COO—, —CO($CH_2$)$_2$CONH—, or —CO($CH_2$)$_2$CONH($CH_2$)$_2$—), and the succinate graft ratio (SU-GR) of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

The recitation "succinate graft ratio" or "SU-GR" of a compound (i.e., FR-targeting excipient), as used herein, refers to the relative abundance of succinate or succinate moiety (i.e., —COCH$_2$CH$_2$CO—) in the compound (i.e., FR-targeting excipient) divided by the relative abundance of functional groups of a polysaccharide (i.e., functionally-modified polysaccharide) in the compound (i.e., FR-targeting excipient), suitably expressed as a percentage. The SU-GR corresponds to the percentage of functional groups of the functionally-modified polysaccharide which are linked to succinate.

The succinate graft ratio may be determined by $^1$H NMR (for example at 293 K in $D_2O$). The succinate graft ratio may be determined by $^1$H NMR and calculated using a suitable equation.

For example, the succinate-graft ratio of HMD may be calculated using the equation (3):

$$SU - GR(\%) = 100 \times \frac{[(CH_2CH_2)SU]}{4 \times [(CHO)GLC]} \quad (3)$$

wherein "[($CH_2CH_2$)SU]" is the integral of protons peaks of succinate at 2.51 and 2.71 ppm ($CH_2CH_2$), "4" is the number of $H^+$ in $CH_2CH_2$ of the succinate (i.e., 4), and "[(CHO)GLC]" is the integral of the peaks of glucose monomer between 3.30 and 4.50 ppm (CHO).

In equation (3), [($CH_2CH_2$)SU]/4 corresponds to (3× [($CH_2CH_2$)SU])/12), wherein "[($CH_2CH_2$)SU]/12" is the relative abundance of succinate in the compound. For the relative abundance of the glucose units of HMD in the compound, the peaks of glucose monomer between 3.30 and 4.50 ppm have been chosen. The 4 in equation (3) corresponds to the number of $H^+$ in $CH_2CH_2$ of the succinate (i.e., 4), multiplied by the number of hydroxyl group per glucose unit (i.e., 3), and divided by the number of $H^+$ of CHO of the glucose units (i.e., 3, corresponding to the $H^+$ of C5 and C6 because C2, C3 and C4 have their hydroxyl groups esterified).

In certain embodiments, the linker may have the Formula X as taught herein, wherein $A^1$ comprises —$CO(CH_2)_2$CO— (i.e., succinate moiety) (i.e., $A^1$ is —$CO(CH_2)_2$COO—, —$CO(CH_2)_2$CONH—, or —$CO(CH_2)_2$CONH$(CH_2)_2$—), $L^1$ is a polyethylene oxide, $A^2$ has the same meaning as that defined herein, and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may comprise a folate moiety as taught herein covalently linked to a polysaccharide or functionally-modified polysaccharide as taught herein via a single bond.

In certain embodiments of the products (such as pharmaceutical formulations or FR-targeting excipients) or uses, as taught herein, the FR-targeting excipient may comprise a folate moiety as defined herein covalently linked to a polysaccharide or functionally-modified polysaccharide as taught herein via a linker as taught herein.

In certain embodiments, the FR-targeting excipient may have the Formula XIa,

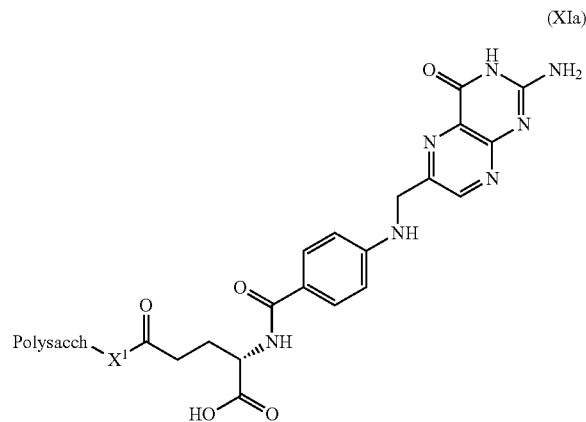

(XIa)

wherein Polysacch is a polysaccharide or functionally-modified polysaccharide as defined herein, and $X^1$ is a single bond or a linker, wherein the linker comprises a polyether, ether, amine, polyamine, amino acid, peptide, a polypeptide, a carbohydrate, or a combination of two or more thereof.

In certain embodiments, the FR-targeting excipient may have the Formula XIa, wherein Polysacch is a polysaccharide or functionally-modified polysaccharide as defined herein, and $X^1$ is a linker having the Formula X as taught herein.

In certain embodiments, the FR-targeting excipient may have the Formula XI,

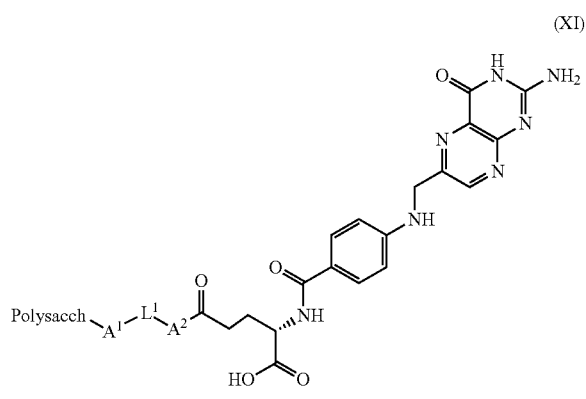

(XI)

wherein Polysacch is a polysaccharide or functionally-modified polysaccharide as defined herein, and $A^1$, $L^1$, and $A^2$ have the same meaning as that defined herein.

In certain embodiments of the products (such as pharmaceutical formulations or FR-targeting excipients) or uses, as taught herein, the FR-targeting excipient may have the Formula XI as taught herein, wherein Polysacch is a polysaccharide or functionally-modified polysaccharide selected from chitosan or functionally-modified chitosan; N-[(2-hydroxy-3-trimethylammonium)propyl] chitosan (HTC) and its salts (such as chloride, acetate, glutamate, or lactate salts) for example HTCC (i.e., chloride salt); N-trimethyl chitosan (TMC) and its salts (such as chloride, acetate, glutamate, or lactate salts); N,O-carboxymethyl chitosan (N,O-CMC) and its salts (such as chloride, acetate, glutamate, or lactate salts); N-carboxymethyl chitosan (N-CMC) and its salts (such as chloride, acetate, glutamate, or lactate salts); N,N-carboxymethyl chitosan (NN-CMC) and its salts (such as chloride, acetate, glutamate, or lactate salts); O-carboxymethyl chitosan (O-CMC) and its salts (such as chloride, acetate, glutamate, or lactate salts); hydrophobically-modified chitosan (HMC) and its salts (such as chloride, acetate, glutamate, or lactate salts); dextran or functionally-modified dextran; hydrophobically-modified dextran (HMD) and its salts (such as chloride, acetate, glutamate, or lactate salts); starch or functionally-modified starch; hydroxypropyl starch; amylose or functionally-modified amylose; amylopectin or functionally-modified amylopectin; cellulose or functionally-modified cellulose; methylcellulose and its salts (such as acetate or acetate phthalate salts); carboxymethylcellulose and its salts (such as acetate or acetate phthalate salts); hydroxyethylcellulose and its salts (such as acetate or acetate phthalate salts); ethylcellulose and its salts (such as acetate or acetate phthalate salts); hydroxyethylmethylcellulose and its salts (such as acetate or acetate phthalate salts); hydroxypropylcellulose and its salts (such as acetate or acetate phthalate salts); hypromellose and its salts (such as acetate or acetate phthalate salts); hypromellose acetate succinate; hypromellose phthalate; croscarmellose and its salts (such as acetate or acetate phthalate salts); chitin; cyclodextrin; dextrate; dextrin; maltodextrin; pullulan; or guar gum; and $A^1$, $L^1$, and $A^2$ have the same meaning as that defined herein.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_3$O—; $L^1$ is a polyethylene oxide having the Formula (CH$_2$CH$_2$O)$_q$ wherein q is an integer selected from 20 to 120; and $A^2$ is —(CH$_2$)$_2$NH—.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_3$O—; $L^1$ is a polyethylene oxide having the Formula (CH$_2$CH$_2$O)$_q$ wherein q is an integer selected from 20 to 120; and $A^2$ is —(CH$_2$)$_2$NH—; and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_2$CONH(CH$_2$)$_2$—; $L^1$ is a polyethylene oxide having the Formula (OCH$_2$CH$_2$)$_q$ wherein q is an integer selected from 20 to 120; and $A^2$ is —NH—.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_2$CONH(CH$_2$)$_2$—; $L^1$ is a polyethylene oxide having the Formula (OCH$_2$CH$_2$)$_q$ wherein q is an integer selected from 20 to 120; and $A^2$ is —NH—; and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_2$CONH(CH$_2$)$_2$—; $L^1$ is a polyethylene oxide having the Formula (OCH$_2$CH$_2$)$_q$ wherein q is an integer selected from 20 to 120; and $A^2$ is —NH—; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_2$CONH(CH$_2$)$_2$—; $L^1$ is a polyethylene oxide having the Formula (OCH$_2$CH$_2$)$_q$ wherein q is an integer selected from 20 to 120; and $A^2$ is —NH—; and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_2$COO—; $L^1$ is a polyethylene oxide having the Formula (CH$_2$CH$_2$O)$_q$ wherein q is an integer selected from 20 to 120; and $A^2$ is —(CH$_2$)$_2$NH—.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_2$COO—; $L^1$ is a polyethylene oxide having the Formula (CH$_2$CH$_2$O)$_q$ wherein q is an integer selected from 20 to 120; and $A^2$ is —(CH$_2$)$_2$NH—; and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_2$COO—; $L^1$ is a polyethylene oxide having the Formula (CH$_2$CH$_2$O)$_q$ wherein q is an integer selected from 20 to 120; and $A^2$ is —(CH$_2$)$_2$NH—; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_2$COO—; $L^1$ is a polyethylene oxide having the Formula (CH$_2$CH$_2$O)$_q$ wherein q is an integer selected from 20 to 120; and $A^2$ is —(CH$_2$)$_2$NH—; and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; $A^1$ is —CO(CH$_2$)$_2$CONH—; $L^1$ is a polyethylene oxide having the Formula (CH$_2$CH$_2$O)$_q$ wherein q is an integer selected from 20 to 120; and $A^2$ is —(CH$_2$)$_2$NH—.

In certain embodiments of the products (such as pharmaceutical formulations or FR-targeting excipients) or uses, as taught herein, the FR-targeting excipient may have the Formula XI as taught herein, wherein Polysacch is HMD; $A^1$ is —CO(CH$_2$)$_2$CONH—; $L^1$ is a polyethylene oxide having the Formula (CH$_2$CH$_2$O)$_q$ wherein q is an integer selected from 20 to 120; and $A^2$ is —(CH$_2$)$_2$NH—; and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; $A^1$ is —CO(CH$_2$)$_2$CONH—; $L^1$ is a polyethylene oxide having the Formula (CH$_2$CH$_2$O)$_q$ wherein q is an integer selected from 20 to 120; and $A^2$ is —(CH$_2$)$_2$NH—; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; $A^1$ is —CO(CH$_2$)$_2$CONH—; $L^1$ is a polyethylene oxide having the Formula (CH$_2$CH$_2$O)$_q$ wherein q is an integer selected from 20 to 120; and $A^2$ is —(CH$_2$)$_2$NH—; and the FA-GR as defined herein of the HMD may be at least about 1%, for example the FA-GR as defined herein of the HMD may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the FA-GR as defined herein of the HMD may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; $A^1$ is —CO(CH$_2$)$_2$CONH—; $L^1$ is a polyethylene oxide having the Formula (CH$_2$CH$_2$O)$_q$ wherein q is an integer selected from 20 to 120; and $A^2$ is —(CH$_2$)$_2$NH—; and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; $A^1$ is —CO(CH$_2$)$_2$CONH—; $L^1$ is a polyethylene oxide having the Formula (CH$_2$CH$_2$O)$_q$ wherein q is an integer selected from 20 to 120; and $A^2$ is —$(CH_2)_2NH$—; and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%; and the FA-GR as defined herein of the HMD may be at least about 1%, for example the FA-GR as defined herein of the HMD may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the FA-GR as defined herein of the HMD may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; $A^1$ is —$CO(CH_2)_2CONH$—; $L^1$ is a polyethylene oxide having the Formula $(CH_2CH_2O)_q$ wherein q is an integer selected from 20 to 120; and $A^2$ is —$(CH_2)_2NH$—; and the FA-GR of the FR-targeting excipients may be at least about 1%, for example, the FA-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the FA-GR of the FR-targeting excipient may be ranging from about 1% to about 100%, from about 1% to about 80%, from about 5% to about 70%, from about 10% to about 60%, or from about 15% to about 50%; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; $A^1$ is —$CO(CH_2)_2CONH$—; $L^1$ is a polyethylene oxide having the Formula $(CH_2CH_2O)_q$ wherein q is an integer selected from 20 to 120; and $A^2$ is —$(CH_2)_2NH$—; and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%; the FA-GR as defined herein of the HMD may be at least about 1%, for example the FA-GR as defined herein of the HMD may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the FA-GR as defined herein of the HMD may be ranging from about 1% to about 100%, from about 1% to about 80%, from about 5% to about 70%, from about 10% to about 60%, or from about 15% to about 50%; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; $A^1$ is —$CO(CH_2)_2COO$—; $L^1$ is a polyethylene oxide having the Formula $(CH_2CH_2O)_q$ wherein q is an integer selected from 20 to 120; and $A^2$ is —$(CH_2)_2NH$—.

In certain embodiments, the FR-targeting excipient may have the Formula XI as taught herein, wherein Polysacch is HMD; $A^1$ is —$CO(CH_2)_2COO$—; $L^1$ is a polyethylene oxide having the Formula $(CH_2CH_2O)_q$ wherein q is an integer selected from 20 to 120; and $A^2$ is —$(CH_2)_2NH$—; and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; $A^1$ is —$CO(CH_2)_2COO$—; $L^1$ is a polyethylene oxide having the Formula $(CH_2CH_2O)_q$ wherein q is an integer selected from 20 to 120; and $A^2$ is —$(CH_2)_2NH$—; and the FA-GR as defined herein of the HMD may be at least about 1%, for example the FA-GR as defined herein of the HMD may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the FA-GR as defined herein of the HMD may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; $A^1$ is —CO(CH$_2$)$_2$COO—; L$^1$ is a polyethylene oxide having the Formula (CH$_2$CH$_2$O)$_q$ wherein q is an integer selected from 20 to 120; and A$^2$ is —(CH$_2$)$_2$NH—; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; A$^1$ is —CO(CH$_2$)$_2$COO—; L$^1$ is a polyethylene oxide having the Formula (CH$_2$CH$_2$O)$_q$ wherein q is an integer selected from 20 to 120; and A$^2$ is —(CH$_2$)$_2$NH—; the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%; and the FA-GR as defined herein of the HMD may be at least about 1%, for example the FA-GR as defined herein of the HMD may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the FA-GR as defined herein of the HMD may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; A$^1$ is —CO(CH$_2$)$_2$COO—; L$^1$ is a polyethylene oxide having the Formula (CH$_2$CH$_2$O)$_q$ wherein q is an integer selected from 20 to 120; and A$^2$ is —(CH$_2$)$_2$NH—; the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HMD; A$^1$ is —CO(CH$_2$)$_2$COO—; L$^1$ is a polyethylene oxide having the Formula (CH$_2$CH$_2$O)$_q$ wherein q is an integer selected from 20 to 120; and A$^2$ is —(CH$_2$)$_2$NH—; the FA-GR as defined herein of the HMD may be at least about 1%, for example the FA-GR as defined herein of the HMD may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the FA-GR as defined herein of the HMD may be ranging from about 1% to about 100%, from about 1% to about 80%, from about 5% to about 70%, from about 10% to about 60%, or from about 15% to about 50%; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_2$CONH—; $L^1$ is a polyethylene oxide having the Formula (CH$_2$CH$_2$O)$_q$ wherein q is an integer selected from 20 to 120; and $A^2$ is —(CH$_2$)$_2$O—.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_2$CONH—; $L^1$ is a polyethylene oxide having the Formula (CH$_2$CH$_2$O)$_q$ wherein q is an integer selected from 20 to 120; and $A^2$ is a single bond or —(CH$_2$)$_2$O—; and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%.

In certain embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_2$CONH—; $L^1$ is a polyethylene oxide having the Formula (CH$_2$CH$_2$O)$_q$ wherein q is an integer selected from 20 to 120; and $A^2$ is a single bond or —(CH$_2$)$_2$O—; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

In certain preferred embodiments of the products (such as pharmaceutical formulations or FR-targeting excipients) or uses, as taught herein, the FR-targeting excipient may have the Formula XI as taught herein, wherein Polysacch is HTCC; $A^1$ is —CO(CH$_2$)$_2$CONH—; $L^1$ is a polyethylene oxide having the Formula (CH$_2$CH$_2$O)$_q$ wherein q is an integer selected from 20 to 120; and $A^2$ is a single bond or —(CH$_2$)$_2$O—; and the GR of the FR-targeting excipients may be at least about 1%, for example, the GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the GR of the FR-targeting excipient may be ranging from about 1% to about 100%, from about 1% to about 80%, from about 5% to about 70%, from about 10% to about 60%, or from about 15% to about 50%; and the SU-GR of the FR-targeting excipient may be at least about 1%, for example, the SU-GR of the FR-targeting excipient may be at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, for example, the SU-GR of the FR-targeting excipient may be ranging from about 1% to about 100%, from about 1% to about 80%, from about 5% to about 70%, from about 10% to about 60%, or from about 15% to about 50%.

The present inventors have surprisingly found that such FR-targeting excipients are able to interact with the antineoplastic agents as taught herein (including hydrophilic antineoplastic agents) and these interactions advantageously lead to a better entrapment and/or encapsulation of the antineoplastic agents in the pharmaceutical formulations. Hence, using such FR-targeting excipients allows high encapsulation efficiency and high loading of the antineoplastic agent in the present pharmaceutical formulations. The present invention also encompasses an FR-targeting excipient as taught herein, preferably an FR-targeting excipient comprising at least one unit selected from the group consisting of units of Formula XIb, XIc, XId, XIe, XIg, XIh, XIj, XIk, XIm, XIn, XIp, and XIq, as taught herein, or any subgroup thereof, wherein $Y^1$, $Y^2$, $Y^3$, $X^4$, $R^1$, $R^2$, $R^3$, $R^4$, $R^{11}$, $R^{20}$, $R^{21}$, $R^{31}$, $R^{34}$, $R^{41}$, $R^{43}$, $R^{53}$, $R^{54}$, $X^1$, and $X^3$ have the same meaning as defined herein.

In certain embodiments, the FR-targeting excipient may be a folate-polysaccharide conjugate as taught herein. In certain embodiments, the FR-targeting excipient may be a folate-polysaccharide conjugate comprising at least one unit of Formula XIb, XIc, XId, XIe, XIg, XIh, XIj, XIk, XIm, XIn, XIp, and/or XIq, as taught herein, or any subgroup thereof, wherein $Y^1$, $Y^2$, $Y^3$, $X^4$, $R^1$, $R^2$, $R^3$, $R^4$, $R^{11}$, $R^{20}$, $R^{21}$, $R^{31}$, $R^{34}$, $R^{41}$, $R^{43}$, $R^{53}$, $R^{54}$, $X^1$, and $X^3$ have the same meaning as defined herein.

In certain embodiments, the FR-targeting excipient may be a folate-polysaccharide conjugate comprising one or more units of Formula XIb, XIc, XId, XIe, XIg, XIh, XIj, XIk, XIm, XIn, XIp, or XIq, as taught herein, or any subgroup thereof, wherein $Y^1$, $Y^2$, $Y^3$, $X^4$, $R^1$, $R^2$, $R^3$, $R^4$, $R^{11}$, $R^{20}$, $R^{21}$, $R^{31}$, $R^{34}$, $R^{41}$, $R^{43}$, $R^{53}$, $R^{54}$, $X^1$, and $X^3$ have the same meaning as defined herein.

The present invention also encompasses an FR-targeting excipient having the Formula XI or XIa, as taught herein, wherein Polysacch, $X^1$, $A^1$, $L^1$, and $A^2$ have the same meaning as that defined herein.

The present invention also encompasses the use of the FR-targeting excipients as taught herein as a pharmaceutical excipient. Such use of the FR-targeting excipients advantageously allows high encapsulation efficiency and high loading of pharmaceutical active ingredients or other components in a pharmaceutical formulation.

A further aspect of the invention also encompasses the FR-targeting excipients as taught herein for use as a pharmaceutical excipient, preferably for use as a pharmaceutical excipient in any one of the diseases as taught herein, and more preferably for use as a pharmaceutical excipient in the treatment of a proliferative disease affecting at least part of the respiratory tract, such as preferably but without limitation a tumour or cancer affecting at least part of the respiratory tract, wherein a FR-targeting excipient is to be administered in vivo together with one or more pharmaceutical active ingredients, preferably one or more antineoplastic agents as taught herein. Further provided is a method for treating any one of the diseases as taught herein, preferably a proliferative disease affecting at least part of the respiratory tract, such as preferably but without limitation a tumour or cancer affecting at least part of the respiratory tract, in a subject in need of such treatment, comprising administering to said subject a FR-targeting excipient as taught herein as a pharmaceutical excipient together with one or more pharmaceutical active ingredients, preferably one or more one or more antineoplastic agents as taught herein.

The present invention also encompasses processes for the preparation of the FR-targeting excipients as taught herein. In the reactions described, it can be necessary to protect reactive functional groups, for example hydroxyl, amino, or carboxyl groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

In certain embodiments, when $X^1$ is a linker as taught herein, the FR-targeting excipient may be synthesized by the following method of preparation. The method for the preparation of the FR-targeting excipients of the invention consists of first coupling the folate moiety as taught herein ($—X^3$) to the linker as taught herein ($—X^1—$) and then coupling $X^1—X^3$ to the polysaccharide or functionally-modified polysaccharide as taught herein (via $—X^2—$).

The carboxylic groups of the folate moiety are first conjugated with the free hydroxyl or amine function of the linker using an appropriate method to form ester or amide group, respectively. The method employed may be an esterification or an amidation synthesis method (e.g. steglich esterification, steglich amidation, acyl chloride method) or a peptide synthesis method (e.g. liquid-phase synthesis, solid-phase synthesis).

The polysaccharide or functionally-modified polysaccharide may be coupled with a carboxylic group for instance using succinic anhydride.

The functional group (e.g., hydroxyl, amine, or carboxyl group) of the polysaccharide or functionally-modified polysaccharide is then coupled to the linker using an appropriate method to form ester or amide group. The method employed may be an esterification or an amidation synthesis method (e.g. steglich esterification, steglich amidation, acyl chloride method) or a peptide synthesis method (e.g. liquid-phase synthesis, solid-phase synthesis).

In certain embodiments, when $X^1$ is a linker of Formula X, one or both of carboxylic groups of folic acid or derivative thereof can be first coupled with a compound of formula (A) H-$A^1$-$L^1$-$A^2$-H, or (B) HO-$A^1$-$L^1$-$A^2$-H, thereby obtaining a compound of formula (A1) H-$A^1$-$L^1$-$A^2$-folate or (B1) HO-$A^1$-$L^1$-$A^2$-folate which can then be reacted with a polysaccharide or functionally-modified polysaccharide as taught herein.

Compounds of formula A, B or folic acid or derivative thereof may contain functional groups that would interfere with the coupling procedures described for the coupling step. In this case it is understood that Compounds of formula A, B or folic acid or derivative can be suitably protected by methods known in the art before conducting the coupling procedure and compounds need to be deprotected after the coupling step by methods known in the art.

In an embodiment, the coupling steps can be performed by coupling methods known in the art, as for example with the help of a coupling agent under basic conditions. Non limiting example of suitable coupling agents can be selected from for example N,N'-dicyclohexylcarbodiimide (DCC), N,N'-carbonyldiimidazole (CDI), 1-(3-dimethylaminopropyl)-3-ethylcarbodiimide hydrochloride (EDC), 1-[bis(dimethylamino)-methylene]-7H-1,2,3-triazolo[4,5-b]pyridinium-3-oxide hexafluorophosphate (HATU), 1-hydroxy-1,2,3-benzotriazo (HOBT), O-benzotriazol-1-yl-N,N,N',N'-tetramethyluronium tetrafluoroborate (TBTU), or O-benzotriazole-N,N,N',N'-tetramethyl-uronium-hexafluoro-phosphate (HBTU). Suitable bases include triethylamine, pyridine, N-methylmorpholine and diisopropylethylamine. The coupling reaction can be performed at a temperature from about −20 to about 90° C., for example from about 0° C. to about 50° C., for example from about 0° C. to about 30° C., for example at room temperature.

In alternative embodiments, when $X^1$ is a single bond, one or both carboxylic groups of folic acid or derivative thereof, preferably the gamma carboxylic group of folic acid or derivative thereof, can be directly coupled with a polysaccharide or modified polysaccharide as taught herein. In an embodiment, this step can be performed by coupling methods known in the art, as for example with the help of a coupling agent under basic conditions. Non limiting example of suitable coupling agents can be selected from for example DCC, CDI, EDC, HATU, TBTU, or HBTU. Suitable bases include triethylamine, pyridine, N-methylmorpholine and diisopropylethylamine. The coupling reaction can be performed at a temperature from about −20 to about 90° C., for example from about 0° C. to about 50° C., for example from about 0° C. to about 30° C., for example at room temperature.

When describing the units or compounds as taught herein, the terms used are to be construed in accordance with the following definitions, unless a context dictates otherwise.

For pharmaceutical use, the units or compounds as taught herein may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by any unit or compound as taught herein with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. No. 6,372,778, U.S. Pat. No. 6,369,086, U.S. Pat. No. 6,369,087 and U.S. Pat. No. 6,372,733.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e., a compound that is sufficiently robust to survive isolation to a useful degree of purity from a reaction mixture, and formulation into a therapeutic agent.

Where groups may be optionally substituted, such groups may be substituted with one or more, such as one, two, or three substituents. Substituents may be selected from but not limited to, for example, the group comprising hydroxyl, alkyl, and alkoxy.

As used herein the terms such as "alkyl, aryl, or cycloalkyl, each being optionally substituted with . . . " or "alkyl, aryl, or cycloalkyl, optionally substituted with . . . " encompasses "alkyl optionally substituted with . . . ", "aryl optionally substituted with . . . " and "cycloalkyl optionally substituted with . . . ".

The term "alkyl", as a group or part of a group, refers to a hydrocarbyl group of Formula $C_nH_{2n+1}$ wherein n is a number of at least 1. Alkyl groups may be linear, or branched and may be substituted as indicated herein. Generally, the alkyl groups comprise from 1 to 20 carbon atoms, preferably from 1 to 12 carbon atoms, preferably from 1 to 10 carbon atoms, preferably from 1 to 6 carbon atoms, more preferably 1, 2, 3, 4, 5, 6 carbon atoms. When a subscript is used herein following a carbon atom, the subscript refers to the number of carbon atoms that the named group may contain. For example, the term "$C_{1-25}$alkyl", as a group or part of a group, refers to a hydrocarbyl group of Formula $C_nH_{2n+1}$ wherein n is a number ranging from 1 to 25. Thus, for example, $C_{1-25}$alkyl groups include all linear, or branched alkyl groups having 1 to 25 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers, heptyl and its isomers, octyl and its isomers, nonyl and its isomers, decyl and its isomers, undecyl and its isomers, dodecyl and its isomers, tridecyl and its isomers, tetradecyl and its isomers, pentadecyl and its isomers, hexadecyl and its isomers, heptadecyl and its isomers, octadecyl and its isomers, nonadecyl and its isomers, icosyl and its isomers, henicosyl and its isomers, docosyl and its isomers, tricosyl and its isomers, tetracosyl and its isomers, pentacosyl and its isomers, and the like. For example, $C_{1-10}$ alkyl includes all linear, or branched alkyl groups having 1 to 10 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers, heptyl and its isomers, octyl and its isomers, nonyl and its isomers, decyl and its isomers and the like. For example, $C_{1-6}$alkyl includes all linear, or branched alkyl groups having 1 to 6 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers. When the suffix "ene" is used in conjunction with an alkyl group, i.e. "alkylene", this is intended to mean the alkyl group as defined herein having two single bonds as points of attachment to other groups. For example, $C_{1-6}$alkylene includes all linear, or branched alkylene groups having 1 to 6 carbon atoms, and thus includes methylene, ethylene, methylmethylene, propylene, ethylethylene, 1,2-dimethylethylene, butylene and its isomers, pentylene and its isomers, hexylene and its isomers. Similarly, where alkenyl groups as defined herein and alkynyl groups as defined herein, respectively, are divalent groups having single bonds for attachment to two other groups, they are termed "alkenylene" and "alkynylene" respectively.

The term "$C_{2-6}$alkenyl" as a group or part of a group, refers to an unsaturated hydrocarbyl group, which may be linear, branched or cyclic, comprising one or more carbon-carbon double bonds. Alkenyl groups preferably comprise between 2 and 6 carbon atoms, preferably between 2 and 4 carbon atoms, still more preferably between 2 and 3 carbon atoms. Non-limiting examples of alkenyl groups are ethenyl, 2-propenyl, 2-butenyl, 3-butenyl, 2-pentenyl and its isomers, 2-hexenyl and its isomers, 2,4-pentadienyl and the like.

The term "$C_{2-6}$alkynyl" as a group or part of a group, refers to a class of monovalent unsaturated hydrocarbyl groups, wherein the unsaturation arises from the presence of one or more carbon-carbon triple bonds. Alkynyl groups thus preferably comprise between 2 and 6 carbon atoms, preferably between 2 and 4 carbon atoms, still more preferably between 2 and 3 carbon atoms. Non-limiting examples of alkynyl groups are ethynyl, 2-propynyl, 2-butynyl, 3-butynyl, 2-pentynyl and its isomers, 2-hexynyl and its isomers and the like.

The term "cycloalkyl", as a group or part of a group, refers to a cyclic alkyl group, that is a monovalent, saturated, hydrocarbyl group having 1 or more cyclic structure, and comprising from 3 to 12 carbon atoms, more preferably from 3 to 9 carbon atoms, more preferably from 3 to 6 carbon atoms, still more preferably from 5 to 6 carbon atoms. Cycloalkyl includes all saturated hydrocarbon groups containing 1 or more rings, including monocyclic or bicyclic groups. The further rings of multi-ring cycloalkyls may be fused, bridged, and/or joined through one or more spino atoms. The term "$C_{3-6}$cycloalkyl", as used herein, refers to a cyclic alkyl group comprising from 3 to 6 carbon atoms, more preferably from 5 to 6 carbon atoms. Non-limiting examples of $C_{3-6}$cycloalkyl groups include cyclopropyl, cyclobutyl, cyclopentyl, cyclohexyl. Cycloalkyl groups may also be considered to be a subset of homocyclic rings discussed hereinafter. When the suffix "ene" is used in conjunction with a cycloalkyl group, i.e. cycloalkylene, this is intended to mean the cycloalkyl group as defined herein having two single bonds as points of attachment to other groups.

The term "homocyclic ring" as a group or part of a group, refers to a ring wherein the ring atoms comprise only carbon atoms. Non limiting examples of homocyclic rings include cycloalkyl, cycloalkenyl, with cycloalkyl being preferred. Where a ring carbon atom is replaced with a heteroatom, preferably nitrogen, oxygen of sulfur, the heteroatom-containing ring resultant from such a replacement is referred to herein as a heterocyclic ring. More than one carbon atom in a ring may be replaced so forming heterocyclic ring having a plurality of heteroatoms.

The term "$C_{1-6}$alkoxy" or "$C_{1-6}$alkyloxy", as a group or part of a group, refers to a group having the Formula —OR' wherein $R^a$ is $C_{1-6}$alkyl as defined herein above. Non-limiting examples of suitable $C_{1-6}$alkoxy include methoxy, ethoxy, propoxy, isopropoxy, butoxy, isobutoxy, sec-butoxy, tert-butoxy, pentyloxy and hexyloxy.

The term "$C_{1-6}$alkoxycarbonyl", as a group or part of a group, refers to a group of formula —C(=O)O$R^a$, wherein $R^a$ is as defined above for $C_{1-6}$alkyl.

The term "$C_{1-6}$alkylcarbonyloxy", as a group or part of a group, refers to a group of Formula —O—C(=O)$R^a$ wherein $R^a$ is as defined above for $C_{1-6}$alkyl.

The term "$C_{6-12}$aryl", as a group or part of a group, refers to a polyunsaturated, aromatic hydrocarbyl group having a single ring (i.e. phenyl) or multiple aromatic rings fused together (e.g. naphthalene), or linked covalently, typically containing 6 to 12 atoms; wherein at least one ring is aromatic. The aromatic ring may optionally include one to two additional rings (cycloalkyl, heterocyclyl, or heteroaryl) fused thereto. Non-limiting examples of suitable aryl include $C_{6-10}$aryl, more preferably $C_{6-8}$aryl. Non-limiting examples of $C_{6-12}$aryl comprise phenyl, biphenylyl, biphenylenyl, or 1- or 2-naphthanelyl; 5- or 6-tetralinyl, 1-, 2-, 3-, 4-, 5-, 6-, 7- or 8-azulenyl, 4-, 5-, 6 or 7-indenyl, 4- or 5-indanyl, 5-, 6-, 7- or 8-tetrahydronaphthyl, 1,2,3,4-tetrahydronaphthyl, and 1,4-dihydronaphthyl. When the suffix "ene" is used in conjunction with an aryl group, this is intended to mean the aryl group as defined herein having two single bonds as points of attachment to other groups. Non-limiting examples of $C_{6-12}$arylene comprise phenylene, biphenylylene, naphthylene, indenylene, and the like. Where a carbon atom in an aryl group is replaced with a heteroatom, the resultant ring is referred to herein as a heteroaryl ring.

The term "carboxyl$C_{1-6}$alkylenecarbonyl" as a group or part of a group, refers to a $C_{1-6}$alkylenecarbonyl as defined herein substituted by one or more carboxyl.

The term "hydroxyC$_{1-6}$alkyl" as a group or part of a group, refers to C$_{1-6}$alkyl as defined above substituted by one or more hydroxyl groups.

The term "carboxylC$_{6-12}$arylenecarbonyl" as a group or part of a group, refers to a group of formula R$^d$—(C=O)- substituted by one or more carboxyl, wherein R$^d$ is C$_{6-12}$arylene as defined herein.

The term "hydroxyl" or "hydroxy" as used herein refers to the group —OH.

The term "amino" refers to the group —NH$_2$.

The term "ammonium" refers to the group —NH$_3^+$.

The term "carboxy" or "carboxyl" refers to the group —CO$_2$H.

The term "halo" or "halogen" as a group or part of a group is generic for fluoro, chloro, bromo, iodo.

The term "halosubstituted" as used herein refers to alkyl groups which have halogen moieties in the place of at least one hydrogen.

The term "nitroso" as used herein refers to the group —N=O.

The term "C$_{1-25}$alkylcarbonyl" refers to a group of Formula —C(=O)—R$^g$ wherein R$^g$ is as defined above for C$_{1-25}$alkyl. Generally, alkyl groups as part of alkylcarbonyl groups as used herein comprise from 1 to 25 carbon atoms, preferably from 1 to 6 carbon atoms, more preferably from 1 to 4 carbon atoms, still more preferably from 1 to 3 carbon atoms, still more preferably 1 to 2 carbon atoms, or alternatively preferably from 3 to 25 carbon atoms, preferably from 5 to 25 carbon atoms, more preferably from 7 to 25 carbon atoms, more preferably from 11 to 23 carbon atoms, still more preferably from 11 to 17 carbon atoms. Alkyl groups may be linear or branched and may be substituted as indicated herein. As used herein, the alkylcarbonyl may form together with the oxygen to which it is bound a saturated fatty acid moiety. Non-limiting examples of suitable saturated fatty acid moieties as taught herein are caprylic acid, capric acid, lauric acid, myristic acid, palmitic acid, stearic acid, arachidic acid, behenic acid, lignoceric acid, and cerotic acid.

The term "C$_{2-25}$alkenylcarbonyl" refers to a group of Formula —C(=O)—R$^h$ wherein R$^h$ is as defined above for alkenyl. Generally, alkenyl groups as part of alkenylcarbonyl groups as used herein comprise from 2 to 25 carbon atoms, preferably from 2 to 6 carbon atoms, more preferably from 2 to 4 carbon atoms, still more preferably from 2 to 3 carbon atoms, or alternatively preferably from 3 to 25 carbon atoms, more preferably from 5 to 23 carbon atoms, more preferably from 11 to 21 carbon atoms, still more preferably from 13 to 21 carbon atoms. Alkenyl groups may be linear or branched and may be substituted as indicated herein. As used herein, the alkenylcarbonyl may form together with the oxygen to which it is bound an unsaturated fatty acid moiety. Non-limiting examples of suitable unsaturated fatty acid moieties as taught herein are myristoleic acid, palmitoleic acid, sapienic acid, oleic acid, elaidic acid, vaccenic acid, linoleic acid, linoelaidic acid, oi-linolenic acid, arachidonic acid, eicosapentaenoic acid, erucic acid, and docosahexaenoic acid.

The term "fatty acid" generally refers to carboxylic acid with a saturated or unsaturated aliphatic chain of carbon atoms. As used herein, the fatty acids are linked through an ester or amide bond to one or more monosaccharide units of a polysaccharide or functionally-modified polysaccharide. The term "fatty acid" includes saturated and unsaturated fatty acids. The fatty acids or fatty acid moieties may be naturally occurring or synthetic fatty acids or fatty acid moieties.

The term "saturated fatty acid" refers to a carboxylic acid with an aliphatic chain of carbon atoms having the Formula CH$_3$(CH$_2$)COOH, wherein n is an integer selected from 2, 3, 4, 5, 6, 7, 8, 9, 10, 11, 12, 13, 14, 15, 16, 17, 18, 19, 20, 21, 22, 23, or 24. A saturated fatty acid comprises from 4 to 26 carbon atoms, preferably from 6 to 26 carbon atoms, more preferably from 8 to 26 carbon atoms, more preferably from 12 to 24 carbon atoms, still more preferably from 12 to 18 carbon atoms. Non-limiting examples of suitable saturated fatty acids are caprylic acid (i.e., octanoic acid), capric acid (i.e., decanoid acid), lauric acid (i.e., dodecanoic acid), myristic acid (i.e., tetradecanoic acid), palmitic acid (i.e., hexadecanoic acid), stearic acid (i.e., octadecanoic acid), arachidic acid (i.e., eicosanoic acid), behenic acid (i.e., docosanoic acid), lignoceric acid (i.e., tetracosanoic acid), and cerotic acid (i.e., hexacosanoic acid).

The term "unsaturated fatty acid" refers to a carboxylic acid with an aliphatic chain of carbon atoms having one or more double bonds between carbon atoms. An unsaturated fatty acid comprises from 4 to 26 carbon atoms, preferably from 6 to 24 carbon atoms, more preferably from 12 to 22 carbon atoms, more preferably from 14 to 22 carbon atoms. Non-limiting examples of suitable unsaturated fatty acids are myristoleic acid (i.e., (Z)-Tetradec-9-enoic acid or 9-cis-tetradecenoic acid), palmitoleic acid (i.e., hexadec-9-enoic acid or 9-cis-hexadecenoic acid), sapienic acid (i.e., (Z)-6-Hexadecenoic acid or cis-6-hexadecenoic acid), oleic acid (i.e., (9Z)-Octadec-9-enoic acid or cis-9-Octadecenoic acid), elaidic acid (i.e., (E)-octadec-9-enoic acid), vaccenic acid (i.e., (E)-Octadec-11-enoic acid), linoleic acid (i.e., (9Z, 12Z)-9,12-Octadecadienoic acid), linoelaidic acid (i.e., (9E, 12E)-octadeca-9,12-dienoic acid or trans, trans-9,12-octadecadienoic acid), α-linolenic acid (i.e., (9Z,12Z,15Z)-9,12, 15-Octadecatrienoic acid), arachidonic acid (i.e., (5Z,8Z, 11Z,14Z)-5,8,11,14-Eicosatetraenoic acid), eicosapentaenoic acid (i.e., (5Z,8Z,11Z,14Z,17Z)-5,8,11,14, 17-icosapentaenoic acid), erucic acid (i.e., Z)-Docos-13-enoic acid), and docosahexaenoic acid (i.e., (4Z,7Z,10Z, 13Z,16Z,19Z)-docosa-4,7,10,13,16,19-hexaenoic acid). The term "monoglycosyl moiety" or "monoglycosyl", as used herein, refers to a monosaccharide connected with its hemiacetal hydroxyl group to a hydroxyl group of the polysaccharide or functionally-modified polysaccharide.

The term "oligoglycosyl moiety" or "oligoglycosyl", as used herein, refers to an oligosaccharide connected with its hemiacetal hydroxyl group to a hydroxyl group of the polysaccharide or functionally-modified polysaccharide.

The term "polyglycosyl moiety" or "polyglycosyl", as used herein, refers to a polysaccharide connected with its hemiacetal hydroxyl group to a hydroxyl group of the polysaccharide or functionally-modified polysaccharide.

The term "oligosaccharide" generally refers to compounds in which 2 to 20 monosaccharide units are joined by glycosidic linkages. According to the number of units, they are called disaccharides, trisaccharides, tetrasaccharides, pentasaccharides etc.

In certain embodiments, the FR-targeting antineoplastic substance or composition comprises at least one antineoplastic agent and at least one FR-targeting excipient.

The term "antineoplastic agent", as used herein, is conceived broadly and generally refers to any substance or composition with pharmacological activity useful in the treatment of proliferative diseases affecting at least part of the respiratory tract.

As used herein, the term "drug" refers to an antineoplastic agent as taught herein.

In certain embodiments, the antineoplastic agent may be a chemotherapeutic agent or a biomolecule, or a combination thereof. Such antineoplastic agents are useful in the treatment of proliferative diseases affecting at least part of the respiratory tract, such as for instance primary or secondary tumours affecting at least part of the respiratory tract.

The term "chemotherapeutic agent" refers to any pharmacologic agent that is known to be of use in the treatment of proliferative diseases.

In certain embodiments, the antineoplastic agent may be a chemotherapeutic agent useful in the treatment of proliferative diseases affecting at least part of the respiratory tract or a biomolecule useful in the treatment of proliferative diseases affecting at least part of the respiratory tract, or a combination thereof.

In certain embodiments, the antineoplastic agent, in particular the chemotherapeutic agent may be an alkylating agent, a cytotoxic compound, an anti-metabolite, a plant alkaloid, a terpenoid, or a topoisomerase inhibitor.

The term "alkylating agent" generally refers to an agent capable to alkylate nucleophilic functional groups under physiological conditions.

Exemplary alkylating agents include but are not limited to cyclophosphamide, carmustine, cisplatin, carboplatin, oxaliplatin, mechlorethamine, melphalan (hydrochloride), chlorambucil, ifosfamide, and busulfan.

The term "cytotoxic compound" generally refers to an agent toxic to a cell.

Exemplary cytotoxic compound include but are not limited to actinomycin (also known as dactinomycin); anthracyclines such as doxorubicin, daunorubicin, valrubicin, idarubicin, and epirubicin; bleomycin; plicamycin; mitoxantrone; and mitomycin.

The term "anti-metabolite" generally refers to an agent capable to inhibit the use of a metabolite such as purines or pyrimidines. Anti-metabolites prevent purines and pyrimidines from becoming incorporated into DNA during the S phase of the cell cycle and thereby stop normal development and division. Exemplary anti-metabolites include but are not limited to azathioprine, fluorouracil, mercaptopurine, methotrexate, nelarabine, and pemetrexed.

Plant alkaloids and terpenoids are derived from plants and block cell division by preventing microtubule function. Non-limiting examples include vinca alkaloids and taxanes.

Exemplary vinca alkaloids include but are not limited to vincristine, vinblastine, vinorelbine, and vindesine.

Exemplary taxanes include but are not limited to paclitaxel, and docetaxel.

The term "topoisomerase inhibitor" generally refers to enzymes that maintain the topology of DNA. Non-limiting examples include type I and type II topoisomerase inhibitors.

Exemplary type I topoisomerase inhibitors include camptothecins such as irinotecan and topotecan.

Exemplary type II topoisomerase inhibitors include amsacrine, etoposide, etoposide phosphate, and teniposide.

In certain embodiments, the antineoplastic agent, in particular the chemotherapeutic agent, may be selected from the group consisting of cyclophosphamide, doxorubicin, idarubicin, mitoxantrone, oxaliplatin, bortezomib, digoxin, digitoxin, hypericin, shikonin, wogonin, sorafenib, everolimus, imatinib, geldanamycin, panobinostat, carmustine, cisplatin, carboplatin, mechlorethamine, melphalan (hydrochloride), chlorambucil, ifosfamide, busulfan, actinomycin, daunorubicin, valrubicin, epirubicin, bleomycin, plicamycin, mitoxantrone, mitomycin, azathioprine, mercaptopurine, fluorouracil, methotrexate, nelarabine, pemetrexed, vincristine, vinblastine, vinorelbine, vindesine, paclitaxel, docetaxel, irinotecan, topotecan, amsacrine, etoposide, etoposide phosphate, teniposide, anastrozole, exemestane, bosutinib, irinotecan, vandetanib, bicalutamide, lomustine, clofarabine, cabozantinib, cytarabine, cytoxan, decitabine, dexamethasone, hydroxyurea, decarbazine, leuprolide, epirubicin, asparaginase, estramustine, vismodegib, amifostine, flutamide, toremifene, fulvestrant, letrozole, degarelix, fludarabine, pralatrexate, floxuridine, gemcitabine, carmustine wafer, eribulin, altretamine, topotecan, axitinib, gefitinib, romidepsin, ixabepilone, ruxolitinib, cabazitaxel, carfilzomib, chlorambucil, sargramostim, cladribine, leuprolide, mitotane, procarbazine, megestrol, mesna, strontium-89 chloride, mitomycin, filgrastim, pegfilgrastim, sorafenib, nilutamide, pentostatin, tamoxifen, pegaspargase, denileukin diftitox, alitretinoin, carboplatin, prednisone, aldesleukin, mercaptopurine, zoledronic acid, lenalidomide, interferon alfa-2a, octreotide, dasatinib, regorafenib, histrelin, sunitinib, peginterferon alfa-2b, omacetaxine, thioguanine, erlotinib, bexarotene, decarbazine, temozolomide, thiotepa, thalidomide, BCG, temsirolimus, bendamustine hydrochloride, triptorelin, arsenic trioxide, lapatinib, valrubicin intravesical, tretinoin, azacitidine, pazopanib, teniposide, leucovorin, crizotinib, capecitabine, enzalutamide, ziv-aflibercept, streptozocin, vemurafenib, goserelin, vorinostat, zoledronic acid, and abiraterone.

In certain embodiments of the pharmaceutical formulations, uses, or methods, as taught herein, the antineoplastic agent, in particular the chemotherapeutic agent, may be selected from temozolomide, cisplatin, paclitaxel, docetaxel, gemcitabine, vinorelbine, etoposide, irinotecan, cyclophosphamide, doxorubicin, vincristine, or a combination thereof, such as a combination of one or more thereof, such as a combination of two, three, four, five, or more thereof. In certain embodiments of the present pharmaceutical formulations, uses, and methods as taught herein, the antineoplastic agent, in particular the chemotherapeutic agent, may be selected from the group consisting of temozolomide, cisplatin, paclitaxel, docetaxel, gemcitabine, vinorelbine, etoposide, irinotecan, cyclophosphamide, doxorubicin, and vincristine. Such antineoplastic agents, in particular chemotherapeutic agents, are satisfactorily efficacious in the treatment of proliferative diseases affecting at least part of the respiratory tract.

In certain preferred embodiments, the antineoplastic agent, in particular the chemotherapeutic agent, may be temozolomide or paclitaxel.

In certain preferred embodiments, the antineoplastic agent, in particular the chemotherapeutic agent, may be paclitaxel.

In certain preferred embodiments, the antineoplastic agent, in particular the chemotherapeutic agent, may be one or more alkylating agents. In certain embodiments, the alkylating agent may be selected from the group consisting of cyclophosphamide, carmustine, cisplatin, carboplatin, oxaliplatin, mechlorethamine, melphalan (hydrochloride), chlorambucil, ifosfamide, and busulfan.

In certain preferred embodiments, the antineoplastic agent, in particular the chemotherapeutic agent, may be cyclophosphamide. Cyclophosphamide is also known as cytophosphane, Endoxan, Cytoxan, Neosar, Procytox, and Revimmune In certain preferred embodiments, the antineoplastic agent, in particular the chemotherapeutic agent, may be one or more cytotoxic antibiotics. In certain embodiments, the cytotoxic antibiotic may be selected from the group consisting of actinomycin, doxorubicin, daunorubicin, valrubicin, idarubicin, epirubicin, bleomycin, plicamycin, mitoxantrone, and mitomycin.

In certain embodiments, the antineoplastic agent, in particular the chemotherapeutic agent, may be a hydrophobic antineoplastic agent. Non-limiting examples of suitable hydrophobic antineoplastic agents are paclitaxel, docetaxel, etoposide, irinotecan, and vincristine.

In certain embodiments, the antineoplastic agent, in particular the chemotherapeutic agent, may be a hydrophilic antineoplastic agent. Non-limiting examples of suitable hydrophilic antineoplastic agents are temozolomide, cisplatin, gemcitabine, vinorelbine, cyclophosphamide, and doxorubicin.

Advantageously, the present inventors have found that the polysaccharides or functionally-modified polysaccharides as taught herein interact with antineoplastic agents as taught herein (including hydrophilic antineoplastic agents as taught herein) and these interactions lead to a better entrapment and/or encapsulation of the antineoplastic agents as taught herein (including hydrophilic antineoplastic agents as taught herein) in the pharmaceutical formulations.

The term "hydrophobic compound" as used in this context may particularly refer to a compound that is substantially insoluble in distilled water at 25° C., such that only a maximum of about 0.05% by weight of said hydrophobic compound will dissolve in water.

The term "hydrophilic compound" as used in this context may particularly refer to a compound that is soluble in distilled water at 25° C.

In certain embodiments, the antineoplastic agent may be a biomolecule, such as preferably a protein, (poly)peptide, peptide, nucleic acid, or small molecule (such as primary metabolite, secondary metabolite, or natural product), or a combination of any two, any three, or any four thereof. Non-limiting examples of suitable biomolecules are aldesleukine, alemtuzumab, bevacizumab, brentuximab vedotine, catumaxomab, cetuximab, ipilimumab, panitumumab, rituximab, tasonermin, and trastuzumab.

In certain embodiments, the antineoplastic agent may be a therapeutic proteins, peptides, nucleic acids, or (poly)peptides, in particular interleukins, cytokines, anti-cytokines and cytokines receptors, vaccines, interferons, tumour necrosis factors (TNFs), enzymes, or antibodies.

The term "biomolecule" refers to any molecule that is produced by a living organism. The terms "protein" or "polypeptide" generally encompass proteins encoded by any open reading frame (ORF) of a genome. Where a single ORF encodes a pre-protein which is processed into one, two or more mature proteins, the term may encompass both the pre-protein and the processed mature proteins. Where a reference is made herein to a protein or polypeptide, such reference is to be understood as also encompassing fragments and/or variants of said protein or polypeptide, particularly including functional fragments and/or variants of said protein or polypeptide.

The term "fragment" generally denotes a N- and/or C-terminally truncated form of a protein or polypeptide. Preferably, a fragment may comprise at least about 30%, e.g., at least 50% or at least 70%, preferably at least 80%, e.g., at least 85%, more preferably at least 90%, and yet more preferably at least 95% or even about 99% of the amino acid sequence length of said protein or polypeptide.

The term "variant" of a given recited protein or polypeptide refers to proteins or polypeptides the amino acid sequence of which is substantially identical (i.e., largely but not wholly identical) to the sequence of said recited protein or polypeptide, e.g., at least about 85% identical, e.g., preferably at least about 90% identical, e.g., at least 91% identical, 92% identical, more preferably at least about 93% identical, e.g., 94% identical, even more preferably at least about 95% identical, e.g., at least 96% identical, yet more preferably at least about 97% identical, e.g., at least 98% identical, and most preferably at least 99% identical. Preferably, a variant may display such degrees of identity to a recited protein or polypeptide when the whole sequence of the recited protein is queried in the sequence alignment (i.e., overall sequence identity).

Sequence identity may be determined using suitable algorithms for performing sequence alignments and determination of sequence identity as know per se. Exemplary but non-limiting algorithms include those based on the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250), for example using the published default settings or other suitable settings (such as, e.g., for the BLASTN algorithm: cost to open a gap=5, cost to extend a gap=2, penalty for a mismatch=−2, reward for a match=1, gap x_dropoff=50, expectation value=10.0, word size=28; or for the BLASTP algorithm: matrix=Blosum62, cost to open a gap=11, cost to extend a gap=1, expectation value=10.0, word size=3).

In an embodiment, a variant of a given protein or polypeptide may be a homologue (e.g., orthologue or paralogue) of said protein or polypeptide. As used herein, the term "homology" generally denotes structural similarity between two macromolecules, particularly between two proteins or polypeptides or polynucleotides, from same or different taxons, wherein said similarity is due to shared ancestry.

The term "functional" denotes that fragments and/or variants at least partly retain the biological activity or functionality of the recited proteins or polypeptides. Preferably, such functional fragments and/or variants may retain at least about 20%, e.g., at least 30%, or at least 40%, or at least 50%, e.g., at least 60%, more preferably at least 70%, e.g., at least 80%, yet more preferably at least 85%, still more preferably at least 90%, and most preferably at least 95% or even 100% or higher of the activity compared to the corresponding recited proteins or polypeptides. For example, such functional fragments and/or variants may retain one or more aspects of the biological activity of the recited proteins or polypeptides, such as, e.g., ability to participate in a complex, ability to participate in a cellular pathway, etc.

The term "peptides" as used herein means a polymer of at most 50 amino acids linked by peptide (amide) bonds.

The term "nucleic acid" as used herein means a polymer of any length composed essentially of nucleotides, e.g., deoxyribonucleotides and/or ribonucleotides. Nucleic acids can comprise purine and/or pyrimidine bases and/or other natural (e.g., xanthine, inosine, hypoxanthine), chemically or biochemically modified (e.g., methylated), non-natural, or derivatised nucleotide bases. The backbone of nucleic acids can comprise sugars and phosphate groups, as can typically be found in RNA or DNA, and/or one or more modified or substituted sugars (such as, e.g., 2'-O-alkylated, e.g., 2'-O-methylated or 2'-O-ethylated; or 2'-0,4'-C-alkynelated, e.g., 2'-0,4'-C-ethylated sugars) and/or one or more modified or substituted phosphate groups (e.g., phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs)). The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g. chemically synthesised) DNA, RNA or DNA/RNA hybrids. A nucleic acid can be naturally occurring, e.g., present in or isolated from nature, can be recombinant, i.e., produced by recombinant DNA technology, and/or can be, partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

By "encoding" is meant that a nucleic acid sequence or part(s) thereof corresponds, by virtue of the genetic code of an organism in question to a particular amino acid sequence, e.g., the amino acid sequence of one or more desired proteins or polypeptides.

Preferably, a nucleic acid encoding one or more proteins or polypeptides (e.g., one or more proteins participating in complexes as taught herein) may comprise an open reading frame (ORF) encoding said protein or polypeptide. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a protein or polypeptide. Hence, the term may be synonymous with "coding sequence" as used in the art.

Expression of proteins can be achieved through operably linking nucleic acid sequences or ORFs encoding said proteins with regulatory sequences allowing for expression of the nucleic acids or ORFs, e.g., in vitro, in a host cell, host organ and/or host organism. Such expression may be achieved, e.g., under suitable (culture) conditions or upon addition of inducers (e.g., where inducible regulatory sequences are used).

An "operable linkage" is a linkage in which regulatory sequences and sequences sought to be expressed are connected in such a way as to permit said expression. For example, sequences, such as, e.g., a promoter and an ORF, may be said to be operably linked if the nature of the linkage between said sequences does not: (1) result in the introduction of a frame-shift mutation, (2) interfere with the ability of the promoter to direct the transcription of the ORF, (3) interfere with the ability of the ORF to be transcribed from the promoter sequence.

The precise nature of regulatory sequences or elements required for expression may vary between expression environments, but typically include a promoter and a transcription terminator, and optionally an enhancer.

Reference to a "promoter" or "enhancer" is to be taken in its broadest context and includes transcriptional regulatory sequences required for accurate transcription initiation and where applicable accurate spatial and/or temporal control of gene expression or its response to, e.g., internal or external (e.g., exogenous) stimuli. More particularly, "promoter" may depict a region on a nucleic acid molecule, preferably DNA molecule, to which an RNA polymerase binds and initiates transcription. A promoter is preferably, but not necessarily, positioned upstream, i.e., 5', of the sequence the transcription of which it controls. Typically, in prokaryotes a promoter region may contain both the promoter per se and sequences which, when transcribed into RNA, will signal the initiation of protein synthesis (e.g., Shine-Dalgarno sequence). In embodiments, promoters contemplated herein may be constitutive or inducible.

The terms "terminator" or "transcription terminator" refer generally to a sequence element at the end of a transcriptional unit which signals termination of transcription. For example, a terminator is usually positioned downstream of, i.e., 3' of ORF(s) encoding a polypeptide of interest. For instance, where a recombinant nucleic acid contains two or more ORFs, e.g., successively ordered and forming together a multi-cistronic transcription unit, a transcription terminator may be advantageously positioned 3' to the most downstream ORF.

The term "vector" generally refers to a nucleic acid molecule, typically DNA, to which nucleic acid segments may be inserted and cloned, i.e., propagated. Hence, a vector will typically contain one or more unique restriction sites, and may be capable of autonomous replication in a defined host or vehicle organism such that the cloned sequence is reproducible. Vectors may include, without limitation, plasmids, phagemids, bacteriophages, bacteriophage-derived vectors, PAC, BAC, linear nucleic acids, e.g., linear DNA, viral vectors, etc., as appropriate. Expression vectors are generally configured to allow for and/or effect the expression of nucleic acids or ORFs introduced thereto in a desired expression system, e.g., in vitro, in a host cell, host organ and/or host organism. For example, expression vectors may advantageously comprise suitable regulatory sequences.

The term "small molecule" refers to compounds, preferably organic compounds, with a size comparable to those organic molecules generally used in pharmaceuticals. The term excludes biological macromolecules (e.g., proteins, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

In certain embodiments, the antineoplastic agent may be an antibody.

As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro, in cell culture, or in vivo.

In certain embodiments, an antibody may be any of IgA, IgD, IgE, IgG and IgM classes, and preferably IgG class antibody.

In certain embodiments, the antibody may be a polyclonal antibody, e.g., an antiserum or immunoglobulins purified there from (e.g., affinity-purified).

In certain preferred embodiments, the antibody may be a monoclonal antibody or a mixture of monoclonal antibodies. Monoclonal antibodies can target a particular antigen or a particular epitope within an antigen with greater selectivity and reproducibility.

By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

In further embodiments, antibody agents may be antibody fragments. "Antibody fragments" comprise a portion of an intact antibody, comprising the antigen-binding or variable region thereof. Non-limiting examples of antibody fragments include Fab, Fab', F(ab')2, Fv and scFv fragments; diabodies; linear antibodies; single-chain antibody molecules; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromaderius*) also including camel heavy-chain antibodies $V_HH$, llama (e.g., *Lama paccos, Lama glama* or *Lama vicugna*) also including llama heavy-chain antibodies $V_HH$, or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

Methods for immunising animals, e.g., non-human animals such as laboratory or farm animals, using immunising antigens (such as, e.g., the herein disclosed complexes) optionally fused to or covalently or non-covalently linked, bound or adsorbed to a presenting carrier, and preparation of antibody or cell reagents from immune sera is well-known per se and described in documents referred to elsewhere in this specification. The animals to be immunised may include any animal species, preferably warm-blooded species, more preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel, llama or horse. The term "presenting carrier" or "carrier" generally denotes an immunogenic molecule which, when bound to a second molecule, augments immune responses to the latter, usually through the provision of additional T cell epitopes. The presenting carrier may be a (poly)peptidic structure or a non-peptidic structure, such as inter alia glycans, polyethylene glycols, peptide mimetics, synthetic polymers, etc. Exemplary non-limiting carriers include human Hepatitis B virus core protein, multiple C3d domains, tetanus toxin fragment C or yeast Ty particles.

In certain embodiments, the antineoplastic agent may be a therapeutic antibody that is cytotoxic or cytostatic against a target cancer cell or tumour cell. For instance, the antineoplastic agent may be a therapeutic antibody that binds to cancer cell-specific or tumour cell-specific antigens and is cytotoxic or cytostatic against a target cancer cell or tumour cell.

In certain embodiments, the antineoplastic agent may be one or more anti-cancer or anti-tumour therapeutic antibodies. In certain embodiments, the anti-cancer or anti-tumour therapeutic antibody may be modified for delivery of a toxin, radioisotope, cytokine or other active conjugate. In certain embodiments, the anti-cancer or anti-tumour therapeutic antibody may be a bispecific antibody that can bind with its Fab region both to target antigen and to a conjugate or effector cell. In certain embodiments, the antineoplastic agent may be a monoclonal anti-cancer therapeutic antibody.

In certain embodiments, the antineoplastic agent, in particular the anti-cancer therapeutic antibody, may be selected from the group consisting of Rituximab, Ofatumumab, Ibritumomab Tiuxetan, Tositumomab, Trastuzumab, Pertuzumab, Alemtuzumab, Brentuximab Vedotin, Gemtuzumab ozogamicin, Cetuximab, Panitumumab, Bevacizumab, Natalizumab, Denosumab, Ipilimumab, Nivolumab, Pidilizumab, Lambrolizumab, BMS-936559, MPDL3280A, and MEDI4736.

In certain embodiments, the antineoplastic agent may be a vaccine. For instance, the antineoplastic agent may be a vaccine that is cytotoxic or cytostatic against a target cancer cell or tumour cell.

In certain embodiments, the antineoplastic agent may be one or more cancer or tumour vaccines such as one or more therapeutic cancer or tumour vaccines.

The term "vaccine" refers to a biological preparation that improves immunity to a particular disease.

The term "cancer or tumour vaccine" refers to a vaccine which is cytotoxic or cytostatic against a target cancer cell or tumour cell.

The term "therapeutic cancer or tumour vaccine" refers to a vaccine which is cytotoxic or cytostatic against a target cancer cell or tumour cell and thereby at least partly treating a proliferative disease.

In certain embodiments, the FR-targeting antineoplastic substance or composition may comprise an antineoplastic agent as taught herein and a FR-targeting excipient as taught herein.

In certain embodiments, the FR-targeting antineoplastic substance or composition may comprise an antineoplastic agent selected from the group consisting of temozolomide, cisplatin, paclitaxel, docetaxel, gemcitabine, vinorelbine, etoposide, irinotecan, cyclophosphamide, doxorubicin, and vincristine, and a FR-targeting excipient having the Formula XI, wherein Polysacch is a polysaccharide or functionally-modified polysaccharide as taught herein, and $A^1$, $L^1$, and $A^2$ have the same meaning as that defined herein.

In certain embodiments, the FR-targeting antineoplastic substance or composition may comprise an antineoplastic agent selected from the group consisting of temozolomide, cisplatin, paclitaxel, docetaxel, gemcitabine, vinorelbine, etoposide, irinotecan, cyclophosphamide, doxorubicin, and vincristine, and a FR-targeting excipient having the Formula XI as taught herein, wherein Polysacch is a polysaccharide or functionally-modified polysaccharide selected from chitosan or functionally-modified chitosan; N-[(2-hydroxy-3-trimethylammonium)propyl] chitosan (HTC) and its salts (such as chloride, acetate, glutamate, or lactate salts) for example HTCC (i.e., chloride salt); N-trimethyl chitosan (TMC) and its salts (such as chloride, acetate, glutamate, or lactate salts); N,O-carboxymethyl chitosan (N,O-CMC) and its salts (such as chloride, acetate, glutamate, or lactate salts); N-carboxymethyl chitosan (N-CMC) and its salts (such as chloride, acetate, glutamate, or lactate salts); N,N-carboxymethyl chitosan (NN-CMC) and its salts (such as chloride, acetate, glutamate, or lactate salts); O-carboxymethyl chitosan (O-CMC) and its salts (such as chloride, acetate, glutamate, or lactate salts); hydrophobically-modified chitosan (HMC) and its salts (such as chloride, acetate, glutamate, or lactate salts); dextran or functionally-modified dextran; hydrophobically-modified dextran (HMD) and its salts (such as chloride, acetate, glutamate, or lactate salts); starch or functionally-modified starch; hydroxypropyl starch; amylose or functionally-modified amylose; amylopectin or functionally-modified amylopectin; cellulose or functionally-modified cellulose; methylcellulose and its salts (such as acetate or acetate phthalate salts); carboxymethylcellulose and its salts (such as acetate or acetate phthalate salts); hydroxyethylcellulose and its salts (such as acetate or acetate phthalate salts); ethylcellulose and its salts (such as acetate or acetate phthalate salts); hydroxyethylmethylcellulose and its salts (such as acetate or acetate phthalate salts); hydroxypropylcellulose and its salts (such as acetate or acetate phthalate salts); hypromellose and its salts (such as acetate or acetate phthalate salts); hypromellose acetate succinate; hypromellose phthalate; croscarmellose and its salts (such as acetate or acetate phthalate salts); chitin; cyclodextrin; dextrate; dextrin; maltodextrin; pullulan; or guar gum; and $A^1$, $L^1$, and $A^2$ have the same meaning as that defined herein.

In certain embodiments of the products (such as pharmaceutical formulations or FR-targeting excipients), uses, or methods, as taught herein, the FR-targeting antineoplastic substance or composition may be comprised in a nanoparticle. In certain embodiments, the FR-targeting antineoplastic substance or composition may be formulated in nanoparticles.

As explained herein, the FR-targeting antineoplastic substance or composition may comprise an antineoplastic agent and a FR-targeting excipient. In certain embodiments of the products (such as pharmaceutical formulations or FR-targeting excipients), uses, or methods, as taught herein, the antineoplastic agent as taught herein and the FR-targeting excipient as taught herein may be comprised in a nanoparticle. In certain embodiments, the antineoplastic agent as taught herein and the FR-targeting excipient as taught herein may form or constitute nanoparticles, in other words the nanoparticles may consist of or consist essentially of the antineoplastic agent as taught herein and the FR-targeting excipient as taught herein.

In certain embodiments, the antineoplastic agent as taught herein and the FR-targeting excipient as taught herein may be comprised in a nanoparticle, wherein the antineoplastic agent and the polysaccharide or functionally-modified polysaccharide are comprised in the nanoparticle core and the folate moiety extends from the nanoparticle surface, for instance via a linker as taught herein.

Formulating the present pharmaceutical formulations as nanoparticles increases the stability and physical integrity of the present pharmaceutical formulations after administration in vivo for instance in comparison with prior art liposomes.

Formulating and/or administering the present pharmaceutical formulations as nanoparticles allow the pharmaceutical formulations to overcome biological barriers and to accumulate in tumours. Moreover, formulating and/or administering the present pharmaceutical formulations as nanoparticles avoids particle phagocytosis by alveolar macrophages and hence, enhances the efficacy of the treatment of a proliferative disease affecting at least part of the respiratory tract.

In certain embodiments, the antineoplastic agent as taught herein and the FR-targeting excipient as taught herein may be non-covalently associated in the nanoparticle.

The term "nanoparticles" as used herein refer to a colloid comprising particles, wherein the Z-average particle size of the particles is ranging from about 2 nm to about 1000 nm (as measured by dynamic light scattering). The nanoparticles may be dispersed in a solvent mixture.

The term "nanoparticles" as used herein encompasses nanomicelles.

The term "nanomicelles" as used herein refers to nanoparticles consisting of spherical or laminar aggregates of polar surface-active molecules. The hydrophilic portion of the molecule interacts with the other members of the aqueous solution (i.e., are oriented outside in water); the hydrophobic ends huddle together within the micelle.

In certain embodiments, the nanoparticles may be essentially spherical. In certain embodiments, the nanoparticles may have a Z-average particle size of at most about 1000 nm, as measured by dynamic light scattering (DLS). For example, the nanoparticles may have a Z-average particle size of at most about 900 nm, at most about 800 nm, at most about 700 nm, at most about 600 nm, at most about 500 nm, at most about 400 nm, at most about 300 nm, at most about 200 nm, or at most about 100 nm, as measured by DLS. For example, the nanoparticles may have a Z-average particle size of at least about 2 nm, at least about 5 nm, at least about 10 nm, at least about 20 nm, at least about 30 nm, at least about 40 nm, or at least about 50 nm, as measured by DLS. For example, the nanoparticles may have a Z-average particle size ranging from about 2 nm to about 500 nm, from about 5 nm to about 500 nm, from about 10 nm to about 400 nm, from about 20 nm to about 300 nm, or from about 50 nm to about 200 nm, as measured by DLS.

The Z-average particle size or particle size distribution of the nanoparticles may be measured, for instance in a solvent mixture, by DLS for instance using a Zetasizer nano ZS (Malvern Instruments, Worcestershire, UK) using Nanosphere™ size standards (Duke Scientific Corporation, Palo Alto, Calif., USA, cat. num. 3300) as internal standard.

In certain embodiments, the nanoparticles may have a particle size below 1000 nm, as measured by dynamic light scattering (DLS). For example, the nanoparticles may have a particle size of at most about 900 nm, at most about 800 nm, at most about 700 nm, at most about 600 nm, at most about 500 nm, at most about 400 nm, at most about 300 nm, at most about 200 nm, or at most about 100 nm, as measured by DLS. For example, the nanoparticles may have a particle size of at least about 2 nm, at least about 5 nm, at least about 10 nm, at least about 20 nm, at least about 30 nm, at least about 40 nm, or at least about 50 nm, as measured by DLS. For example, the nanoparticles may have a particle size ranging from about 2 nm to about 500 nm, from about 5 nm to about 500 nm, from about 10 nm to about 400 nm, from about 20 nm to about 300 nm, or from about 50 nm to about 200 nm, as measured by DLS.

In certain embodiments, at least 50% of the nanoparticles may have a particle size below 700 nm, as measured by dynamic light scattering (DLS). For example, at least 50% of the nanoparticles may have a particle size of below 600 nm, below 500 nm, below 400 nm, below 300 nm, below 200 nm, or below 100 nm, as measured by DLS.

In certain embodiments, the nanoparticles may have a zeta potential (ZP) ranging from about −35 mV to about +35 mV. For example, the nanoparticles may have a ZP ranging from about −30 mV to about +30 mV, from about −25 mV to about +25 mV, from about −20 mV to about +20 mV, or from about −15 mV to about +15 mV.

The zeta potential of the nanoparticles may be measured, for instance in a solvent mixture, using a zetasizer (Zetasizer nano ZS, Malvern Instruments, Worcestershire, UK) using Zeta potential Transfer Standard (Malvern Instruments, Worcestershire, UK, cat. num. DTS1230).

In certain embodiments, the drug loading of the nanoparticles may be at least about 0.5% (w/w). For example, the drug loading of the nanoparticles may be at least about 0.6% (w/w), at least about 0.7% (w/w), at least about 0.8% (w/w), at least about 0.9% (w/w), at least about 1.0% (w/w), at least about 1.1% (w/w), at least about 1.2% (w/w), at least about 1.3% (w/w), at least about 1.4% (w/w), at least about 1.5% (w/w), at least about 1.6% (w/w), at least about 1.7% (w/w), at least about 1.8% (w/w), at least about 1.9% (w/w), at least about 2.0% (w/w), at least about 2.5% (w/w), at least about 3.0% (w/w), at least about 3.5% (w/w), at least about 4.0% (w/w), at least about 4.5% (w/w), at least about 5.0% (w/w), at least about 6.0% (w/w), at least about 7.0% (w/w), at least about 8.0% (w/w), at least about 9.0 (w/w), at least about 10% (w/w), at least about 20% (w/w), at least about 30% (w/w), at least about 40% (w/w), at least about 50% (w/w), at least about 60% (w/w), at least about 70% (w/w), or at least about 80% (w/w). For example, the drug loading of the nanoparticles may be ranging from about 0.5% (w/w) to about 80% (w/w), from about 1.0% (w/w) to about 60% (w/w), from about 2.0% (w/w) to about 40% (w/w), from about 3.0% (w/w) to about 20% (w/w), or from about 4.0% (w/w) to about 8.0% (w/w).

As used herein, the term "drug loading" or "DL" of the nanoparticles refers to the ratio of the mass of the antineoplastic agent as taught herein (expressed in grams) at least partially coated or dispersed with the FR-targeting excipient as taught herein, to the sum of the mass of the antineoplastic agent and the excipients employed (i.e., the FR-targeting excipient and any further excipient, such as polymeric excipient and/or lipid excipient and/or tensioactive agent) (expressed in grams), suitably expressed as a percentage.

The drug loading may be measured using any technique known in the art such as reversed-phase chromatography, for instance reversed-phase chromatography coupled with an (UV) detector.

In certain embodiments, the encapsulation efficiency of the nanoparticles may be at least about 1.0% (w/w). For example, the encapsulation efficiency of the nanoparticles may be at least about 1.1% (w/w), at least about 1.2% (w/w), at least about 1.3% (w/w), at least about 1.4% (w/w), at least about 1.5% (w/w), at least about 1.6% (w/w), at least about 1.7% (w/w), at least about 1.8% (w/w), at least about 1.9% (w/w), at least about 2.0% (w/w), at least about 2.5% (w/w), at least about 3.0% (w/w), at least about 3.5% (w/w), at least about 4.0% (w/w), at least about 4.5% (w/w), at least about 5.0% (w/w), at least about 5.5% (w/w), at least about 6.0% (w/w), at least about 6.5% (w/w), at least about 7.0% (w/w), at least about 7.5% (w/w), at least about 8.0% (w/w), at least about 8.5% (w/w), at least about 9.0 (w/w), at least about 9.5% (w/w), at least about 10% (w/w), at least about 11% (w/w), at least about 12% (w/w), at least about 13% (w/w), at least about 14% (w/w), at least about 15% (w/w), at least about 20% (w/w), at least about 30% (w/w), at least about 40% (w/w), at least about 50% (w/w), at least about 60% (w/w), at least about 70% (w/w), at least about 80% (w/w), at least about 90% (w/w), or at least about 100% (w/w). For example, the encapsulation efficiency of the nanoparticles may be ranging from about 1.0% (w/w) to about 100% (w/w), from about 2.0% (w/w) to about 80% (w/w), from about 4.0% (w/w) to about 60% (w/w), from about 6.0% (w/w) to about 40% (w/w), from about 8.0% (w/w) to about 20% (w/w).

As used herein, the term "encapsulation efficiency" or "EE" of the nanoparticles refers to the ratio of the mass of the antineoplastic agent as taught herein (expressed in grams) at least partially coated or dispersed with the FR-targeting excipient as taught herein, to the total mass of the antineoplastic agent as taught herein (expressed in grams) added to the FR-targeting excipient as taught herein, suitably expressed as a percentage.

The encapsulation efficiency may be measured using any technique known in the art such as reversed-phase chromatography, for instance reversed-phase chromatography coupled with an (UV) detector.

Provided herein is a method for preparing the pharmaceutical formulation as taught herein, the method comprising the steps of:
(a) preparing in a first solvent a first composition comprising: (i) at least one FR-targeting antineoplastic substance or composition as taught herein, and (ii) optionally one or more polymeric excipients and/or one or more lipid excipients and/or one or more tensioactive agents, wherein the at least one FR-targeting antineoplastic substance or composition is in solution in the first solvent, and the optional one or more polymeric excipients and/or one or more lipid excipients and/or one or more tensioactive agents are solubilised or dispersed in the first solvent;
(b) preparing in a second solvent a second composition comprising: (i') a FR-targeting excipient as taught herein, and (ii') optionally one or more polymeric excipients and/or one or more lipid excipients and/or one or more tensioactive agents, wherein the FR-targeting excipient is in solution or in dispersion in the second solvent, and the optional one or more polymeric excipients and/or one or more lipid excipients and/or one or more tensioactive agents are solubilised or dispersed in the second solvent, and wherein the at least one antineoplastic agent is more soluble in the first solvent than in the second solvent;
(c) mixing of the first composition of step (a) and the second composition of step (b) to produce nanoparticles (in the solvent mixture), wherein the nanoparticles comprise the at least one FR-targeting antineoplastic substance or composition.

Also provided herein is a method for preparing the pharmaceutical formulation as taught herein, the method comprising the steps of:
(a) preparing in a first solvent a first composition comprising: (i) at least one FR-targeting antineoplastic substance or composition as taught herein, and (ii) optionally one or more polymeric excipients and/or one or more lipid excipients and/or one or more tensioactive agents, wherein the at least one FR-targeting antineoplastic substance or composition is in solution in the first solvent, and the optional one or more polymeric excipients and/or one or more lipid excipients and/or one or more tensioactive agents are solubilised or dispersed in the first solvent;
(b) preparing in a second solvent a second composition comprising: (i') a FR-targeting excipient as taught herein, and (ii') optionally one or more polymeric excipients and/or one or more lipid excipients and/or one or more tensioactive agents, wherein the FR-targeting excipient is in solution or in dispersion in the second solvent, and the optional one or more polymeric excipients and/or one or more lipid excipients and/or one or more tensioactive agents are solubilised or dispersed in the second solvent, and wherein the at least one FR-targeting antineoplastic substance or composition is more soluble in the first solvent than in the second solvent;
(c) mixing of the first composition of step (a) and the second composition of step (b) to produce nanoparticles (in the solvent mixture), wherein the nanoparticles comprise the at least one FR-targeting antineoplastic substance or composition.

For example, the first solvent may be an organic water-miscible solvent, organic water-non-miscible solvent, aqueous buffer, or a combination of any two or three thereof.

For example, the second solvent may be an organic water-miscible solvent, organic water-non-miscible solvent, aqueous buffer, or a combination of any two or three thereof The terms "solution" or "solubilized" generally refer to a homogeneous mixture composed of only one phase. In a solution, a solute is dissolved in another substance, known as a solvent.

The terms "dispersion" or "dispersed" generally refers to a material comprising more than one phase where at least one of the phases consists of finely divided phase domains, often in the colloidal size range, dispersed throughout a continuous phase. There are three main types of dispersions: suspension (or coarse dispersion), colloid, and solution.

The term "suspension" refers to a heterogeneous mixture containing solid particles that are sufficiently large for sedimentation. Usually the particles are larger than 1 micrometer. Typically, the internal phase (solid) is dispersed throughout the external phase (fluid) through mechanical agitation, with the use of certain excipients or suspending agents.

The term "colloid" refers to a substance microscopically dispersed throughout another substance. The dispersed-phase particles usually have a diameter of between about 2 nm and about 1 micrometer, more usually between about 2 nm and about 500 nm.

The first composition of step (a) as defined above and the second composition of step (b) as defined above may comprise one or more polymeric excipients and/or one or more lipid excipients and/or one or more tensioactive agents.

Non-limiting examples of suitable polymeric excipients are chitosan derivatives (HTC, TMC, CMC, chitosan) and their salts (such as hydrochloride, acetate, glutamate, or lactate salts), or dextran.

Non-limiting examples of suitable lipid excipients are phospholipids, lecithin, lipids (such as cholesterol), or vitamins (such as generally regarded as save (GRAS)-modified vitamins). The phospholipid may be selected from phosphatic acids, phosphatidyl choline (saturated and unsaturated), phosphatidyl ethanol amine (such as DSPE), phosphatidyl glycerol, phosphatidyl serine, or phosphatidyl inositol.

Non-limiting examples of suitable tensioactive agents or surfactants are phospholipids, lecithin, lipids, cholic acid derivatives and their salts (sodium glycocholate, sodium taurocholate), vitamins (such as generally regarded as save (GRAS)-modified vitamins), or any combination thereof. The phospholipids may be selected from phosphatic acids, phosphatidylcholine (saturated and unsaturated), phosphatidylethanolamine, phosphatidylglycerol, phosphatidylserine, or phosphatidylinositol.

In certain embodiments of the methods as taught herein, step (c) may be achieved by addition of an energy source. Addition of an energy source may advantageously improve homogenization efficiency. Non-limiting examples of the energy source are magnetic stirring, an ultrasonic probe, a high speed homogenizer, a high pressure homogenizer, etc.

In certain embodiments, the method for preparing the nanoparticles as taught herein, may comprise the steps of:
(a) preparing in a first solvent a first composition comprising: (i) at least one antineoplastic agent as taught herein, (ii) at least one FR-targeting excipient as taught herein, and (iii) optionally one or more polymeric excipients and/or one or more lipid excipients and/or one or more tensioactive agents, wherein the at least one antineoplastic agent and the at least one FR-targeting excipient are in solution in the first solvent, and the optional one or more polymeric excipients and/or one or more lipid excipients and/or one or more tensioactive agents are solubilised or dispersed in the first solvent;
(b) preparing in a second solvent a second composition comprising: (i') a FR-targeting excipient as taught herein, and (ii') optionally one or more polymeric excipients and/or one or more lipid excipients and/or one or more tensioactive agents, wherein the FR-targeting excipient is in solution or in dispersion in the second solvent, and the optional one or more polymeric excipients and/or one or more lipid excipients and/or one or more tensioactive agents are solubilised or dispersed in the second solvent, and wherein the at least one antineoplastic agent is more soluble in the first solvent than in the second solvent,
(c) mixing of the first composition of step (a) and the second composition of step (b) to produce nanoparticles, wherein the at least one antineoplastic agent is at least partly coated or dispersed in the at least one FR-targeting excipient.

Also provided herein is a method for preparing the pharmaceutical formulation as taught herein, the method comprising the step of mixing at least one FR-targeting antineoplastic substance or composition as taught herein or at least one antineoplastic agent as taught herein with at least one FR-targeting excipient as taught herein to produce nanomicelles. This method is also referred to herein as a co-solubilisation method.

In certain embodiments, the method for preparing the pharmaceutical formulation as taught herein may comprise the steps of:
(a) preparing in a first solvent a first composition comprising at least one antineoplastic agent as taught herein, wherein the at least one antineoplastic agent is in solution in the solvent;
(b) preparing in a second solvent a second composition comprising at least one FR-targeting excipient as taught herein, wherein the at least one FR-targeting excipient is in solution or in dispersion in the solvent,
(c) mixing of the first composition of step (a) and the second composition of step (b) to produce nanomicelles, wherein the at least one antineoplastic agent is at least partly coated or dispersed in the at least one FR-targeting excipient.

The first solvent and the second solvent may be the same or different.

The pharmaceutical formulations as taught herein may comprise one or more pharmaceutically acceptable excipients in addition to the other herein recited elements (e.g. FR-targeting antineoplastic substance or composition, or antineoplastic agent and FR-targeting excipient)

The term "pharmaceutically acceptable" as used herein is consistent with the art and means compatible with the other ingredients of a pharmaceutical formulation and not deleterious to the recipient thereof.

As used herein, "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, antioxidants, tonicity controlling agents, absorption delaying agents, and the like. The use of such media and agents for pharmaceutical formulations is well known in the art. Except insofar as any conventional media or agent is incompatible with the active compounds, its use in the therapeutic compositions may be contemplated. In certain embodiments of the products (such as pharmaceutical formulations or FR-targeting excipients), uses, or methods, as taught herein, the nanoparticles may be comprised in microparticles.

The term "microparticles", as used herein, refers to a dry powder comprising particles, wherein the mass median aerodynamic diameter (MMAD) of the particles is ranging from about 0.1 µm to about 10 µm. This range is helpful to allow the particles to satisfactorily reach the respiratory tract such as the lower respiratory tract.

The terms "microparticles", "nano-contained microparticles", "NCMs", "nano-embedded microparticles", or "NEMs" may be used interchangeably herein.

In certain embodiments, the microparticles may have a mass median aerodynamic diameter (MMAD) of at most about 10.0 μm. For example, the microparticles may have a MMAD of at most about 9.0 μm, at most about 8.0 μm, at most about 7.0 μm, at most about 6.0 μm, at most about 5.0 μm, at most about 4.0 μm, or at most about 3.0 μm. In certain embodiments, the microparticles may have a MMAD of at least about 0.1 μm. For example, the microparticles may have a MMAD of at least about 0.2 μm, at least about 0.3 μm, at least about 0.4 μm, at least about 0.5 μm, at least about 0.6 μm, at least about 0.7 μm, at least about 0.8 μm, at least about 0.9 μm, or at least about 1.0 μm. In certain embodiments, the microparticles may have a MMAD ranging from about 0.1 μm to about 10.0 μm, from about 0.5 μm to about 5.0 μm, from about 1.0 μm to about 5.0 μm, from about 3.0 μm to about 5.0 μm, or from about 1.0 μm to about 3.0 μm.

The terms "aerodynamic diameter" or "$d_{ae}$" of an irregular particle is defined as the diameter of a spherical particle with a density of 1 $g/cm^3$ and the same settling velocity as the irregular particle. In other words, the aerodynamic diameter of a particle may be defined as the diameter of a sphere with a unit density (i.e., density of 1 $g/cm^3$) that has the same settling velocity in still air as the particle in consideration.

The aerodynamic diameter provides a useful measurement of inhalable particles and takes into account factors that affect their aerodynamic properties. Aerodynamic diameter can be used to compare droplets of differing physical size and takes into account the density of the particle as well as its size.

Experimental results are usually express as mass median aerodynamic diameter (MMAD). The MMAD refers to the diameter of the particles deposited in an impactor for which 50% (w/w) of particles have a lower diameter and 50% (w/w) have a higher diameter. In other words, the MMAD refers to the median of the distribution of airborne particle mass with respect to the aerodynamic diameter. The MMAD is usually accompanied by the geometric standard deviation (g or sigma g) which characterizes the variability of the particle size distribution.

Experimentally, the aerodynamic diameter can be determined by employing a gravitational settling method, whereby the time for an ensemble of particles to settle a certain distance is used to infer directly the aerodynamic diameter of the particles. Indirect methods for measuring the mass median aerodynamic diameter (MMAD) are methods described in the European or US Pharmacopeas using an impactor or impaction apparatus such as glass impinger, multi-stage liquid impinger (MsLI), Andersen cascade impactor, or next-generation impinger (NGI).

For example, the mass median aerodynamic diameter may be determined using a laser diffraction technique used a Spraytec® (Malvern Instruments, Worcestershire, UK) diffraction-based device equipped with an inhalation cell, specifically modified for measuring the aerodynamic diameter of particles generated from medicinal aerosols including dry powder inhalators (DPIs). The technique uses a Spraytec® unit with a throat held in place by the inhalation cell and a connection for a MsLI or a NGI. The entire assembly is a closed system and allows for a controlled airflow rate (100 l/min during 2.4 sec for low resistance device) in the measurement zone. This allows the size properties of DPI formulations (including mass median aerodynamic diameter, aerodynamic profile, fine particle dose, fine particle fraction, and particle size distribution) to be measured under simulated normal breathing conditions. The amount of antineoplastic agent sampled at each stage of the impactor can be plot against the cut-off diameter for the stage, resulting in a collection efficiency curve. The total dose of particles with aerodynamic diameters smaller than 5 μm can be calculated by interpolation from the collection efficiency curve and considered as the fine particle dose (FPD) or fine particle fraction (FPF), expressed as a percentage of the total antineoplastic agent dose (and not of the emitted dose).

The term "emitted dose" refers to the dose delivered by the inhaler to the patient or to the impactor device. Hence, the emitted dose corresponds to the dose previously contained in the DPI device (the total antineoplastic agent dose) before activation without the fractions of the dose remaining in the DPI device after inhalation.

The term "(in vitro) pulmonary deposition" refers to the proportion of mass of the antineoplastic agent sampled at each stage of the impactor (e.g. DPI, throat, stage 1 to 5) relative to the mass of the nominal dose (i.e. the mass of the dose loaded in the inhalation device).

The term "fine particle dose" or "FPD" generally refers to the mass of the particles with an aerodynamic diameter below 5 μm relative to the mass of the nominal dose (i.e. the mass of the dose loaded in the inhalation device).

The fine particle dose or fine particle fraction represents the fraction of the pharmaceutical formulation that can be deeply inhaled and is theoretically available for pharmacological activity (Dunbar et al, *Kona* 16: 7-45, 1998).

In certain embodiments, the microparticles may be essentially spherical. In certain embodiments, the microparticles may have a mass median geometric diameter (MMGD) ranging from about 0.1 µm to about 30.0 µm, from about 0.5 µm to about 20.0 µm, from about 1.0 µm to about 10.0 µm, from about 1.0 µm to about 5.0 µm, or from about 1.0 µm to about 3.0 µm.

The terms "mass median geometric diameter (MMGD)", "particle size diameter (PSD)", "median diameter", or "mass median diameter (MMD)" may be used interchangeably.

The particle size diameter of the particles, for example, their MMGD, can be measured using a laser diffraction technique used a Spraytec® (Malvern Instruments, Worcestershire, UK) diffraction-based device equipped with an inhalation cell, as described herein above. Other methods for measuring particle diameter are described in the European or US Pharmacopeas.

In certain embodiments, the nanoparticles reversibly agglomerate to form microparticles (e.g. during the (spray) drying step).

In certain embodiments, the nanoparticles may be combined with (i.e. dispersed in, embedded in, or physically mixed with) at least one carrier.

In certain embodiments, the microparticles may comprise at least one carrier. In certain embodiments, the microparticles may comprise the nanoparticles and at least one carrier.

In certain embodiments, the carrier may be selected from sugar alcohols; polyols (such as sorbitol, mannitol and xylitol); crystalline sugars including monosaccharides (such as glucose, arabinose) and disaccharides (such as lactose, maltose, saccharose, dextrose, trehalose, maltitol); inorganic salts (such as sodium chloride and calcium carbonate); organic salts (such as sodium lactate, potassium or sodium phosphate, sodium citrate, urea); polysaccharides (such as dextran, chitosan, starch, cellulose, and their derivatives); oligosaccharides (such as cyclodextrins and dextrins); titanium dioxide; silicone dioxide; magnesium stearate; lecithin; amino acids (such as leucine, isoleucine, histidine, threonine, lysine, valine, methionine, phenylalanine); derivatives of an amino acid (such as acesulfame K, aspartame); lauric acid or derivatives (such as esters and salts); palmitic acid or derivatives (such as esters and salts); stearic acid or derivatives (such as esters and salts); erucic acid or derivatives (such as esters and salts); behenic acid or derivatives (such as esters and salts); sodium stearyl fumarate; sodium stearyl lactylate; phosphatidylcholines; phosphatidylglycerols; natural and synthetic lung surfactants; lauric acid and its salts (such as sodium lauryl sulphate, magnesium lauryl sulphate); triglycerides; sugar esters; phospholipids; cholesterol; talc.

In certain preferred embodiments, the carrier is mannitol, dextran, or lactose.

In certain preferred embodiments, the carrier is phospholipids or cholesterol.

In certain preferred embodiments, the carrier is mannitol, dextran, lactose, phospholipids, or cholesterol.

In certain preferred embodiments, the carrier is mannitol, dextran, phospholipids, or cholesterol. Such carriers advantageously allow that the nanoparticles comprised in the microparticles are released and/or reformed as nanoparticles when the microparticles are dissolved or dispersed in an aqueous medium such as a physiological medium.

In certain embodiments, the nanoparticles combined with the carrier may constitute, form, or be comprised in microparticles. In certain embodiments, the nanoparticles combined with the carrier may constitute, form, or be comprised in microparticles configured for dry powder inhalation.

In certain embodiments, the mass of the nanoparticles as taught herein (expressed in grams) comprised in microparticles may be at least about 1% (w/w), relative to or compared with the total mass of the microparticle (expressed in grams). For example, the mass of the nanoparticles as taught herein (expressed in grams) comprised in microparticles may be at least about 5% (w/w), at least about 10% (w/w), at least about 15% (w/w), at least about 20% (w/w), at least about 25% (w/w), at least about 30% (w/w), at least about 35% (w/w), at least about 40% (w/w), at least about 45% (w/w), at least about 50% (w/w), at least about 60% (w/w), at least about 70% (w/w), at least about 80% (w/w), at least about 90% (w/w), at least about 95% (w/w), at least about 99% (w/w), or about 100% (w/w), relative to or compared with the total mass of the microparticle (expressed in grams). For example, the mass of the nanoparticles as taught herein (expressed in grams) comprised in a microparticle may be ranging from about 5% (w/w) to about 95% (w/w), from about 10% (w/w) to about 90% (w/w), from about 20% (w/w) to about 80% (w/w), from about 30% (w/w) to about 70% (w/w), or from about 40% (w/w) to about 60% (w/w).

In certain embodiments of the products (such as pharmaceutical formulations or FR-targeting excipients), uses, or methods, as taught herein, the pharmaceutical formulation as taught herein may be formulated as a dry powder. Such dry powder-based pharmaceutical formulations advantageously are in a solid state, which is more stable for long-term storage and better adapted to poorly water-soluble drugs such as antineoplastic agents.

As used herein, the terms "dry powder" and "microparticles" can be used interchangeably.

The term "dry powder" as used herein refers to particles, wherein the mass median aerodynamic diameter (MMAD) of the particles is ranging from about 0.1 μm to about 10 μm. This range is helpful to allow the particles to satisfactorily reach the respiratory tract such as the lower respiratory tract.

The terms "dry powder inhalation formulation", "dry powder inhalation pharmaceutical formulation", "DPI formulation", or "DPI pharmaceutical formulation" can be used interchangeably herein and refer to a formulation or pharmaceutical formulation which is formulated as a dry powder.

In certain embodiments, the pharmaceutical formulations as taught herein may thus be configured for dry powder inhalation.

In certain embodiments, the method for preparing microparticles configured for dry powder inhalation may comprise the steps of:

(a") preparing (preferably in a solvent) a composition comprising: (i") nanoparticles as taught herein, (ii") optionally at least one carrier as taught herein, and (iii") one or more surfactants, wherein the nanoparticles are dispersed in the solvent, the optional carrier is in suspension or solution or dispersed in the solvent, and the one or more surfactants are in solution in the solvent, and (b") drying, preferably spray drying, the composition of step (a") to produce microparticles containing the nanoparticles.

Such method advantageously allows manipulating and controlling mean particle size and particle size distribution, particle shape and density, in addition to macroscopic properties such as bulk density, flow ability, and dispersibility of the present pharmaceutical formulations.

For example, the solvent may be an organic water-miscible solvent, organic water-non-miscible solvent, aqueous buffer, or a combination of any two or three thereof.

Non-limiting examples of suitable surfactants are phospholipids, lecithin, lipids, cholic acid derivatives and its salts (sodium glycocholate, sodium taurocholate), vitamins (such as GRAS-modified vitamins), sorbitan esters (for example SPAN 85), polyethoxylated sorbitan (for example Tween 80), or any combination thereof. The phospholipid may be selected from phosphatic acids, phosphatidylcholine (saturated and unsaturated), phosphatidylethanolamine, phosphatidylglycerol, phosphatidylserine, phosphatidylinositol, or natural or synthetic lung surfactants.

In certain embodiments, the microparticles as defined herein may be dissolved or dispersed in an aqueous solution to reconstitute the nanoparticles comprised in the microparticles. The term "reconstituted nanoparticles" as used herein refers to nanoparticles which are released and/or reformed after dissolution or dispersion of the microparticles as defined herein in an aqueous medium such as a physiological solution or bodily fluid.

In certain embodiments of the pharmaceutical formulations, inhalers, uses, and methods, as taught herein, at least 10% of the reconstituted nanoparticles may have a particle size distribution which is corresponding to the particle size distribution of the nanoparticles (before they were) comprised in the microparticles. For example, at least 20% of the reconstituted nanoparticles, at least 30% of the reconstituted nanoparticles, at least 40% of the reconstituted nanoparticles, at least 50% of the reconstituted nanoparticles, at least 60% of the reconstituted nanoparticles, at least 70% of the reconstituted nanoparticles, at least 80% of the reconstituted nanoparticles, or at least 90% of the reconstituted nanoparticles may have a particle size distribution which is corresponding to the particle size distribution of the nanoparticles (before they were) comprised in the microparticles.

In certain embodiments of the pharmaceutical formulations, inhalers, uses, and methods, as taught herein, after dissolving or dispersing the microparticles as defined herein in an aqueous medium, such as a physiological solution or bodily fluid, the particle size distribution of at least 10% of the reconstituted nanoparticles may correspond to the particle size distribution of the nanoparticles (before they were) comprised in the microparticles. For example, after dissolving or dispersing the microparticles as defined herein in an aqueous medium, such as a physiological solution or bodily fluid, the particle size distribution of at least 20% of the reconstituted nanoparticles, of at least 30% of the reconstituted nanoparticles, of at least 40% of the reconstituted nanoparticles, of at least 50% of the reconstituted nanoparticles, of at least 60% of the reconstituted nanoparticles, of at least 70% of the reconstituted nanoparticles, of at least 80% of the reconstituted nanoparticles, or of at least 90% of the reconstituted nanoparticles may correspond to the particle size distribution of the nanoparticles (before they were) comprised in the microparticles.

In certain embodiments of the method for preparing microparticles configured for dry powder inhalation, the method may further comprise dissolving or dispersing the microparticles in an aqueous medium to reconstitute the nanoparticles.

In certain embodiments of the method for preparing microparticles configured for dry powder inhalation, the method may further comprise dissolving or dispersing the microparticles in an aqueous medium to reconstitute the nanoparticles, wherein the particle size distribution of at least 10% of the reconstituted nanoparticles corresponds to the particle size distribution of the nanoparticles (before they were) comprised in the microparticles. For example, the method for preparing microparticles configured for dry powder inhalation may further comprise dissolving or dispersing the microparticles in an aqueous medium to reconstitute the nanoparticles, wherein the particle size distribution of at least 20% of the reconstituted nanoparticles, of at least 30% of the reconstituted nanoparticles, of at least 40% of the reconstituted nanoparticles, of at least 50% of the reconstituted nanoparticles, of at least 60% of the reconstituted nanoparticles, of at least 70% of the reconstituted nanoparticles, of at least 80% of the reconstituted nanoparticles, or of at least 90% of the reconstituted nanoparticles corresponds to the particle size distribution of the nanoparticles (before they were) comprised in the microparticles.

The present invention also encompasses an inhaler comprising the pharmaceutical formulations as taught herein. A further aspect provides a powder inhaler comprising the pharmaceutical formulations as taught herein. A yet further aspect provides a dry powder inhaler (DPI) comprising the pharmaceutical formulations as taught herein. Such DPIs offer many advantages. Indeed, DPIs allow storing the pharmaceutical formulations in a solid state, which is more stable for long-term storage and better adapted to poorly water-soluble drugs such as antineoplastic agents. Moreover, such DPIs are activated and driven by the patient's inspiratory flow and require a short administration time. Further, the DPIs increase the user's comfort because they are easily transportable and do not require a large set of equipment. Also, the present DPIs are less expensive, require less maintenance, and can be manufactured as disposable inhalers to limit environmental contamination.

The term "dry powder inhaler" or "DPI" generally refers to a (medical) device that delivers medication such as a pharmaceutical formulation to at least part of the respiratory tract, such as for instance to the lungs, in the form of a dry powder. DPIs are an alternative to nebulizers or aerosol-based inhalers commonly called metered-dose inhaler (or MDI).

The present pharmaceutical formulations may be used in DPIs. The DPI can be for example a multidose system (reservoir system), or a monodose system in which the powder is pre-packaged in either capsules (hard gelatin, hydroxypropylmethylcellulose (HPMC), or other pharmaceutically acceptable capsules) or in blisters (Islam and Gladki, *Int J Pharm* 360:1-11, 2008).

An aspect provides a pharmaceutical formulation as taught herein, for use as a medicament.

A further aspect provides a pharmaceutical formulation as taught herein, for use in the treatment of a proliferative disease affecting at least part of the respiratory tract, such as preferably but without limitation a tumour or cancer affecting at least part of the respiratory tract. The use of the pharmaceutical formulations as taught herein in the treatment of a proliferative disease affecting at least part of the respiratory tract is advantageous, since the pharmaceutical formulations allow selectively and specifically targeting antineoplastic cells affecting at least part of the respiratory system.

Also provided according to the present invention is the use of a pharmaceutical formulation as taught herein for the manufacture of a medicament for the treatment of a proliferative disease affecting at least part of the respiratory tract, such as preferably but without limitation a tumour or cancer affecting at least part of the respiratory tract.

Also provided according to the present invention is a method for treating a proliferative disease affecting at least part of the respiratory tract, such as preferably but without limitation a tumour or cancer affecting at least part of the respiratory tract, in a subject in need of such treatment, comprising administering to said subject a therapeutically or prophylactically effective amount of a pharmaceutical formulation as taught herein.

A further aspect provides a pharmaceutical formulation comprising an antineoplastic agent and a FR-targeting excipient, for use in the treatment of a proliferative disease affecting at least part of the respiratory tract, such as preferably but without limitation a tumour or cancer affecting at least part of the respiratory tract. In certain embodiments of the pharmaceutical formulations, uses, or methods, as taught herein, the pharmaceutical formulation may be administered by inhalation. In certain preferred embodiments, the pharmaceutical formulation may be administered by dry powder inhalation. The use of a pharmaceutical formulation comprising an antineoplastic agent and a FR-targeting excipient in the treatment of a proliferative disease affecting at least part of the respiratory tract is advantageous, since the pharmaceutical formulations allow selectively and specifically targeting antineoplastic cells affecting at least part of the respiratory system.

Also provided according to the present invention is the use of a pharmaceutical formulation comprising an antineoplastic agent and a FR-targeting excipient for the manufacture of a medicament for the treatment of a proliferative disease affecting at least part of the respiratory tract, such as preferably but without limitation a tumour or cancer affecting at least part of the respiratory tract.

Also provided according to the present invention is a method for treating a proliferative disease affecting at least part of the respiratory tract, such as preferably but without limitation a tumour or cancer affecting at least part of the respiratory tract, in a subject in need of such treatment, comprising administering to said subject a therapeutically or prophylactically effective amount of a pharmaceutical formulation comprising an antineoplastic agent and a FR-targeting excipient.

In some embodiments, the antineoplastic agent and the FR-targeting excipient may be comprised in a kit of parts, preferably in a pharmaceutical kit of parts. Accordingly, a further aspect provides a kit of parts, preferably a pharmaceutical kit of parts, comprising an antineoplastic agent as taught herein and a FR-targeting excipient as taught herein, wherein the antineoplastic agent and the FR-targeting excipient are configured to allow for producing a pharmaceutical formulation as taught herein.

The term "proliferative disease or disorder" generally refers to any disease or disorder characterized by neoplastic cell growth and proliferation, whether benign, pre-malignant, or malignant. The term proliferative disease generally includes all transformed cells and tissues and all cancerous cells and tissues. Proliferative diseases or disorders include, but are not limited to abnormal cell growth, benign tumours, premalignant or precancerous lesions, malignant tumours, and cancer.

The term "respiratory tract" generally refers to the part of the anatomy involved with the process of respiration. The respiratory tract is typically divided into three segments: (1) the upper respiratory tract comprising the nose and nasal passages, paranasal sinuses, and throat or pharynx, (2) the respiratory airways comprising the voice box or larynx, trachea, bronchi, and bronchioles, and (3) the lungs comprising respiratory bronchioles, alveolar ducts, alveolar sacs, and alveoli.

In certain embodiments, at least part of the respiratory tract may be the lungs or at least part of the lungs.

The recitation "a proliferative disease affecting at least part of the respiratory tract" as used herein refers to primary proliferative diseases affecting at least part of the respiratory tract (such as small cell lung cancer or non-small cell lung cancer), secondary proliferative diseases affecting at least part of the respiratory tract (such as a metastatic tumour affecting at least part of the respiratory tract or metastatic cancer affecting at least part of the respiratory tract), or a combination thereof.

The term "primary proliferative disease" refers to a proliferative disease whereby the neoplastic cells have not migrated to secondary sites in the subject's body, i.e., sites other than the site of the original tumour or cancer.

The term "secondary proliferative disease" refers to a proliferative disease arising from metastasis, whereby the neoplastic cells have migrated to secondary sites in the subject's body, i.e., sites that are different from the site of the original tumour or cancer.

Non-limiting examples of proliferative diseases affecting at least part of the respiratory tract are benign, pre-malignant, and malignant neoplasms located in any tissue or organ of the respiratory tract.

In certain embodiments, the proliferative disease affecting at least part of the respiratory tract may be a tumour affecting at least part of the respiratory tract or cancer affecting at least part of the respiratory tract.

In certain embodiments, the proliferative disease affecting at least part of the respiratory tract may be a tumour affecting at least part of the respiratory tract or may be characterized by the presence of a tumour affecting at least part of the respiratory tract.

As used herein, the terms "tumour" or "tumour tissue" refer to an abnormal mass of tissue resulting from excessive cell division. A tumour or tumour tissue comprises "tumour cells" which are neoplastic cells with abnormal growth properties and no useful bodily function. Tumours, tumour tissue and tumour cells may be benign, pre-malignant or malignant, or may represent a lesion without any cancerous potential. A tumour or tumour tissue may also comprise "tumour-associated non-tumour cells", e.g., vascular cells which form blood vessels to supply the tumour or tumour tissue. Non-tumour cells may be induced to replicate and develop by tumour cells, for example, the induction of angiogenesis in a tumour or tumour tissue.

In certain embodiments, the proliferative disease affecting at least part of the respiratory tract may be malignancy affecting at least part of the respiratory tract.

As used herein, the term "malignancy" refers to a non-benign tumour or a cancer.

In certain embodiments, the proliferative disease affecting at least part of the respiratory tract may be cancer affecting at least part of the respiratory tract.

As used herein, the term "cancer" refers to a malignant neoplasm characterized by deregulated or unregulated cell growth.

The term "cancer" includes primary malignant cells or tumours (e.g., those whose cells have not migrated to sites in the subject's body other than the site of the original malignancy or tumour) and secondary malignant cells or tumours (e.g., those arising from metastasis, the migration of malignant cells or tumour cells to secondary sites that are different from the site of the original tumour).

In certain embodiments, the proliferative disease affecting at least part of the respiratory tract, in particular the primary proliferative disease affecting at least part of the respiratory tract, may be squamous cell cancer (e.g., epithelial squamous cell cancer), lung cancer including small-cell lung cancer (SCLC), non-small cell lung cancer (NSCLC), adenocarcinoma of the lung, squamous carcinoma of the lung, or large cell carcinoma of the lung.

In certain embodiments, the proliferative disease affecting at least part of the respiratory tract, in particular the primary proliferative disease affecting at least part of the respiratory tract, may be SCLC or NSCLC. The treatment of subjects having SCLC or NSCLC with a pharmaceutical formulation as taught herein or with a pharmaceutical formulation comprising an antineoplastic agent and a FR-targeting excipient, may advantageously decrease tumour growth and increase the subjects' survival rate in comparison with untreated subjects.

In certain embodiments, the proliferative disease affecting at least part of the respiratory tract, in particular the secondary proliferative disease affecting at least part of the respiratory tract, may be a metastatic tumour affecting at least part of the respiratory tract or metastatic cancer affecting at least part of the respiratory tract.

In certain embodiments, the proliferative disease affecting at least part of the respiratory tract, in particular the secondary proliferative disease affecting at least part of the respiratory tract, may be a metastasis affecting at least part of the respiratory tract.

The term "metastatic" or "metastasis" generally refers to the spread of a cancer from one organ or tissue to another non-adjacent organ or tissue. The occurrence of the proliferative disease in the other non-adjacent organ or tissue is referred to as metastasis.

In certain embodiments, the proliferative disease affecting at least part of the respiratory tract, in particular the secondary proliferative disease affecting at least part of the respiratory tract, may be selected from the group consisting of squamous cell cancer (e.g., epithelial squamous cell cancer), cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, head cancer and neck cancer.

In the context of the present invention, it will be understood that a pharmaceutical formulation as taught herein and a pharmaceutical formulation comprising an antineoplastic agent and a FR-targeting excipient will be selectively taken up by cells comprising expression of a folate receptor.

In certain embodiments, the proliferative disease affecting at least part of the respiratory tract may comprise a cell expressing a folate receptor.

The term "folate receptor" refers to any cell-based receptor that binds folate and reduced folic acid derivatives and mediates delivery of tetrahydrofolate to the interior of the cell.

The terms "folate receptor" and "folate binding protein" can be used interchangeably herein. Human folate receptors include Folate receptor alpha, Folate receptor beta, Folate receptor gamma and Retbindin.

The terms "folate receptor alpha" or "FR alpha" may be used interchangeably.

Exemplary human folate receptor alpha protein sequences may be as annotated under NCBI Genbank (http://www.ncbi.nlm.nih.gov/) accession number NP_057936.1 or NP_057937.1.

The terms "folate receptor beta", "FR beta", "BETA HFR" or "FBP/PL 1" may be used interchangeably.

Exemplary human folate receptor beta protein sequences may be as annotated under NCBI Genbank (http://www.ncbi.nlm.nih.gov/) accession number NP_000794.3, NP_001107007.1, NP_001107006.1, or NP_001107008.1.

The terms "folate receptor gamma", "FR gamma", "FR G", or "gamma HFR" may be used interchangeably.

Exemplary human folate receptor gamma protein sequence may be as annotated under NCBI Genbank (http://www.ncbi.nlm.nih.gov/) accession number NP_000795.2.

The terms "Retbindin" or "RTBDN" may be used interchangeably.

Exemplary human RTBDN protein sequences may be as annotated under NCBI Genbank (http://www.ncbi.nlm.nih.gov/) accession number NP_113617.1 or NP_001257369.1.

Wherein a cell is said to be positive for (or to express or comprise expression of) a particular marker, this means that a skilled person will conclude the presence or evidence of a distinct signal, e.g., antibody-detectable or detection by reverse transcription polymerase chain reaction, for that marker when carrying out the appropriate measurement, compared to suitable controls. Where the method allows for quantitative assessment of the marker, positive cells may on average generate a signal that is significantly different from the control, e.g., but without limitation, at least 1.5-fold higher than such signal generated by control cells, e.g., at least 2-fold, at least 4-fold, at least 10-fold, at least 20-fold, at least 30-fold, at least 40-fold, at least 50-fold higher or even higher.

Non-limiting examples of suitable antibodies for the detection of human folate receptor alpha are Rabbit Anti-Folate receptor alpha antibody, Polyclonal (LS-B5727, Lifespan Biosciences, or PA5-27465, Thermo Fisher Scientific, Inc.) or Rabbit Anti-Folate receptor alpha antibody, Monoclonal[EPR4708(2)] (LS-C139001, Lifespan Biosciences). Non-limiting examples of suitable antibodies for the detection of human folate receptor beta are Rabbit Anti-Folate receptor beta antibody, Polyclonal (LS-C46883, Lifespan Biosciences, or PA5-24953, Thermo Fisher Scientific, Inc.) or Mouse Anti-Folate receptor beta antibody, Monoclonal[4B12] (H00002350-M04, Abnova).

The expression of the above cell-specific markers can be detected using any suitable immunological technique known in the art, such as immuno-cytochemistry or affinity adsorption, Western blot analysis, FACS, ELISA, etc., or by any suitable biochemical assay of enzyme activity, or by any suitable technique of measuring the quantity of the marker mRNA, e.g., Northern blot, semi-quantitative or quantitative RT-PCR, etc. Sequence data for molecules listed in this disclosure are known and can be obtained from public databases such as GenBank (http://www.ncbi.nlm.nih.gov/).

It will be understood, however, that specific dose level and frequency of dosage for any particular patient may be varied and will depend upon a variety of factors including the activity of the specific antineoplastic substance or composition employed, the metabolic stability and length of action of that antineoplastic substance or composition, the breathing pattern (i.e. flow rate, ventilation volume, and end-inspiratory breath-holding), the age, body weight, general health, sex, diet, mode and time of administration, rate of excretion, combination of active compounds, the severity of the particular condition, and the subject undergoing therapy.

The dosage or amount of the present pharmaceutical formulations used, optionally in combination with one or more other active compound to be administered, depends on the individual case and is, as is customary, to be adapted to the individual circumstances to achieve an optimum effect. Thus, it depends on the nature and the severity of the disorder to be treated, and also on the sex, age, body weight, general health, diet, mode and time of administration, and individual responsiveness of the human or animal to be treated, efficacy, metabolic stability and duration of action of the compounds used, on whether the therapy is acute or chronic or prophylactic, or on whether other active compounds are administered in addition to the agent(s) of the invention.

Without limitation, depending on the type and severity of the disease, a typical daily dosage of the present pharmaceutical formulations might range from about 1 µg/kg to 1 g/kg of body weight or more, depending on the factors mentioned above. For instance, a daily dosage of the present pharmaceutical formulations may range from about 1 mg/kg to 1 g/kg of body weight. For repeated administrations over several days or longer, depending on the condition, the treatment is sustained until a desired suppression of disease symptoms occurs. A preferred dosage of the present pharmaceutical formulations may be in the range from about 10.0 mg/kg to about 500 mg/kg of body weight. Thus, one or more doses of about 10.0 mg/kg, 20.0 mg/kg, 50.0 mg/kg, 100 mg/kg, 200 mg/kg, 300 mg/kg, 400 mg/kg, or 500 mg/kg (or any combination thereof) may be administered to the patient. Such doses may be administered intermittently, e.g., every day, every week or every two or three weeks.

In certain embodiments, the pharmaceutical formulation as taught herein may be used alone or in combination with one or more active compounds that are suitable in the treatment of a proliferative disease affecting at least part of the respiratory tract. The latter can be administered before, after, or simultaneously with the administration of the pharmaceutical formulation as taught herein. The recitations "active compound" or "active pharmaceutical ingredient" refer to a substance or composition other than the pharmaceutical formulations as taught herein.

The term "active" in the recitations "active compound" or "active pharmaceutical ingredient" refers to "pharmacologically active".

Except when noted, "subject" or "patient" are used interchangeably and refer to animals, preferably warm-blooded animals, more preferably vertebrates, even more preferably mammals, still more preferably primates, and specifically includes human patients and non-human mammals and primates. Preferred patients are human subjects.

The term "mammal" includes any animal classified as such, including, but not limited to, humans, domestic and farm animals, zoo animals, sport animals, pet animals, companion animals and experimental animals, such as, for example, mice, rats, hamsters, rabbits, dogs, cats, guinea pigs, cattle, cows, sheep, horses, pigs and primates, e.g., monkeys and apes. Particularly preferred are human subjects, including both genders and all age categories thereof The term "diseased subject" as used herein refers to a subject diagnosed with or having a proliferative disease affecting at least part of the respiratory tract, such as a tumour affecting at least part of the respiratory tract or cancer affecting at least part of the respiratory tract.

As used herein, a phrase such as "a subject in need of treatment" includes subjects that would benefit from treatment of a given condition, particularly proliferative diseases. Such subjects may include, without limitation, those that have been diagnosed with said condition, those prone to develop said condition and/or those in whom said condition is to be prevented.

The terms "treat" or "treatment" encompass both the therapeutic treatment of an already developed disease or condition, such as the therapy of an already developed proliferative disease, as well as prophylactic or preventive measures, wherein the aim is to prevent or lessen the chances of incidence of an undesired affliction, such as to prevent occurrence, development and progression of proliferative diseases. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

The term "prophylactically effective amount" refers to an amount of an active compound or pharmaceutical agent that inhibits or delays in a subject the onset of a disorder as being sought by a researcher, veterinarian, medical doctor or other clinician. The term "therapeutically effective amount" as used herein, refers to an amount of active compound or pharmaceutical agent that elicits the biological or medicinal response in a subject that is being sought by a researcher, veterinarian, medical doctor or other clinician, which may include inter alia alleviation of the symptoms of the disease or condition being treated. Methods are known in the art for determining therapeutically and prophylactically effective doses for the pharmaceutical formulation as taught herein.

The above aspects and embodiments are further supported by the following non-limiting examples.

EXAMPLES

Example 1: Synthesis of an FR-Targeting Excipient According to an Embodiment of the Present Invention (Folate-PEO-HTCC 1)

The carboxylic groups of folic acid were first conjugated with the free primary amine of O-[2-aminoethyl]-O'-[3-carboxypropyl]polyethylene glycol ($NH_2CH_2CH_2$—PEO-O$(CH_2)_3COOH$) (Iris Biotech GmbH, Marktredwitz, Germany, catalogue number (cat. num.) PEG1096, 3000 Da) using carbodiimide chemistry (Hermanson G. T, *Bioconjugate Techniques*, $2^{nd}$ Edition, Academic Press, Elsevier, 2008). Briefly, 1.1 g of folic acid (Sigma-Aldrich, St. Louis, Mo., USA, cat. num. F7876) was dissolved in 15 ml of anhydrous dimethylsulfoxide (DMSO) (Sigma-Aldrich, St. Louis, Mo., USA, cat. num. 276855) containing 700 µL, of triethylamine (TEA) (Sigma-Aldrich, St. Louis, Mo., USA, cat. num. T0886) by sonication. 1 g of N,N'-Dicylclohexylcarbodiimide (DCC) (Sigma-Aldrich, St. Louis, Mo., USA, cat. num. D80002), 580 mg of N-Hydroxysuccinimide (NHS) (Sigma-Aldrich, St. Louis, Mo., USA, cat. num. 130672) and 60 mg of 4-(Dimethylamino)pyridine (DMAP) (Sigma-Aldrich, St. Louis, Mo., USA, cat. num. 522805) were added to this DMSO solution and the mixture was stirred at room temperature in the dark overnight. The precipitated byproduct, N,N'-Dicyclohexylurea (DCU), was filtrated and the filtrate was added dropwise to 350 ml of an anhydrous solution of acetone (Sigma-Aldrich, St. Louis, Mo., USA, cat. num. 179124)/diethyl ether (Sigma-Aldrich, St. Louis, Mo., USA, cat. num. 32203) (30:70) at 0° C. The yellow precipitate obtained was collected and wash with 3 times 20 ml of cold acetone/diethyl ether solution to remove any trace of reagents and DMSO. This precipitate corresponding to activated folic acid was dissolved in 15 ml of anhydrous DMSO containing 700 µl of TEA in presence of 1.6 g of $NH_2CH_2CH_2$—PEO-$O(CH_2)_3COOH$. This solution was stirred in the dark at room temperature for 24 h. The reaction mixture was first dialyzed against NaOH 0.1 M (molecular weight cutoff (MWCO)=1 kDa, Spectra/Por, Spectrum Labs, Breda, The Netherlands) in order to eliminate DMSO, ultrafiltrated (MWCO=1 kDa, Ultracel, Merck Millipore, Darmstadt, Germany) against NaOH 0.1 M and then against ultrapure water and finally lyophilized (Freeze-dryer Epsilon 1-6, Martin Christ GmbH, Osterode, Germany). Folate-$NHCH_2CH_2$—PEO-$O(CH_2)_3COOH$ molecular structure was confirmed by $^1H$ NMR (Bruker Avance 300 spectrometer, Bruker, Wissembourg, France) at 293 K in $D_2O$ (Sigma-Aldrich, St. Louis, Mo., USA, cat. num. 633178). Chemical shifts (δ) are given in parts per million (ppm) relative to trimethylsilane (TMS). $^1H$ NMR ($D_2O$, 300 MHz, δ ppm): 3.71 (PEO), 6.86, 7.69, 8.76 (Folate). Folate content value determined by quantitative UV spectrophotometry of the folate-polysaccharide conjugate in methanol using the folic acid extinction coefficient E value of 28400 $M^{-1}$ $cm^{-1}$ at $\lambda_{max}$ of 285 nm (Agilent 8453 UV/Visible Spectrophotometer, Agilent, Santa Clara, Calif., USA). Folate content value was 0.234±0.002 mmol/g (87.6±0.9% of the theoretical value namely 0.270 mmol/g).

The free carboxylic group of folate-$NHCH_2CH_2$—PEO-$O(CH_2)_3COOH$ was afterwards coupled with the free primary amines of N-[(2-hydroxy-3-trimethylammonium)propyl] chitosan chloride (HTCC) with Mw of 92 kDa, a degree of acetylation of 20% (corresponding of a degree of deacetylation of 80%), and a degree of modification (by HT) of 33%. (Kitozyme, Herstal, Belgium), using carbodiimide chemistry (Hermanson G. T., 2008, supra). Briefly, 420 mg of HTCC was dissolved in 35 ml of ultrapure water under magnetic stirring. 1.15 g folate-$NHCH_2CH_2$—PEO-O$(CH_2)_3$ COOH, 100 mg of N-(3-Dimethylaminopropyl)-N'-ethylcarbodiimide hydrochloride (EDC) (Sigma-Aldrich, St. Louis, Mo., USA, cat. num. E6383) and 75 mg of NHS were added to this aqueous solution and the mixture was stirred at room temperature for 48 h. The reaction mixture was ultrafiltrated (MWCO=30 kDa, Ultracel, Merck Millipore, Darmstadt, Germany) against 0.001 M HCl and then lyophilized (Freeze-dryer Epsilon 1-6, Martin Christ GmbH, Osterode, Germany)

Folate-$NHCH_2CH_2$—PEO-$O(CH_2)_3C0$-HTCC 1 (also referred to herein as folate-PEO-HTCC 1) molecular structure was confirmed by $^1H$ NMR (Bruker Avance 300 spectrometer, Bruker, Wissembourg, France) at 293 K in $D_2O$ and the graft ratio (GR) of PEO on HTCC was determined by $^1H$ NMR (Bruker Avance 300 spectrometer, Bruker, Wissembourg, France) at 293 K in $D_2O$ using the following equation (1):

$$GR(\%) = \frac{[PEG] \times DQ \times 9}{nH^+ PEG \times [N^+(CH_3)_3]} \quad (1)$$

wherein [PEG] is the integral of proton peak of PEO at 3.7 ppm ($CH_2O$); DQ is the degree of quaternization or degree of substitution of HTCC (%) given by the supplier (DQ=33%); 9 is the number of $H^+$ in $N^+(CH_3)_3$; $nH^+PEG$ is the number of proton per PEO chain according to the molecular weight of PEO given by the supplier (Mw=3219 Da, $nH^+PEG$=288); and $[N^+(CH_3)_3]$ is the integral of the peak at 3.3 ppm ($N^+(CH_3)_3$)

$^1$H-NMR ($D_2O$, 300 MHz, δ ppm): 2.06 (s, 3H, —CO—$CH_3$), 2.78 (s, 2H, —NH—$CH_2$—CH—), 3.23 (s, 9H, —N+$(CH_3)_3$), 3.71 (PEG, s, 288H, —$CH_2$—O—), 4.30 (s, 1H, —$CH_2$—CHOH—$CH_2$—), 6.86, 7.69, 8.76 (Folate). The graft ratio (GR) of PEO on HTCC was 7%.

Example 2: Synthesis of an FR-Targeting Excipient According to an Embodiment of the Present Invention (Folate-PEO-HTCC 2)

A carboxylic group was first graft on Boc-NH-PEO—$(CH_2)_2NH_2$ (Iris Biotech GmbH, Marktredwitz, Germany, cat. num. PEG1068, 3000 Da) using succinic anhydride (Sigma-Aldrich, St. Louis, Mo., USA, cat. num. 239690). Briefly, 2 g of Boc-NH-PEO—$(CH_2)_2NH_2$ and 340 mg of succinic anhydride were dissolved in 50 ml of dichloromethane (DCM) (Sigma-Aldrich, St. Louis, Mo., USA, cat. num. 443484) under magnetic stirring and the mixture was let to stir overnight at room temperature. DCM was evaporated under vacuum and the resulting powder was dissolved in 20 ml of ultrapure water. The solution was ultrafiltrated (MWCO=1 kDa, Ultracel, Merck Millipore, Darmstadt, Germany) against ultrapure water and lyophilized (Freeze-dryer Epsilon 1-6, Martin Christ GmbH, Osterode, Germany). Boc-NH-PEO—$(CH_2)_2NHCO$—$(CH_2)_2$—COOH molecular structure was confirmed by $^1H$ NMR (Bruker Avance 300 spectrometer, Bruker, Wissembourg, France) at 293 K in DMSO-d6 (Sigma-Aldrich, St. Louis, Mo., USA, cat. num. 156914). Chemical shifts (δ) are given in ppm relative to DMSO. $^1H$ NMR (DMSO-d6, 300 MHz, δ ppm): 3.50 (PEG), 2.1 and 2.2 (succinate), 1.37 (Boc).

The Boc group of Boc-NH-PEO—$(CH_2)_2NHCO$—$(CH_2)_2$—COOH was then removed in order to form a primary amine. Boc-NH-PEO—$(CH_2)_2NHCO$—$(CH_2)_2$—COOH was dissolved in 10 ml of DCM under magnetic stirring. 10 ml of trifluoroacetic acid (TFA) (Sigma-Aldrich, St. Louis, Mo., USA, cat. num. 302031) were added and the mixture was let to stir overnight. DCM was evaporated under vacuum. The resulting TFA solution were carefully added dropwise directly in a beaker containing 11.25 g of $NaHCO_3$ and 13 g of ice. The neutralization occurs until the end of the production of gas bubbles corresponding of $CO_2$ formation. The reaction mixture were ultrafiltrated (MWCO=1 kDa, Ultracel, Merck Millipore, Darmstadt, Germany) against ultrapure water and lyophilized (Freeze-dryer Epsilon 1-6, Martin Christ GmbH, Osterode, Germany). The deprotection of the primary amine to form $NH_2$—PEO—$(CH_2)_2NHCO$—$(CH_2)_2$—COOH was evaluated by $^1H$ NMR (Bruker Avance 300 spectrometer, Bruker, Wissembourg, France) in DMSO-d6 at 293 K.

The carboxylic groups of folic acid were then conjugated with the free primary amine of $NH_2$—PEO—$(CH_2)_2$NHCO—$(CH_2)_2$—COOH using carbodiimide chemistry (Hermanson G. T., 2008, supra). Briefly, 1.1 g of folic acid (Sigma-Aldrich, St. Louis, Mo., USA, cat. num. F7876) was dissolved in 15 ml of anhydrous DMSO (Sigma-Aldrich, St. Louis, Mo., USA, cat. num. 276855) containing 700 μL of TEA (Sigma-Aldrich, St. Louis, Mo., USA, cat. num. T0886) by sonication. 1 g of DCC (Sigma-Aldrich, St. Louis, Mo., USA, cat. num. D80002), 580 mg of NHS (Sigma-Aldrich, St. Louis, Mo., USA, cat. num. 130672) and 60 mg of DMAP (Sigma-Aldrich, St. Louis, Mo., USA, cat. num. 522805) were added to this DMSO solution and the mixture was stirred at room temperature in the dark overnight. The precipitated byproduct, DCU, was filtrated and the filtrate was added dropwise to 350 ml of an anhydrous solution of acetone (Sigma-Aldrich, St. Louis, Mo., USA, cat. num. 179124)/diethyl ether (Sigma-Aldrich, St. Louis, Mo., USA, cat. num. 32203) (30:70) at 0° C. The yellow precipitate obtained was collected and wash with 3 times 20 ml of cold acetone/diethyl ether solution to remove any trace of reagents and DMSO. This precipitate corresponding to activated folic acid was dissolved in 15 ml of anhydrous DMSO containing 700 µl of TEA in presence of 1.6 g of $NH_2$—PEO—$(CH_2)_2$NHCO—$(CH_2)_2$—COOH. This solution was stirred in the dark at room temperature for 24 h. The reaction mixture was first dialyzed against NaOH 0.1 M (MWCO=1 kDa, Spectra/Por, Spectrum Labs, Breda, The Nederlands) in order to eliminate DMSO, ultrafiltrated (MWCO=1 kDa, Ultracel, Merck Millipore, Darmstadt, Germany) against NaOH 0.1M and then against ultrapure water and finally lyophilized (Freeze-dryer Epsilon 1-6, Martin Christ GmbH, Osterode, Germany). Folate-NH-PEO—$(CH_2)_2$NHCO—$(CH_2)_2$—COOH molecular structure was confirmed by $^1$H NMR (Bruker Avance 300 spectrometer, Bruker, Wissembourg, France) and folate content value determined by quantitative UV spectrophotometry of the conjugate (Agilent 8453 UV/Visible Spectrophotometer, Agilent, Santa Clara, Calif., USA). $^1$H NMR analysis and determination of the folate content value was performed as described in Example 1. $^1$H NMR ($D_2O$, 300 MHz, δ ppm): 2.1 and 2.2 (succinate), 3.71 (PEG), 6.86, 7.69, 8.76 (Folate). Folate content value was 0.240±0.001 mmol/g (89.7±0.6% of the theoretical value, 0.27 mmol/g).

The free carboxylic group of folate-NH-PEO—$(CH_2)_2$NHCO—$(CH_2)_2$—COOH was afterwards coupled with the free primary amines of HTCC (Mw of 92 kDa, a degree of acetylation of 20% (corresponding of a degree of deacetylation of 80%), and a degree of modification (by HT) of 33%. (Kitozyme, Herstal, Belgium)) using carbodiimide chemistry (Hermanson G. T, 2008, supra). Briefly, 420 mg of HTCC was dissolved in 35 ml of ultrapure water under magnetic stirring. 1.15 g folate-NH-PEO—$(CH_2)_2$NHCO—$(CH_2)_2$—COOH, 100 mg of EDC (Sigma-Aldrich, St. Louis, Mo., USA, cat. num. E6383) and 75 mg of NHS were added to this aqueous solution and the mixture was stirred at room temperature for 48 h. The reaction mixture was ultrafiltrated (MWCO=30 kDa, Ultracel, Merck Millipore, Darmstadt, Germany) against HCl 0.001 M and then lyophilized (Freeze-dryer Epsilon 1-6, Martin Christ GmbH, Osterode, Germany).

Folate-NH-PEO—$(CH_2)_2$NHCO—$(CH_2)_2$—CO-HTCC 2 (also referred to herein as folate-PEO-HTCC 2) molecular structure was confirmed by $^1$H NMR (Bruker Avance 300 spectrometer, Bruker, Wissembourg, France) in $D_2O$ at 293 K and the graft ratio (GR) was determined by $^1$H NMR (Bruker Avance 300 spectrometer, Bruker, Wissembourg, France) in $D_2O$ at 293 K using the equation (1).

$^1$H-NMR ($D_2O$, 300 MHz, δ ppm): 2.06 (s, 3H, —CO—$CH_3$), 2.78 (s, 2H, —NH—$CH_2$—CH—), 3.23 (s, 9H, —N+$(CH_3)_3$), 3.71 (PEG, s, 288H, —$CH_2$—O—), 4.30 (s, 1H, —$CH_2$—CHOH—$CH_2$—), 6.86, 7.69, 8.76 (Folate). The GR was 7%.

Example 3: Synthesis of an FR-Targeting Excipient According to an Embodiment of the Present Invention (Folate-PEO-HTCC 3)

The carboxylic groups of folic acid were first conjugated with the free primary amine of 0-(2-aminoethyl)polyethylene oxide (HO-PEO—$(CH_2)_2NH_2$) (Iris Biotech GmbH, Marktredwitz, Germany, cat. num. PEG1007) using carbodiimide chemistry (Hermanson G. T., 2008, supra). Briefly, 1.1 g of folic acid was dissolved in 15 ml of anhydrous DMSO containing 700 µL of TEA by sonication. 1 g DCC, 580 mg of NHS and 60 mg of DMAP were added to this DMSO solution and the mixture was stirred at room temperature in the dark overnight. The precipitated byproduct, DCU, was filtrated and the filtrate was added to 700 µl of TEA in presence of 1.6 g of HO-PEO—$(CH_2)_2NH_2$. This solution was stirred in the dark at room temperature for 24 h. The reaction mixture was first dialyzed against NaOH 0.1 M (MWCO=1 kDa, Spectra/Por, Spectrum Labs, Breda, The Nederlands) in order to eliminate DMSO, ultrafiltrated (MWCO=1 kDa, Ultracel, Merck Millipore, Darmstadt, Germany) against NaOH 0.1M and then against ultrapure water and finally lyophilized (Freeze-dryer Epsilon 1-6, Martin Christ GmbH, Osterode, Germany). Folate-NH—$(CH_2)_2$—PEO-OH molecular structure was confirmed by $^1$H NMR (Bruker Avance 300 spectrometer, Bruker, Wissembourg, France) and folate content value determined by quantitative UV spectrophotometry of the folate-polysaccharide conjugate (Agilent 8453 UV/Visible Spectrophotometer, Agilent, Santa Clara, Calif., USA). $^1$H NMR analysis and determination of the folate content value was performed as described in Example 1. $^1$H NMR ($D_2O$, 300 MHz, δ ppm): 3.71 (PEG), 6.86, 7.69, 8.76 (Folate). Folate content value was 0.2422±0.0001 mmol/g (90.59±0.05% of the theoretical value, 0.27 mmol/g).

A carboxylic group was graft on folate-NH—$(CH_2)_2$—PEO-OH using succinic anhydride. Briefly 1.1 g of folate-NH—$(CH_2)_2$—PEO-OH was dissolved in 30 ml of $CHCl_3$ (Sigma-Aldrich, St. Louis, Mo., USA, cat. num. 472476) under magnetic stirring at room temperature. 170 mg of succinic anhydride (Sigma-Aldrich, St. Louis, Mo., USA, cat. num. 239690), 220 µl of TEA and 37 mg of DMAP were added and the mixture was stirred at 50° C. overnight. The $CHCl_3$ was evaporated under vacuum and the product was ultrafiltrated (MWCO=1 kDa, Ultracel, Merck Millipore, Darmstadt, Germany) against ultrapure water and finally lyophilized (Freeze-dryer Epsilon 1-6, Martin Christ GmbH, Osterode, Germany). Folate-NH—$(CH_2)_2$—PEO-O—(CO)$(CH_2)_2$COOH molecular structure was confirmed by $^1$H NMR (Bruker Avance 300 spectrometer, Bruker, Wissembourg, France) in $D_2O$ at 293 K. $^1$H NMR ($D_2O$, 300 MHz, δ ppm): 2.6 and 2.7 (succinate), 3.71 (PEG), 6.86, 7.69, 8.76 (Folate).

The free carboxylic group of folate-NH—$(CH_2)_2$—PEO-O—(CO)$(CH_2)_2$COOH was afterwards coupled with the free primary amines of HTCC (Mw of 92 kDa, a degree of acetylation of 20% (corresponding of a degree of deacetylation of 80%), and a degree of modification (by HT) of 33%. (Kitozyme, Herstal, Belgium)) using carbodiimide chemistry (Hermanson G. T, 2008, supra). Briefly, 420 mg of HTCC was dissolved in 35 ml of ultrapure water under magnetic stirring. 1.15 g folate-NH—$(CH_2)_2$—PEO-O—(CO)$(CH_2)_2$COOH, 100 mg of EDC and 75 mg of NHS were added to this aqueous solution and the mixture was stirred at room temperature for 48 h. The reaction mixture was ultrafiltrated (MWCO=30 kDa, Ultracel, Merck Millipore, Darmstadt, Germany) against ultrapure water and then lyophilized (Freeze-dryer Epsilon 1-6, Martin Christ GmbH, Osterode, Germany)

Folate-NH—$(CH_2)_2$—PEO-O—(CO)$(CH_2)_2$(CO)-HTCC 3 (also referred to herein as folate-PEO-HTCC 3) molecular structure was confirmed by $^1$H NMR (Bruker Avance 300 spectrometer, Bruker, Wissembourg, France) in $D_2O$ at 293 K and the graft ration (GR) was determined by $^1$H NMR (Bruker Avance 300 spectrometer, Bruker, Wissembourg, France) in $D_2O$ at 293 K using the equation (1). $^1$H-NMR ($D_2O$, 300 MHz, δ ppm): 2.06 (s, 3H, —CO—$CH_3$), 2.78 (s, 2H, —NH—$CH_2$—CH—), 3.23 (s, 9H, —N+$(CH_3)_3$), 3.71

(PEG, s, 288H, —CH$_2$—O—), 4.30 (s, 1H, —CH$_2$—CHOH—CH$_2$—), 6.86, 7.69, 8.76 (Folate). The GR was 7%.

Example 4: Synthesis of an FR-Targeting Excipient According to an Embodiment of the Present Invention (Folate-PEO-HMD 1)

The carboxylic groups of folic acid were first conjugated with the free primary amine of Boc-NH-PEO—(CH$_2$)$_2$NH$_2$ (Iris Biotech GmbH, Marktredwitz, Germany, cat. num. PEG1068) using carbodiimide chemistry (Hermanson G. T., 2008, supra). Briefly, 1.51 g of folic acid was dissolved in 10 ml of anhydrous DMSO containing 420 μL of TEA by sonication. 630 mg of DCC, 350 mg of NHS and 40 mg of DMAP were added to this DMSO solution and the mixture was stirred at room temperature in the dark overnight. The precipitated byproduct, DCU, was filtrated and the filtrate was added to 420 μl of TEA in presence of 1.1 g of Boc-NH-PEO—(CH$_2$)$_2$NH$_2$. This solution was stirred in the dark at room temperature for 24 h. The reaction mixture was first dialyzed against NaOH 0.1 M (MWCO=1 kDa, Spectra/Por, Spectrum Labs, Breda, The Nederlands) in order to eliminate DMSO, ultrafiltrated (MWCO=1 kDa, Ultracel, Merck Millipore, Darmstadt, Germany) against NaOH 0.1M and then against ultrapure water and finally lyophilized (Freeze-dryer Epsilon 1-6, Martin Christ GmbH, Osterode, Germany) Folate-NH—(CH$_2$)$_2$—PEO—NH-Boc molecular structure was confirmed by $^1$H NMR (Bruker Avance 300 spectrometer, Bruker, Wissembourg, France) and folate content value determined by quantitative UV spectrophotometry of the folate-polysaccharide conjugate (Agilent 8453 UV/Visible Spectrophotometer, Agilent, Santa Clara, Calif., USA). $^1$H NMR analysis and determination of the folate content value was performed as described in Example 1. $^1$H NMR (D$_2$O, 300 MHz, δ ppm): 1.37 (Boc), 3.71 (PEG), 6.86, 7.69, 8.76 (Folate). Folate content value was 0.26±0.01 mmol/g (98±5% of the theoretical value, 0.27 mmol/g).

The Boc group of folate-NH—(CH$_2$)$_2$—PEO—NH-Boc was then removed in order to form a primary amine. Folate-NH—(CH$_2$)$_2$—PEO—NH-Boc was dissolved in 4 ml of DCM under magnetic stirring. 4 ml of TFA were added and the mixture was let to stir overnight. DCM was evaporated under vacuum. The resulting TFA solution were carefully added dropwise directly in a beaker containing 4.5 g of NaHCO$_3$ and 5 g of ice. The neutralization occurs until the end of the production of gas bubbles corresponding of CO$_2$ formation. The reaction mixture were ultrafiltrated (MWCO=1 kDa, Ultracel, Merck Millipore, Darmstadt, Germany) against ultrapure water and lyophilized (Freeze-dryer Epsilon 1-6, Martin Christ GmbH, Osterode, Germany) The deprotection of the primary amine to form folate-NH—(CH$_2$)$_2$—PEO-NH$_2$ was evaluated by $^1$H NMR (Bruker Avance 300 spectrometer, Bruker, Wissembourg, France) in DMSO-d6 at 293 K.

The carboxylic group of stearic acid was grafted on hydroxyl group of dextran using carbodiimide chemistry (Hermanson G. T, 2008, supra) in order to increase hydrophobicity of dextran. Briefly, 100 mg of dextran (Pharmacosmos, Holbaek, Denmark, cat. num. 55100010) was dissolved in 7 ml of anhydrous DMSO under magnetic stirring. 90 mg of stearic acid (Fagron, Waregem, Belgium, cat. num. 610688), 135 mg of DCC and 20 mg of DMAP were added to this DMSO solution and the mixture was stirred at 60° C. for 24 h. The reaction mixture was dialyzed (MWCO=10 kDa, Spectra/Por, Spectrum Labs, Breda, The Nederlands) against ultrapure water and the dialysate was filtrated in order to remove the byproduct DCU and unreacted DCC and stearic acid. The filtrate was finally lyophilized (Freeze-dryer Epsilon 1-6, Martin Christ GmbH, Osterode, Germany). Molecular structure of hydrophobically-modified dextran (HMD) was confirmed by $^1$H NMR (Bruker Avance 300 spectrometer, Bruker, Wissembourg, France) in DMSO-d6 at 293 K. Chemical shifts (δ) are given in ppm relative to DMSO. The fatty acid-graft ratio (FA-GR) was determined by $^1$H NMR (Bruker Avance 300 spectrometer, Bruker, Wissembourg, France) in DMSO-d6 at 293 K using the following equation (2):

$$FA - GR(\%) = 100 \times \frac{[(CH_3)FA]}{9 \times [(CHO)GLC]} \quad (2)$$

wherein [(CH$_3$)FA] is the integral of proton peak of stearate at 0.85 ppm (CH$_3$CH$_2$); 9 is the number of H$^+$ in CH$_3$ (i.e., 3) multiplied by the number of hydroxyl group per glucose unit (i.e., 3); and [(CHO)GLC] is the integral of the peak of glucose monomer at 4.68 ppm (CHO).

$^1$H-NMR (DMSO-d6, 300 MHz, δ ppm): 0.85 and 1.24 (stearate), 3.00-4.00, 4.68 (glucose), 4.47, 4.90 (glucose-stearate). The FA-GR was 3%

A carboxylic group was also graft on dextran using succinic anhydride. Briefly 100 mg of HMD was dissolved in 8 ml of anhydrous DMSO under magnetic stirring at room temperature. 30 mg of succinic anhydride, 80 μl of TEA and 12 mg of DMAP were added and the mixture was stirred at 40° C. overnight. The reaction mixture was dialyzed (MWCO=10 kDa, Spectra/Por, Spectrum Labs, Breda, The Nederlands) against ultrapure water and finally lyophilized (Freeze-dryer Epsilon 1-6, Martin Christ GmbH, Osterode, Germany). HMD-(CO)—(CH$_2$)$_2$—COOH molecular structure was confirmed by $^1$H NMR (Bruker Avance 300 spectrometer, Bruker, Wissembourg, France)) in D$_2$O at 293 K. Chemical shifts (δ) are given in ppm relative to TMS. The succinate-graft ratio (SU-GR) was determined by $^1$H NMR (Bruker Avance 300 spectrometer, Bruker, Wissembourg, France) using the following equation (3):

$$SU - GR(\%) = 100 \times \frac{[(CH_2CH_2)SU]}{4 \times [(CHO)GLC]} \quad (3)$$

wherein [(CH$_2$CH$_2$)SU] is the integral of protons peaks of succinate at 2.52 and 2.71 ppm (CH$_2$CH$_2$); 4 is the number of H$^+$ in CH$_2$CH$_2$ of the succinate (i.e., 4), multiplied by the number of hydroxyl group per glucose unit (i.e., 3), and divided by the number of H$^+$ of CHO of the glucose units (i.e., 3, corresponding to the H$^+$ of C5 and C6 because C2, C3 and C4 have their hydroxyl groups esterified); and [(CHO)GLC] is the integral of the peaks of glucose monomer between 3.30 and 4.50 ppm (CHO).

$^1$H-NMR (D$_2$O, 300 MHz, δ ppm): 0.91 and 1.29 (stearate), 2.52, 2.71 (succinate), 3.30-4.50 (glucose) The SU-GR was 13%.

The free primary amine group of folate-NH—(CH$_2$)$_2$—PEO-NH$_2$ was afterwards coupled with the free carboxylic group of HMD-(CO)—(CH$_2$)$_2$—COOH using carbodiimide chemistry (Hermanson G. T., 2008, supra). Briefly, 45 mg of HMD-(CO)—(CH$_2$)$_2$—COOH was dissolved in presence of 210 mg of folate-NH—(CH$_2$)$_2$—PEO-NH$_2$ in 10 ml of anhydrous DMSO under magnetic stirring. 25 mg of DCC, 15 mg of NHS, 16 μl of TEA and 5 mg of DMAP were added to this solution and the mixture was stirred at 40° C. for 24 h. The reaction mixture was dialyzed (MWCO=10 kDa, Spectra/Por, Spectrum Labs, Breda, The Nederlands) against ultrapure water in order to remove DMSO, ultrafiltrated (MWCO=10 kDa, Ultracel, Merck Millipore, Darmstadt, Germany) against a 70% (v/v) ethanol solution. Ethanol was evaporated under vacuum and the resulting aqueous solution was lyophilized (Freeze-dryer Epsilon 1-6, Martin Christ GmbH, Osterode, Germany). Folate-NH—(CH$_2$)$_2$—PEO-NH—(CO)—(CH$_2$)$_2$—(CO)-HMD (also referred to herein as folate-PEO-HMD 1) molecular structure was confirmed by $^1$H NMR (Bruker Avance 300 spectrometer, Bruker, Wissembourg, France) in D$_2$O at 293 K. Chemical shifts (δ) are given in ppm relative to TMS. The graft ratio (GR) of PEG on HMD was determined by $^1$H NMR (Bruker Avance 300 spectrometer, Bruker, Wissembourg, France) in D$_2$O at 293 K using the following equation (4):

$$GR(\%) = \frac{12 \times [PEG] \times [SU - GR]}{nH^+PEG \times [(CH_2CH_2)SU]} \quad (4)$$

wherein 12 is the number of H$^+$ in CH$_2$CH$_2$ (i.e., 4) multiplied by the number of hydroxyl group per glucose unit (i.e., 3); [PEG] is the integral of proton peak of PEG at 3.7 ppm (CH$_2$O); [SU-GR] is the SU-Graft ratio (expressed in %) of HMD-COOH; nH$^+$PEG is the number of proton per PEG chain according to the molecular weight of PEG given by the supplier (Mw=3317, n H$^+$PEG=288); and [(CH$_2$CH$_2$)SU] is the integral of protons peaks of succinate at 2.52 and 2.71 ppm (CH$_2$CH$_2$).

$^1$H-NMR (D$_2$O, 300 MHz, δ ppm): 0.91 (t, 3H, CH$_2$—CH$_3$) and 1.29 (s, 28H, C$_{14}$H$_{28}$—CH$_3$) (stearate), 2.52, 2.71 (2s, 4H, —NH—CO—CH$_2$CH$_2$—COO—, succinate), 3.30-4.50 (m, CHO, glucose), 3.7 (s, 288H, —CH$_2$—O—, PEG), 6.86, 7.69, 8.76 (Folate). The GR was 12%.

Example 5: Synthesis of an FR-Targeting Excipient According to an Embodiment of the Present Invention (Folate-PEO-HMD 2)

The carboxylic groups of folic acid were first conjugated with the free primary amine of HO-PEO—(CH$_2$)$_2$NH$_2$ using carbodiimide chemistry as described in Example 3. The free hydroxyl group of folate-NH—(CH$_2$)$_2$—PEO-OH was afterwards coupled with the free carboxylic group of HMD-(CO)—(CH$_2$)$_2$—COOH (synthesized according to Example 4) using carbodiimide chemistry (Hermanson G. T, 2008, supra). Briefly, 45 mg of HMD-(CO)—(CH$_2$)$_2$—COOH was dissolved in presence of 210 mg of folate-NH—(CH$_2$)$_2$—PEO-OH in 10 ml of anhydrous DMSO under magnetic stirring. 25 mg of DCC, 15 mg of NHS, 16 μl of TEA and 5 mg of DMAP were added to this solution and the mixture was stirred at 40° C. for 24 h. The reaction mixture was dialyzed (MWCO=10 kDa, Spectra/Por, Spectrum Labs, Breda, The Nederlands) against ultrapure water in order to remove DMSO, ultrafiltrated (MWCO=10 kDa, Ultracel, Merck Millipore, Darmstadt, Germany) against a 70% (v/v) ethanol solution. Ethanol was evaporated under vacuum and the resulting aqueous solution was lyophilized (Freeze-dryer Epsilon 1-6, Martin Christ GmbH, Osterode, Germany). Folate-NH—(CH$_2$)$_2$—PEO-O—(CO)—(CH$_2$)$_2$—(CO)-HMD (also referred to herein as folate-PEO-HMD 2) molecular structure was confirmed by $^1$H NMR (Bruker Avance 300 spectrometer, Bruker, Wissembourg, France) in D$_2$O at 293 K and the graft ratio (GR) of PEG on HMD was determined by $^1$H NMR (Bruker Avance 300 spectrometer, Bruker, Wissembourg, France) in D$_2$O at 293 K using the equation (4).

$^1$H NMR (D$_2$O, 300 MHz, δ ppm): 0.91 (t, 3H, CH$_2$—CH$_3$) and 1.29 (s, 28H, C$_{14}$H$_{28}$—CH$_3$) (stearate), 2.60, 2.71 (2s, 4H, —OOC—CH$_2$CH$_2$—COO—, succinate), 3.30-4.50 (m, CHO, glucose), 3.7 (s, 288H, —CH$_2$—O—, PEG), 6.86, 7.69, 8.76 (Folate). The GR was 12%.

Example 6: Synthesis of an FR-Targeting Excipient According to an Embodiment of the Present Invention (Folate-PEO-HTCC 4)

The carboxylic groups of folic acid were first conjugated with the free hydroxyl group of HO—(CH$_2$)$_2$—PEO-NHCO—(CH$_2$)$_2$—COOH (Iris Biotech GmbH, Marktredwitz, Germany, cat. num. PEG1093) using carbodiimide chemistry (Hermanson G. T., 2008, supra). Briefly, 1.1 g of folic acid was dissolved in 15 ml of anhydrous DMSO containing 700 μL of TEA by sonication. 1 g of DCC, 580 mg of NHS and 60 mg of DMAP were added to this DMSO solution and the mixture was stirred at room temperature in the dark overnight. The precipitated byproduct, DCU, was filtrated and the filtrate was added dropwise to 350 ml of an anhydrous solution of acetone/diethyl ether (30:70) at 0° C. The yellow precipitate obtained was collected and wash with 3×20 ml of cold acetone/diethyl ether solution to remove any trace of reagents and DMSO. This precipitate corresponding to activated folic acid was dissolved in 15 ml of anhydrous DMSO containing 700 μl of TEA in presence of 1.6 g of HO—(CH$_2$)$_2$—PEO-NHCO—(CH$_2$)$_2$—COOH. This solution was stirred in the dark at 70° C. for 48 h. The reaction mixture was first dialyzed against NaOH 0.1 M (MWCO=1 kDa, Spectra/Por, Spectrum Labs, Breda, The Nederlands) in order to eliminate DMSO, ultrafiltrated (MWCO=1 kDa, Ultracel, Merck Millipore, Darmstadt, Germany) against NaOH 0.1M and then against ultrapure water and finally lyophilized (Freeze-dryer Epsilon 1-6, Martin Christ GmbH, Osterode, Germany). Folate-PEO-NHCO—(CH$_2$)$_2$—COOH molecular structure was confirmed by $^1$H NMR (Bruker Avance 300 spectrometer, Bruker, Wissembourg, France) and folate content value determined by quantitative UV spectrophotometry of the folate-polysaccharide conjugate (Agilent 8453 UV/Visible Spectrophotometer, Agilent, Santa Clara, Calif., USA). $^1$H NMR analysis and determination of the folate content value was performed as described in Example 1. $^1$H NMR (D$_2$O, 300 MHz, δ ppm):3.71 (PEG), 6.86, 7.69, 8.76 (Folate). Folate content value was 0.14±0.03 mmol/g (51±4% of the theoretical value, 0.27 mmol/g).

The free carboxylic group of folate-PEO-NHCO—(CH$_2$)$_2$—COOH was afterwards coupled with the free primary amines of N-[(2-hydroxy-3-trimethylammonium)propyl] chitosan (HTCC) (Mw of 92 kDa, a degree of acetylation of 20% (corresponding of a degree of deacetylation of 80%), and a degree of modification (by HT) of 33%. (Kitozyme, Herstal, Belgium)) using carbodiimide chemistry (Hermanson G. T, 2008, supra). Briefly, 420 mg of HTCC was dissolved in 35 ml of ultrapure water under magnetic stirring. 1.15 g folate-PEO-NHCO—(CH$_2$)$_2$—COOH, 100 mg of EDC and 75 mg of NHS were added to this aqueous solution and the mixture was stirred at room temperature for 48 h. The reaction mixture was ultrafiltrated (MWCO=30 kDa, Ultracel, Merck Millipore, Darmstadt, Germany) against ultrapure water and then lyophilized (Freeze-dryer Epsilon 1-6, Martin Christ GmbH, Osterode, Germany)

Folate-PEO-NHCO—$(CH_2)_2$—CO-HTCC 4 (also referred to herein as folate-PEO-HTCC 4) molecular structure was confirmed by $^1H$ NMR (Bruker Avance 300 spectrometer, Bruker, Wissembourg, France) in $D_2O$ at 293 K and the graft ratio (GR) of PEG on HTCC was determined by $^1H$ NMR (Bruker Avance 300 spectrometer, Bruker, Wissembourg, France) in $D_2O$ at 293 K using the equation (1).

$^1H$-NMR ($D_2O$, 300 MHz, δ ppm): 2.06 (s, 3H, —CO—$CH_3$), 2.78 (s, 2H, —NH—$CH_2$—CH—), 3.23 (s, 9H, —N+$(CH_3)_3$), 3.71 (PEG, s, 288H, —$CH_2$—O—), 4.30 (s, 1H, —$CH_2$—CHOH—$CH_2$—), 6.86, 7.69, 8.76 (Folate). The GR was 7%.

Example 7: Preparation of Nanoparticles According to an Embodiment of the Present Invention (Temozolomide-Loaded Folate-PEO-HTCC 1 NPs)

Temozolomide (TMZ)-loaded folate-PEO-HTCC 1 nanoparticles (NPs) were produced by a controlled nanoprecipitation method at room temperature. Folate-PEO-HTCC 1 was synthesized according to Example 1.

Folate-PEO-HTCC 1 was dissolved in a DMSO/pH5 acetate buffer (0.1 M) (4:10 v/v) at a concentration of 7.15 mg/ml under magnetic stirring. A quantity of TMZ (Shilpa Madicare Ld, Raichur, India) of 6 mg/ml was added in the solution and the solution was stirred at room temperature for at least 48 h in order to prepare TMZ-saturated solution. This solution was then centrifuged and the supernatant collected. The saturation concentration of TMZ in DMSO/PH5 acetate buffer in presence of folate-PEO-HTCC 1 was determined in triplicate by a validated high-pressure liquid chromatography (HPLC) method coupled with UV detector. The chromatographic system (HP 1200 series, Agilent Technologies, Brussels, Belgium) was equipped with a quaternary pump, an auto sampler and a diode array detector. The separations were performed on a reverse-phase Hypersil Gold C-18 column (5 μm, 250 mm×4.6 mm) (Thermo Fisher Scientific, Waltham, USA). The mobile phase consisted of 0.5% v/v aqueous acetic acid/acetonitrile (90:10 v/v), which was delivered at a flow rate of 1.0 ml/min. The quantification was performed at 329 nm. The calibration curve was linear in the 1-250 μg/ml range. The TMZ samples and calibration standards were diluted in the mobile phase. The volume injected was 10 μl, the temperature was set at 25° C. and the analysis time was 10 min. Saturation concentration of TMZ in pH5 acetate buffer in presence of folate-PEO-HTCC 1 was 5.7±0.4 mg/ml. The TMZ-saturated solution containing folate-PEO-HTCC 1 was poured into isopropanol containing 0.05 mg/ml of sodium taurocholate (Sigma-Aldrich, St. Louis, Mo., USA, cat. num. T0750) (TMZ solution-isopropanol volume ratio was 0.0.35) under sonication using ultrasonic probe (Vibra-Cell VCX 500, Sonics and Materials, Newtown, USA) and the precipitation immediately occurred. The sonication was applied in an ice bath in order to avoid an increase of temperature with the following conditions, amplitude=40% during 5 min under magnetic stirring.

Z-average particle size and size distribution of NPs were measured by dynamic light scattering (DLS) (Zetasizer nano ZS, Malvern Instruments, Worcestershire, UK) using Nanosphere™ size standards (Duke Scientific Corporation, Palo Alto, Calif., USA, cat. num. 3300) as internal standard. Size distribution is presented in FIG. 2. The Z-average particle size was 186±4 nm. Polydispersity index: 0.39±0.05.

Figure 2:
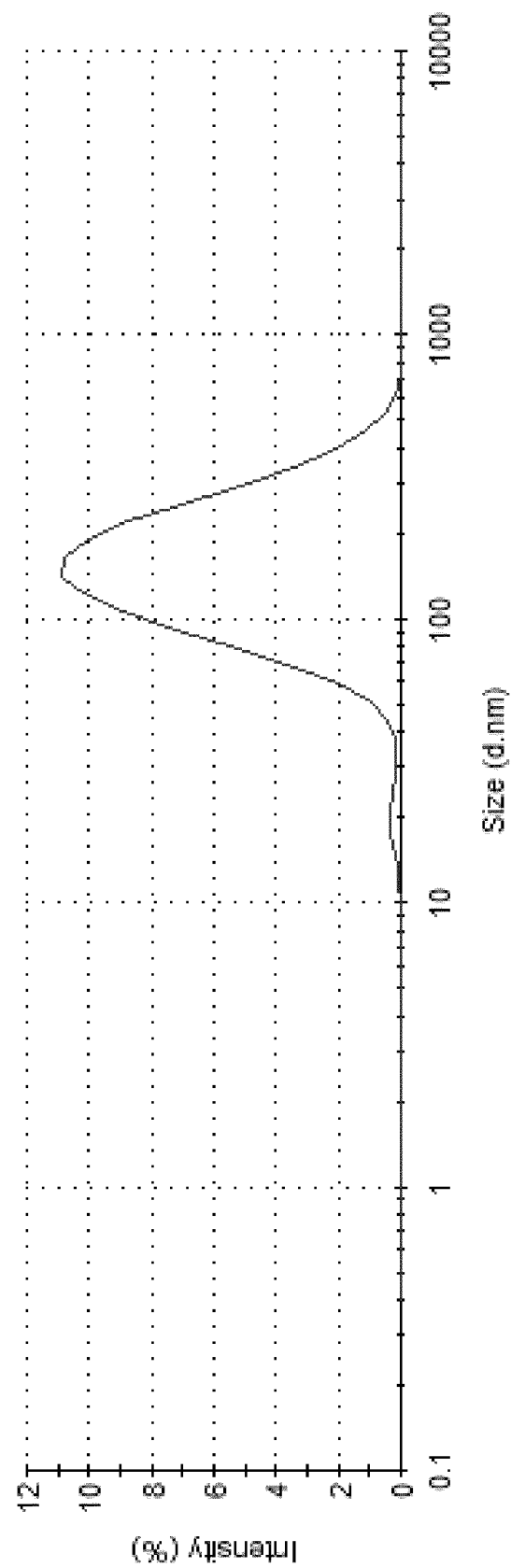
FIG. 2 represents a graph illustrating laser diffraction particle size distribution (Z-Average) of TMZ-loaded folate-PEO-HTCC 1 NPs prepared according to example 7 (n=3), as measured with Zetasizer nano ZS (Malvern Instruments, Worcestershire, UK).

FIG. 2 shows the laser diffraction particle size distribution (Z-average) of TMZ-loaded folate-PEO-HTCC 1 NPs prepared according to Example 7 (n=3) (Zetasizer nano ZS, Malvern Instruments, Worcestershire, UK).

The zeta potential (ZP) of NPs was measured using a zetasizer (Zetasizer nano ZS, Malvern Instruments, Worcestershire, UK) using Zeta potential Transfer Standard (Malvern Instruments, Worcestershire, UK, cat. num. DTS1230). The zeta potential of the nanoparticles was 16±1 mV.

Formulation was ultrafiltrated (MWCO=300 kDa, Ultracel, Merck Millipore, Darmstadt, Germany) and the filtrate was collected. The TMZ drug loading (DL) and encapsulation efficiency (EE) of TMZ-loaded folate-PEO-HTCC 1 NPs were determined using equation (5) and equation (6), respectively.

The drug loading (DL) was determined using the equation (5):

$$DL(\%) = 1 - \frac{\text{amount of drug in supernatant}}{\text{amount of drug added} + \text{amount of excipients added}} \times 100$$

The amount of antineoplastic agent (i.e., temozolomide) in the supernatant was determined in triplicate by the validated HPLC method coupled with UV detector as described above. The drug loading was 4.1±0.2%.

The encapsulation efficiency (EE) was determined using the equation (6):

$$EE(\%) = 1 - \frac{\text{amount of drug in supernatant}}{\text{amount of drug added}} \times 100 \qquad (6)$$

The amount of antineoplastic agent (i.e., temozolomide) in the supernatant was determined in triplicate by the validated HPLC method coupled with UV detector described above. The encapsulation efficiency was 7.5±0.1%.

Example 8: Preparation of Nanoparticles According to an Embodiment of the Present Invention (TMZ-Loaded Folate-PEO-HTCC 2 NPs)

TMZ-loaded folate-PEO-HTCC 2 nanoparticles (NPs) are produced by the controlled nanoprecipitation method at room temperature. Folate-PEO-HTCC 2 is synthesized according to Example 2.

Folate-PEO-HTCC 2 is dissolved in DMSO/pH5 acetate buffer (0.1 M) (4:10 v/v) at a concentration of 7.15 mg/ml under magnetic stirring. A quantity of TMZ of 8 mg/ml is added in the solution and the solution is stirred at room temperature for at least 48 h in order to prepare TMZ-saturated solution. This solution is then centrifuged and the supernatant collected. The saturation concentration of TMZ in DMSO/PH5 acetate buffer in presence of folate-PEO-HTCC 2 is determined in triplicate by a validated HPLC method coupled with UV detector (described in example 7). Saturation concentration of TMZ in PH5 acetate buffer in presence of folate-PEO-HTCC 2=5.7±0.4 mg/ml. The TMZ-saturated solution containing folate-PEO-HTCC 2 is poured into isopropanol containing 0.05 mg/ml of sodium taurocholate (TMZ solution-isopropanol volume ratio=0.035) under sonication using ultrasonic probe (Vibra-Cell VCX 500, Sonics and Materials, Newtown, USA) and the precipitation immediately occurs. The sonication is applied in an ice bath in order to avoid an increase of temperature with the following conditions, amplitude=40% during 5 min under magnetic stirring.

Z-average particle size and size distribution of NPs are measured by DLS (Zetasizer nano ZS, Malvern Instruments, Worcestershire, UK) as described in Example 7. The results are in line with those obtained in Example 7.

The ZP of NPs is measured using a zetasizer (Zetasizer nano ZS, Malvern Instruments, Worcestershire, UK) as described in Example 7. The results are in line with those obtained in Example 7.

The formulation is ultrafiltrated (MWCO=300 kDa, Ultracel, Merck Millipore, Darmstadt, Germany) and the filtrate collected. The TMZ drug loading and encapsulation efficiency of TMZ-loaded folate-PEO-HTCC 2 NPs are determined in triplicate by a validated HPLC method coupled with UV detector (described in example 8). The drug loading and encapsulation efficiency are determined using equations (5) and (6) respectively. The results are in line with those obtained in Example 7.

Example 9: Preparation of Nanoparticles According to an Embodiment of the Present Invention (TMZ-Loaded Folate-PEO-HTCC 3 NPs)

TMZ-loaded folate-PEO-HTCC 3 NPs are produced by the controlled nanoprecipitation method at room temperature. Folate-PEO-HTCC 3 is synthesized according to Example 3.

Folate-PEO-HTCC 3 is dissolved in DMSO/pH5 acetate buffer (0.1 M) (4:10 v/v) at a concentration of 7.15 mg/ml under magnetic stirring. A quantity of TMZ of 8 mg/ml is added in the solution and the solution is stirred at room temperature for at least 48 h in order to prepare TMZ-saturated solution. This solution is then centrifuged and the supernatant collected. The saturation concentration of TMZ in DMSO/PH5 acetate buffer in presence of folate-PEO-HTCC 3 is determined in triplicate by a validated HPLC method coupled with UV detector (described in example 7). Saturation concentration of TMZ in PH5 acetate buffer in presence of folate-PEO-HTCC 3=5.7±0.4 mg/ml. The TMZ-saturated solution containing folate-PEO-HTCC 3 is poured into isopropanol containing 0.05 mg/ml of sodium taurocholate (TMZ solution-isopropanol volume ratio=0.035) under sonication using ultrasonic probe (Vibra-Cell VCX 500, Sonics and Materials, Newtown, USA) and the precipitation immediately occurs. The sonication is applied in an ice bath in order to avoid an increase of temperature with the following conditions, amplitude=40% during 5 min under magnetic stirring.

Z-average particle size and size distribution of NPs are measured by DLS (Zetasizer nano ZS, Malvern Instruments, Worcestershire, UK) as described in Example 7. The results are in line with those obtained in Example 7.

The ZP of NPs is measured using a zetasizer (Zetasizer nano ZS, Malvern Instruments, Worcestershire, UK) as described in Example 7. The results are in line with those obtained in Example 7.

The formulation is ultrafiltrated (MWCO=300 kDa, Ultracel, Merck Millipore, Darmstadt, Germany) and the filtrate collected. The TMZ drug loading and encapsulation efficiency of TMZ-loaded folate-PEO-HTCC NPs are determined in triplicate by a validated HPLC method coupled with UV detector (described in example 7). The drug loading and encapsulation efficiency are determined using equations (5) and (6) respectively. The results are in line with those obtained in Example 7.

Example 10: Preparation of Nanoparticles According to an Embodiment of the Present Invention (TMZ-Loaded Folate-PEO-HMD 1 NPs)

TMZ-loaded folate-PEO-HMD 1 NPs were produced by the controlled nanoprecipitation method at room temperature. Folate-PEO-HMD 1 was synthesized according to Example 4.

Folate-PEO-HMD 1 was dissolved in DMSO at a concentration of 50 mg/ml under magnetic stirring. A quantity of TMZ of 40 mg/ml was added in the solution and the solution was stirred at room temperature for at least 48 h in order to prepare TMZ-saturated solution. This solution was then centrifuged and the supernatant collected. The saturation concentration of TMZ in DMSO in presence of folate-PEO-HMD 1 was determined in triplicate by a validated HPLC method coupled with UV detector (described in example 7). Saturation concentration of TMZ in DMSO in presence of folate-PEO-HMD 1 was 24.4±0.2 mg/ml. The solution was poured into isopropanol containing 0.1 mg/ml of sodium taurocholate (DMSO/isopropanol volume ratio=1/40) under sonication using ultrasonic probe (Vibra-Cell VCX 500, Sonics and Materials, Newtown, USA) and the precipitation immediately occurred. The sonication was applied in an ice bath in order to avoid an increase of temperature with the following conditions, amplitude=40% during 5 min under magnetic stirring.

Z-average particle size and size distribution of NPs were measured by DLS (Zetasizer nano ZS, Malvern Instruments, Worcestershire, UK) as described in Example 7. The Z-average particle size was 122±1 nm Polydispersity index: 0.15±0.06.

Figure 3:
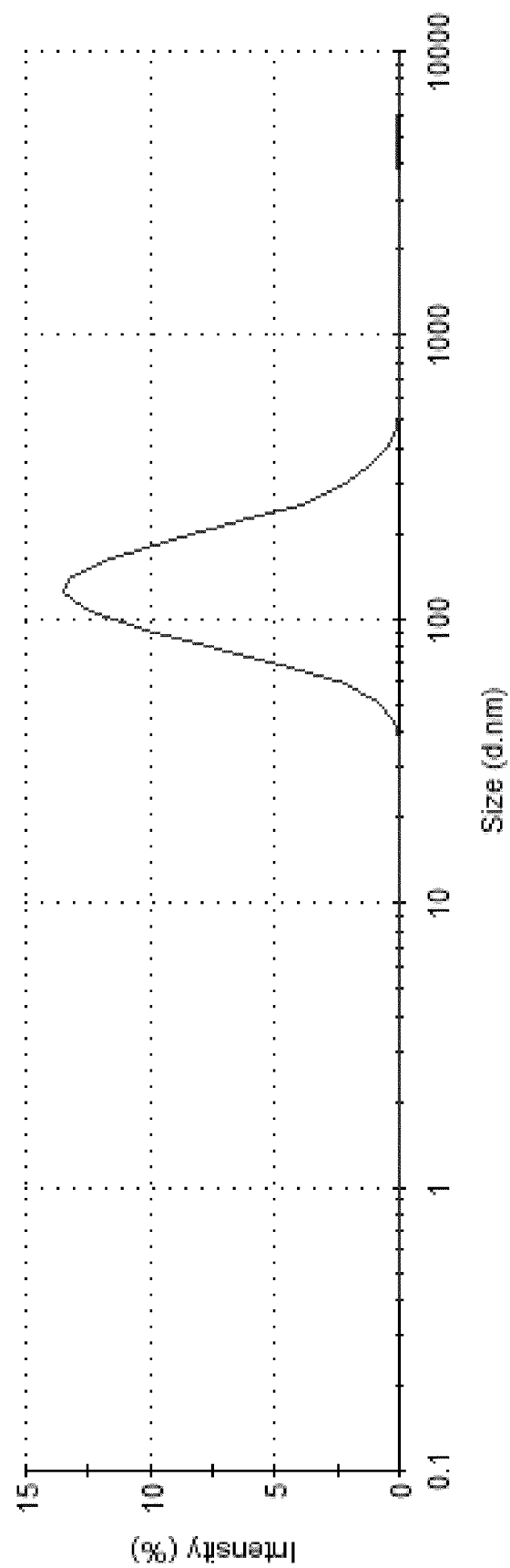
FIG. 3 represents a graph illustrating laser diffraction particle size distribution (Z-Average) of TMZ-loaded folate-PEO-HMD 1 NPs prepared according to example 10 (n=3) (Zetasizer nano ZS, Malvern Instruments, Worcestershire, UK).

FIG. 3 shows laser diffraction particle size distribution (Z-Average) of TMZ-loaded folate-PEO-HMD 1 NPs prepared according to example 10 (n=3) (Zetasizer nano ZS, Malvern Instruments, Worcestershire, UK).

The ZP of NPs were measured using a zetasizer (Zetasizer nano ZS, Malvern Instruments, Worcestershire, UK) as described in Example 7. The zeta potential of the NPs was 35±1 mV.

Formulation was ultrafiltrated (MWCO=300 kDa, Ultracel, Merck Millipore, Darmstadt, Germany) and the filtrate was collected. The TMZ drug loading and encapsulation efficiency of TMZ-loaded folate-PEO-HMD 1 NPs were determined in triplicate by a validated HPLC method coupled with UV detector (described in example 7). The drug loading and the encapsulation efficiency were determined using equations (5) and (6) respectively.

The drug loading was 6±1%. The encapsulation efficiency (EE) was 10±2%.

Example 11: Preparation of Nanoparticles According to an Embodiment of the Present Invention (TMZ-Loaded Folate-PEO-HMD 2 NPs)

TMZ-loaded folate-PEO-HMD 2 NPs are produced by the controlled nanoprecipitation method at room temperature. Folate-PEO-HMD 2 is synthesized according to Example 5.

Folate-PEO-HMD 2 is dissolved in DMSO at a concentration of 50 mg/ml under magnetic stirring. A quantity of TMZ of 40 mg/ml is added in the solution and the solution is stirred at room temperature for at least 48 h in order to prepare TMZ-saturated solution. This solution is then centrifuged and the supernatant collected. The saturation concentration of TMZ in DMSO in presence of folate-PEO-HMD 2 is determined in triplicate by a validated HPLC method coupled with UV detector (described in example 7). Saturation concentration of TMZ in DMSO in the presence of folate-PEO-HMD 2=24.4±0.2 mg/ml. The solution is poured into isopropanol containing 0.1 mg/ml of sodium taurocholate (DMSO/isopropanol volume ratio=1/40) under sonication using ultrasonic probe (Vibra-Cell VCX 500, Sonics and Materials, Newtown, USA) and the precipitation immediately occurs. The sonication is applied in an ice bath in order to avoid an increase of temperature with the following conditions, amplitude=40% during 5 min under magnetic stirring.

Z-average particle size and size distribution of NPs are measured by DLS (Zetasizer nano ZS, Malvern Instruments, Worcestershire, UK). The results are in line with those obtained in Example 10.

The ZP of NPs are measured using a zetasizer (Zetasizer nano ZS, Malvern Instruments, Worcestershire, UK). The results are in line with those obtained in Example 10.

The formulation is ultrafiltrated (MWCO=300 kDa, Ultracel, Merck Millipore, Darmstadt, Germany) and the filtrate was collected. The TMZ drug loading and encapsulation efficiency of TMZ-loaded folate-PEO-HMD NPs are determined in triplicate by a validated HPLC method coupled with UV detector (described in example 7). The drug loading and the encapsulation efficiency are determined using equations (5) and (6) respectively. The results are in line with those obtained in Example 10.

Example 12: Preparation of Nanoparticles According to an Embodiment of the Present Invention (TMZ-Loaded Folate-PEO-HTCC 4 NPs)

TMZ-loaded folate-PEO-HTCC 4 NPs are produced by the controlled nanoprecipitation method at room temperature. Folate-PEO-HTCC 4 is synthesized according to Example 6.

Folate-PEO-HTCC 4 is dissolved in DMSO/pH5 acetate buffer (0.1 M) (4:10 v/v) at a concentration of 7.15 mg/ml under magnetic stirring. A quantity of TMZ of 8 mg/ml is added in the solution and the solution is stirred at room temperature for at least 48 h in order to prepare TMZ-saturated solution. This solution is then centrifuged and the supernatant collected. The saturation concentration of TMZ in DMSO/PH5 acetate buffer in presence of folate-PEO-HTCC 4 is determined in triplicate by a validated HPLC method coupled with UV detector (described in example 7). Saturation concentration of TMZ in PH5 acetate buffer in presence of folate-PEO-HTCC 4=5.7±0.4 mg/ml. The TMZ-saturated solution containing folate-PEO-HTCC 4 is poured into isopropanol containing 0.05 mg/ml of sodium taurocholate (TMZ solution-isopropanol volume ratio=0.035) under sonication using ultrasonic probe (Vibra-Cell VCX 500, Sonics and Materials, Newtown, USA) and the precipitation immediately occurs. The sonication is applied in an ice bath in order to avoid an increase of temperature with the following conditions, amplitude=40% during 5 min under magnetic stirring.

Z-average particle size and size distribution of NPs are measured by DLS (Zetasizer nano ZS, Malvern Instruments, Worcestershire, UK) as described in Example 7. The results are in line with those obtained in Example 7.

The ZP of NPs was measured using a zetasizer (Zetasizer nano ZS, Malvern Instruments, Worcestershire, UK) as described in Example 7. The results are in line with those obtained in Example 7.

The formulation is ultrafiltrated (MWCO=300 kDa, Ultracel, Merck Millipore, Darmstadt, Germany) and the filtrate is collected. The TMZ drug loading and encapsulation efficiency of TMZ-loaded folate-PEO-HTCC NPs are determined in triplicate by a validated HPLC method coupled with UV detector (described in example 7). The drug loading and the encapsulation efficiency are determined using equations (5) and (6) respectively. The results are in line with those obtained in Example 7.

Example 13: Preparation of Formulation for Dry Powder Inhalation (DPI) According to an Embodiment of the Present Invention (NEMs Containing TMZ-Loaded Folate-PEO-HTCC 1 NPs and Mannitol)

TMZ-loaded folate-PEO-HTCC 1 NPs were prepared according to Example 7.

Nano-embedded microparticles (NEMs) were produced by spray-drying the dispersion of TMZ-loaded folate-PEO-HTCC 1 NPs in presence of mannitol (Paerlitol 400 DC, Roquette, Lestrem, France). Briefly, the dispersion of NPs was ultrafiltrated (MWCO=300 kDa, Ultracel, Merck Millipore, Darmstadt, Germany) against a solution of 1% (w/v) mannitol in a mixture of isopropanol/ultrapure water (70:30). The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 2.7 g/min; nozzle diameter 0.7 mm; inlet temperature 80° C. corresponding to an outlet temperature of about 28° C. The NPs dispersion was kept in an ice bath during the spray-drying process in order to prevent NPs aggregation and dissolution of TMZ.

The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 µm, in particular in the range of 1-5 µm. Hence, the pharmaceutical formulation illustrating the present invention is configured for administration by inhalation.

Example 14: Preparation of Formulation for Dry Powder Inhalation (DPI) According to an Embodiment of the Present Invention (NEMs Containing TMZ-Loaded Folate-PEO-HTCC 1 NPs, Mannitol and Leucine)

TMZ-loaded folate-PEO-HTCC 1 NPs were prepared according to Example 7.

NEMs were produced by spray-drying the dispersion of TMZ-loaded folate-PEO-HTCC 1 NPs in presence of mannitol (Paerlitol 400 DC, Roquette, Lestrem, France) and leucine (Merck, Darmstadt, Germany, cat. num. 105020). Briefly, the dispersion of NPs was ultrafiltrated (MWCO=300 kDa, Ultracel, Merck Millipore, Darmstadt, Germany) against a solution of 0.7% (w/v) mannitol and 0.3% (w/v) leucine in a mixture of isopropanol/ultrapure water (70:30). The dispersion was spray-dried (Mini Spray Dryer B-290, Büchi Laboratory-Techniques, Flawil, Switzerland) under the following conditions: spraying air flow 800 l/hour; drying air flow 35 m³/hour; solution feed rate 2.7 g/min; nozzle diameter 0.7 mm; inlet temperature 80° C. corresponding to an outlet temperature of about 28° C. The NPs dispersion was kept in an ice bath during the spray-drying process in order to prevent NPs aggregation and dissolution of TMZ.

The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

Example 15: Preparation of Formulation for Dry Powder Inhalation (DPI) According to an Embodiment of the Present Invention (NEMs Containing TMZ-Loaded Folate-PEO-HTCC 2 NPs and Mannitol)

TMZ-loaded folate-PEO-HTCC 2 NPs were prepared according to Example 8.

NEMs were produced by spray-drying the dispersion of TMZ-loaded folate-PEO-HTCC 2 NPs in presence of mannitol (Paerlitol 400 DC, Roquette, Lestrem, France). Briefly, the dispersion of NPs was ultrafiltrated (MWCO=300 kDa, Ultracel, Merck Millipore, Darmstadt, Germany) against a solution of 1% (w/v) mannitol and 0.01% (w/v) sodium taurocholate (Sigma-Aldrich, St. Louis, Mo., USA, cat. num. T0750) in a mixture of isopropanol/ultrapure water (70:30 v/v). The dispersion was spray-dried (Mini Spray Dryer B-290, Büchi Laboratory-Techniques, Flawil, Switzerland) under the following conditions: spraying air flow 800 l/hour; drying air flow 35 m³/hour; solution feed rate 3.8 g/min; nozzle diameter 0.7 mm; inlet temperature 80° C. corresponding to an outlet temperature of about 33° C. The NPs dispersion was kept in an ice bath during the spray-drying process in order to prevent NPs aggregation and dissolution of TMZ.

The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

Example 16: Preparation of Formulation for Dry Powder Inhalation (DPI) According to an Embodiment of the Present Invention (NEMs Containing TMZ-Loaded Folate-PEO-HTCC 2 NPs, Mannitol and Leucine)

TMZ-loaded folate-PEO-HTCC 2 NPs were prepared according to Example 8.

NEMs were produced by spray-drying the dispersion of TMZ-loaded folate-PEO-HTCC 2 NPs in presence of mannitol (Paerlitol 400 DC, Roquette, Lestrem, France) and leucine (Merck, Darmstadt, Germany, cat. num. 105020). Briefly, the dispersion of NPs was ultrafiltrated (MWCO=300 kDa, Ultracel, Merck Millipore, Darmstadt, Germany) against a solution of 0.7% (w/v) mannitol, 0.3% (w/v) leucine and 0.01% (w/v) sodium taurocholate (Sigma-Aldrich, St. Louis, Mo., USA, cat. num. T0750) in a mixture of isopropanol/ultrapure water (70:30 v/v). The dispersion was spray-dried (Mini Spray Dryer B-290, Büchi Laboratory-Techniques, Flawil, Switzerland) under the following conditions: spraying air flow 800 l/hour; drying air flow 35 m³/hour; solution feed rate 3.8 g/min; nozzle diameter 0.7 mm; inlet temperature 80° C. corresponding to an outlet temperature of about 33° C. The NPs dispersion was kept in an ice bath during the spray-drying process in order to prevent NPs aggregation and dissolution of TMZ. The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

Example 17: Preparation of Formulation for Dry Powder Inhalation (DPI) According to an Embodiment of the Present Invention (NEMs Containing TMZ-Loaded Folate-PEO-HTCC 3 NPs and Mannitol)

TMZ-loaded folate-PEO-HTCC 3 NPs were prepared according to Example 9.

NEMs were produced by spray-drying the dispersion of TMZ-loaded folate-PEO-HTCC 3 NPs in presence of mannitol (Paerlitol 400 DC, Roquette, Lestrem, France). Briefly, the dispersion of NPs was ultrafiltrated (MWCO=300 kDa, Ultracel, Merck Millipore, Darmstadt, Germany) against a solution of 1% (w/v) mannitol and 0.01% (w/v) sodium taurocholate (Sigma-Aldrich, St. Louis, Mo., USA, cat. num. T0750) in a mixture of isopropanol/ultrapure water (70:30 v/v). The dispersion was spray-dried (Mini Spray Dryer B-290, Büchi Laboratory-Techniques, Flawil, Switzerland) under the following conditions: spraying air flow 800 l/hour; drying air flow 35 m³/hour; solution feed rate 3.8 g/min; nozzle diameter 0.7 mm; inlet temperature 80° C. corresponding to an outlet temperature of about 33° C. The NPs dispersion was kept in an ice bath during the spray-drying process in order to prevent NPs aggregation and dissolution of TMZ.

The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

Example 18: Preparation of Formulation for Dry Powder Inhalation (DPI) According to an Embodiment of the Present Invention (NEMs Containing TMZ-Loaded Folate-PEO-HTCC 3 NPs, Mannitol and Leucine)

TMZ-loaded folate-PEO-HTCC 3 NPs were prepared according to Example 9.

NEMs were produced by spray-drying the dispersion of TMZ-loaded folate-PEO-HTCC 3 NPs in presence of mannitol (Paerlitol 400 DC, Roquette, Lestrem, France) and leucine (Merck, Darmstadt, Germany, cat. num. 105020). Briefly, the dispersion of NPs was ultrafiltrated (MWCO=300 kDa, Ultracel, Merck Millipore, Darmstadt, Germany) against a solution of 0.7% (w/v) mannitol, 0.3% (w/v) leucine and 0.01% (w/v) sodium taurocholate (Sigma-Aldrich, St. Louis, Mo., USA, cat. num. T0750) in a mixture of isopropanol/ultrapure water (70:30 v/v). The dispersion was spray-dried (Mini Spray Dryer B-290, Büchi Laboratory-Techniques, Flawil, Switzerland) under the following conditions: spraying air flow 800 l/hour; drying air flow 35 $m^3$/hour; solution feed rate 3.8 g/min; nozzle diameter 0.7 mm; inlet temperature 80° C. corresponding to an outlet temperature of about 33° C. The NPs dispersion was kept in an ice bath during the spray-drying process in order to prevent NPs aggregation and dissolution of TMZ. The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

Example 19: Preparation of Formulation for Dry Powder Inhalation (DPI) According to an Embodiment of the Present Invention (NEMs Containing TMZ-Loaded Folate-PEO-HMD 1 NPs and Mannitol)

TMZ-loaded folate-PEO-HMD 1 NPs were prepared according to Example 10.

NEMs were produced by spray-drying the dispersion of TMZ-loaded folate-PEO-HMD 1 NPs in presence of mannitol (Paerlitol 400 DC, Roquette, Lestrem, France). Briefly, the dispersion of NPs was ultrafiltrated (MWCO=300 kDa, Ultracel, Merck Millipore, Darmstadt, Germany) against a solution of 1% (w/v) mannitol and 0.01% (w/v) sodium taurocholate (Sigma-Aldrich, St. Louis, Mo., USA, cat. num. T0750) in a mixture of isopropanol/ultrapure water (70:30). The dispersion was spray-dried (Mini Spray Dryer B-290, Büchi Laboratory-Techniques, Flawil, Switzerland) under the following conditions: spraying air flow 800 l/hour; drying air flow 35 $m^3$/hour; solution feed rate 3.8 g/min; nozzle diameter 0.7 mm; inlet temperature 80° C. corresponding to an outlet temperature of about 33° C. The NPs dispersion was kept in an ice bath during the spray-drying process in order to prevent NPs aggregation and dissolution of TMZ.

The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

Example 20: Preparation of Formulation for Dry Powder Inhalation (DPI) According to an Embodiment of the Present Invention (NEMs Containing TMZ-Loaded Folate-PEO-HMD 1 NPs, Mannitol and Leucine)

TMZ-loaded folate-PEO-HMD 1 NPs were prepared according to Example 10.

NEMs were produced by spray-drying the dispersion of TMZ-loaded folate-PEO-HMD 1 NPs in presence of mannitol (Paerlitol 400 DC, Roquette, Lestrem, France) and leucine (Merck, Darmstadt, Germany, cat. num. 105020). Briefly, the dispersion of NPs was ultrafiltrated (MWCO=300 kDa, Ultracel, Merck Millipore, Darmstadt, Germany) against a solution of 0.7% (w/v) mannitol, 0.3% (w/v) leucine and 0.01% (w/v) sodium taurocholate (Sigma-Aldrich, St. Louis, Mo., USA, cat. num. T0750) in a mixture of isopropanol/ultrapure water (70:30 v/v). The dispersion was spray-dried (Mini Spray Dryer B-290, Büchi Laboratory-Techniques, Flawil, Switzerland) under the following conditions: spraying air flow 800 l/hour; drying air flow 35 $m^3$/hour; solution feed rate 3.8 g/min; nozzle diameter 0.7 mm; inlet temperature 80° C. corresponding to an outlet temperature of about 33° C. The NPs dispersion was kept in an ice bath during the spray-drying process in order to prevent NPs aggregation and dissolution of TMZ.

The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

Example 21: Preparation of Formulation for Dry Powder Inhalation (DPI) According to an Embodiment of the Present Invention (NEMs Containing TMZ-Loaded Folate-PEO-HMD 2 NPs and Mannitol)

TMZ-loaded folate-PEO-HMD 2 NPs were prepared according to Example 11.

NEMs were produced by spray-drying the dispersion of TMZ-loaded folate-PEO-HMD 2 NPs in presence of mannitol (Paerlitol 400 DC, Roquette, Lestrem, France). Briefly, the dispersion of NPs was ultrafiltrated (MWCO=300 kDa, Ultracel, Merck Millipore, Darmstadt, Germany) against a solution of 1% (w/v) mannitol and 0.01% (w/v) sodium taurocholate (Sigma-Aldrich, St. Louis, Mo., USA, cat. num. T0750) in a mixture of isopropanol/ultrapure water (70:30). The dispersion was spray-dried (Mini Spray Dryer B-290, Büchi Laboratory-Techniques, Flawil, Switzerland) under the following conditions: spraying air flow 800 l/hour; drying air flow 35 $m^3$/hour; solution feed rate 3.8 g/min; nozzle diameter 0.7 mm; inlet temperature 80° C. corresponding to an outlet temperature of about 33° C. The NPs dispersion was kept in an ice bath during the spray-drying process in order to prevent NPs aggregation and dissolution of TMZ.

The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

Example 22: Preparation of Formulation for Dry Powder Inhalation (DPI) According to an Embodiment of the Present Invention (NEMs Containing TMZ-Loaded Folate-PEO-HMD 2 NPs, Mannitol and Leucine)

TMZ-loaded folate-PEO-HMD 2 NPs were prepared according to Example 11.

NEMs were produced by spray-drying the dispersion of TMZ-loaded folate-PEO-HMD 2 NPs in presence of mannitol (Paerlitol 400 DC, Roquette, Lestrem, France) and leucine (Merck, Darmstadt, Germany, cat. num. 105020). Briefly, the dispersion of NPs was ultrafiltrated (MWCO=300 kDa, Ultracel, Merck Millipore, Darmstadt, Germany) against a solution of 0.7% (w/v) mannitol, 0.3% (w/v) leucine and 0.01% (w/v) sodium taurocholate (Sigma-Aldrich, St. Louis, Mo., USA, cat. num. T0750) in a mixture of isopropanol/ultrapure water (70:30 v/v). The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 3.8 g/min; nozzle diameter 0.7 mm; inlet temperature 80° C. corresponding to an outlet temperature of about 33° C. The NPs dispersion was kept in an ice bath during the spray-drying process in order to prevent NPs aggregation and dissolution of TMZ. The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

Example 23: Preparation of Formulation for Dry Powder Inhalation (DPI) According to an Embodiment of the Present Invention (NEMs Containing TMZ-Loaded Folate-PEO-HTCC 4 NPs and Mannitol)

TMZ-loaded folate-PEO-HTCC 4 NPs were prepared according to Example 12.

NEMs were produced by spray-drying the dispersion of TMZ-loaded folate-PEO-HTCC 4 NPs in presence of mannitol (Paerlitol 400 DC, Roquette, Lestrem, France). Briefly, the dispersion of NPs was ultrafiltrated (MWCO=300 kDa, Ultracel, Merck Millipore, Darmstadt, Germany) against a solution of 1% (w/v) mannitol and 0.01% (w/v) sodium taurocholate (Sigma-Aldrich, St. Louis, Mo., USA, cat. num. T0750) in a mixture of isopropanol/ultrapure water (70:30 v/v). The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 3.8 g/min; nozzle diameter 0.7 mm; inlet temperature 80° C. corresponding to an outlet temperature of about 33° C. The NPs dispersion was kept in an ice bath during the spray-drying process in order to prevent NPs aggregation and dissolution of TMZ.

The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

Example 24: Preparation of Formulation for Dry Powder Inhalation (DPI) According to an Embodiment of the Present Invention (NEMs Containing TMZ-Loaded Folate-PEO-HTCC 4 NPs, Mannitol and Leucine)

TMZ-loaded folate-PEO-HTCC 4 NPs were prepared according to example 12.

NEMs were produced by spray-drying the dispersion of TMZ-loaded folate-PEO-HTCC 4 NPs in presence of mannitol (Paerlitol 400 DC, Roquette, Lestrem, France) and leucine (Merck, Darmstadt, Germany, cat. num. 105020). Briefly, the dispersion of NPs was ultrafiltrated (MWCO=300 kDa, Ultracel, Merck Millipore, Darmstadt, Germany) against a solution of 0.7% (w/v) mannitol, 0.3% (w/v) leucine and 0.01% (w/v) sodium taurocholate (Sigma-Aldrich, St. Louis, Mo., USA, cat. num. T0750) in a mixture of isopropanol/ultrapure water (70:30 v/v). The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 3.8 g/min; nozzle diameter 0.7 mm; inlet temperature 80° C. corresponding to an outlet temperature of about 33° C. The NPs dispersion was kept in an ice bath during the spray-drying process in order to prevent NPs aggregation and dissolution of TMZ. The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

Example 25: Preparation of Formulation for Dry Powder Inhalation (DPI) Containing Cisplatin-Loaded Folate-PEO-HTCC 1 NPs and Mannitol Cisplatin-loaded folate-PEO-HTCC 1 NPs are prepared in the same way as described in Example 7. Nano-embedded microparticles (NEMS) are produced by spray-drying the dispersion of cisplatin-loaded folate-PEO-HTCC 1 NPs in presence of mannitol (Paerlitol 400 DC, Roquette, Lestrem, France). Briefly, the dispersion of NPs is ultrafiltrated (MWCO=300 kDa, Ultracel, Merck Millipore, Darmstadt, Germany) against a solution of 1% (w/v) mannitol in a mixture of isopropanol/ultrapure water (70:30). The dispersion is spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 2.7 g/min; nozzle diameter 0.7 mm; inlet temperature 80° C. corresponding to an outlet temperature of about 28° C. The NPs dispersion is kept in an ice bath during the spray-drying process in order to prevent NPs aggregation and dissolution of cisplatin.

The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

Example 26: Preparation of Formulation for Dry Powder Inhalation (DPI) Containing Paclitaxel-Loaded Folate-PEO-HTCC 1 NPs and Mannitol Paclitaxel-loaded folate-PEO-HTCC 1 NPs are prepared in the same way as described in Example 7.

Nano-embedded microparticles (NEMS) are produced by spray-drying the dispersion of paclitaxel-loaded folate-PEO-HTCC 1 NPs in presence of mannitol (Paerlitol 400 DC, Roquette, Lestrem, France). Briefly, the dispersion of NPs is ultrafiltrated (MWCO=300 kDa, Ultracel, Merck Millipore, Darmstadt, Germany) against a solution of 1% (w/v) mannitol in a mixture of isopropanol/ultrapure water (70:30). The dispersion is spray-dried (Mini Spray Dryer B-290, Büchi Laboratory-Techniques, Flawil, Switzerland) under the following conditions: spraying air flow 800 l/hour; drying air flow 35 m³/hour; solution feed rate 2.7 g/min; nozzle diameter 0.7 mm; inlet temperature 80° C. corresponding to an outlet temperature of about 28° C. The NPs dispersion is kept in an ice bath during the spray-drying process in order to prevent NPs aggregation and dissolution of paclitaxel. The obtained pharmaceutical formulation illustrating the present invention is evaluated by determining its aerodynamic profile, mass median aerodynamic diameter, and particle size distribution. The mass median aerodynamic diameter of the DPI formulation illustrating the present invention is in the range of 1-10 μm, in particular in the range of 1-5 μm. Hence, the pharmaceutical formulation illustrating the present invention is configured for administration by inhalation.

In the same way, pharmaceutical formulations illustrating the present invention comprising an antineoplastic agent selected from docetaxel, gemcitabine, vinorelbine, etoposide, irinotecan, cyclophosphamide, doxorubicin, or vincristine, and an FR-targeting excipient are prepared. The obtained pharmaceutical formulations illustrating the present invention are evaluated by determining the aerodynamic profile, mass median aerodynamic diameter, and particle size distribution. The mass median aerodynamic diameter of the DPI formulations illustrating the present invention is in the range of 1-10 μm, in particular in the range of 1-5 μm. Hence, the pharmaceutical formulations illustrating the present invention are configured for administration by inhalation.

Example 27: In Vitro Evaluation of the Selectivity of the Anti-Proliferative Properties of a Dry Powder Inhalation (DPI) Formulation According to an Embodiment of the Present Invention for FR-Expressing Cells The cytotoxic effects of a dry powder inhalation (DPI) formulation illustrating the present invention on FR-expressing cells (including human HeLa cervical adenocarcinoma and murine M109 lung carcinoma cell lines) compared with FR-depleted cells (including murine B16F10 melanoma cell line) are determined by means of the colorimetric 3-(4,5-dimethylthiazol-2-yl)-2,5-diphenyl tetrazolium bromide (Sigma-Aldrich, St. Louis, Mo., USA, cat. num. M2128) (referred to herein as MTT) assay. The test measures the number of metabolically active living cells that are able to transform the yellow product MTT into the blue product formazan dye by mitochondrial reduction. The amount of formazan obtained at the end of the experiment, measured by means of a spectrophotometer, is directly proportional to the number of living cells. Optical density determination thus allows a quantitative measurement of the effect of the investigated formulations as compared with the control condition (untreated cells) and/or to other references such as a TMZ solution.

To perform the assay, cells are allowed to grow in 96-well plate with a flat bottom with an amount of 100 μl of cell suspension per well with 5,000 to 8,000 cells/well depending on the cell type used. Each cell line is seeded in its appropriate culture medium.

The detailed experimental procedure is the following: after a 24-hour period of incubation at 37° C., the culture medium is replaced by 100 μl of fresh medium in which the DPI formulation illustrating the present invention (prepared according to Example 13, 14, 15, 16, 17, 18, 19, 20, 21, 22, 23, or 24) is previously dispersed at the following TMZ-relative molar concentrations: $5 \cdot 10^{-7}$ M, $10^{-6}$ M, $5 \cdot 10^{-6}$ M, $10^{-5}$ M, $5 \cdot 10^{-5}$ M, $10^{-4}$ M, $5 \cdot 10^{-4}$ M, and $10^{-3}$ M. Each experiment is performed six times.

After 3 to 6 days of incubation at 37° C. without (control condition) or with the DPI formulation illustrating the present invention (experimental conditions), the medium is replaced by 100 μl MTT dissolved in RPMI (1640 without phenol red) at a concentration of 0.5 or 1 mg/ml. The micro-wells are subsequently incubated during 3 hours and a half at 37° C. and centrifuged at 200×g during 10 minutes. MTT is removed and formazan crystals formed are dissolved in 100 μl DMSO. The micro-wells are shaken for 5 minutes and read on a spectrophotometer at wavelengths of 570 nm (maximal formazan absorbance).

Advantageously, it is observed that the DPI formulations according to embodiments of the present invention have higher cytotoxic effect on FR-expressing cells (e g human HeLa cervical adenocarcinoma and murine M109 lung carcinoma cell lines) than on FR-depleted cells (e.g. murine B16F10 melanoma cell line). The results illustrate the selectively of the formulations illustrating the present invention for FR-expressing cells and the pharmacological efficacy of the antineoplastic agent comprised in the formulations illustrating the present invention.

Example 28: In Vitro Evaluation of the Preferential Incorporation of TMZ-Loaded Folate-PEO-HTCC 1 NPs into FR-Expressing Cells Compared with FR-Depleted Cells The incorporation of the TMZ-loaded folate-PEO-HTCC 1 NPs (prepared according to Example 13) into FR-expressing cells (e.g. human HeLa cervical adenocarcinoma and murine M109 lung carcinoma cell lines) compared with FR-depleted cells (e.g. murine B16F10 melanoma cell line) is evaluated using fluorescent microscopy techniques (and flow cytometry techniques).

A fluorescent dye (FITC) is linked to the TMZ-loaded folate-PEO-HTCC 1 NPs.

To perform the assay, cells are allowed to grow in 6-well plate with a flat bottom with an amount of 5,000 to 8,000 cells/well depending on the cell type used. Each cell line is seeded in its appropriate culture medium.

The detailed experimental procedure is the following: after a 24-hour period of incubation at 37° C., the culture medium is replaced by fresh medium in which the formulation illustrating the present invention was previously dispersed. Each well is observed after 30 minutes and after 3 hours under a fluorescent microscope. Each experiment is performed in triplicate (3 times).

Advantageously, higher fluorescence is observed in FR-expressing cells (e.g. human HeLa cervical adenocarcinoma and murine M109 lung carcinoma cell lines) compared with FR-depleted cells (e.g. murine B16F10 melanoma cell line), illustrating that the formulations illustrating the present invention are selectively incorporated in FR-expressing cells and not in FR-depleted cells.

Example 29: In Vitro Evaluation of the Mucoadhesive Properties of NPs Illustrating the Present Invention The in vitro mucoadhesive properties of NPs illustrating the present invention (prepared according to Examples 7 to 12) are determined by evaluating the interactions between mucin and the NPs in aqueous media. Mucin is incubated in an aqueous buffer in presence of the NPs illustrating the present inventions (prepared according to Examples 7 to 12) and the amount of adsorption of mucin on NPs surface is determined.

The results illustrate that the nanoparticles illustrating the present invention comprising the chitosan or functionally-modified chitosan have good bioadhesive properties compared with prior art nanoparticles.

Example 30: In Vivo Evaluation of the Efficacy of the DPI Formulations on FR-Expressing M109 Lung Carcinoma-Bearing Mice M109 lung carcinoma tumours are obtained by the intralobar injection (left lung) of $1.4 \times 10^6$ M109 cells (20 µl) on BALB/c mice. Mice are randomised on the $6^{th}$ day post-tumour grafting, and treatments begin on the $7^{th}$ day post-tumour grafting.

The experimental groups are:
Control group: administration of anaesthetic medications via intraperitoneal injection of 112.5 mg/kg body weight of ketamine and 1.5 mg/kg body weight of xylazine,
Group 1: administration of temozolomide (TMZ) via intravenous (i.v.) injection (40 mg/kg body weight),
Group 2: administration of DPI formulation containing non-targeted TMZ-loaded NPs (formulation and dose to be determined).
Group 3: administration of DPI formulation illustrating the present invention (prepared according to Example 13, 14, 15, 16, 17, 18, 19, 20, 21, 22, 23, or 24) containing folate-targeted TMZ-loaded NPs (formulation and dose to be determined).

TMZ is administrated via i.v. (200 µl of an i.v. solution at 0.4% TMZ (m/v) in the tail vein) three times a week for three consecutive weeks. DPI formulations is administered directly to the lungs using a dry powder endotracheal insufflator device the Penn-Century Dry Powder Insufflator for mice (DP-4M®) as previously described (Duret et al., Eur J Pharm Biopharm 81:627-634, 2012) three times a week for three consecutive weeks.

Mouse survival was checked two times a day. Mouse weight was recorded three times a week. Each M109 lung carcinoma-bearing mouse was sacrificed when it had lost 20% of its weight (compared to that determined at the time of the tumour graft) or if it was suffocating. The lungs were removed, fixed in buffered formalin, embedded in paraffin and then processed for conventional histopathological analyses. Based on the measurement of survival it is observed that the efficacy of the formulations of the present invention is significantly higher in comparison with the efficacy of formulations administered systemically (i.e., intravenously) or of non FR-targeting formulations administered by inhalation.

Example 31: Preparation of Nanoparticles According to an Embodiment of the Present Invention (Temozolomide-Loaded Folate-PEO-HTCC 1 NPs)

Temozolomide (TMZ)-loaded folate-PEO-HTCC 1 nanoparticles (NPs) were produced by a controlled nanoprecipitation method at room temperature. Folate-PEO-HTCC 1 was synthesized according to Example 1.

Folate-PEO-HTCC 1 was dissolved in a pH 5 acetate buffer (0.1 M) at a concentration of 10 mg/ml in an ultrasonic bath at 50° C. After complete dissolution of folate-PEO-HTCC 1, a quantity of TMZ of 6 mg/ml was solubilized in the buffer at the same temperature. A second TMZ solution was prepared in DMSO at a concentration of 65 mg/ml at 50° C. The two TMZ solutions were then cooled at room temperature and were poured into a TMZ-saturated isopropanol solution containing 1 mg/ml of sodium taurocholate under sonication using ultrasonic probe (Vibra-Cell VCX 500, Sonics and Materials, Newtown, USA) leading to an immediate NP precipitation (buffer-DMSO-isopropanol proportion 19.9/0.4/79.7). The sonication was applied in an ice bath in order to avoid an increase of temperature with the following conditions, amplitude=40% during 5 min.

Figure 4:
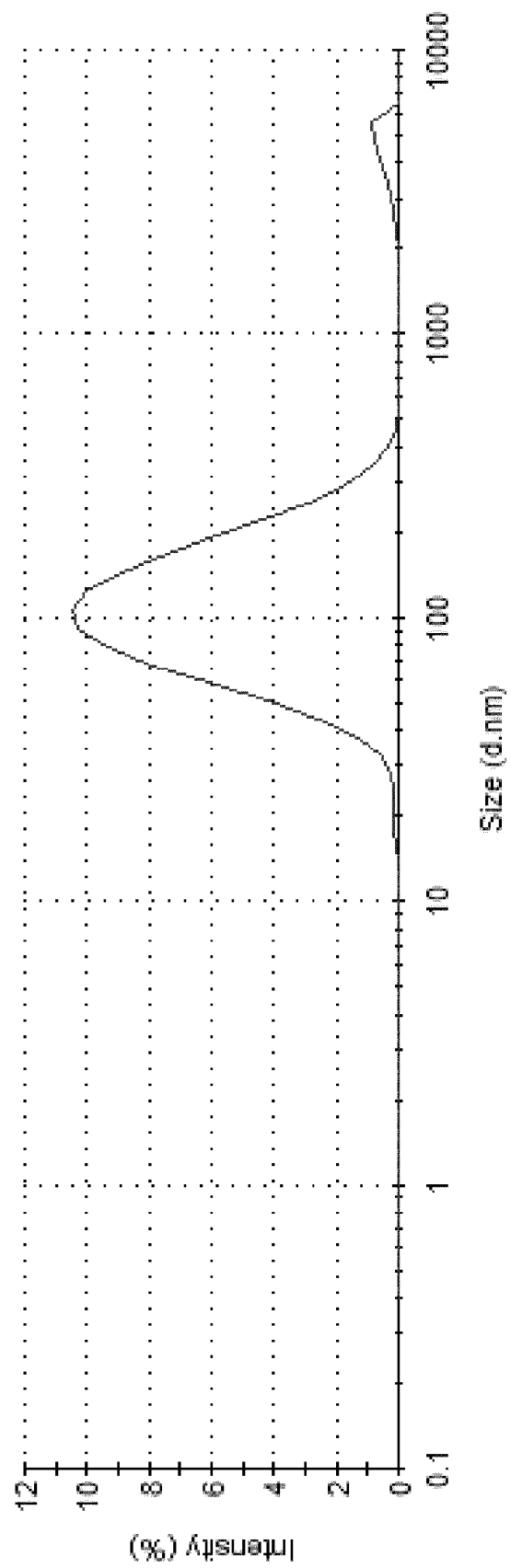
FIG. 4 represents a graph illustrating laser diffraction particle size distribution (Z-average) of TMZ-loaded folate-PEO-HTCC 1 NPs prepared according to Example 31 (n=3), as measured with Zetasizer nano ZS (Malvern Instruments, Worcestershire, UK).

Z-average particle size and size distribution of NPs were measured by dynamic light scattering (DLS) (Zetasizer nano ZS, Malvern Instruments, Worcestershire, UK) using Nanosphere™ size standards (Duke Scientific Corporation, Palo Alto, Calif., USA, cat. num. 3300) as internal standard. Size distribution is presented in FIG. 4. The Z-average particle size was 99±2 nm. Polydispersity index: 0.25±0.01. FIG. 4 shows the laser diffraction particle size distribution (Z-average) of TMZ-loaded folate-PEO-HTCC 1 NPs prepared according to Example 31 (n=3) (Zetasizer nano ZS, Malvern Instruments, Worcestershire, UK).

The zeta potential (ZP) of NPs was measured using a zetasizer (Zetasizer nano ZS, Malvern Instruments, Worcestershire, UK) using Zeta potential Transfer Standard (Malvern Instruments, Worcestershire, UK, cat. num. DTS1230). The zeta potential of the nanoparticles was 14±1 mV.

Formulation was ultrafiltrated (MWCO=10 kDa, Ultracel, Merck Millipore, Darmstadt, Germany) and the filtrate was collected. The TMZ drug loading (DL) and encapsulation efficiency (EE) of TMZ-loaded folate-PEO-HTCC 1 NPs were determined using equation (5) and equation (6), respectively.

The drug loading (DL) was determined using the equation (5):

$$DL(\%) = 1 - \frac{\text{amount of drug in supernatant}}{\text{amount of drug added + amount of excipients added}} \times 100 \quad (5)$$

The amount of antineoplastic agent (i.e., temozolomide) in the supernatant was determined in triplicate by the validated high-pressure liquid chromatography (HPLC) method coupled with UV detector. The chromatographic system (HP 1200 series, Agilent Technologies, Brussels, Belgium) was equipped with a quaternary pump, an auto sampler and a diode array detector. The separations were performed on a reverse-phase Hypersil Gold C-18 column (5 µm, 250 mm×4.6 mm) (Thermo Fisher Scientific, Waltham, USA). The mobile phase consisted of 0.5% v/v aqueous acetic acid/acetonitrile (90:10 v/v), which was delivered at a flow rate of 1.0 ml/min. The quantification was performed at 329 nm. The calibration curve was linear in the 1-250 µg/ml range. The TMZ samples and calibration standards were diluted in the mobile phase. The volume injected was 10 µl, the temperature was set at 25° C. and the analysis time was 10 min. The drug loading was 9±1%.

The encapsulation efficiency (EE) was determined using the equation (6):

$$EE(\%) = 1 - \frac{\text{amount of drug in supernatant}}{\text{amount of drug added}} \times 100$$

The amount of antineoplastic agent (i.e., temozolomide) in the supernatant was determined in triplicate by the validated HPLC method coupled with UV detector described above. The encapsulation efficiency was 14±1%.

Example 32: Preparation of Nanoparticles According to an Embodiment of the Present Invention (TMZ-Loaded Folate-PEO-HTCC 2 NPs)

TMZ-loaded folate-PEO-HTCC 2 nanoparticles (NPs) are produced by the controlled nanoprecipitation method at room temperature. Folate-PEO-HTCC 2 is synthesized according to Example 2.

Folate-PEO-HTCC 2 was dissolved in a pH 5 acetate buffer (0.1 M) at a concentration of 10 mg/ml in an ultrasonic bath at 50° C. After complete dissolution of folate-PEO-HTCC 2, a quantity of TMZ of 6 mg/ml was solubilized in the buffer at the same temperature. A second TMZ solution was prepared in DMSO at a concentration of 65 mg/ml at 50° C. The two TMZ solutions were then cooled at room temperature and were poured into a TMZ-saturated isopropanol solution containing 1 mg/ml of sodium taurocholate under sonication using ultrasonic probe (Vibra-Cell VCX 500, Sonics and Materials, Newtown, USA) leading to an immediate NP precipitation (buffer-DMSO-isopropanol proportion 19.9/0.4/79.7). The sonication was applied in an ice bath in order to avoid an increase of temperature with the following conditions, amplitude=40% during 5 min.

Z-average particle size and size distribution of NPs are measured by DLS (Zetasizer nano ZS, Malvern Instruments, Worcestershire, UK) as described in Example 31. The results are in line with those obtained in Example 31.

The ZP of NPs is measured using a zetasizer (Zetasizer nano ZS, Malvern Instruments, Worcestershire, UK) as described in Example 31. The results are in line with those obtained in Example 31.

The formulation is ultrafiltrated (MWCO=10 kDa, Ultracel, Merck Millipore, Darmstadt, Germany) and the filtrate collected. The TMZ drug loading and encapsulation efficiency of TMZ-loaded folate-PEO-HTCC 2 NPs are determined in triplicate by a validated HPLC method coupled with UV detector (described in example 31). The drug loading and encapsulation efficiency are determined using equations (5) and (6) respectively. The results are in line with those obtained in Example 31.

Example 33: Preparation of Nanoparticles According to an Embodiment of the Present Invention (TMZ-Loaded Folate-PEO-HTCC 3 NPs)

TMZ-loaded folate-PEO-HTCC 3 NPs are produced by the controlled nanoprecipitation method at room temperature. Folate-PEO-HTCC 3 is synthesized according to Example 3.

Folate-PEO-HTCC 3 was dissolved in a pH 5 acetate buffer (0.1 M) at a concentration of 10 mg/ml in an ultrasonic bath at 50° C. After complete dissolution of folate-PEO-HTCC 3, a quantity of TMZ of 6 mg/ml was solubilized in the buffer at the same temperature. A second TMZ solution was prepared in DMSO at a concentration of 65 mg/ml at 50° C. The two TMZ solutions were then cooled at room temperature and were poured into a TMZ-saturated isopropanol solution containing 1 mg/ml of sodium taurocholate under sonication using ultrasonic probe (Vibra-Cell VCX 500, Sonics and Materials, Newtown, USA) leading to an immediate NP precipitation (buffer-DMSO-isopropanol proportion 19.9/0.4/79.7). The sonication was applied in an ice bath in order to avoid an increase of temperature with the following conditions, amplitude=40% during 5 min.

Z-average particle size and size distribution of NPs are measured by DLS (Zetasizer nano ZS, Malvern Instruments, Worcestershire, UK) as described in Example 31. The results are in line with those obtained in Example 31.

The ZP of NPs is measured using a zetasizer (Zetasizer nano ZS, Malvern Instruments, Worcestershire, UK) as described in Example 31. The results are in line with those obtained in Example 31.

The formulation is ultrafiltrated (MWCO=10 kDa, Ultracel, Merck Millipore, Darmstadt, Germany) and the filtrate collected. The TMZ drug loading and encapsulation efficiency of TMZ-loaded folate-PEO-HTCC NPs are determined in triplicate by a validated HPLC method coupled with UV detector (described in example 31). The drug loading and encapsulation efficiency are determined using equations (5) and (6) respectively. The results are in line with those obtained in Example 31.

Example 34: Preparation of Nanoparticles According to an Embodiment of the Present Invention (Paclitaxel-Loaded Folate-PEO-HTCC 1 NPs)

Paclitaxel (PTX)-loaded folate-PEO-HTCC 1 NPs or PTX-loaded folate-PEO-HTCC 1-coated solid lipid nanoparticles (SLNs) were produced by the controlled nanoprecipitation method at room temperature. Folate-PEO-HTCC 1 was synthesized according to Example 1.

First, PTX-loaded solid lipid nanoparticles (SLNs) were prepared. A solution containing 1.5 mg/ml of PTX (Carbosynth Limited, Berkshire, United Kingdom, cat. num. FP10637), 5 mg/ml of glyceryl-stearate (Geleol, Gattefosse, Saint-Priest, France, cat. num. 5154) and 30 mg/ml of cholesterol (Fagron, Waregem, Belgium, cat. num. 610546) in acetone was prepared in an ultrasonic bath. The solution was poured into ultrapure water containing 0.15 mg/ml of d-alpha tocopherol polyethylene glycol-succinate (TPGS) (Fagron, Waregem, Belgium, cat. num. 610972) and 0.1 mg/ml of sodium taurocholate (acetone/water volume ratio=1/10) under magnetic stirring (1300 RPM) and the precipitation immediately occurred. Z-average particle size and size distribution of SLNs were measured by DLS (Zetasizer nano ZS, Malvern Instruments, Worcestershire, UK) as described in Example 31. The Z-average particle size was 186±16 nm Polydispersity index: 0.22±0.03.

The ZP of NPs were measured using a zetasizer (Zetasizer nano ZS, Malvern Instruments, Worcestershire, UK) as described in Example 31. The zeta potential of the NPs was −17±1 mV.

Formulation was ultrafiltrated (MWCO=10 kDa, Amicon, Merck Millipore, Darmstadt, Germany) and the filtrate was collected. The PTX drug loading and encapsulation efficiency of PTX-loaded folate-PEO-HMD 1 NPs were determined in triplicate by a validated HPLC method coupled with UV detector. The chromatographic system (HP 1200 series, Agilent Technologies, Brussels, Belgium) was equipped with a quaternary pump, an auto sampler and a diode array detector. The separations were performed on a reverse-phase Hypersil Gold C-18 column (5 µm, 250 mm×4.6 mm) (Thermo Fisher Scientific, Waltham, USA). The mobile phase consisted of ultrapure water/acetonitrile (47:53 v/v), which was delivered at a flow rate of 1.0 ml/min. The quantification was performed at 227 nm. The calibration curve was linear in the 50-1000 ng/ml range. The PTX samples and calibration standards were diluted in the mobile phase. The volume injected was 100 µl, the temperature was set at 30° C. and the analysis time was 10 min. The drug loading and the encapsulation efficiency were determined using equations (5) and (6) respectively.

The drug loading was 5.9±0.2%. The encapsulation efficiency (EE) was 99.0±0.3%.

PTX-loaded SLNs were then coated with folate-PEO-HTCC 1. Folate-PEO-HTCC 1 was dissolved in ultrapure water at a concentration of 1.5 mg/ml under magnetic stirring. This solution was then poured to the SLNs dispersion.

Z-average particle size and size distribution of NPs were measured by DLS (Zetasizer nano ZS, Malvern Instruments, Worcestershire, UK) as described in Example 31. The Z-average particle size was 313±41 nm Polydispersity index: 0.39±0.09.

Figure 5:
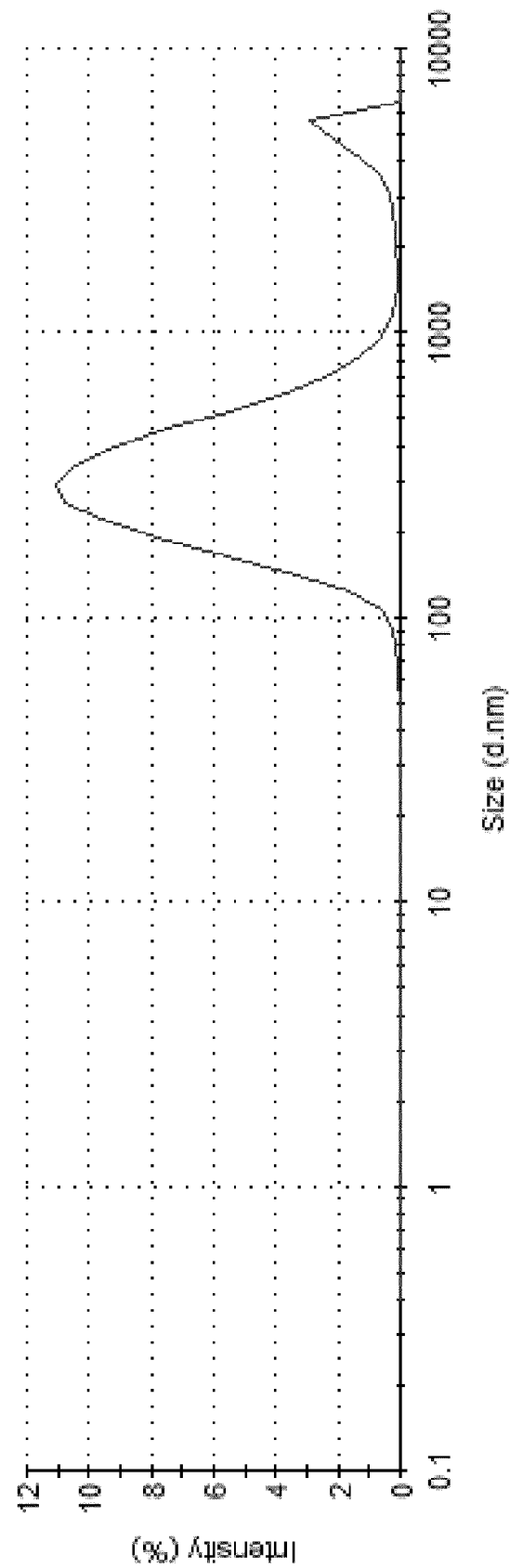
FIG. 5 represents a graph illustrating laser diffraction particle size distribution (Z-Average) of PTX-loaded folate- PEO-HTCC 1 NPs prepared according to Example 34 (n=3), as measured with Zetasizer nano ZS (Malvern Instruments, Worcestershire, UK).

FIG. 5 shows laser diffraction particle size distribution (Z-Average) of PTX-loaded folate-PEO-HTCC 1 NPs prepared according to Example 34 (n=3) (Zetasizer nano ZS, Malvern Instruments, Worcestershire, UK).

The ZP of NPs were measured using a zetasizer (Zetasizer nano ZS, Malvern Instruments, Worcestershire, UK) as described in Example 31. The zeta potential of the NPs was 32.2±0.8 mV.

Example 35: Preparation of Nanoparticles According to an Embodiment of the Present Invention (Paclitaxel-Loaded Folate-PEO-HTCC 2 NPs)

PTX-loaded folate-PEO-HTCC 2 NPs or PTX-loaded folate-PEO-HTCC 2-coated solid lipid nanoparticles (SLNs) were produced by the controlled nanoprecipitation method at room temperature. Folate-PEO-HTCC 2 was synthesized according to Example 2.

First, PTX-loaded SLNs were prepared as described in Example 34.

PTX-loaded SLNs were then coated with folate-PEO-HTCC 2. Folate-PEO-HTCC 2 was dissolved in ultrapure water at a concentration of 1.5 mg/ml under magnetic stirring. This solution was then poured to the SLNs dispersion.

Z-average particle size and size distribution of NPs were measured by DLS (Zetasizer nano ZS, Malvern Instruments, Worcestershire, UK) as described in Example 31. The results are in line with those obtained in Example 34.

The ZP of NPs were measured using a zetasizer (Zetasizer nano ZS, Malvern Instruments, Worcestershire, UK) as described in Example 31. The results are in line with those obtained in Example 34.

Example 36: Preparation of Nanoparticles According to an Embodiment of the Present Invention (Paclitaxel-Loaded Folate-PEO-HTCC 3 NPs)

PTX-loaded folate-PEO-HTCC 3 NPs or PTX-loaded folate-PEO-HTCC 3-coated solid lipid nanoparticles (SLNs) were produced by the controlled nanoprecipitation method at room temperature. Folate-PEO-HTCC 3 was synthesized according to Example 3.

First, PTX-loaded SLNs were prepared as described in Example 34.

PTX-loaded SLNs were then coated with folate-PEO-HTCC 3. Folate-PEO-HTCC 3 was dissolved in ultrapure water at a concentration of 1.5 mg/ml under magnetic stirring. This solution was then poured to the SLNs dispersion.

Z-average particle size and size distribution of NPs were measured by DLS (Zetasizer nano ZS, Malvern Instruments, Worcestershire, UK) as described in Example 31. The results are in line with those obtained in Example 34.

The ZP of NPs were measured using a zetasizer (Zetasizer nano ZS, Malvern Instruments, Worcestershire, UK) as described in Example 31. The results are in line with those obtained in Example 34.

Example 37: Preparation of Nanoparticles According to an Embodiment of the Present Invention (PTX-Loaded Folate-PEO-HMD 1 NPs)

PTX-loaded folate-PEO-HMD 1 NPs were produced by the controlled nanoprecipitation method at room temperature in presence of a dialysis membrane. Folate-PEO-HMD 1 was synthesized according to Example 4.

A solution containing folate-PEO-HMD 1 at a concentration of 67 mg/ml and PTX at a concentration of 1 mg/ml in DMSO was prepared in an ultrasonic bath. The solution was dialyzed (MWCO=10 kDa, Spectra/Por, Spectrum Labs, Breda, The Nederlands) against ultrapure water and formation of NPs progressively occurs.

Particle size distribution of NPs were measured by dynamic light scattering (Zetasizer nano ZS, Malvern Instruments, Worcestershire, UK) as described in Example 31.

Figure 6:
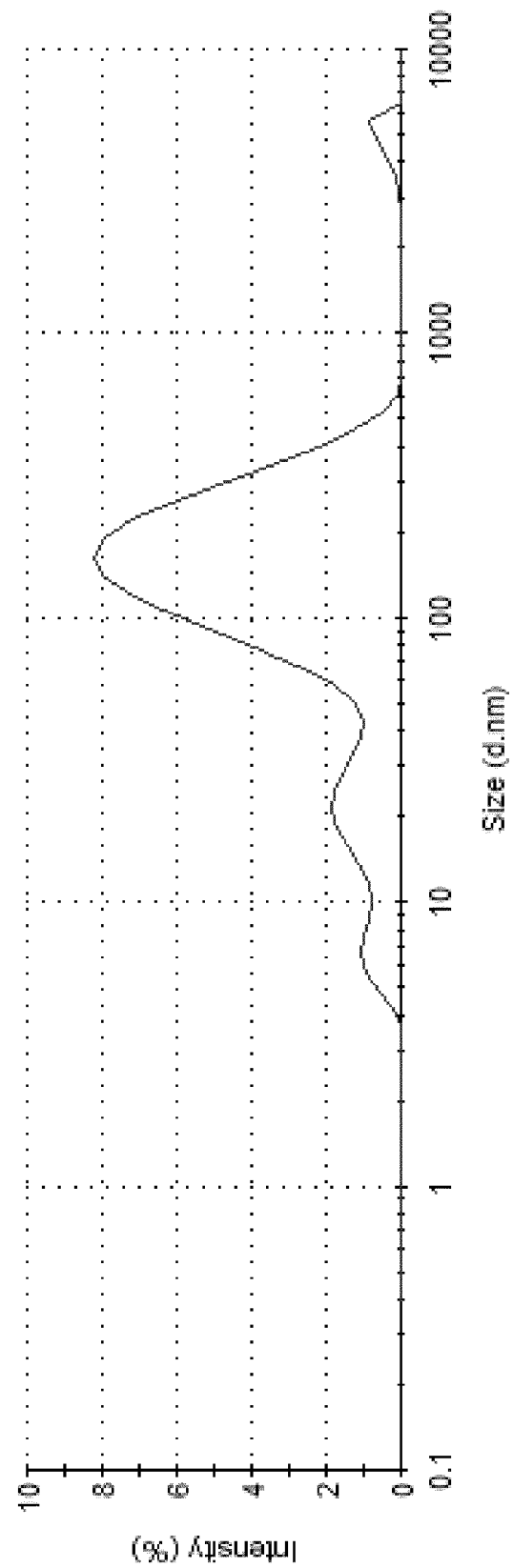
FIG. 6 represents a graph illustrating laser diffraction particle size distribution of PTX-loaded folate-PEO-HMD 1 NPs prepared according to example 37 (n=3), as measured with Zetasizer nano ZS (Malvern Instruments, Worcestershire, UK).

FIG. 6 shows laser diffraction particle size distribution of PTX-loaded folate-PEO-HMD 1 NPs prepared according to example 37 (n=3) (Zetasizer nano ZS, Malvern Instruments, Worcestershire, UK).

The ZP of NPs were measured using a zetasizer (Zetasizer nano ZS, Malvern Instruments, Worcestershire, UK) as described in Example 31. The zeta potential of the NPs was −14±2 mV.

Formulation was ultrafiltrated (MWCO=10 kDa, Amicon, Merck Millipore, Darmstadt, Germany) and the filtrate was collected. The PTX drug loading and encapsulation efficiency of PTX-loaded folate-PEO-HMD 1 NPs were determined in triplicate by the validated HPLC method coupled with UV detector described in Example 34. The drug loading and the encapsulation efficiency were determined using equations (5) and (6) respectively.

The drug loading was 1.2±0.2%. The encapsulation efficiency (EE) was 99±2%.

Example 38: Preparation of Nanoparticles According to an Embodiment of the Present Invention (PTX-Loaded Folate-PEO-HMD 2 NPs)

PTX-loaded folate-PEO-HMD 2 NPs or PTX-loaded folate-PEO-HMD 2 nanomicelles were produced by the dialysis method at room temperature. Folate-PEO-HMD 2 was synthesized according to Example 5.

A solution containing folate-PEO-HMD 2 at a concentration of 67 mg/ml and PTX at a concentration of 1 mg/ml in DMSO was prepared in an ultrasonic bath. The solution was dialyzed (MWCO=10 kDa, Spectra/Por, Spectrum Labs, Breda, The Nederlands) against ultrapure water and formation of NPs progressively occurs.

Particle size distribution of NPs were measured by dynamic light scattering (Zetasizer nano ZS, Malvern Instruments, Worcestershire, UK) as described in Example 31. The results are in line with those obtained in Example 37.

The ZP of NPs were measured using a zetasizer (Zetasizer nano ZS, Malvern Instruments, Worcestershire, UK) as described in Example 31. The results are in line with those obtained in Example 37.

Formulation was ultrafiltrated (MWCO=10 kDa, Amicon, Merck Millipore, Darmstadt, Germany) and the filtrate was collected. The PTX drug loading and encapsulation efficiency of PTX-loaded folate-PEO-HMD 1 NPs were determined in triplicate by the validated HPLC method coupled with UV detector described in Example 34. The drug loading and the encapsulation efficiency were determined using equations (5) and (6) respectively.

The results are in line with those obtained in Example 37.

Example 39: Preparation of Nanoparticles According to an Embodiment of the Present Invention (TMZ-Loaded Folate-PEO-HMD 1 NPs)

TMZ-loaded folate-PEO-HMD 1 NPs were produced by the co-solubilization method. Folate-PEO-HMD 1 was synthesized according to Example 4.

Folate-PEO-HMD 1 was dissolved at a concentration of 1 mg/ml in presence of 4 mg/ml of TMZ at 50° C. in an ultrasonic bath. The dispersion was then cooled at room temperature and NPs formation progressively occurs.

Particle size distribution of NPs were measured by dynamic light scattering (Zetasizer nano ZS, Malvern Instruments, Worcestershire, UK) as described in Example 31.

Figure 7:
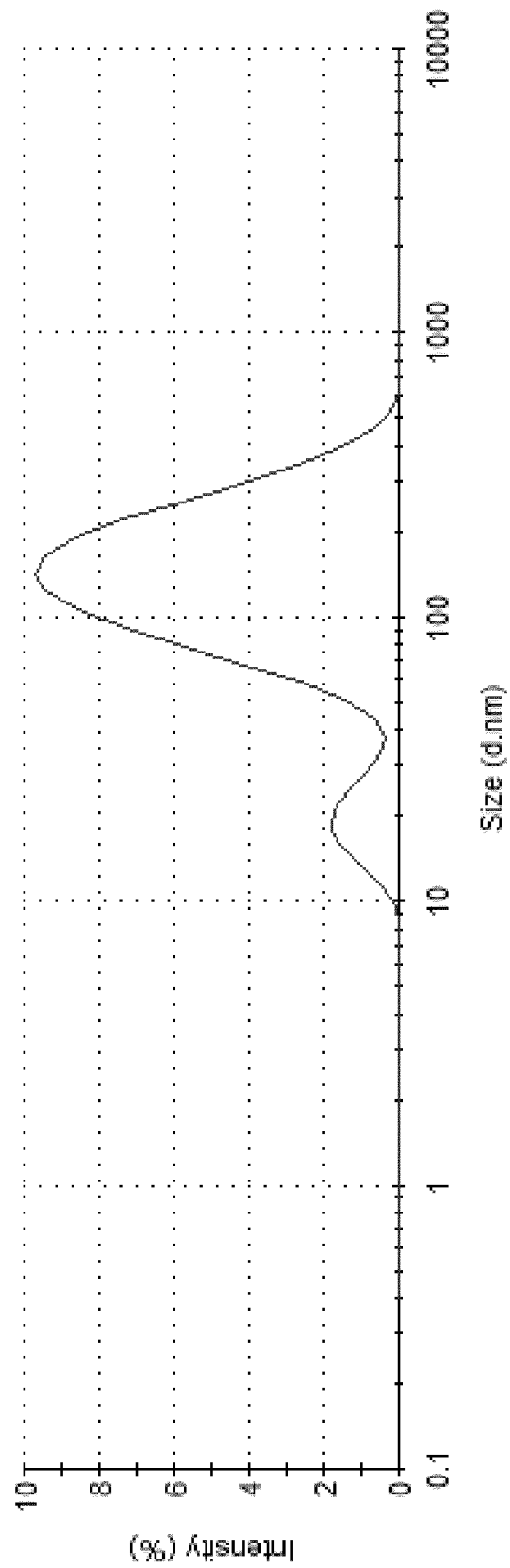
FIG. 7 represents a graph illustrating laser diffraction particle size distribution of TMZ-loaded folate-PEO-HMD 1 NPs prepared according to Example 39 (n=3) (Zetasizer nano ZS, Malvern Instruments, Worcestershire, UK).

FIG. 7 shows laser diffraction particle size distribution of TMZ-loaded folate-PEO-HMD 1 NPs prepared according to Example 39 (n=3) (Zetasizer nano ZS, Malvern Instruments, Worcestershire, UK).

The ZP of NPs were measured using a zetasizer (Zetasizer nano ZS, Malvern Instruments, Worcestershire, UK) as described in Example 31. The zeta potential of the NPs was 0.7±0.2 mV.

Formulation was ultrafiltrated (MWCO=10 kDa, Amicon, Merck Millipore, Darmstadt, Germany) and the filtrate was collected. The TMZ drug loading and encapsulation efficiency of TMZ-loaded folate-PEO-HMD 1 NPs were determined in triplicate by a validated HPLC method coupled with UV detector (described in example 31). The drug loading and the encapsulation efficiency were determined using equations (5) and (6) respectively.

The drug loading was 1.3±0.5%. The encapsulation efficiency (EE) was 3±1%.

Example 40: Preparation of Nanoparticles According to an Embodiment of the Present Invention (TMZ-Loaded Folate-PEO-HMD 2 NPs)

TMZ-loaded folate-PEO-HMD 2 NPs are produced by the co-solubilization method. Folate-PEO-HMD 2 is synthesized according to Example 5.

Folate-PEO-HMD 1 was dissolved at a concentration of 3 mg/ml in presence of 4 mg/ml of TMZ at 50° C. in an ultrasonic bath. The dispersion was then cooled at room temperature and NPs formation progressively occurs.

Particle size distribution of NPs are measured by DLS (Zetasizer nano ZS, Malvern Instruments, Worcestershire, UK). The results are in line with those obtained in Example 39.

The ZP of NPs are measured using a zetasizer (Zetasizer nano ZS, Malvern Instruments, Worcestershire, UK). The results are in line with those obtained in Example 39.

The formulation is ultrafiltrated (MWCO=10 kDa, Ultracel, Merck Millipore, Darmstadt, Germany) and the filtrate was collected. The TMZ drug loading and encapsulation efficiency of TMZ-loaded folate-PEO-HMD NPs are determined in triplicate by a validated HPLC method coupled with UV detector (described in example 31). The drug loading and the encapsulation efficiency are determined using equations (5) and (6) respectively. The results are in line with those obtained in Example 39.

Example 41: Preparation of Nanoparticles According to an Embodiment of the Present Invention (TMZ-Loaded Folate-PEO-HTCC 4 NPs)

TMZ-loaded folate-PEO-HTCC 4 NPs are produced by the controlled nanoprecipitation method at room temperature. Folate-PEO-HTCC 4 is synthesized according to Example 6.

Folate-PEO-HTCC 4 was dissolved in a pH 5 acetate buffer (0.1 M) at a concentration of 10 mg/ml in an ultrasonic bath at 50° C. After complete dissolution of folate-PEO-HTCC 4, a quantity of TMZ of 6 mg/ml was solubilized in the buffer at the same temperature. A second TMZ solution was prepared in DMSO at a concentration of 65 mg/ml at 50° C. The two TMZ solutions were then cooled at room temperature and were poured into a TMZ-saturated isopropanol solution containing 1 mg/ml of sodium taurocholate under sonication using ultrasonic probe (Vibra-Cell VCX 500, Sonics and Materials, Newtown, USA) leading to an immediate NP precipitation (buffer-DMSO-isopropanol proportion 19.9/0.4/79.7). The sonication was applied in an ice bath in order to avoid an increase of temperature with the following conditions, amplitude=40% during 5 min.

Z-average particle size and size distribution of NPs are measured by DLS (Zetasizer nano ZS, Malvern Instruments, Worcestershire, UK) as described in Example 31. The results are in line with those obtained in Example 31.

The ZP of NPs was measured using a zetasizer (Zetasizer nano ZS, Malvern Instruments, Worcestershire, UK) as described in Example 31. The results are in line with those obtained in Example 31.

The formulation is ultrafiltrated (MWCO=10 kDa, Ultracel, Merck Millipore, Darmstadt, Germany) and the filtrate is collected. The TMZ drug loading and encapsulation efficiency of TMZ-loaded folate-PEO-HTCC NPs are determined in triplicate by a validated HPLC method coupled with UV detector (described in example 31). The drug loading and the encapsulation efficiency are determined using equations (5) and (6) respectively. The results are in line with those obtained in Example 31.

Example 42: Preparation of Nanoparticles According to an Embodiment of the Present Invention (Paclitaxel-Loaded Folate-PEO-HTCC 4 NPs)

PTX-loaded folate-PEO-HTCC 4 NPs or PTX-loaded folate-PEO-HTCC 4-coated solid lipid nanoparticles (SLNs) were produced by the controlled nanoprecipitation method at room temperature. Folate-PEO-HTCC 4 was synthesized according to Example 6.

First, PTX-loaded SLNs were prepared as described in Example 34.

PTX-loaded SLNs were then coated with folate-PEO-HTCC 4. Folate-PEO-HTCC 4 was dissolved in ultrapure water at a concentration of 1.5 mg/ml under magnetic stirring. This solution was then poured to the SLNs dispersion.

Z-average particle size and size distribution of NPs were measured by DLS (Zetasizer nano ZS, Malvern Instruments, Worcestershire, UK) as described in Example 31. The results are in line with those obtained in Example 34.

The ZP of NPs were measured using a zetasizer (Zetasizer nano ZS, Malvern Instruments, Worcestershire, UK) as described in Example 31. The results are in line with those obtained in Example 34.

Example 43: Preparation of Formulation for Dry Powder Inhalation (DPI) According to an Embodiment of the Present Invention (NEMS Containing TMZ-Loaded Folate-PEO-HTCC 1 NPs and Mannitol)

TMZ-loaded folate-PEO-HTCC 1 NPs were prepared according to Example 31.

Nano-embedded microparticles (NEMS) were produced by spray-drying the dispersion of TMZ-loaded folate-PEO-HTCC 1 NPs in the presence of mannitol (Paerlitol 400 DC, Roquette, Lestrem, France). Briefly, the dispersion of NPs was concentrated (factor 2) by ultrafiltration (MWCO=10 kDa, Ultracel, Merck Millipore, Darmstadt, Germany). Mannitol was dissolved in the concentrated NPs dispersion at a concentration of 10 mg/ml using an ultrasonic probe at 40% during 1 min in an ice bath The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 4.5 g/min; nozzle diameter 0.7 mm; inlet temperature 80° C. corresponding to an outlet temperature of about 45° C.

The actual TMZ content of the obtained pharmaceutical formulation according to an embodiment of the present invention is determined using the validated HPLC coupled with UV detector described in Example 31. Actual TMZ content=10.7±0.3%.

Figure 8:
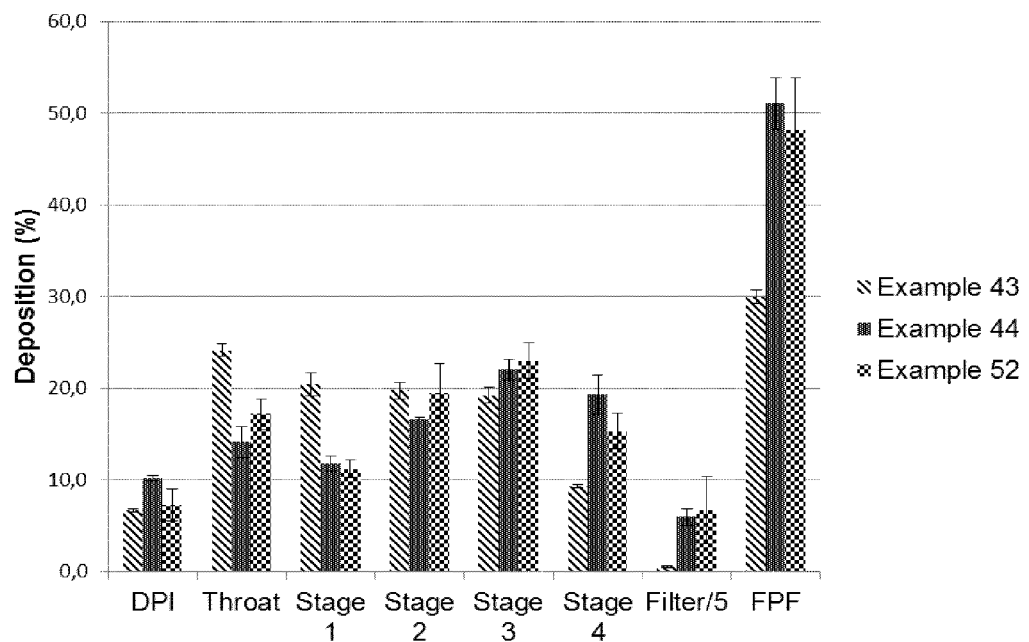
FIG. 8 represents a graph illustrating the in vitro pulmonary deposition (in percentage) and fine particle fraction (FPF, in percentage) of the pharmaceutical formulation according to embodiments of the present invention, i.e. pharmaceutical formulation prepared in Example 43, Example 44, and Example 52. DPI: dry powder inhaler, FPF: fine particle fraction.

The obtained pharmaceutical formulation illustrating the present invention is evaluated by determining its in vitro pulmonary deposition, mass median aerodynamic diameter (MMAD) and fine particle fraction (FPF) by performing impaction tests using a Multi-Stage Liquid Impinger (MSLI) from the Axahaler® (SMB Laboratories, Brussels, Belgium) dry powder inhaler (DPI) (100 L/min, 2.4s and No 3 HPMC capsules filled with 20 mg of dry powder, three discharges per capsule, one capsule per test, n=3). The cut-off diameters at this flow rate were 5.27, 2.40 and 1.32 μm between stages 2 to 3, 3 to 4 and 4 to 5, respectively. The FPF was expressed as a percentage of the total dose recovered but not of the delivered dose. The in vitro pulmonary deposition and fine particle fraction (FPF) of the pharmaceutical formulation according to an embodiment of the present invention are presented in FIG. 8. FPF=30.0±0.7%, MMAD=4.6±0.9 μm.

Example 44: Preparation of Formulation for DPI According to an Embodiment of the Present Invention (NEMs Containing TMZ-Loaded Folate-PEO-HTCC 1 NPs and Lipids)

TMZ-loaded folate-PEO-HTCC 1 NPs were prepared according to Example 31.

NEMs were produced by spray-drying the dispersion of TMZ-loaded folate-PEO-HTCC 1 NPs in the presence of cholesterol and phospholipids.

Briefly, the dispersion of NPs was concentrated (factor 2) by ultrafiltration (MWCO=10 kDa). Cholesterol (Fagron, Waregem, Belgium, cat. num. 610546) and phospholipids (Phospholipon 90H, Nattermann Phospholipid GmbH, Koeln, Germany, cat. num. 368174) were dissolved in the concentrated NPs dispersion at a concentration of 9 mg/ml and 2 mg/ml, respectively, using an ultrasonic probe at 40% during 1 min in an ice bath The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 4.5 g/min; nozzle diameter 0.7 mm; inlet temperature 80° C. corresponding to an outlet temperature of about 45° C.

The actual TMZ content of the obtained pharmaceutical formulation according to an embodiment of the present invention is determined using the validated HPLC coupled with UV detector described in Example 31. Actual TMZ content=12.45±0.01%.

The obtained pharmaceutical formulation illustrating the present invention is evaluated by determining its in vitro pulmonary deposition, MMAD and FPF by performing impaction tests by performing impaction tests as described in Example 43. The in vitro pulmonary deposition and the fine particle fraction of the pharmaceutical formulation according to an embodiment of the present invention are presented in FIG. 8. FPF=51±3%, MMAD=2.8±0.5 μm.

Example 45: Preparation of Formulation for DPI According to an Embodiment of the Present Invention (NEMs Containing PTX-Loaded Folate-PEO-HTCC 1 NPs and Dextran)

PTX-loaded folate-PEO-HTCC 1 NPs were prepared according to Example 34.

NEMs were produced by spray-drying the dispersion of PTX-loaded folate-PEO-HTCC 1 NPs in the presence of dextran.

Briefly, dextran (Pharmacosmos, Holbaek, Denmark, cat. num. 55100010) were dissolved in the NPs dispersion at a concentration of 28.4 mg/ml using an ultrasonic bath at room temperature. The dispersion was placed in an ice bath and 25% (v/v) of isopropanol was added to the dispersion. The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 4.75 g/min; nozzle diameter 0.7 mm; inlet temperature 100° C. corresponding to an outlet temperature of about 43° C. The NPs dispersion was kept in an ice bath during the spray-drying process in order to prevent NPs aggregation and dissolution of PTX.

The actual PTX content of the obtained pharmaceutical formulation according to an embodiment of the present invention is determined using the validated HPLC coupled with UV detector described in Example 34. Actual PTX content=0.58±0.03%.

Figure 9:
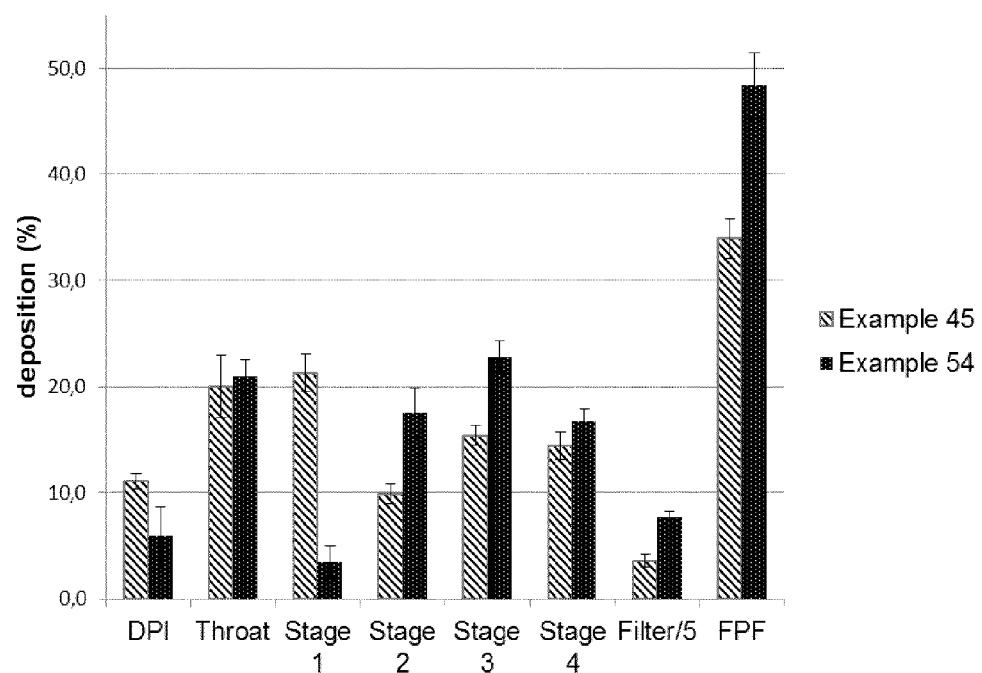
FIG. 9 represents a graph illustrating the in vitro pulmonary deposition (in percentage) and fine particle fraction (FPF, in percentage) of the pharmaceutical formulation according to embodiments of the present invention, i.e. pharmaceutical formulation prepared in Example 45, and Example 54. DPI: dry powder inhaler, FPF: fine particle fraction.

The obtained pharmaceutical formulation illustrating the present invention is evaluated by determining its in vitro pulmonary deposition, MMAD and FPF by performing impaction tests using a MSLI from the Axahaler® DPI (100 L/min, 2.4s and No 3 HPMC capsules filled with 20 mg of dry powder, three discharges per capsule, one capsule per test, n=3). The cut-off diameters at this flow rate were 5.27, 2.40 and 1.32 μm between stages 2 to 3, 3 to 4 and 4 to 5, respectively. The fine particle fraction (FPF) was expressed as a percentage of the total dose recovered but not of the delivered dose. The in vitro pulmonary deposition and the FPF of the pharmaceutical formulation according to an embodiment of the present invention are presented in FIG. 9. FPF=34±2%, MMAD=2.9±0.2 μm.

Example 46: Preparation of Formulation for DPI According to an Embodiment of the Present Invention (NEMs Containing TMZ-Loaded Folate-PEO-HTCC 2 NPs and Mannitol)

TMZ-loaded folate-PEO-HTCC 2 NPs were prepared according to Example 32.

NEMs were produced by spray-drying the dispersion of TMZ-loaded folate-PEO-HTCC 2 NPs in the presence of mannitol.

Briefly, the dispersion of NPs was concentrated (factor 2) by ultrafiltration (MWCO=10 kDa). Mannitol was dissolved in the concentrated NPs dispersion at a concentration of 10 mg/ml using an ultrasonic probe at 40% during 1 min in an ice bath The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 4.5 g/min; nozzle diameter 0.7 mm; inlet temperature 80° C. corresponding to an outlet temperature of about 45° C.

The actual TMZ content of the obtained pharmaceutical formulation according to an embodiment of the present invention is determined using the validated HPLC coupled with UV detector described in Example 31. The results are in line with those obtained in Example 43.

The obtained pharmaceutical formulation illustrating the present invention is evaluated by determining its in vitro pulmonary deposition, MMAD and FPF by performing impaction tests by performing impaction tests as described in Example 43. The results are in line with those obtained in Example 43.

Example 47: Preparation of Formulation for DPI According to an Embodiment of the Present Invention (NEMs Containing TMZ-Loaded Folate-PEO-HTCC 2 NPs and Lipids)

TMZ-loaded folate-PEO-HTCC 2 NPs were prepared according to Example 32.

NEMs were produced by spray-drying the dispersion of TMZ-loaded folate-PEO-HTCC 2 NPs in the presence of cholesterol and phospholipids.

Briefly, the dispersion of NPs was concentrated (factor 2) by ultrafiltration (MWCO=10 kDa). Cholesterol and phospholipids were dissolved in the concentrated NPs dispersion at a concentration of 9 mg/ml and 2 mg/ml, respectively, using an ultrasonic probe at 40% during 1 min in an ice bath The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 4.5 g/min; nozzle diameter 0.7 mm; inlet temperature 80° C. corresponding to an outlet temperature of about 45° C.

The actual TMZ content of the obtained pharmaceutical formulation according to an embodiment of the present invention is determined using the validated HPLC coupled with UV detector described in Example 31. The results are in line with those obtained in Example 44.

The obtained pharmaceutical formulation illustrating the present invention is evaluated by determining its in vitro pulmonary deposition, MMAD and FPF by performing impaction tests as described in Example 43. The results are in line with those obtained in Example 44.

Example 48: Preparation of Formulation for DPI According to an Embodiment of the Present Invention (NEMs Containing PTX-Loaded Folate-PEO-HTCC 2 NPs and Dextran)

PTX-loaded folate-PEO-HTCC 2 NPs were prepared according to Example 35.

NEMs were produced by spray-drying the dispersion of PTX-loaded folate-PEO-HTCC 2 NPs in presence of dextran.

Briefly, dextran was dissolved in the NPs dispersion at a concentration of 28.4 mg/ml using an ultrasonic bath at room temperature. The dispersion was placed in an ice bath and 25% (v/v) of isopropanol was added to the dispersion. The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 4.75 g/min; nozzle diameter 0.7 mm; inlet temperature 100° C. corresponding to an outlet temperature of about 43° C. The NPs dispersion was kept in an ice bath during the spray-drying process in order to prevent NPs aggregation and dissolution of PTX.

The obtained pharmaceutical formulation illustrating the present invention is evaluated by determining its in vitro pulmonary deposition, MMAD and FPF by performing impaction tests using as described in Example 45. The results are in line with those obtained in Example 45.

Example 49: Preparation of Formulation for DPI According to an Embodiment of the Present Invention (NEMs Containing TMZ-Loaded Folate-PEO-HTCC 3 NPs and Mannitol)

TMZ-loaded folate-PEO-HTCC 3 NPs were prepared according to Example 33.

NEMs were produced by spray-drying the dispersion of TMZ-loaded folate-PEO-HTCC 3 NPs in presence of mannitol.

Briefly, the dispersion of NPs was concentrated (factor 2) by ultrafiltration (MWCO=10 kDa). Mannitol was dissolved in the concentrated NPs dispersion at a concentration of 10 mg/ml using an ultrasonic probe at 40% during 1 min in an ice bath The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 4.5 g/min; nozzle diameter 0.7 mm; inlet temperature 80° C. corresponding to an outlet temperature of about 45° C.

The actual TMZ content of the obtained pharmaceutical formulation according to an embodiment of the present invention is determined using the validated HPLC coupled with UV detector described in Example 31. The results are in line with those obtained in Example 43.

The obtained pharmaceutical formulation illustrating the present invention is evaluated by determining its in vitro pulmonary deposition, MMAD and FPF by performing impaction tests by performing impaction tests as described in Example 43. The results are in line with those obtained in Example 43.

Example 50: Preparation of Formulation for DPI According to an Embodiment of the Present Invention (NEMs Containing TMZ-Loaded Folate-PEO-HTCC 3 NPs and Lipids)

TMZ-loaded folate-PEO-HTCC 3 NPs were prepared according to Example 33.

NEMs were produced by spray-drying the dispersion of TMZ-loaded folate-PEO-HTCC 3 NPs in the presence of cholesterol and phospholipids.

Briefly, the dispersion of NPs was concentrated (factor 2) by ultrafiltration (MWCO=10 kDa). Cholesterol and phospholipids were dissolved in the concentrated NPs dispersion at a concentration of 9 mg/ml and 2 mg/ml, respectively, using an ultrasonic probe at 40% during 1 min in an ice bath The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 4.5 g/min; nozzle diameter 0.7 mm; inlet temperature 80° C. corresponding to an outlet temperature of about 45° C.

The actual TMZ content of the obtained pharmaceutical formulation according to an embodiment of the present invention is determined using the validated HPLC coupled with UV detector described in Example 31. The results are in line with those obtained in Example 44.

The obtained pharmaceutical formulation illustrating the present invention is evaluated by determining its in vitro pulmonary deposition, MMAD and FPF by performing impaction tests as described in Example 43. The results are in line with those obtained in Example 44.

Example 51: Preparation of Formulation for DPI According to an Embodiment of the Present Invention (NEMs Containing PTX-Loaded Folate-PEO-HTCC 3 NPs and Dextran)

PTX-loaded folate-PEO-HTCC 3 NPs were prepared according to Example 36.

NEMs were produced by spray-drying the dispersion of PTX-loaded folate-PEO-HTCC 2 NPs in presence of dextran.

Briefly, dextran was dissolved in the NPs dispersion at a concentration of 28.4 mg/ml using an ultrasonic bath at room temperature. The dispersion was placed in an ice bath and 25% (v/v) of isopropanol was added to the dispersion. The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 4.75 g/min; nozzle diameter 0.7 mm; inlet temperature 100° C. corresponding to an outlet temperature of about 43° C. The NPs dispersion was kept in an ice bath during the spray-drying process in order to prevent NPs aggregation and dissolution of PTX.

The obtained pharmaceutical formulation illustrating the present invention is evaluated by determining its in vitro pulmonary deposition, MMAD and FPF by performing impaction tests as described in Example 45. The results are in line with those obtained in Example 45.

Example 52: Preparation of Formulation for DPI According to an Embodiment of the Present Invention (NEMs Containing TMZ-Loaded Folate-PEO-HMD 1 NPs and Mannitol and Leucine)

TMZ-loaded folate-PEO-HMD 1 NPs were prepared according to Example 39.

NEMs were produced by spray-drying the dispersion of TMZ-loaded folate-PEO-HMD 1 NPs in presence of mannitol and leucine.

Briefly, mannitol and leucine were dissolved in the NPs dispersion at a concentration of 27.4 mg/ml and 8 mg/ml, respectively, using an ultrasonic bath at room temperature. The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 4.4 g/min; nozzle diameter 0.7 mm; inlet temperature 160° C. corresponding to an outlet temperature of about 69° C. The actual TMZ content of the obtained pharmaceutical formulation according to an embodiment of the present invention is determined using the validated HPLC coupled with UV detector described in Example 31. Actual TMZ content=8.4±0.2%.

The obtained pharmaceutical formulation illustrating the present invention is evaluated by determining its in vitro pulmonary deposition, MMAD and FPF by performing impaction tests as described in Example 43. The in vitro pulmonary deposition and the FPF of obtained formulation are presented in FIG. 8. FPF=48±6%, MMAD=3.4±0.5 μm.

Example 53: Preparation of Formulation for DPI According to an Embodiment of the Present Invention (NEMs Containing TMZ-Loaded Folate-PEO-HMD 2 NPs and Mannitol and Leucine)

TMZ-loaded folate-PEO-HMD 2 NPs were prepared according to Example 40.

NEMs were produced by spray-drying the dispersion of TMZ-loaded folate-PEO-HMD 2 NPs in presence of mannitol and leucine.

Briefly, mannitol and leucine were dissolved in the NPs dispersion at a concentration of 27.4 mg/ml and 8 mg/ml, respectively, using an ultrasonic bath at room temperature. The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 4.4 g/min; nozzle diameter 0.7 mm; inlet temperature 160° C. corresponding to an outlet temperature of about 69° C. The actual TMZ content of the obtained pharmaceutical formulation according to an embodiment of the present invention is determined using the validated HPLC coupled with UV detector described in Example 31. The results are in line with those obtained in Example 52.

The obtained pharmaceutical formulation illustrating the present invention is evaluated by determining its in vitro pulmonary deposition, MMAD and FPF by performing impaction tests as described in Example 43. The results are in line with those obtained in Example 52.

Example 54: Preparation of Formulation for DPI According to an Embodiment of the Present Invention (NEMs Containing PTX-Loaded Folate-PEO-HMD 1 NPs and Mannitol and Leucine)

PTX-loaded folate-PEO-HMD 1 NPs were prepared according to Example 37.

NEMs were produced by spray-drying the dispersion of PTX-loaded folate-PEO-HMD 1 NPs in presence of mannitol and leucine.

Briefly, the NPs dispersion was diluted in a solution containing mannitol and leucine to have a concentration of F-PEG-HMD, mannitol and leucine of 2 mg/ml, 30 mg/ml and 8 mg/ml, respectively. The dispersion was spray-dried (Mini Spray Dryer B-290, Büchi Laboratory-Techniques, Flawil, Switzerland) under the following conditions: spraying air flow 800 l/hour; drying air flow 35 m³/hour; solution feed rate 4.5 g/min; nozzle diameter 0.7 mm; inlet temperature 130° C. corresponding to an outlet temperature of about 55° C. The dispersion was kept in an ice bath during the process in order to avoid dissolution of PTX.

The actual PTX content of the obtained pharmaceutical formulation according to an embodiment of the present invention is determined using the validated HPLC coupled with UV detector described in Example 34. Actual PTX content=0.068±0.002%.

The obtained pharmaceutical formulation illustrating the present invention is evaluated by determining its in vitro pulmonary deposition, MMAD and FPF by performing impaction tests using a MSLI from the Axahaler® DPI (100 L/min, 2.4s and No 3 HPMC capsules filled with 30 mg of dry powder, three discharges per capsule, two capsules per test, n=3). The cut-off diameters at this flow rate were 5.27, 2.40 and 1.32 μm between stages 2 to 3, 3 to 4 and 4 to 5, respectively. The FPF was expressed as a percentage of the total dose recovered but not of the delivered dose. The in vitro pulmonary deposition and the FPF of obtained formulation are presented in FIG. 9. FPF=48±3%, MMAD=3.1±0.2 μm.

Example 55: Preparation of Formulation for DPI According to an Embodiment of the Present Invention (NEMs Containing PTX-Loaded Folate-PEO-HMD 2 NPs and Mannitol and Leucine)

PTX-loaded folate-PEO-HMD 2 NPs were prepared according to Example 38.

NEMs were produced by spray-drying the dispersion of PTX-loaded folate-PEO-HMD 2_NPs in presence of mannitol and leucine.

Briefly, the NPs dispersion was diluted in a solution containing mannitol and leucine to have a concentration of F-PEG-HMD, mannitol and leucine of 2 mg/ml, 30 mg/ml and 8 mg/ml, respectively. The dispersion was spray-dried (Mini Spray Dryer B-290, Büchi Laboratory-Techniques, Flawil, Switzerland) under the following conditions: spraying air flow 800 l/hour; drying air flow 35 m³/hour; solution feed rate 4.5 g/min; nozzle diameter 0.7 mm; inlet temperature 130° C. corresponding to an outlet temperature of about 55° C. The dispersion was kept in an ice bath during the process in order to avoid dissolution of PTX.

The actual PTX content of the obtained pharmaceutical formulation according to an embodiment of the present invention is determined using the validated HPLC coupled with UV detector described in Example 34. The results are in line with those obtained in Example 54.

The obtained pharmaceutical formulation illustrating the present invention is evaluated by determining its in vitro pulmonary deposition, MMAD and FPF by performing impaction tests using a MSLI from the Axahaler® DPI (100 L/min, 2.4s and No 3 HPMC capsules filled with 30 mg of dry powder, three discharges per capsule, two capsules per test, n=3). The cut-off diameters at this flow rate were 5.27, 2.40 and 1.32 μm between stages 2 to 3, 3 to 4 and 4 to 5, respectively. The FPF was expressed as a percentage of the total dose recovered but not of the delivered dose. The results are in line with those obtained in Example 54.

Example 56: Preparation of Formulation for DPI According to an Embodiment of the Present Invention (NEMs Containing TMZ-Loaded Folate-PEO-HTCC 4 NPs and Mannitol)

TMZ-loaded folate-PEO-HTCC 4 NPs were prepared according to Example 41.

NEMs were produced by spray-drying the dispersion of TMZ-loaded folate-PEO-HTCC 4 NPs in the presence of mannitol.

Briefly, the dispersion of NPs was concentrated (factor 2) by ultrafiltration (MWCO=10 kDa). Mannitol was dissolved in the concentrated NPs dispersion at a concentration of 10 mg/ml using an ultrasonic probe at 40% during 1 min in an ice bath The dispersion was spray-dried (Mini Spray Dryer B-290, Büchi Laboratory-Techniques, Flawil, Switzerland) under the following conditions: spraying air flow 800 l/hour; drying air flow 35 m³/hour; solution feed rate 4.5 g/min; nozzle diameter 0.7 mm; inlet temperature 80° C. corresponding to an outlet temperature of about 45° C.

The actual TMZ content of the obtained pharmaceutical formulation according to an embodiment of the present invention is determined using the validated HPLC coupled with UV detector described in Example 31. The results are in line with those obtained in Example 43.

The obtained pharmaceutical formulation illustrating the present invention is evaluated by determining its in vitro pulmonary deposition, MMAD and FPF by performing impaction tests by performing impaction tests as described in Example 43. The results are in line with those obtained in Example 43.

Example 57: Preparation of Formulation for DPI According to an Embodiment of the Present Invention (NEMs Containing TMZ-Loaded Folate-PEO-HTCC 4 NPs and Lipids)

TMZ-loaded folate-PEO-HTCC 4 NPs were prepared according to Example 41.

NEMs were produced by spray-drying the dispersion of TMZ-loaded folate-PEO-HTCC 4 NPs in presence of cholesterol and phospholipids.

Briefly, the dispersion of NPs was concentrated (factor 2) by ultrafiltration (MWCO=10 kDa). Cholesterol and phospholipids were dissolved in the concentrated NPs dispersion at a concentration of 9 mg/ml and 2 mg/ml, respectively, using an ultrasonic probe at 40% during 1 min in an ice bath The dispersion was spray-dried (Mini Spray Dryer B-290, Büchi Laboratory-Techniques, Flawil, Switzerland) under the following conditions: spraying air flow 800 l/hour; drying air flow 35 m³/hour; solution feed rate 4.5 g/min; nozzle diameter 0.7 mm; inlet temperature 80° C. corresponding to an outlet temperature of about 45° C.

The actual TMZ content of the obtained pharmaceutical formulation according to an embodiment of the present invention is determined using the validated HPLC coupled with UV detector described in Example 31. The results are in line with those obtained in Example 44.

The obtained pharmaceutical formulation illustrating the present invention is evaluated by determining its in vitro pulmonary deposition, MMAD and FPF by performing impaction tests as described in Example 43. The results are in line with those obtained in Example 44.

Example 58: Preparation of Formulation for DPI According to an Embodiment of the Present Invention (NEMs Containing PTX-Loaded Folate-PEO-HTCC 4 NPs and Dextran)

PTX-loaded folate-PEO-HTCC 4 NPs were prepared according to Example 41.

NEMs were produced by spray-drying the dispersion of PTX-loaded folate-PEO-HTCC 4 NPs in presence of dextran.

Briefly, dextran was dissolved in the NPs dispersion at a concentration of 28.4 mg/ml using an ultrasonic bath at room temperature. The dispersion was placed in an ice bath and 25% (v/v) of isopropanol was added to the dispersion. The dispersion was spray-dried (Mini Spray Dryer B-290, Büchi Laboratory-Techniques, Flawil, Switzerland) under the following conditions: spraying air flow 800 l/hour; drying air flow 35 m$^3$/hour; solution feed rate 4.75 g/min; nozzle diameter 0.7 mm; inlet temperature 100° C. corresponding to an outlet temperature of about 43° C. The NPs dispersion was kept in an ice bath during the spray-drying process in order to prevent NPs aggregation and dissolution of PTX.

The obtained pharmaceutical formulation illustrating the present invention is evaluated by determining its in vitro pulmonary deposition, MMAD and FPF by performing impaction tests using as described in Example 45. The results are in line with those obtained in Example 45.

Example 59: In Vitro Evaluation of the Anti-Proliferative Properties of a DPI Formulation According to an Embodiment of the Present Invention for FR-Expressing Cells The cytotoxic effect of a DPI formulation illustrating the present invention on FR-expressing cells (human HeLa cervical adenocarcinoma cell line) was determined by means of the colorimetric assay using 3-(4,5-dimethylthiazol-2-yl)-2,5-diphenyl tetrazolium bromide (Sigma-Aldrich, St. Louis, Mo., USA, cat. num. M2128) (referred to herein as MTT). The test measures the number of metabolically active living cells that are able to transform the yellow product MTT into the blue product formazan dye by mitochondrial reduction. The amount of formazan obtained at the end of the experiment, measured by means of a spectrophotometer, is directly proportional to the number of living cells. Optical density determination thus allows a quantitative measurement of the effect of the investigated formulations as compared with the control condition (untreated cells) and/or to other references such as a paclitaxel solution.

To perform the assay, cells were allowed to grow in 96-well plate with a flat bottom with an amount of 100 µl of cell suspension per well with 1800 cells/well. The HeLa cell line was seeded in folate-free RPMI 1640 culture medium (Life Technologies, Gent, Belgium, cat. num. 27016021) supplemented with 10% of foetal bovine serum (Life Technologies, Gent, Belgium, cat. num. 16000036).

The detailed experimental procedure was the following: after a 24-hour period of incubation at 37° C., the culture medium was replaced by 100 µl of fresh medium in which the DPI formulation illustrating the present invention (prepared according to Example 45) was previously dispersed at the following PTX-relative molar concentrations: $10^{-10}$ M, $5·10^{-10}$ M, $10^{-9}$ M, $5·10^{-9}$M, $10^{-8}$ M, $5·10^{-8}$ M, $10^{-7}$M, $5·10^{-7}$ M, $10^{-6}$ M. Each experiment was performed six times.

After 2 hours of incubation at 37° C. without (control condition) or with the DPI formulation illustrating the present invention, the medium was replaced by fresh medium and the cells were let to incubate under normal culture conditions. After 3 days of incubation, the medium was replaced by 100 µl MTT dissolved in RPMI (1640 without phenol red) at a concentration of 0.5 mg/ml. The micro-wells were subsequently incubated during 3 hours at 37° C. and centrifuged at 200×g during 5 minutes. MTT was removed and formazan crystals formed were dissolved in 100 µl DMSO. The micro-wells were shaken for 5 minutes and read on a spectrophotometer at wavelengths of 570 nm (maximal formazan absorbance).

DPI formulations illustrating the present invention (prepared according to Example 45) were incubated in folate free RPMI or in presence of folic acid (RPMI 1640 medium, Life Technologies, Gent, Belgium, cat. num. 61870044). In the presence of folic acid, the folic acid enters in competition with the DPI formulation illustrating the present invention for the folate receptors and may inhibit interactions between the DPI formulation illustrating the present invention and folate receptors.

A non-targeted formulation was prepared by the same protocol than the one described in Example 45 using the non-targeted excipient, PEO-HTCC (synthesis described below), instead of folate-PEO-HTCC 1 in order to investigate the role of folic acid in folate-PEO-HTCC 1 as targeting agent.

Water-soluble formulation of paclitaxel was used as positive control (composition: paclitaxel 6 mg/ml, Cremophor EL (BASF, Limburgerhof, Germany) 50% (v/v) in ethanol) under the following concentrations: $10^{-9}$ M, $5·10^{-9}$M, $10^{-8}$ M, $5·10^{-8}$ M, $10^{-7}$M, $5·10^{-7}$ M, $10^{-6}$ M, $5·10^{-6}$ M, $10^{-5}$ M.

Figure 10:
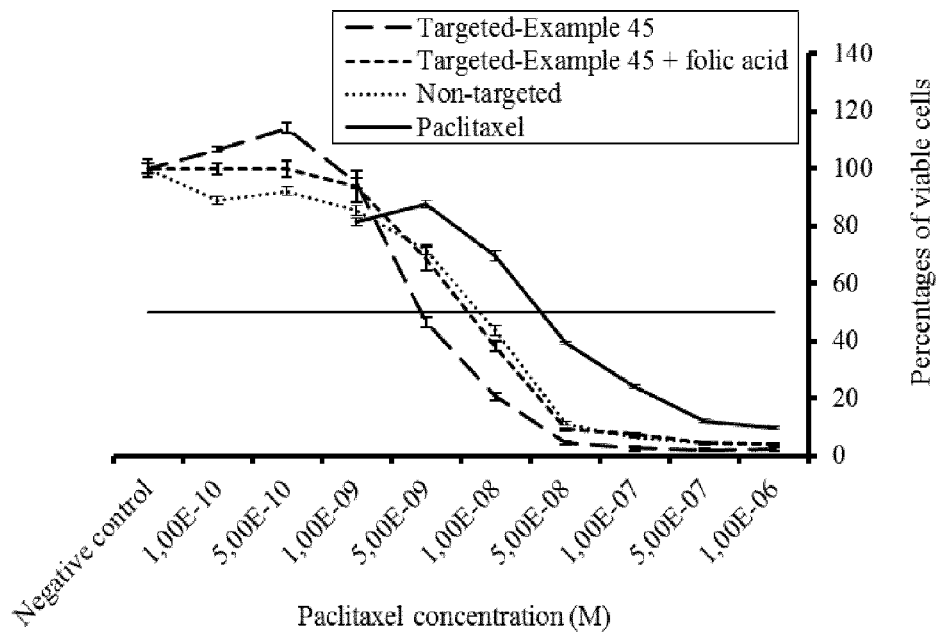
FIG. 10 represents a graph illustrating the percentage of viable cells in function of paclitaxel concentration for cells incubated with a DPI formulation according to an embodiment of the present invention (Targeted-Example 45), with a DPI formulations according to an embodiment of the present invention in presence of folic acid (Targeted-Example 45+folic acid), with non-targeted formulation (Non-targeted), or with water-soluble formulation of paclitaxel (Paclitaxel).

The percentage of viable cells in function of PTX concentration is presented in FIG. 10.

It was observed that the DPI formulation according to an embodiment of the present invention has higher cytotoxic effect on FR-expressing cells than paclitaxel and the non-targeted formulation. The results illustrate the role of the folic acid as targeting agent in the dry powder formulation illustrating the present invention for FR-expressing cells and the pharmacological efficacy of the antineoplastic agent comprised in the formulations illustrating the present invention.

Synthesis of PEO-HTCC: The free carboxylic group of HO—$CH_2CH_2$—PEO-NHCO$(CH_2)_2$COOH (Iris Biotech GmbH, Marktredwitz, Germany, cat. num. PEG1093) was coupled with the free primary amines of N-[(2-hydroxy-3-trimethylammonium)propyl] chitosan chloride (HTCC) with Mw of 92 kDa, a degree of acetylation of 20% (corresponding of a degree of deacetylation of 80%), and a degree of modification (by HT) of 33%. (Kitozyme, Herstal, Belgium), using carbodiimide chemistry (Hermanson G. T, 2008, supra). Briefly, 420 mg of HTCC was dissolved in 35 ml of ultrapure water under magnetic stirring. 1.15 g HO—$CH_2CH_2$—PEO-NHCO$(CH_2)_2$COOH, 100 mg of N-(3-Dimethylaminopropyl)-N'-ethylcarbodiimide hydrochloride (EDC) (Sigma-Aldrich, St. Louis, Mo., USA, cat. num. E6383) and 75 mg of NHS were added to this aqueous solution and the mixture was stirred at room temperature for 48 h. The reaction mixture was ultrafiltrated (MWCO=30 kDa, Ultracel, Merck Millipore, Darmstadt, Germany) against 0.001 M HCl and then lyophilized (Freeze-dryer Epsilon 1-6, Martin Christ GmbH, Osterode, Germany)

Example 60: In Vitro Evaluation of the Anti-Proliferative Properties of a DPI Formulation According to an Embodiment of the Present Invention for FR-Expressing Cells The cytotoxic effect of a DPI formulation illustrating the present invention on FR-expressing cells (human HeLa cervical adenocarcinoma cell line) was determined by means of the colorimetric MTT assay as described in Example 59.

The DPI formulations illustrating the present invention (prepared according Example 54) were incubated in folate free RPMI or in presence of folic acid (RPMI 1640 medium, Life Technologies, Gent, Belgium, cat. num. 61870044). In the presence of folic acid, the folic acid enters in competition with the formulation illustrating the present invention for the folate receptors and inhibits interactions between the formulation illustrating the present invention and folate receptors.

A non-targeted formulation was prepared by the same protocol than the one described in Example 59 using the non-targeted excipient PEO-HMD (synthesis described below) instead of folate-PEO-HMD 1 in order to investigate the role of folic acid in folate-PEO-HMD 1 as targeting agent.

Figure 11:
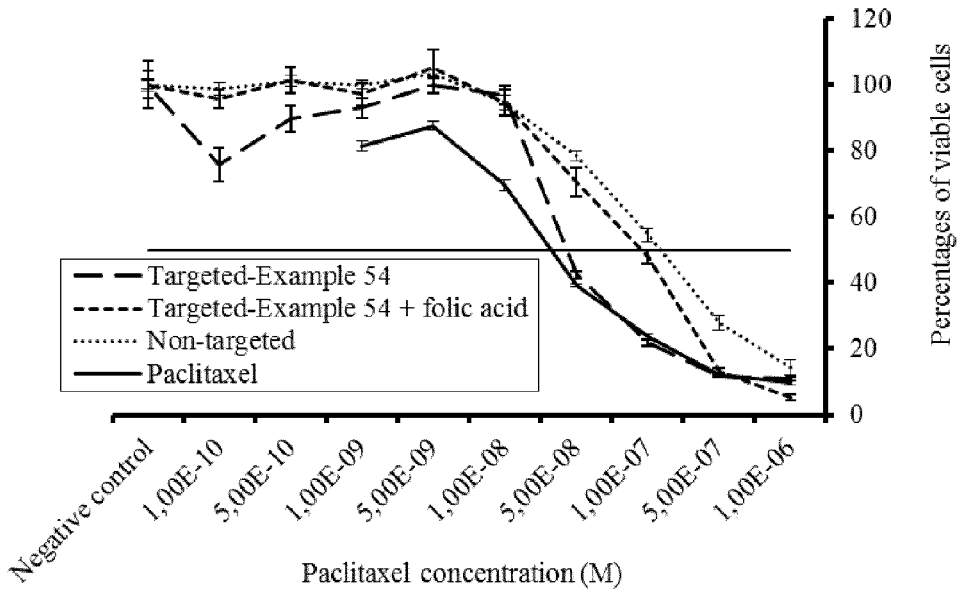
FIG. 11 represents a graph illustrating the percentage of viable cells in function of paclitaxel concentration for cells incubated with a DPI formulation according to an embodiment of the present invention (Targeted-Example 54), with a DPI formulations according to an embodiment of the present invention in presence of folic acid (Targeted-Example 54+folic acid), with non-targeted formulation (Non-targeted), or with water-soluble formulation of paclitaxel (Paclitaxel).

The percentage of viable cells in function of PTX concentration is presented in FIG. 11. It was observed that the DPI formulation according to an embodiment of the present invention has higher cytotoxic effect on FR-expressing cells than the non-targeted formulation. The results illustrate the role of the folic acid as targeting agent in the formulation illustrating the present invention for FR-expressing cells and the pharmacological efficacy of the antineoplastic agent comprised in the formulations illustrating the present invention.

Synthesis of PEO-HMD: First, $HMD-(CO)-(CH_2)_2-COOH$ was synthesized as described in Example 4. The free primary amine group of $HO-(CH_2)_2-PEO-NH_2$ (Iris Biotech GmbH, Marktredwitz, Germany, cat. num. PEG1007) was afterwards coupled with the free carboxylic group of $HMD-(CO)-(CH_2)_2-COOH$ using carbodiimide chemistry (Hermanson G. T., 2008, supra). Briefly, 45 mg of $HMD-(CO)-(CH_2)_2-COOH$ was dissolved in presence of 210 mg of $folate-NH-(CH_2)_2-PEO-NH_2$ in 10 ml of anhydrous DMSO under magnetic stirring. 25 mg of DCC, 15 mg of NHS, 16 µl of TEA and 5 mg of DMAP were added to this solution and the mixture was stirred at 40° C. for 24 h. The reaction mixture was dialyzed (MWCO=10 kDa, Spectra/Por, Spectrum Labs, Breda, The Nederlands) against ultrapure water in order to remove DMSO, ultrafiltrated (MWCO=10 kDa, Ultracel, Merck Millipore, Darmstadt, Germany) against a 70% (v/v) ethanol solution. Ethanol was evaporated under vacuum and the resulting aqueous solution was lyophilized (Freeze-dryer Epsilon 1-6, Martin Christ GmbH, Osterode, Germany)

Example 61: In Vitro Evaluation of the Incorporation of 3,3'-Dioctadecyloxacarbocyanine Perchlorate (DiO)-Loaded Folate-PEO-HTCC 1 NPs into FR-Expressing Cells The incorporation of the DiO-loaded folate-PEO-HTCC 1 NPs into FR-expressing cells (e.g. human HeLa cervical adenocarcinoma) was compared to the incorporation of the DiO-loaded PEO-HTCC using flow cytometry techniques.

DiO-loaded folate-PEO-HTCC 1 NPs were prepared according to Example 34 by using DiO (Sigma-Aldrich, St. Louis, Mo., USA, cat. num. D4292) at a concentration of 0.05 mg/ml instead of PTX in the acetone solution. DiO-loaded PEO-HTCC NPs were prepared according to Example 34 by using at a concentration of 0.05 mg/ml instead of PTX in the acetone solution, and by using PEO-HTCC (synthesis described in Example 59) instead of folate-PEO-HTCC 1.

To perform the assay, cells were allowed to grow in T25 culture flasks in folate-free RPMI 1640 supplemented with 10% of foetal bovine serum until they were confluent The detailed experimental procedure was the following: once cells were confluent, the culture medium was removed and cells were washed with 3 ml of cold phosphate buffer saline (PBS, Life Technologies, Gent, Belgium, cat. num. 10010015). Fresh medium, in which the NP formulation (DiO-loaded folate-PEO-HTCC 1 NPs or DiO-loaded PEO-HTCC NPs) was dispersed, was then added into the flasks. Each flask was incubated at 37° C. After a 30 minute or after a 3 hour period of incubation, cells were washed with cold PBS, detached by trypsin-EDTA (Life Technologies, Gent, Belgium, cat. num. 25200056) treatment, centrifuged, and suspended in 0.5 ml cold PBS. Suspensions of cells were analysed with a flow cytometer Quanta SC flow (Beckman Coulter Analis, Suarlee, Belgium). Results are expressed as mean green fluorescent signal (FL1 mean) per 10000 cells which is directly proportional to the number of nanoparticles interacting with FR-expressing cells. The date were analysed via the Student's t-test using Microsoft Excel (Microsoft Corporation, Redmond, USA). Experimental conditions were realized in triplicate.

Figure 12:
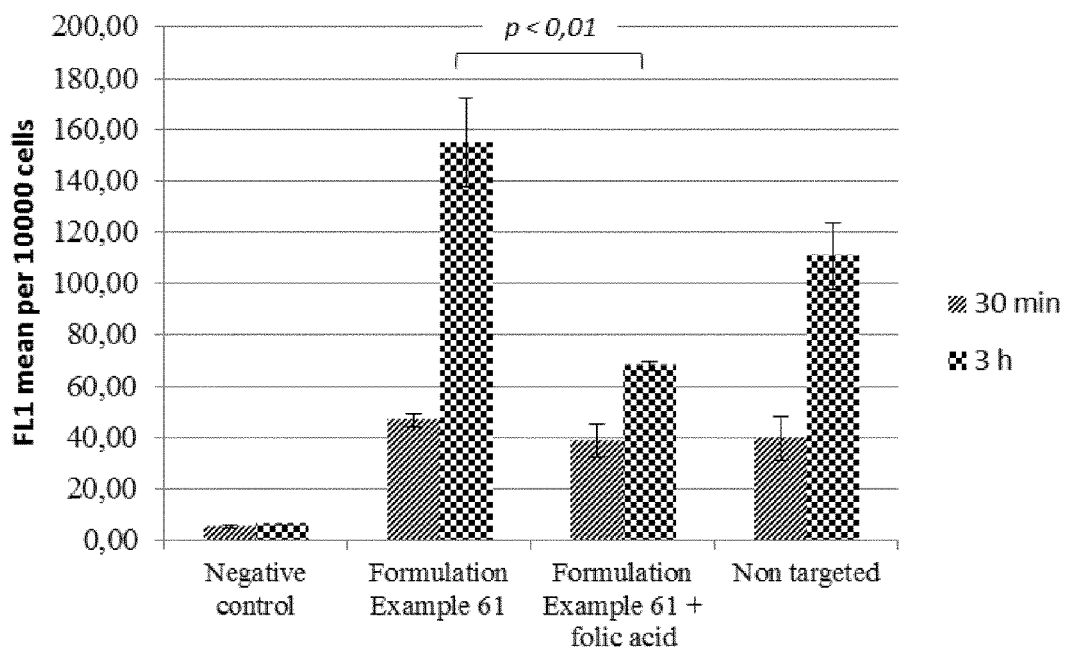
FIG. 12 represents a graph illustrating the mean green fluorescent signal (FL1 mean) per 10000 cells (proportional to the number of nanoparticles interacting with FR-expressing cells) after 30 minutes and 3 hours incubation of FR-expressing cells with fresh medium (Negative control), fresh medium containing DiO-loaded folate-PEO-HTCC 1 NPs (Formulation Example 61), fresh medium containing DiO-loaded folate-PEO-HTCC 1 NPs and folic acid (Formulation Example 61+folic acid), and fresh medium containing DiO-loaded PEO-HTCC NPs (Non targeted).

DiO-loaded folate-PEO-HTCC 1 NPs was incubated in folate free RPMI or in presence of folic acid (RPMI 1640 medium, Life Technologies, Gent, Belgium, cat. num. 61870044). In the presence of folic acid, the folic acid enters in competition with the DiO-loaded folate-PEO-HTCC 1 NPs for the folate receptors and inhibits interactions between the DiO-loaded folate-PEO-HTCC 1 NPs and folate receptors. Results are presented in FIG. 12.

No difference of interaction between DiO-loaded folate-PEO-HTCC 1 NPs and the cells were observed after the 30 minute incubation time.

After a 3 hour incubation time, the DiO-loaded folate-PEO-HTCC 1 NPs incubated in a folate-free medium showed the highest level of interaction with the cells compared to the non-targeted NPs (i.e. DiO-loaded PEO-HMD NPs). Moreover, the incubation of the same DiO-loaded folate-PEO-HTCC 1 NPs in presence of folic acid in the medium lead to a statistically significant lower level of interaction compared to incubation in a folate free medium. These results indicate that DiO-loaded folate-PEO-HTCC 1 NPs at least partially interact with the cells though the folate receptors. Hence, these results suggest that the formulations illustrating the present invention advantageously interact at least partially with FR-expressing cells though their folate receptors.

Example 62: In Vitro Evaluation of the Incorporation of 3,3'-Dioctadecyloxacarbocyanine Perchlorate (DiO)-Loaded Folate-PEO-HMD 1 NPs into FR-Expressing Cells The incorporation of the DiO-loaded folate-PEO-HMD 1 NPs into FR-expressing cells (e.g. human HeLa cervical adenocarcinoma) was compared to the incorporation of the DiO-loaded PEO-HMD using flow cytometry techniques.

DiO-loaded folate-PEO-HMD 1 NPs were prepared according to Example 39 by using DiO (Sigma-Aldrich, St. Louis, Mo., USA, cat. num. D4292) at a concentration of 0.5 mg/ml instead of PTX in DMSO. DiO-loaded PEO-HMD NPs were prepared according to Example 39 by using at a concentration of 0.5 mg/ml instead of PTX in DMSO, and by using PEO-HMD (synthesis described in Example 60) instead of folate-PEO-HMD 1.

To perform the assay, cells were allowed to grow in T25 culture flasks in folate-free RPMI 1640 supplemented with 10% of foetal bovine serum until they were confluent.

The detailed experimental procedure was the following: once cells were confluent, the culture medium was removed and cells were washed with 3 ml of cold phosphate buffer saline (PBS, Life Technologies, Gent, Belgium, cat. num. 10010015). Fresh medium, in which the NP formulation (DiO-loaded folate-PEO-HMD 1 NPs or DiO-loaded PEO-HMD NPs) was dispersed, was then added into the flasks. Each flask was incubated at 37° C. After a 30 minute or after a 3 hour period of incubation, cells were washed with cold PBS, detached by trypsin-EDTA Life Technologies, Gent, Belgium, cat. num. 25200056) treatment, centrifuged, and suspended in 0.5 ml cold PBS. Suspensions of cells were analysed with a flow cytometer Quanta SC flow (Beckman Coulter Analis, Suarlee, Belgium). Results are expressed as mean green fluorescent signal (FL1 mean) per 10000 cells which is directly proportional to the number of nanoparticles interacting with FR-expressing cells. The date were analysed via the Student's t-test using Microsoft Excel (Microsoft Corporation, Redmond, USA). Experimental conditions were realized in triplicate.

Figure 13:
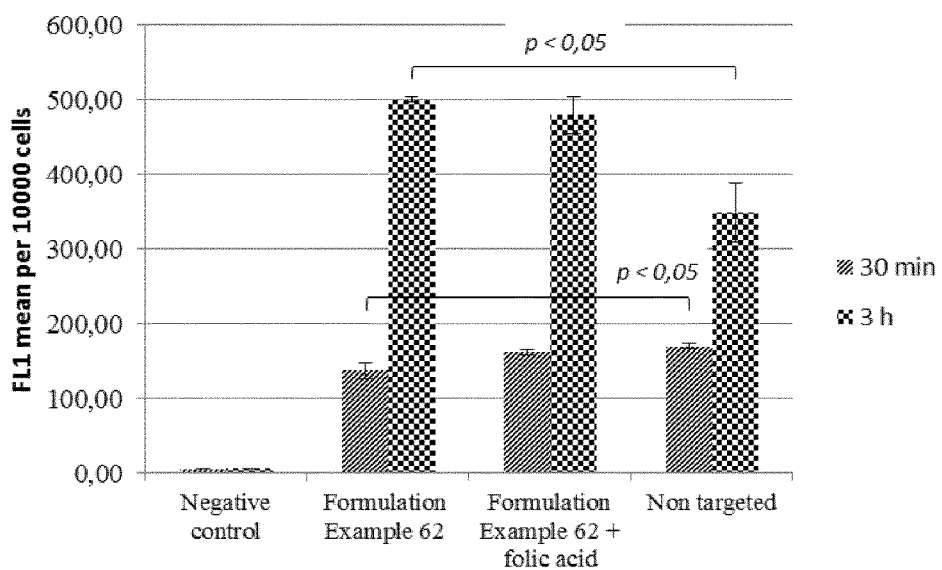
FIG. 13 represents a graph illustrating the mean green fluorescent signal (FL1 mean) per 10000 cells (proportional to the number of nanoparticles interacting with FR-expressing cells) after 30 minutes and 3 hours incubation of FR-expressing cells with fresh medium (Negative control), fresh medium containing DiO-loaded folate-PEO-HMD 1 NPs (Formulation Example 62), fresh medium containing DiO-loaded folate-PEO-HMD 1 NPs and folic acid (Formulation Example 62+folic acid), and fresh medium containing DiO-loaded PEO-HMD NPs (Non targeted).

DiO-loaded folate-PEO-HMD 1 NPs was incubated in folate free RPMI or in presence of folic acid (RPMI 1640 medium, Life Technologies, Gent, Belgium, cat. num. 61870044). In the presence of folic acid, the folic acid enters in competition with the DiO-loaded folate-PEO-HMD 1 NPs for the folate receptors and inhibits interactions between the DiO-loaded folate-PEO-HMD 1 NPs and folate receptors. Results are presented in FIG. 13.

After a 30 minutes incubation time, the level of interaction of DiO-loaded PEO-HMD NPs with the cells was slightly higher than the interaction of folate-PEO-HMD 1 NPs with the cells. However, this relative high level of interaction seemed to be only furtive with regard to results for a 3 hour incubation time. After a 3 hour incubation time, the DiO-loaded folate-PEO-HMD 1 NPs incubated in a folate-free medium showed the highest level of interaction with the cells. These results indicate that DiO-loaded folate-PEO-HTCC 1 NPs interact at least partially with the cells though the folate receptors. Hence, these results suggest that the formulations illustrating the present invention advantageously interact at least partially with FR-expressing cells though their folate receptors.

Example 63: Dispersion of a DPI Formulation Illustrating the Present Invention in Aqueous Medium Example 63 shows the potential of the spray-drying method described in the present invention to produce DPI formulations capable to reform the initial NPs (i.e., NPs before the spray drying process) in aqueous media.

Particle size distribution of NPs prepared according to Example 34 were measured by dynamic light scattering (DLS) (Zetasizer nano ZS, Malvern Instruments, Worcestershire, UK) as described in Example 31. The sum of the Mean Intensity % values below a diameter of 955.4 nm ($MI_{<955.4}$) of the PTX-loaded folate-PEO-HTCC 1 NPs was considered 100%. 10 mg of DPI formulation prepared according to Example 45 was dispersed in 1.5 ml of ultrapure water using vortex during 2 times 60 seconds. Particle size distribution of reconstituted NPs were measured by DLS (Zetasizer nano ZS, Malvern Instruments, Worcestershire, UK) as described in Example 31. The sum of the Mean Intensity % values below a diameter of 955.4 nm was calculated and expressed as a percentage ($MI_{<955.4}$) by considering the $MI_{<955.4}$ of the PTX-loaded folate-PEO-HTCC 1 NPs as 100%. $MI_{<955.4}$ of the dispersed DPI formulation prepared according to Example 45 was 48%.

Example 64: Dispersion of a DPI Formulation Illustrating the Present Invention in Aqueous Medium Example 64 shows the potential of the spray-drying method described in the present invention to produce DPI formulations able to reform the initial NPs (i.e., NPs before the spray drying process) in aqueous media.

Particle size distribution of NPs prepared according to Example 37 were measured by DLS (Zetasizer nano ZS, Malvern Instruments, Worcestershire, UK) as described in Example 31. The sum of the Mean Intensity % value below a diameter of 615.1 nm ($MI_{<615.1}$) of the PTX-loaded folate-PEO-HMD 1 NPs was considered 100%.

10 mg of DPI formulation prepared according to Example 54 was dispersed in 1.5 ml of ultrapure water using vortex during 2 times 60 seconds. Particle size distribution of NPs were measured by DLS (Zetasizer nano ZS, Malvern Instruments, Worcestershire, UK) as described in Example 31. The sum of the Mean Intensity % value below a diameter of 615.1 nm was calculated and expressed as a percentage ($MI_{<615.1}$) by considering the $MI_{<615.1}$ of the PTX-loaded folate-PEO-HMD 1 NPs as 100%. $MI_{<615.1}$ of the dispersed DPI formulation prepared according to Example 54 was 93%.

The invention claimed is:

1. A dry powder pharmaceutical formulation configured for administration by inhalation, comprising microparticles formed by at least one carrier and, embedded in the microparticles, nanoparticles comprising at least one antineoplastic agent and at least one folate receptor (FR)-targeting compound, wherein the at least one carrier comprises mannitol or dextran or mannitol and leucine, and wherein the at least one carrier is configured to allow for reconstitution of the nanoparticles when the microparticles are dissolved or dispersed in an aqueous medium.

2. The pharmaceutical formulation according to claim 1, wherein the FR-targeting is effected by at least one folate moiety.

3. The pharmaceutical formulation according to claim 1, wherein the FR-targeting compound is a folate-polysaccharide conjugate comprising at least one folate moiety covalently linked to a polysaccharide or functionally-modified polysaccharide.

4. The pharmaceutical formulation according to claim 3, wherein the polysaccharide or functionally-modified polysaccharide is selected from chitosan or functionally-modified chitosan; N-[(2-hydroxy-3-trimethylammonium)propyl] chitosan (HTC) and its salts; N-trimethyl chitosan (TMC) and its salts; N,O-carboxymethyl chitosan (N,O-CMC) and its salts; N-carboxymethyl chitosan (N-CMC) and its salts; N,N-carboxymethyl chitosan (N,N-CMC) and its salts; O-carboxymethyl chitosan (O-CMC) and its salts; hydrophobically-modified chitosan (HMC) and its salts; dextran or functionally-modified dextran; hydrophobically-modified dextran (HMD) and its salts; starch or functionally-modified starch; hydroxypropyl starch; amylose or functionally-modified amylose; amylopectin or functionally-modified amylopectin; cellulose or functionally-modified cellulose; methylcellulose and its salts; carboxymethylcellulose and its salts; hydroxyethylcellulose and its salts; ethylcellulose and its salts; hydroxyethylmethylcellulose and its salts; hydroxypropylcellulose and its salts; hypromellose and its salts; hypromellose acetate succinate; hypromellose phthalate; croscarmellose and its salts; chitin; cyclodextrin; dextrate; dextrin; maltodextrin; pullulan; or guar gum.

5. The pharmaceutical formulation according to claim 3, wherein the polysaccharide or functionally-modified polysaccharide is covalently bound to the folate moiety via a single bond or via a linker, wherein the linker comprises a polyether, ether, amine, polyamine, amino acid, peptide, a polypeptide, a carbohydrate, or a combination of two or more thereof.

6. The pharmaceutical formulation according to claim 5, wherein the linker comprises or consists essentially of a polyether selected from polyethylene oxide (PEO), polypropylene oxide (PPO), or a block co-polymer of PEO and PPO.

7. The pharmaceutical formulation according to claim 5, wherein the linker comprises or consists essentially of a PEO.

8. The pharmaceutical formulation according to claim 1, wherein the FR-targeting compound is a folate-polysaccharide conjugate comprising at least one unit selected from the group consisting of units of Formula XIb, XIc, XId, and XIe, or a stereoisomer, tautomer, salt, hydrate or solvate thereof, or any subgroup thereof, wherein

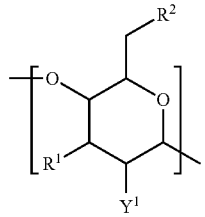
(XIb)

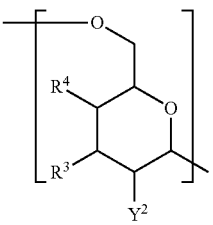
(XIc)

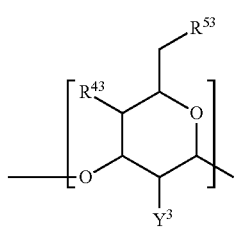
(XId)

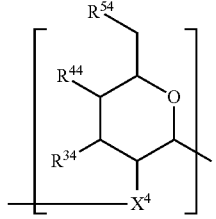
(XIe)

$Y^1$ is —$X^2$—$X^1$—$X^3$, or a group selected from —$OR^{10}$, —$N(R^{100})R^{101}$, or —$N^+(R^{100})(R^{101})R^{102}$, $Y^2$ is —$X^2$—$X^1$—$X^3$, or a group selected from —$OR^{20}$, —$N(R^{200})R^{201}$, or —$N^+(R^{200})(R^{201})R^{202}$, $Y^3$ is —$X^2$—$X^1$—$X^3$, or a group selected from —$OR^{30}$, —$N(R^{300})R^{301}$, or —$N^+(R^{300})(R^{301})R^{302}$, $R^1$ is —$OR^1$ or —$X^2$—$X^1$—$X^3$,
$R^2$ is —$OR^{21}$ Or —$X^2$—$X^1$—$X^3$,
$R^3$ is —$OR^{31}$ or —$X^2$—$X^1$—$X^3$,
$R^4$ is —$OR^{41}$ or —$X^2$—$X^1$—$X^3$,
$R^{34}$ is —$OR^{31}$ or —$X^2$—$X^1$—$X^3$,
$R^{43}$ is —$OR^{41}$ or —$X^2$—$X^1$—$X^3$,
$R^{44}$ is —$OR^{41}$ or —$X^2$—$X^1$—$X^3$,
$R^{53}$ is —$OR^{51}$ or —$X^2$—$X^1$—$X^3$,
$R^{54}$ is —$OR^{51}$ or —$X^2$—$X^1$—$X^3$,
wherein at least one of $Y^1$, $R^1$, or $R^2$ is —$X^2$—$X^1$—$X^3$;
wherein at least one of $Y^2$, $R^3$, or $R^4$ is —$X^2$—$X^1$—$X^3$;
wherein at least one of $Y^3$, $R^{43}$, or $R^{53}$ is —$X^2$—$X^1$—$X^3$;
wherein at least one of $R^{34}$, $R^{44}$, or $R^{54}$ is —$X^2$—$X^1$—$X^3$;
wherein $R^{10}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, —$C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$R^{11}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$R^{20}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—$OR^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein $R^{12}$ is selected from hydrogen or $C_{1-6}$alkyl;

$R^{21}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

R$^{30}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

R$^{31}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

R$^{41}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

R$^{51}$ is selected from hydrogen, a mono-, oligo-, or poly-glycosyl moiety, or a group consisting of $C_{1-25}$alkyl, $C_{1-25}$alkylcarbonyl, $C_{2-25}$alkenylcarbonyl, $C_{1-6}$alkylene-CO—OR$^{12}$, carboxyl$C_{1-6}$alkylenecarbonyl, hydroxy$C_{1-6}$alkyl, carboxyl$C_{6-12}$arylenecarbonyl, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, or $C_{1-6}$alkoxy, wherein R$^{12}$ is selected from hydrogen or $C_{1-6}$alkyl;

R$^{100}$ is selected from hydrogen, or a group consisting of $C_{1-25}$alkyl, $C_{1-6}$alkylene-N(R$^{111}$)R$^{112}$, $C_{1-6}$alkylene-N$^+$(R$^{111}$)(R$^{112}$)R$^{113}$, $C_{1-25}$alkylcarbonyl, $C_{2-25}$alkenylcarbonyl, $C_{1-6}$alkylene-CO—OR$^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein R$^{111}$ is selected from hydrogen or $C_{1-6}$alkyl, R$^{112}$ is selected from hydrogen or $C_{1-6}$alkyl, R$^{113}$ is selected from hydrogen or $C_{1-6}$alkyl, and R$^{114}$ is selected from hydrogen or $C_{1-6}$alkyl;

R$^{101}$ is selected from hydrogen, or a group consisting of $C_{1-25}$alkyl, $C_{1-6}$alkylene-N(R$^{111}$)R$^{112}$, $C_{1-6}$alkylene-N$^+$(R$^{111}$)(R$^{112}$)R$^{113}$, $C_{1-25}$alkylcarbonyl, $C_{2-25}$alkenylcarbonyl, $C_{1-6}$alkylene-CO—OR$^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein R$^{11}$ is selected from hydrogen or $C_{1-6}$alkyl, R$^{112}$ is selected from hydrogen or $C_{1-6}$alkyl, R$^{113}$ is selected from hydrogen or $C_{1-6}$alkyl, and R$^{114}$ is selected from hydrogen or $C_{1-6}$alkyl;

R$^{102}$ is selected from hydrogen, or a group consisting of $C_{1-25}$alkyl, $C_{1-6}$alkylene-N(R$^{111}$)R$^{112}$, $C_{1-6}$alkylene-N$^+$(R$^{111}$)(R$^{112}$)R$^{113}$, $C_{1-25}$alkylcarbonyl, $C_{2-25}$alkenylcarbonyl, $C_{1-6}$alkylene-CO—OR$^{114}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein R$^{11}$ is selected from hydrogen or $C_{1-6}$alkyl, R$^{112}$ is selected from hydrogen or $C_{1-6}$alkyl, R$^{113}$ is selected from hydrogen or $C_{1-6}$alkyl, and R$^{114}$ is selected from hydrogen or $C_{1-6}$alkyl;

R$^{200}$ is selected from hydrogen, or a group consisting of $C_{1-25}$alkyl, $C_{1-6}$alkylene-N(R$^{211}$)R$^{212}$, $C_{1-6}$alkylene-N$^+$(R$^{211}$)(R$^{212}$)R$^{213}$, $C_{1-25}$alkylcarbonyl, $C_{2-25}$alkenylcarbonyl, $C_{1-6}$alkylene-CO—OR$^{214}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein R$^{211}$ is selected from hydrogen or $C_{1-6}$alkyl, R$^{212}$ is selected from hydrogen or $C_{1-6}$alkyl, R$^{213}$ is selected from hydrogen or $C_{1-6}$alkyl, and R$^{214}$ is selected from hydrogen or $C_{1-6}$alkyl;

R$^{201}$ is selected from hydrogen, or a group consisting of $C_{1-25}$alkyl, $C_{1-6}$alkylene-N(R$^{211}$)R$^{212}$, $C_{1-6}$alkylene-N$^+$(R$^{211}$)(R$^{212}$)R$^{213}$, $C_{1-25}$alkylcarbonyl, $C_{2-25}$alkenylcarbonyl, $C_{1-6}$alkylene-CO—OR$^{214}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein R$^{211}$ is selected from hydrogen or $C_{1-6}$alkyl, R$^{212}$ is selected from hydrogen or $C_{1-6}$alkyl, R$^{213}$ is selected from hydrogen or $C_{1-6}$alkyl, and R$^{214}$ is selected from hydrogen or $C_{1-6}$alkyl;

R$^{202}$ is selected from hydrogen, or a group consisting of $C_{1-25}$alkyl, $C_{1-6}$alkylene-N(R$^{211}$)R$^{212}$, $C_{1-6}$alkylene-N$^+$(R$^{211}$)(R$^{212}$)R$^{213}$, $C_{1-25}$alkylcarbonyl, $C_{2-25}$alkenylcarbonyl, $C_{1-6}$alkylene-CO—OR$^{214}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein R$^{211}$ is selected from hydrogen or $C_{1-6}$alkyl, R$^{212}$ is selected from hydrogen or $C_{1-6}$alkyl, R$^{213}$ is selected from hydrogen or $C_{1-6}$alkyl, and R$^{214}$ is selected from hydrogen or $C_{1-6}$alkyl;

R$^{300}$ is selected from hydrogen, or a group consisting of $C_{1-25}$alkyl, $C_{1-6}$alkylene-N(R$^{211}$)R$^{212}$, $C_{1-6}$alkylene- $N^+(R^{211})(R^{212})R^{213}$, $C_{1-25}$alkylcarbonyl, $C_{2-25}$alkenylcarbonyl, $C_{1-6}$alkylene-CO—$OR^{314}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{311}$ is selected from hydrogen or $C_{1-6}$alkyl, $R^{312}$ is selected from hydrogen or $C_{1-6}$alkyl, $R^{313}$ is selected from hydrogen or $C_{1-6}$alkyl, and $R^{314}$ is selected from hydrogen or $C_{1-6}$alkyl;

$R^{301}$ is selected from hydrogen, or a group consisting of $C_{1-25}$alkyl, $C_{1-6}$alkylene-$N(R^{211})R^{212}$, $C_{1-6}$alkylene-$N^+(R^{211})(R^{212})R^{213}$, $C_{1-25}$alkylcarbonyl, $C_{2-25}$alkenylcarbonyl, $C_{1-6}$alkylene-CO—$OR^{314}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{311}$ is selected from hydrogen or $C_{1-6}$alkyl, $R^{312}$ is selected from hydrogen or $C_{1-6}$alkyl, $R^{313}$ is selected from hydrogen or $C_{1-6}$alkyl, and $R^{314}$ is selected from hydrogen or $C_{1-6}$alkyl;

$R^{302}$ is selected from hydrogen, or a group consisting of $C_{1-25}$alkyl, $C_{1-6}$alkylene-$N(R^{211})R^{212}$, $C_{1-6}$alkylene-$N^+(R^{211})(R^{212})R^{213}$, $C_{1-25}$alkylcarbonyl, $C_{2-25}$alkenylcarbonyl, $C_{1-6}$alkylene-CO—$OR^{314}$, $C_{2-6}$alkenyl, $C_{2-6}$alkynyl, $C_{3-6}$cycloalkyl, and $C_{6-10}$aryl, each group being optionally substituted with one or more substituents each independently selected from hydroxyl, halogen, $C_{1-6}$alkyl, carboxyl, or $C_{1-6}$alkoxy, wherein $R^{311}$ is selected from hydrogen or $C_{1-6}$alkyl, $R^{312}$ is selected from hydrogen or $C_{1-6}$alkyl, $R^{313}$ is selected from hydrogen or $C_{1-6}$alkyl, and $R^{314}$ is selected from hydrogen or $C_{1-6}$alkyl;

$X^2$ is —O— or —$N(R^{103})$—, wherein $R^{103}$ is selected from hydrogen or $C_{1-6}$alkyl;

$X^1$ is a single bond or a linker comprising a polyether, ether, amine, polyamine, amino acid, peptide, a polypeptide, a carbohydrate, or a combination of two or more thereof, $X^3$ is a folate moiety-having the structural Formula XII, or a stereoisomer, tautomer, salt, hydrate or solvate thereof, wherein

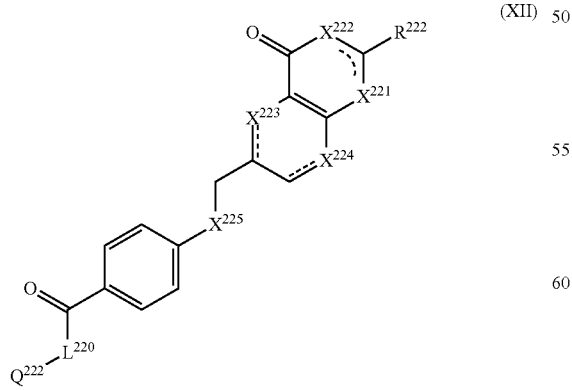

(XII)

$X^{221}$ is selected from N, $NR^{221}$, or O; $X^{222}$ is selected from N, $NR^{221}$, or O; $X^{223}$ is selected from N, $NR^{223}$, or O; $X^{224}$ is selected from N, $NR^{224}$ or O; $X^{225}$ is selected from $NR^{224}$ or O; $R^{221}$ is selected from hydrogen, or a group consisting of nitroso, $C_{1-12}$alkyl, —OR', —COR', and halosubstituted —COR', wherein R' is H or $C_{1-8}$alkyl; $R^{222}$ is selected from the group consisting of —N(H)$R^{225}$, hydrogen, halogen, $C_{1-12}$alkyl, $C_{2-12}$alkenyl, $C_{2-12}$alkynyl, —$OR^{225}$, —CO—$R^{125}$, —CO—O—$R^{225}$, and —CO—N(H)$R^{225}$, wherein $R^{225}$ is selected from the group consisting of hydrogen, halo, $C_{1-12}$alkyl, $C_{2-12}$alkenyl, $C_{2-12}$alkynyl, —OR', —CO—R', —CO—OR', and —NHR', wherein R' is H or $C_{1-8}$alkyl; $R^{223}$ is selected from hydrogen, or a group consisting of $C_{1-12}$alkyl, nitroso, —(C=O), —OR', —COR', and halosubstituted —COR', wherein R' is H or $C_{1-8}$alkyl; $R^{224}$ is selected from hydrogen, or a group consisting of nitroso, $C_{1-12}$alkyl, —(C=O), —OR', —COR', and halosubstituted —COR', wherein R' is H or $C_{1-8}$alkyl; $L^{220}$ is selected from

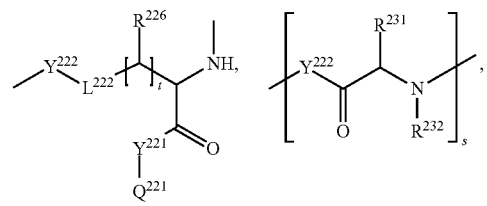

or a group consisting of $C_{1-6}$alkylene, $C_{1-6}$alkylenecarbonyl, —$C_{1-6}$alkylene-$N(R^{227})$—, $C_{2-6}$alkenylene, $C_{2-6}$alkynylene, $C_{3-6}$cycloalkylene, $C_{6-10}$arylene, —(C=O)—$C_{1-6}$alkylene, —O—, $C_{1-6}$alkylene-O—$C_{1-6}$alkylene, $C_{2-6}$alkenylene-O—$C_{2-6}$alkenylene, $C_{2-6}$alkynylene-O—$C_{2-6}$alkynylene, $C_{3-6}$cycloalkylene-O—$C_{3-6}$cycloalkylene, $C_{1-6}$alkylene-(CO)—O—$C_{1-6}$alkylene, $C_{2-6}$alkenylene-(CO)—O—$C_{2-6}$alkenylene, $C_{2-6}$alkynylene-(CO)—O—$C_{2-6}$alkynylene, $C_{3-6}$cycloalkylene-(CO)—O—$C_{3-6}$cycloalkylene, $C_{1-6}$alkylene-O—(CO)—$C_{1-6}$alkylene, $C_{2-6}$alkenylene-O—(CO)—$C_{2-6}$alkenylene, $C_{2-6}$alkynylene-O—(CO)—$C_{2-6}$alkynylene, $C_{3-6}$cycloalkylene-O—(CO)—$C_{3-6}$cycloalkylene, —$N(R^{228})$—, —$N(R^{228})$—(CO)—, and —(CO)—$N(R^{228})$—, each group being optionally substituted with one or more substituents each independently selected from hydroxyl or $C_{1-6}$alkyl; wherein the $Y^{222}$ is attached to $Q^{222}$ and —NH— is attached to —(CO)—, or wherein the left side of each group is attached to $Q^{222}$ and the right side of each group is attached to —(CO)—; wherein $Y^{221}$ is selected from a single bond, —O—, —$N(R^{229})$—, or —S—; $Y^{222}$ is selected from a single bond, —O—, —$NR^{229}$—, —$N(R^{229})$—C(=NH)—N($R^{230}$)—, or —S—; $L^{222}$ is a single bond, $C_{6-10}$arylene, or —(C=O)—; t is an integer selected from 1, 2, 3, or 4; s is an integer selected from 1 to 20; $R^{226}$ is hydrogen or $C_{1-6}$alkyl; $R^{227}$ is hydrogen or $C_{1-6}$alkyl; $R^{228}$ is hydrogen or $C_{1-6}$alkyl; $R^{229}$ is hydrogen or $C_{1-6}$alkyl; $R^{230}$ is hydrogen or $C_{1-6}$alkyl; each $R^{231}$ is independently selected from the group consisting of hydrogen or the amino acid side chain of arginine, histidine, lysine, aspartic acid, glutamic acid, serine, threonine, asparagine, glutamine, cysteine, glycine, alanine, valine, isoleucine, leucine, methionine, phenylalanine, tyrosine, and tryptophan; $R^{232}$ is hydrogen or $R^{231}$ and $R^{232}$ together with the atoms to with they are attached form a pyrrolidine ring; $Q^{221}$ is hydrogen or is a single bond connected to $X^1$; $Q^{222}$ is hydrogen or is a single bond connected to $X^1$; wherein at least one of $Q^{221}$ and $Q^{222}$ is a single bond connected to $X^1$; the dotted bond represents a single bond or a double bond;

$X^4$ is —O— or —N($R^{403}$)—, wherein $R^{403}$ is selected from hydrogen or $C_{1-6}$alkyl.

9. The pharmaceutical formulation according to claim 1, wherein the antineoplastic agent is selected from temozolomide, cisplatin, carboplatin, paclitaxel, docetaxel, gemcitabine, vinorelbine, etoposide, irinotecan, cyclophosphamide, doxorubicin, vincristine, or a combination thereof.

10. The pharmaceutical formulation according to claim 1, wherein the antineoplastic agent and the FR-targeting compound are non-covalently associated in the nanoparticle.

11. The pharmaceutical formulation according to claim 1, wherein the at least one FR-targeting compound is a polysaccharide or functionally-modified polysaccharide comprising at least one FR-targeting moiety.

12. The pharmaceutical formulation according to claim 11, wherein the FR-targeting moiety is a folate moiety.

13. The pharmaceutical formulation according to claim 1, wherein the particle size distribution of at least 10% of the nanoparticles, when reconstituted by dissolving or dispersing the microparticles in an aqueous medium, corresponds to the particle size distribution of the nanoparticles before they were comprised in the microparticles.

14. The pharmaceutical formulation according to claim 1, wherein the particle size distribution of at least 90% of the nanoparticles, when reconstituted by dissolving or dispersing the microparticles in an aqueous medium, corresponds to the particle size distribution of the nanoparticles before they were comprised in the microparticles.

15. An inhaler comprising the pharmaceutical formulation according to claim 1.

16. A method for treating a proliferative disease affecting at least part of the respiratory tract, comprising administering a therapeutically or prophylactically effective amount of the pharmaceutical formulation of claim 1 to a subject in need thereof.

17. The method of claim 16, wherein the pharmaceutical formulation is administered by inhalation.

18. The method of claim 16, wherein the proliferative disease affecting at least part of the respiratory tract is a tumour affecting at least part of the respiratory tract or cancer affecting at least part of the respiratory tract.

19. The method of claim 16, wherein the proliferative disease affecting at least part of the respiratory tract is small cell lung cancer (SCLC) or non-small cell lung cancer (NSCLC).

20. The method of claim 16, wherein the proliferative disease affecting at least part of the respiratory tract is a metastatic tumour affecting at least part of the respiratory tract or metastatic cancer affecting at least part of the respiratory tract.

21. The method of claim 16, wherein the pharmaceutical formulation is administered by dry powder inhalation.

22. A method for preparing the microparticles of claim 1, the steps of:
(a) producing nanoparticles comprising at least one antineoplastic agent and at least one FR-targeting compound;
(b) preparing in a solvent a composition comprising (i) nanoparticles produced in step (a), (ii) at least one carrier comprising mannitol or dextran or mannitol and leucine, and (iii) one or more surfactants, wherein the nanoparticles are dispersed in the solvent, the carrier is in suspension or solution or dispersed in the solvent, and the one or more surfactants are in solution in the solvent, and
(c) drying the composition of step (b) to produce microparticles containing the nanoparticles,
wherein the method is for preparing microparticles configured for dry powder inhalation.

23. The method according to claim 22, wherein the method further comprises dissolving or dispersing the microparticles in an aqueous medium to reconstitute the nanoparticles, wherein the particle size distribution of at least 10% of the reconstituted nanoparticles corresponds to the particle size distribution of the nanoparticles (before they were) comprised in the microparticles.

24. The method of claim 22, wherein the composition of step (b) is dried by spray drying.

* * * * *